(12) United States Patent
Carpino et al.

(10) Patent No.: US 6,432,945 B1
(45) Date of Patent: Aug. 13, 2002

(54) DIPEPTIDE DERIVATIVES

(75) Inventors: Philip Albert Carpino, Groton; David Andrew Griffith, Old Saybrook; Bruce Allen Lefker, Gales Ferry, all of CT (US)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 09/822,095

(22) Filed: Mar. 30, 2001

Related U.S. Application Data

(62) Division of application No. 09/380,887, filed as application No. PCT/IB98/00873 on Jun. 5, 1998, now Pat. No. 6,251,902.
(60) Provisional application No. 60/050,764, filed on Jun. 25, 1997.

(51) Int. Cl.[7] .................... A61K 31/542; C07D 513/04
(52) U.S. Cl. .................. 514/222.8; 514/19; 514/226.5; 514/249; 544/10; 544/47; 544/48; 544/350
(58) Field of Search .............................. 544/10, 47, 48, 544/350; 514/19, 222.8, 226.5, 249

(56) References Cited

U.S. PATENT DOCUMENTS 4,411,890 A    10/1983    Momany .................... 424/177

FOREIGN PATENT DOCUMENTS

| WO | WO9411012 | 5/1994 |
| WO | WO9413696 | 6/1994 |
| WO | WO9513069 | 5/1995 |
| WO | WO9709060 | 3/1997 |
| WO | WO9724369 | 7/1997 |
| WO | WO9734604 | 9/1997 |

OTHER PUBLICATIONS

Jorgensen, J. O. L., et al, Lancet 1:1221–1227 1989.
Richelsen, B. et al, Am. J. Physiol, 266:E211,–E216, 1994.
Rudman, D. et al, Horm Res 36(Suppl 1):73–81, 1991.
Gertz, B. J. et al, J. Clin. Endocrinil. Metab., 79:745–749, 1994.
Arvat, E., et al., J. Clin Endocrinol., Metab., 79:1440–1443, 1994.
Maccario, M. et al, Metabolish, 44:134–138, 1995.
Aloi, J. A. et al., J. Clin. Endocrinol. Metab., 79:943–949, 1994.
Jacks, T. et al., J. Endocrinol, 143:399–409, 1993.

Primary Examiner—Richard L. Raymond
(74) Attorney, Agent, or Firm—Peter C. Richardson; Gregg C. Benson; John A. Wichtowski

(57) ABSTRACT

This invention is directed to compounds of the formula

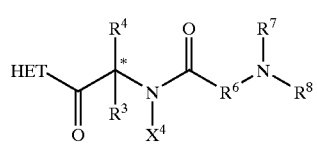

and the pharmaceutically-acceptable salts thereof, where the substituents are as defined in the Specification, which are growth hormone secretogogues and which increase the level of endogenous growth hormone. The compounds of this invention are useful for the treatment and prevention of osteoporosis and/or frailty, congestive heart failure, frailty associated with aging, obesity; accelerating bone fracture repair, attenuating protein catabolic response after a major operation, reducing cachexia and protein loss due to chronic illness, accelerating wound healing, or accelerating the recovery of burn patients or patients having undergone major surgery; improving muscle strength, mobility, maintenance of skin thickness, metabolic homeostasis or renal homeostasis. The compounds of the present invention are also useful in treating osteoporosis and/or frailty when used in combination with: a bisphosphonate compound such as alendronate; estrogen, premarin, and optionally progesterone; an estrogen agonist or antagonist; or calcitonin, and pharmaceutical compositions useful therefor. Further, the present invention is directed to pharmaceutical compositions useful for increasing the endogenous production or release of growth hormone in a human or other animal which comprises an effective amount of a compound of the present invention and a growth hormone secretagogue selected from GHRP-6, Hexarelin, GHRP-1, growth hormone releasing factor (GRF), IGF-1, IGF-2 or B-HT920. The invention is also directed to intermediates useful in the preparation of compounds of Formula I.

48 Claims, No Drawings

DIPEPTIDE DERIVATIVES

CROSS-REFERENCE TO RELATED APPLICATIONS

This is a division of U.S. Ser. No. 09/380,887, filed Sep. 8, 199, now U.S. Pat. No. 6,251,902, which is a 371 of PCT/IB98/008,731 filed Jun, 5, 1998, entitled "Dipeptide Derivatives as Growth Hormone Secretagogues," and claims benefit to U.S. Proviosional Application No. 60/050,764, filed Jun. 25, 1997.

BACKGROUND OF THE INVENTION

Growth hormone (GH), which is secreted from the pituitary gland, stimulates growth of all tissues of the body that are capable of growing. In addition, growth hormone is known to have the following basic effects on the metabolic processes of the body:

1. Increased rate of protein synthesis in substantially all cells of the body;
2. Decreased rate of carbohydrate utilization in cells of the body; and
3. Increased mobilization of free fatty acids and use of fatty acids for energy.

Deficiency in growth hormone results in a variety of medical disorders. In children, it causes dwarfism. In adults, the consequences of acquired GH deficiency include profound reduction in lean body mass and concomitant increase in total body fat, particularly in the truncal region. Decreased skeletal and cardiac muscle mass and muscle strength lead to a significant reduction in exercise capacity. Bone density is also reduced. Administration of exogenous growth hormone has been shown to reverse many of the metabolic changes. Additional benefits of therapy have included reduction in LDL cholesterol and improved psychological well-being.

In cases where increased levels of growth hormone were desired, the problem was generally solved by providing exogenous growth hormone or by administering an agent which stimulated growth hormone production and/or release. In either case the peptidyl nature of the compound necessitated that it be administered by injection. Initially the source of growth hormone was the extraction of the pituitary glands of cadavers. This resulted in an expensive product, and carried with it the risk that a disease associated with the source of the pituitary gland could be transmitted to the recipient of the growth hormone (e.g., Jacob-Creutzfeld disease). Recently, recombinant growth hormone has become available which, while no longer carrying any risk of disease transmission, is still a very expensive product which must be given by injection or nasal spray.

Most GH deficiencies are caused by defects in GH release, not primary defects in pituitary synthesis of GH. Therefore, an alternative strategy for normalizing serum GH levels is by stimulating its release from somatotrophs. Increasing GH secretion can be achieved by stimulating or inhibiting various neurotransmitter systems in the brain and hypothalamus. As a result, the development of synthetic growth hormone-releasing agents to stimulate pituitary GH secretion are being pursued, and may have several advantages over expensive and inconvenient GH replacement therapy. By acting along physiologic regulatory pathways, the most desirable agents would stimulate pulsatile GH secretion, and excessive levels of GH that have been associated with the undesirable side effects of exogenous GH administration would be avoided by virtue of intact negative feedback loops.

Physiologic and pharmacologic stimulators of GH secretion, which include arginine, L-3,4-dihydroxyphenylalanine (L-DOPA), glucagon, vasopressin, and insulin induced hypoglycemia, as well as activities such as sleep and exercise, indirectly cause growth hormone to be released from the pituitary by acting in some fashion on the hypothalamus perhaps either to decrease somatostatin secretion or to increase the secretion of the known secretagogue growth hormone releasing factor (GHRF) or an unknown endogenous growth hormone-releasing hormone or all of these.

Obesity is a major risk factor for diabetes, and a large fraction of NIDDM patients are obese. Both conditions are characterized by elevated circulating insulin levels and suppressed GH levels. GH treatment of GH-deficient adults (Jorgensen, J. O. L., et al., Lancet 1:1221 (1989)), obese women (Richelsen, B., et al., Am J Physiol, 266:E211 (1994)) and elderly men (Rudman, D., et al, Horm Res 36 (Suppl 1):73 (1991)) has been shown to produce increases in lean body, hepatic and muscle mass while decreasing fat mass. Thus, GH therapy for obesity would seem attractive except for the diabetogenic effects of GH.

An alternative to exogenous GH administration is therapy that stimulates endogenous GH secretion. It has been shown that a substantial pituitary reserve of GH is present in pituitary-intact GH-deficient patients and the elderly so that decreased serum GH levels are due to hyposecretion.

Hyposecretion of GH in several clinical settings (obesity, aging, glucocorticoid suppression) is relatively resistant to stimulation by GHRH (Gertz, B. J., et al., J Clin Endocrinol Metab, 79:745 (1994); Arvat, E., et al., J Clin Endocrinol Metab, 79:1440 (1994); Maccardo, M., et al., Metabolism, 44:134 (1995)). In contrast, administration of a GHRP or combined administration of GHRH and a GHRP in these patients can elicit a robust GH response (Aloi, J. A., et al., J Clin Endocrinol Metab, 79:943; (1994)). Single dose studies of GHRPs have demonstrated the absence of an acute effect on circulating insulin or glucose levels. Insulin and glucose have generally not been monitored in chronic studies except to document the absence of unfavorable changes (Jacks, T., et al., J Endocrinol. 143:399 (1993)).

Prior to the present invention, the use of GHRPs or GHRP mimetics to improve glycemic control has not specifically been explored. The method of treating insulin resistance in a mammal comprising the administration of a compound of Formula I of this invention is practiced preferentially in patients who have a functional hypothalamic-pituitary axis capable of GH secretory responses to GHRPs and who have pancreatic beta-cells capable of secreting insulin.

Other compounds have been developed which stimulate the release of endogenous growth hormone such as analogous peptidyl compounds related to GRF or the peptides of U.S. Pat. No. 4,411,890. These peptides, while considerably smaller than growth hormones, are still susceptible to various proteases. As with most peptides, their potential for oral bioavailability is low.

WO 94/13696 refers to certain spiropiperidines and homologues which promote release of growth hormone. Preferred compounds described therein are of the general structure shown below.

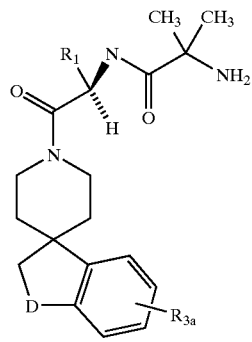

WO 94/11012 refers to certain dipeptides that promote release of growth hormone. These dipeptides have the general structure

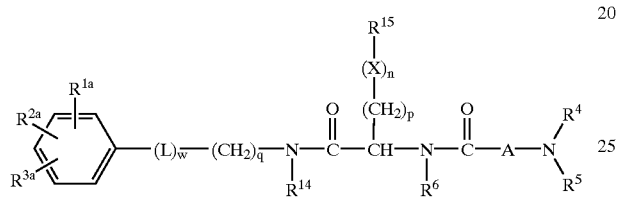

where L is

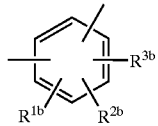

The compounds of WO 94/11012 and WO 94/13696 are reported to be useful in the treatment of osteoporosis in combination with parathyroid hormone or a bisphosphonate.

PCT publication WO 97/09060 discloses the use of growth hormone releasing hormone or a functional analog thereof in the treatment of insulin resistance in mammals.

SUMMARY OF THE INVENTION

This invention provides compounds of the formula:

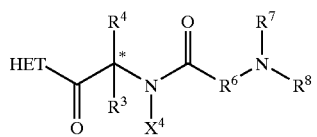

or a stereoisomeric mixture thereof, diastereomerically enriched, diastereomerically pure, enantiomerically enriched or enantiomerically pure isomer thereof, or a prodrug of such compound, mixture or isomer thereof, or a pharmaceutically acceptable salt of the compound, mixture, isomer or prodrug, wherein HET is a heterocyclic moiety selected from the group consisting of

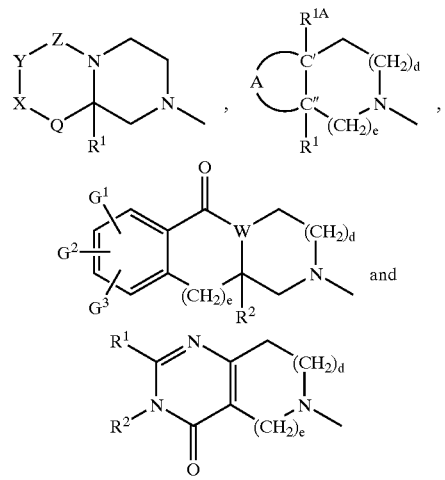

d is 0, 1 or 2;
e is 1 or 2;
A is a divalent radical, where the left hand side of the radical as shown below is connected to C''' and the right hand side of the radical as shown below is connected to C', selected from the group consisting of
—$NR^2$—C(O)—$NR^2$—,
—$NR^2$—S(O)$_2$—$NR^2$—,
—O—C(O)—$NR^2$—,
—$NR^2$—C(O)—O—,
—C(O)—$NR^2$—C(O)—,
—C(O)—$NR^2$—C($R^9R^{10}$)—,
—C($R^9R^{10}$)—$NR^2$—C(O)—,
—C($R^9R^{10}$)—C($R^9R^{10}$)—C($R^9R^{10}$)—,
—S(O)$_2$—C($R^9R^{10}$)—C($R^9R^{10}$)—,
—C($R^9R^{10}$)—O—C(O)—,
—C($R^9R^{10}$)—O—C($R^9R^{10}$)—,
—$NR^2$—C(O)—C($R^9R^{10}$)—,
—O—C(O)—C($R^9R^{10}$)—,
—C($R^9R^{10}$)—C(O)—$NR^2$—,
—C(O)—$NR^2$—C(O)—,
—C($R^9R^{10}$)—C(O)—O—,
—C(O)—$NR^2$—C($R^9R^{10}$)—C($R^9R^{10}$)—,
—C(O)—O—C($R^9R^{10}$)—,
—C($R^9R^{10}$)—C($R^9R^{10}$)—C($R^9R^{10}$)—C($R^9R_{10}$)—,
—S(O)$_2$—$NR^2$—C($R^9R^{10}$)—C($R^9R^{10}$)—,
—C($R^9R^{10}$)—C($R^9R^{10}$)—$NR^2$—C(O)—,
—C($R^9R^{10}$)—C($R^9R^{10}$)—O—C(O)—,
—$NR^2$—C(O)—C($R^9R^{10}$)—C($R^9R^{10}$)—,
—$NR^2$—S(O)$_2$—C($R^9R^{10}$)—C($R^9R^{10}$)—,
—O—C(O)—C($R^9R^{10}$)—C($R^9R^{10}$)—,
—C($R^9R^{10}$)—C($R^9R^{10}$)—C(O)—$NR^2$—,
—C($R^9R^{10}$)—C($R^9R^{10}$)—C(O)—,
—C($R^9R^{10}$)—$NR^2$—C(O)—O—,
—C($R^9R^{10}$)—O—C(O)—$NR^2$,
—C($R^9R^{10}$)—$NR^2$—C(O)—$NR^2$—,
—$NR^2$—C(O)—O—C($R^9R^{10}$)—,
—$NR^2$—C(O)—$NR^2$—C($R^9R^{10}$)—,
—$NR^2$—S(O)$_2$—$NR^2$—C($R^9R^{10}$)—,
—O—C(O)—$NR^2$—C($R^9R^{10}$)—,
—C(O)—N=C($R^{11}$)—$NR^2$—,
—C(O)—$NR^2$—C($R^{11}$)=N—,
—C($R^9R^{10}$)—$NR^{12}$—C($R^9R^{10}$)—,
—$NR^{12}$—C($R^9R^{10}$)—,
—$NR^{12}$—C($R^9R^{10}$)—C($R^9R^{10}$)—,
—C(O)—O—C($R^9R^{10}$)—C($R^9R^{10}$)—,
—$NR^2$—C($R^{11}$)=N—C(O)—, —C(R$^9$R$^{10}$)—C(R$^9$R$^{10}$)—N(R$^{12}$)—,
—C(R$^9$R$^{10}$)—NR$^{12}$—,
—N=C(R$^{11}$)—NR$^2$—C(O)—,
—C(R$^9$R$^{10}$)—C(R$^9$R$^{10}$)—NR$^2$—S(O)$_2$—,
—C(R$^9$R$^{10}$)—C(R$^9$R$^{10}$)—S(O)$_2$—NR$^2$—,
—C(R$^9$R$^{10}$)—C(R$^9$R$^{10}$)—C(O)—O—,
—C(R$^9$R$^{10}$)—S(O)$_2$—C(R$^9$R$^{10}$)—,
—C(R$^9$R$^{10}$)—C(R$^9$R$^{10}$)—S(O)$_2$—,
—O—C(R$^9$R$^{10}$)—C(R$^9$R$^{10}$)—,
—C(R$^9$R$^{10}$)—C(R$^9$R$^{10}$)—O—,
—C(R$^9$R$^{10}$)—C(O)—C(R$^9$R$^{10}$)—,
—C(O)—C(R$^9$R$^{10}$)—C(R$^9$R$^{10}$)— and
—C(R$^9$R$^{10}$)—NR$^2$—S(O)$_2$—NR$^2$—;

Q is a covalent bond or CH$_2$;
W is CH or N;
X is CR$^9$R$^{10}$, C=CH$_2$ or C=O;
Y is CR$^9$R$^{10}$, O or NR$^2$;
Z is C=O, C=S or S(O)$_2$;
G$^1$ is hydrogen, halo, hydroxy, nitro, amino, cyano, phenyl, carboxyl, —CONH$_2$, —(C$_1$–C$_4$)alkyl optionally independently substituted with one or more phenyl, one or more halogens or one or more hydroxy groups, —(C$_1$–C$_4$)alkoxy optionally independently substituted with one or more phenyl, one or more halogens or one or more hydroxy groups, —(C$_1$–C$_4$)alkylthio, phenoxy, —COO(C$_1$–C$_4$)alkyl, N,N-di-(C$_1$–C$_4$)alkylamino, —(C$_2$–C$_6$)alkenyl optionally independently substituted with one or more phenyl, one or more halogens or one or more hydroxy groups, —(C$_2$–C$_6$)alkynyl optionally independently substituted with one or more phenyl, one or more halogens or one or more hydroxy groups, —(C$_3$–C$_6$)cycloalkyl optionally independently substituted with one or more (C$_1$–C$_4$)alkyl groups, one or more halogens or one or more hydroxy groups, —(C$_1$–C$_4$)alkylamino carbonyl or di-(C$_1$–C$_4$)alkylamino carbonyl; G$^2$ and G$^3$ are each independently selected from the group consisting of hydrogen, halo, hydroxy, —(C$_1$–C$_4$)alkyl optionally independently substituted with one to three halo groups and —(C$_1$–C$_4$)alkoxy optionally independently substituted with one to three halo groups;
R$^1$ is hydrogen, —CN, —(CH$_2$)$_q$N(X$^6$)C(O)X$^6$, —(CH$_2$)$_q$N(X$^6$)C(O)(CH$_2$)$_t$—A$^1$, —(CH$_2$)$_q$N(X$^6$)S(O)$_2$(CH$_2$)$_t$—A$^1$, —(CH$_2$)$_q$N(X$^6$)S(C)$_2$X$^6$, —(CH$_2$)$_q$N(X$^6$)C(O)N(X$^6$)(CH$_2$)$_t$—A$^1$, —(CH$_2$)$_q$N(X$^6$)C(O)N(X$^6$)(X$^6$), —(CH$_2$)$_q$C(O)N(X$^6$)(X$^6$), —(CH$_2$)$_q$C(O)N(X$^6$)(CH$_2$)$_t$—A$^1$, —(CH$_2$)$_q$C(O)OX$^6$, —(CH$_2$)$_q$C(O)O(CH$_2$)$_t$—A$^1$, —(CH$_2$)$_q$OX$^6$, —(CH$_2$)$_q$OC(O)X$^6$, —(CH$_2$)$_q$OC(O)(CH$_2$)$_t$—A$^1$, —(CH$_2$)$_q$OC(O)N(X$^6$)(CH$_2$)$_t$—A$^1$, —(CH$_2$)$_q$OC(O)N(X$^6$)(X$^6$), —(CH$_2$)$_q$C(O)X$^6$, —(CH$_2$)$_q$C(O)(CH$_2$)$_t$—A$^1$, —(CH$_2$)$_q$N(X$^6$)C(O)OX$^6$, —(CH$_2$)$_q$N(X$^6$)S(O)$_2$N(X$^6$)(X$^6$), —(CH$_2$)$_q$S(O)$_m$X$^6$, —(CH$_2$)$_q$S(O)$_m$(CH$_2$)$_t$—A$^1$, —(C$_1$–C$_{10}$)alkyl, —(CH$_2$)$_t$—A$^1$, —(CH$_2$)$_q$—(C$_3$–C$_7$)cycloalkyl, —(CH$_2$)$_q$—Y$^1$—(C$_1$–C$_6$)alkyl, —(CH$_2$)$_q$—Y$^1$—(CH$_2$)$_t$—A$^1$ or —(CH$_2$)$_q$—Y$^1$—(CH$_2$)$_t$—(C$_3$–C$_7$)cycloalkyl;
where the alkyl and cycloalkyl groups in the definition of R$^1$ are optionally substituted with (C$_1$–C$_4$)alkyl, hydroxy, (C$_1$–C$_4$)alkoxy, carboxyl, —CONH$_2$, —S(O)$_m$(C$_1$–C$_6$)alkyl, —CO$_2$(C$_1$–C$_4$)alkyl ester, 1H-tetrazol-5-yl or 1, 2 or 3 fluoro groups;
Y$^1$ is O, S(O)$_m$, —C(O)NX$^6$—, —CH=CH—, —C≡C—, —N(X$^6$)C(O)—, —C(O)NX$^6$—, —C(O)O—, —OC(O)N(X$^6$)— or —OC(O)—;
q is 0, 1, 2, 3 or 4;
t is 0, 1, 2 or 3;
said (CH$_2$)$_q$ group and (CH$_2$)$_t$ group in the definition of R$^1$ are optionally independently substituted with hydroxy, (C$_1$–C$_4$)alkoxy, carboxyl, —CONH$_2$, —S(O)$_m$(C$_1$–C$_6$)alkyl, —CO$_2$(C$_1$–C$_4$)alkyl ester, 1H-tetrazol-5-yl, 1, 2 or 3 fluoro groups or 1 or 2 (C$_1$–C$_4$)alkyl groups;
R$^{1A}$ is selected from the group consisting of hydrogen, F, Cl, Br, I, (C$_1$–C$_6$)alkyl, phenyl(C$_1$–C$_3$)alkyl, pyridyl(C$_1$–C$_3$)alkyl, thiazolyl(C$_1$–C$_3$)alkyl and thienyl(C$_1$–C$_3$)alkyl, provided that R$^{1A}$ is not F, Cl, Br or I when a heteroatom is vicinal to C";
R$^2$ is hydrogen, (C$_1$–C$_8$)alkyl, —(C$_0$–C$_3$)alkyl-(C$_3$–C$_8$)cycloalkyl, —(C$_1$–C$_4$)alkyl-A$^1$ or A$^1$;
where the alkyl groups and the cycloalkyl groups in the definition of R$^2$ are optionally substituted with hydroxy, —C(O)OX$^6$, —C(O)N(X$^6$)(X$^6$), —N(X$^6$)(X$^6$), —S(O)$_m$(C$_1$–C$_6$)alkyl, —C(O)A$^1$, —C(O)(X$^6$), CF$_3$, CN or 1, 2 or 3 independently selected halo groups;
R$^3$ is selected from the group consisting of A$^1$, (C$_1$–C$_{10}$)alkyl, —(C$_1$–C$_6$)alkyl-A$^1$, —(C$_1$–C$_6$)alkyl-(C$_3$–C$_7$)cycloalkyl, —(C$_1$–C$_5$)alkyl-X$^1$—(C$_1$–C$_5$)alkyl, —(C$_1$–C$_5$)alkyl-X$^1$—(C$_0$–C$_5$)alkyl-A$^1$ and —(C$_1$–C$_5$)alkyl-X$^1$—(C$_1$–C$_5$)alkyl-(C$_3$–C$_7$)cycloalkyl;
where the alkyl groups in the definition of R$^3$ are optionally substituted with —S(O)$_m$(C$_1$–C$_6$)alkyl, —C(O)OX$^3$, 1, 2, 3, 4 or 5 independently selected halo groups or 1, 2 or 3 independently selected —OX$^3$ groups;
X$^1$ is O, S(O)$_m$, —N(X$^2$)C(O)—, —C(O)N(X$^2$)—, —OC(O)—, —C(O)O—, —CX$^2$=CX$^2$—, —N(X$^2$)C(O)O—, —OC(O)N(X$^2$)— or —C=C—;
R$^4$ is hydrogen, (C$_1$–C$_6$)alkyl or (C$_3$–C$_7$)cycloalkyl, or R$^4$ is taken together with R$^3$ and the carbon atom to which they are attached and form (C$_5$–C$_7$)cycloalkyl, (C$_5$–C$_7$)cycloalkenyl, a partially saturated or fully saturated 4- to 8-membered ring having 1 to 4 heteroatoms independently selected from the group consisting of oxygen, sulfur and nitrogen, or is a bicyclic ring system consisting of a partially saturated or fully saturated 5- or 6-membered ring, fused to a partially saturated, fully unsaturated or fully saturated 5- or 6-membered ring, optionally having 1 to 4 heteroatoms independently selected from the group consisting of nitrogen, sulfur and oxygen;
X$^4$ is hydrogen or (C$_1$–C$_6$)alkyl or X$^4$ is taken together with R$^4$ and the nitrogen atom to which X$^4$ is attached and the carbon atom to which R$^4$ is attached and form a five to seven membered ring;
R$^6$ is a bond or is where a and b are each independently 0, 1, 2 or 3;
X$^5$ and X$^{5a}$ are each independently selected from the group consisting of hydrogen, CF$_3$, A$^1$ and optionally substituted (C$_1$–C$_6$)alkyl;
the optionally substituted (C$_1$–C$_6$)alkyl in the definition of X$^5$ and X$^{5a}$ is optionally substituted with a substituent selected from the group consisting of A$^1$, OX$^2$, —S(O)$_m$(C$_1$–C$_6$)alkyl, —C(O)OX$^2$, (C$_3$–C$_7$)cycloalkyl, —N(X$^2$)(X$^2$) and —C(O)N(X$^2$)(X$^2$);

or the carbon bearing $X^5$ or $X^{5a}$ forms one or two alkylene bridges with the nitrogen atom bearing $R^7$ and $R^8$ wherein each alkylene bridge contains 1 to 5 carbon atoms, provided that when one alkylene bridge is formed then only one of $X^5$ or $X^{5a}$ is on the carbon atom and only one of $R^7$ or $R^8$ is on the nitrogen atom and further provided that when two alkylene bridges are formed then $X^5$ and $X^{5a}$ cannot be on the carbon atom and $R^7$ and $R^8$ cannot be on the nitrogen atom;

or $X^5$ is taken together with $X^{5a}$ and the carbon atom to which they are attached and form a partially saturated or fully saturated 3- to 7-membered ring, or a partially saturated or fully saturated 4- to 8-membered ring having 1 to 4 heteroatoms independently selected from the group consisting of oxygen, sulfur and nitrogen;

or $X^5$ is taken together with $X^{5a}$ and the carbon atom to which they are attached and form a bicyclic ring system consisting of a partially saturated or fully saturated 5- or 6-membered ring, optionally having 1 or 2 heteroatoms independently selected from the group consisting of nitrogen, sulfur and oxygen, fused to a partially saturated, fully saturated or fully unsaturated 5- or 6-membered ring, optionally having 1 to 4 heteroatoms independently selected from the group consisting of nitrogen, sulfur and oxygen;

$Z^1$ is a bond, O or N—$X^2$, provided that when a and b are both 0 then $Z^1$ is not N—$X^2$ or O;

$R^7$ and $R^8$ are each independently hydrogen or optionally substituted $(C_1-C_6)$alkyl;

where the optionally substituted $(C_1-C_6)$alkyl in the definition of $R^7$ and $R^8$ is optionally independently substituted with $A^1$, —C(O)O—$(C_1-C_6)$alkyl, —S(O)$_m$$(C_1-C_6)$alkyl, 1 to 5 halo groups, 1 to 3 hydroxy groups, 1 to 3 —O—C(O)$(C_1-C_{10})$alkyl groups or 1 to 3 $(C_1-C_6)$alkoxy groups; or $R^7$ and $R^8$ can be taken together to form —(CH$_2$)$_r$—L—(CH$_2$)$_r$—;

where L is C($X^2$)($X^2$), S(O)$_m$ or N($X^2$);

$R^9$ and $R^{10}$ are each independently selected from the group consisting of hydrogen, fluoro, hydroxy and $(C_1-C_5)$alkyl optionally independently substituted with 1–5 halo groups;

$R^{11}$ is selected from the group consisting of $(C_1-C_5)$alkyl and phenyl optionally substituted with 1–3 substitutents each independently selected from the group consisting of $(C_1-C_5)$alkyl, halo and $(C_1-C_5)$alkoxy;

$R^{12}$ is selected from the group consisting of $(C_1-C_5)$alkylsulfonyl, $(C_1-C_5)$alkanoyl and $(C_1-C_5)$alkyl where the alkyl portion is optionally independently substituted by 1–5 halo groups;

$A^1$ for each occurrence is independently selected from the group consisting of $(C_5-C_7)$cycloalkenyl, phenyl, a partially saturated, fully saturated or fully unsaturated 4- to 8-membered ring optionally having 1 to 4 heteroatoms independently selected from the group consisting of oxygen, sulfur and nitrogen and a bicyclic ring system consisting of a partially saturated, fully unsaturated or fully saturated 5- or 6-membered ring, optionally having 1 to 4 heteroatoms independently selected from the group consisting of nitrogen, sulfur and oxygen, fused to a partially saturated, fully saturated or fully unsaturated 5- or 6-membered ring, optionally having 1 to 4 heteroatoms independently selected from the group consisting of oxygen, sulfur and nitrogen;

$A^1$ for each occurrence is independently optionally substituted, on one or optionally both rings if $A^1$ is a bicyclic ring system, with up to three substituents, each substituent independently selected from the group consisting of F, Cl, Br, I, OCF$_3$, OCF$_2$H, CF$_3$, CH$_3$, OCH$_3$, —OX$^6$, —C(O)N($X^6$)($X^6$), —C(O) OX$^6$, oxo, $(C_1-C_6)$alkyl, nitro, cyano, benzyl, —S(O)$_m$$(C_1-C_6)$alkyl, 1H-tetrazol-5-yl, phenyl, phenoxy, phenylalkyloxy, halophenyl, methylenedioxy, —N($X^6$)($X^6$), —N($X^6$)C(O)($X^6$), —S(O)$_2$N($X^6$)($X^6$), —N($X^6$)S(O)$_2$-phenyl, —N($X^6$)S(O)$_2$$X^6$, —CONX$^{11}$X$^{12}$, —S(O)$_2$NX$^{11}$X$^{12}$, —NX$^6$S(O)$_2$X$^{12}$, —NX$^6$CONX$^{11}$X$^{12}$, —NX$^6$S(O)$_2$NX$^{11}$X$^{12}$, —NX$^6$C(O)X$^{12}$, imidazolyl, thiazolyl and tetrazolyl, provided that if $A^1$ is optionally substituted with methylenedioxy then it can only be substituted with one methylenedioxy;

where $X^{11}$ is hydrogen or optionally substituted $(C_1-C_6)$alkyl;

the optionally substituted $(C_1-C_6)$alkyl defined for $X^{11}$ is optionally independently substituted with phenyl, phenoxy, $(C_1-C_6)$alkoxycarbonyl, —S(O)$_m$$(C_1-C_6)$alkyl, 1 to 5 halo groups, 1 to 3 hydroxy groups, 1 to 3 $(C_1-C_{10})$alkanoyloxy groups or 1 to 3 $(C_1-C_6)$alkoxy groups;

$X^{12}$ is hydrogen, $(C_1-C_6)$alkyl, phenyl, thiazolyl, imidazolyl, furyl or thienyl, provided that when $X^{12}$ is not hydrogen, the $X^{12}$ group is optionally substituted with one to three substituents independently selected from the group consisting of Cl, F, CH$_3$, OCH$_3$, OCF$_3$ and CF$_3$;

or $X^{11}$ and $X^{12}$ are taken together to form —(CH$_2$)$_r$—L$^1$—(CH$_2$)$_r$—;

L$^1$ is C($X^2$)($X^2$), O, S(O)$_m$ or N($X^2$);

r for each occurrence is independently 1, 2 or 3;

$X^2$ for each occurrence is independently hydrogen, optionally substituted $(C_1-C_6)$alkyl or optionally substituted $(C_3-C_7)$cycloalkyl, where the optionally substituted $(C_1-C_6)$alkyl and optionally substituted $(C_3-C_7)$cycloalkyl in the definition of $X^2$ are optionally independently substituted with —S(O)$_m$$(C_1-C_6)$ alkyl, —C(O)OX$^3$, 1 to 5 halo groups or 1–3 OX$^3$ groups;

$X^3$ for each occurrence is independently hydrogen or $(C_1-C_6)$alkyl;

$X^6$ for each occurrence is independently hydrogen, optionally substituted $(C_1-C_6)$alkyl, $(C_2-C_6)$ halogenated alkyl, optionally substituted $(C_3-C_7)$ cycloalkyl, $(C_3-C_7)$-halogenated cycloalkyl, where optonally substituted $(C_1-C_6)$alkyl and optionally substituted $(C_3-C_7)$cycloalkyl in the definition of $X^6$ is optionally independently mono- or di-substituted with $(C_1-C_4)$alkyl, hydroxy, $(C_1-C_4)$alkoxy, carboxyl, CONH$_2$, —S(O)$_m$$(C_1-C_6)$alkyl, carboxylate $(C_1-C_4)$alkyl ester or 1H-tetrazol-5-yl; or when there are two $X^6$ groups on one atom and both $X^6$ are independently $(C_1-C_6)$alkyl, the two $(C_1-C_6)$alkyl groups may be optionally joined and; together with the atom to which the two $X^6$ groups are attached, form a 4- to 9-membered ring optionally having oxygen, sulfur or NX$^7$ as a ring member;

$X^7$ is hydrogen or $(C_1-C_6)$alkyl optionally substituted with hydroxy;

m for each occurrence is independently 0, 1 or 2;

with the proviso that:

$X^6$ and $X^{12}$ cannot be hydrogen when attached to C(O) or S(O)$_2$ in the form C(O)X$^6$, C(O)X$^{12}$, S(O)$_2$X$^6$ or S(O)$_2$X$^{12}$; and when $R^6$ is a bond then L is $N(X^2)$ and each r in the definition —$(CH_2)_r$—L—$(CH_2)_r$— is independently 2 or 3.

From herein on, the word "compounds" includes a stereoisomeric mixture thereof, diastereomerically enriched, diastereomercally pure, enantiomerically enriched or enantiomerically pure isomer thereof, or a prodrug of such compound, mixture or isomer thereof, or a pharmaceutically acceptable salt of the compound, mixture, isomer or prodrug unless otherwise more specifically stated.

A preferred group of the foregoing compounds, designated the A Group compounds, are those compounds of formula I wherein $R^4$ is hydrogen or methyl; $X^4$ is hydrogen;

$R^6$ is

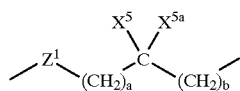

where $Z^1$ is a bond and a is 0 or 1; $X^5$ and $X^{5a}$ are each independently selected from the group consisting of hydrogen, $CF_3$, phenyl and optionally substituted $(C_1-C_6)$alkyl;

where the optionally substituted $(C_1-C_6)$alkyl in the definition of $X^5$ and $X^{5a}$ is optionally substituted with $OX^2$ or $A^1$;

where $A^1$ in the definition of $X^5$ and $X^{5a}$ is imidazolyl, phenyl, indolyl, p-hydroxyphenyl, $(C_5-C_7)$ cycloalkyl, —$S(O)_m(C_1-C_6)$alkyl, —$N(X^2)(X^2)$ or —$C(O)N(X^2)(X^2)$;

$R^7$ is hydrogen or $(C_1-C_3)$alkyl;

or $X^5$ and $R^7$ are taken together and form a $(C_1-C_5)$ alkylene bridge; and $R^8$ is hydrogen or $(C_1-C_3)$alkyl optionally substituted with one or two hydroxy groups.

A group of compounds which is preferred among the A Group compounds, designated the B Group, are those compounds of the A Group wherein b is 0; $X^5$ and $X^{5a}$ are each independently selected from the group consisting of hydrogen, $(C_1-C_3)$alkyl and hydroxy$(C_1-C_3)$alkyl; and $R^3$ is selected from the group consisting of thienyl-$CH_2$—O—$CH_2$—, pyridyl-$CH_2$—O—$CH_2$—, thiazolyl-$CH_2$—O—$CH_2$—, 1-indolyl-$CH_2$—, 2-indolyl-$CH_2$—, 3-indolyl-$CH_2$—, 1-naphthyl-$CH_2$, 2-naphthyl-$CH_2$—, 1-benzimidazolyl-$CH_2$—, 2-benzimidazolyl-$CH_2$—, phenyl-$(C_1-C_4)$alkyl, 2-pyridyl-$(C_1-C_4)$alkyl-, 3-pyrdyl-$(C_1-C_4)$alkyl-, 4-pyridyl-$(C_1-C_4)$alkyl-, phenyl-$CH_2$—S—$CH_2$, thienyl-$(C_1-C_4)$alkyl-, phenyl-$(C_0-C_3)$alkyl-O—$CH_2$—, phenyl-$CH_2$—O-phenyl-$CH_2$—, phenyl-O—$CH_2CH_2$— and 3-benzothienyl-$CH_2$—;

where the aryl portion(s) of the groups defined for $R^3$ are each optionally substituted with one to three substituents, each substituent being independently selected from the group consisting of methylenedioxy, F, Cl, $CH_3$, $OCH_3$, $OCF_3$, $OCF_2H$ and $CF_3$.

A group of compounds which is preferred among the B Group compounds, designated the C Group, are those compounds of the B Group wherein $R^4$ is hydrogen; a is 0;

$X^5$ and $X^{5a}$ are each independently selected from the group consisting of hydrogen, methyl or hydroxymethyl, provided that when $X^5$ is hydrogen then $X^{5a}$ is not hydrogen;

$R^7$ and $R^8$ are each hydrogen; and $R^3$ is selected from the group consisting of 3-indolyl-$CH_2$—, 1-naphthyl-$CH_2$—, 2-naphthyl-$CH_2$—, phenyl-$(C_1-C_4)$alkyl-, 2-pyridyl-$(C_1-C_4)$alkyl-, 3-pyridyl-$(C_1-C_4)$alkyl-, 4-pyridyl-$(C_1-C_4)$alkyl-, phenyl-$CH_2$—S—$CH_2$—, thienyl-$(C_2-C_4)$alkyl-, phenyl-$(C_0-C_3)$alkyl-O—$CH_2$—, 3-benzothienyl-$CH_2$—, thienyl-$CH_2$—O—$CH_2$—, thiazolyl-$CH_2$—O—$CH_2$—, pyridyl-$CH_2$—O—$CH_2$— and phenyl-O—$CH_2$—$CH_2$—;

where the aryl portion(s) of the groups defined for $R^3$ are each optionally substituted with one to three substituents, each substituent being independently selected from the group consisting of methylenedioxy, F, Cl, $CH_3$, $OCH_3$, $OCF_3$, $OCF_2H$ and $CF_3$.

A group of compounds which is preferred among the C Group compounds, designated the D Group, are those compounds of the C Group wherein $R^1$ is —$(CH_2)_t$—$A^1$, —$(CH_2)_q$—$(C_3-C_7)$cycloalkyl or $(C_1-C_{10})$alkyl;

$A^1$ in the definition of $R^1$ is phenyl, pyridyl, thiazolyl or thienyl, optionally substituted with one to three substituents, each substituent being independently selected from the group consisting of F, Cl, $CH_3$, $OCH_3$, $OCF_2H$, $OCF_3$ and $CF_3$;

the cycloalkyl and alkyl groups in the definition of $R^1$ are optionally substituted with $(C_1-C_4)$alkyl, hydroxy, $(C_1-C_4)$alkoxy or 1 to 3 fluoro atoms;

q is 1 or 2; t is 1 or 2;

$R^3$ is phenyl-$CH_2$—O—$CH_2$—, phenyl-$CH_2$—S—$CH_2$—, pyridyl-$CH_2$—O—$CH_2$—, thienyl-$CH_2$—O—$CH_2$—, thiazolyl-$CH_2$—O—$CH_2$—, phenyl-$(CH_2)_3$— or 3-indolyl-$CH_2$—;

where the carbon atom bearing the substituent $R^3$ is of the (R)-configuration;

where the aryl portion of the groups defined for $R^3$ is optionally substituted with one to three substituents, each substituent being independently selected from the group consisting of F, Cl, $CH_3$, $OCH_3$, $OCF_2H$, $OCF_3$ and $CF_3$; and $X^5$ and $X^{5a}$ are each methyl.

A group of compounds which is preferred among the D Group compounds, designated the E Group, are those compounds of the D Group wherein HET is

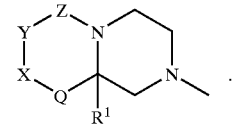

A group of compounds which is preferred among the E Group compounds, designated the F Group, are those compounds of the E Group wherein Z is $S(O)_2$; Q is a covalent bond; X is $CH_2$; and Y is $CH_2$ or $NR^2$;

$R^2$ is hydrogen, $(C_1-C_5)$alkyl or —$(C_0-C_2)$alkyl-$(C_3-C_8)$cycloalkyl;

where the alkyl and cycloalkyl groups in the definition of $R^2$ are optionally substituted with 1, 2 or 3 fluoro groups.

A group of compounds which is preferred among the F Group compounds, designated the G Group, are those compounds of the F Group wherein Y is $CH_2$.

A group of compounds which is preferred among the G Group compounds, designated the H Group, are those compounds of the G Group wherein $R^1$ is —$CH_2$—$A^1$ where $A^1$ is phenyl, pyridyl or thiazolyl, optionally substituted with one to three substituents, each substituent being independently selected from the group consisting of F, Cl, $CH_3$, $OCH_3$, $OCF_2H$, $OCF_3$ and $CF_3$; and $R^3$ is selected from the group consisting of 3-indolyl-$CH_2$—, phenyl-$(CH_2)_3$—, phenyl-$CH_2$—O—$CH_2$— and thiazolyl-$CH_2$—O—$CH_2$—, where the aryl portion of the groups defined for $R^3$ is optionally substituted with one to three substituents, each substituent being independently selected from the group consisting of methylenedioxy, F, Cl, $CH_3$, $OCH_3$, $OCF_3$, $OCF_2H$ and $CF_3$.

A preferred compound of the H Group is the 3a(R,S),1(R) diastereomeric mixture, the 3a(R),1(R) diastereomer or the 3a(S),1(R) diastereomer of 2-amino-N-[2-(3a-benzyl-1,1-dioxo-hexahydro-1-thia-5,7a-diaza-inden-5-yl)-1-benzyloxymethyl-2-oxo-ethyl]-2-methyl-propionamide.

Another group of compounds which is preferred among the E Group compounds, designated the I Group, are those compounds of the E Group wherein Z is C=O; Q is a covalent bond; X is $CH_2$; and Y is $NR^2$; $R^2$ is hydrogen, $(C_1-C_5)$alkyl or —$(C_0-C_2)$alkyl-$(C_3-C_8)$cycloalkyl;

where the alkyl and cycloalkyl groups in the definition of $R^2$ are optionally substituted with 1, 2 or 3 fluoro groups.

A group of compounds which is preferred among the I Group compounds, designated the J Group, are those compounds of the I Group wherein $R^1$ is —$CH_2$—$A^1$ where $A^1$ is phenyl, pyridyl or thiazolyl, optionally substituted with one to three substituents, each substituent being independently selected from the group consisting of F, Cl, $CH_3$, $OCH_3$, $OCF_2H$, $OCF_3$ and $CF_3$;

$R^2$ is hydrogen or $(C_1-C_3)$alkyl optionally substituted with 1–3 fluoro groups; and $R^3$ is selected from the group consisting of 3-indolyl-$CH_2$—, phenyl-$(CH_2)_3$—, phenyl-$CH_2$—O—$CH_2$— and thiazolyl-$CH_2$—O—$CH_2$—, where the aryl portion of the groups defined for $R^3$ is optionally substituted with one to three substituents, each substituent being independently selected from the group consisting of methylenedioxy, F, Cl, $CH_3$, $OCH_3$, $OCF_3$, $OCF_2H$ and $CF_3$.

A preferred compound of the J Group is the 8a(R,S),1(R) diastereomeric mixture, the 8a(R),1(R) diastereomer or the 8a(S),1(R) diastereomer of 2-amino-N-[2-(8a-benzyl-2-methyl-3-oxo-hexahydro-imidazo[1,5-a]pyrazin-7-yl)-1-benzyloxymethyl-2-oxo-ethyl]-2-methyl-propionamide.

Another group of compounds which is preferred among the E Group compounds, designated the K Group, are those compounds of the E Group wherein Z is C=O; Q is a covalent bond; X is $CH_2$; and Y is O.

A group of compounds which is preferred among the K Group compounds, designated the L Group, are those compounds of the K Group wherein $R^1$ is —$CH_2$—$A^1$ where $A^1$ is phenyl, pyridyl or thiazolyl, optionally substituted with one to three substituents, each substituent being independently selected from the group consisting of F, Cl, $CH_3$, $OCH_3$, $OCF_2H$, $OCF_3$ and $CF_3$; and $R^3$ is selected from the group consisting of 3-indolyl-$CH_2$—, phenyl-$(CH_2)_3$—, phenyl-$CH_2$—O—$CH_2$— and thiazolyl-$CH_2$—O—$CH_2$—, where the aryl portion of the groups defined for $R^3$ is optionally substituted with one to three substituents, each substituent being independently selected from the group consisting of methylenedioxy, F, Cl, $CH_3$, $OCH_3$, $OCF_3$, $OCF_2H$ and $CF_3$.

A group of compounds which is preferred among the L Group compounds, designated the M Group, are where the compound is the 8a(R,S),1(R) diastereomeric mixture, the 8a(R),1(R) diastereomer or the 8a(S),1(R) diastereomer of the compound selected from the group consisting of 2-amino-N-[2-(8a-benzyl-3-oxo-tetrahydro-oxazolo[3,4-a]pyrazin-7-yl)-1-benzyloxymethyl-2-oxo-ethyl]-2-methyl-propionamide, 2-amino-N-[1-benzyloxymethyl-2-oxo-2-(3-oxo-8a-thiazol-4-ylmethyl-tetrahydro-oxazolo[3,4-a]pyrazin-7-yl)-ethyl]-2-methyl-propionamide and 2-amino-N-[1-benzyloxymethyl-2-oxo-2-(3-oxo-8a-pyridin-3-ylmethyl-tetrahydro-oxazolo[3,4-a]pyrazin-7-yl)-ethyl]-2-methyl-propionamide.

Another group of compounds which is preferred among the E Group compounds, designated the N Group, are those compounds of the E Group wherein Z is C=O or $S(O)_2$; Q is a covalent bond; X is C=O; and Y is $NR^2$;

$R^2$ is hydrogen, $(C_1-C_5)$alkyl or —$(C_0-C_2)$alkyl-$(C_3-C_8)$cycloalkyl;

where the alkyl and cycloalkyl groups in the definition of $R^2$ are optionally substituted with 1, 2 or 3 fluoro groups.

A group of compounds which is preferred among the N Group compounds, designated the O Group, are those compounds of the N Group wherein Z is C=O; $R^1$ is —$CH_2$—$A^1$, where $A^1$ in the definition of $R^1$ is phenyl or pyridyl where said phenyl or pyridyl is optionally substituted with one to three substituents, each substituent being independently selected from the group consisting of F, Cl, $CH_3$, $OCH_3$, $OCF_2H$, $OCF_3$ and $CF_3$; and $R^3$ is phenyl-$CH_2$—O—$CH_2$—, pyridyl-$CH_2$—O—$CH_2$—, phenyl-$(CH_2)$—, 3-indolyl-$CH_2$— or thiazolyl-$CH_2$—O—$CH_2$—, where the aryl portion of the groups defined for $R^3$ is optionally substituted with one to three substituents, each substituent being independently selected from the group consisting of methylenedioxy, F, Cl, $CH_3$, $OCH_3$, $OCF_3$, $OCF_2H$ and $CF_3$.

A group of compounds which is preferred among the O Group compounds, designated the P Group, are those compounds of the O Group wherein $R^2$ is hydrogen or $(C_1-C_3)$ alkyl where the alkyl group is optionally substituted with 1–3 fluoro groups.

A group of compounds which is preferred among the P Group compounds, designated the Q Group, are those compounds of the P Group wherein $R^3$ is phenyl-$CH_2$—O—$CH_2$— or phenyl-$(CH_2)_3$—, where the phenyl in the definition of $R^3$ is optionally substituted with one to three substituents, each substituent being independently selected from the group consisting of methylenedioxy, F, Cl, $CH_3$, $OCH_3$, $OCF_3$, $OCF_2H$ and $CF_3$.

A group of compounds which is preferred among the Q Group compounds, designated the R Group, are those compounds of the Q Group wherein $R^1$ is —$CH_2$—$A^1$ where $A^1$ is phenyl, 2-pyridyl, 3-pyridyl, optionally substituted with 1–3 fluoro groups or 1–3 Chloro groups;

R² is methyl or ethyl where the ethyl group is optionally substituted with 1–3 fluoro groups; and R³ is phenyl-CH₂—O—CH₂—, where the phenyl is optionally substituted with 1–3 fluoro groups, 1–3 Chloro groups or 1–2 CF₃ groups.

A preferred compound of the R Group is the 1(R),8a(R,S) diastereomeric mixture, the 1(R),8a(R) diastereomer or the 1(R),8a(S) diastereomer of 2-amino-N-{1-(2,4-difluoro-benzyloxymethyl)-2-[1,3-dioxo-8a-pyridin-3-ylmethyl-2-(2,2,2-trifluoro-ethyl)-hexahydro-imidazo[1,5-a]pyrazin-7-yl]-2-oxo-ethyl}-2-methyl-propionamide.

A group of compounds which is preferred among the R Group compounds, designated the S Group, are those compounds of the R Group wherein R¹ is —CH₂—A¹ where A¹ is phenyl optionally substituted with 1–2 chloro groups or 1–2 fluoro groups;

R² is methyl or —CH₂CF₃; and

R³ is phenyl-CH₂—O—CH₂—, optionally substituted with 1–3 fluoro groups, 1–3 chloro groups or 1–2 CF₃ groups.

A group of compounds which is preferred among the S Group compounds, designated the T Group, are those compounds of the S Group where the compound is selected from the group consisting of 2-amino-N-[2-(8a-(R,S)-benzyl-2-methyl-1,3-dioxo-hexahydro-imidazo[1,5-a]pyrazin-7-yl)-1-(R)-benzyloxymethyl-2-oxo-ethyl]-2-methyl-propionamide, 2-amino-N{1-(R)-benzyloxymethyl-2-[8a-(R,S)-(4-fluoro-benzyl)-2-methyl-1,3-dioxo-hexahydroimidazo[1,5-a]pyrazin-7-yl]-2-oxo-ethyl}-2-methyl-propionamide and 2-amino-N-{2-[8a-(R,S)-benzyl-1,3-dioxo-2-(2,2,2-trifluoro-ethyl)-hexahydro-imidazo[1,5-a]pyrazin-7-yl]-1-(R)-benzyloxymethyl-2-oxo-ethyl}-2-methyl-propionamide.

The following compounds are particularly preferred of the T Group compounds:

2-amino-N-[2-(8a-(R)-benzyl-2-methyl-1,3-dioxo-hexahydro-imidazo[1,5-a]pyrazin-7-yl)-1-(R)-benzyloxymethyl-2-oxo-ethyl]-2-methyl-propionamide;

2-amino-N-[2-(8a-(S)-benzyl-2-methyl-1,3-dioxo-hexahydro-imidazo[1,5a]pyrazin-7-yl)-1-(R)-benzyloxymethyl-2-oxo-ethyl]-2-methyl-propionamide;

2-amino-N-{1-(R)-benzyloxymethyl-2-[8a-(R)-(4-fluoro-benzyl)-2-methyl-1,3-dioxo-hexahydro-imidazo[1,5-a]pyrazin-7-yl]-2-oxo-ethyl}-2-methyl-propionamide;

2-amino-N-{1-(R)-benzyloxymethyl-2-[8a-(S)-(4-fluoro-benzyl)-2-methyl-1,3-dioxo-hexahydro-imidazo[1,5-a]pyrazin-7-yl]-2-oxo-ethyl}-2-methyl-propionamide;

2-amino-N-{2-[8a-(R)-benzyl-1,3-dioxo-2-(2,2,2-trifluoro-ethyl)-hexahydro-imidazo[1,5-a]pyrazin-7-yl]-1-(R)-benzyloxymethyl-2-oxo-ethyl}-2-methyl-propionamide; and 2-amino-N-{2-[8a-(S)-benzyl-1,3-dioxo-2-(2,2,2-trifluoro-ethyl)-hexahydro-imidazo[1,5-a]pyrazin-7-yl]-1-(R)-benzyloxymethyl-2-oxo-ethyl}-2-methyl-propionamide.

Another group of compounds which is preferred among the R Group compounds, designated the U Group, are those compounds of the R Group wherein R¹ is —CH₂A¹ where A¹ is 2-pyridyl optionally substituted with 1–2 chloro groups;

R² is methyl or —CH₂CF₃; and

R³ is phenyl-CH₂—O—CH₂, optionally substituted with 1–3 fluoro groups, 1–3 chloro groups or 1–2 CF₃ groups.

A group of compounds which is preferred among the U Group compounds, designated the V Group, are those compounds of the U Group where the compound is 2-amino-N-[1-(R)-benzyloxymethyl-2-(2-methyl-1,3-dioxo-8a-(R,S)-pyridin-2-ylmethyl-hexahydro-imidazo[1,5-a]pyrazin-7-yl)-2-oxo-ethyl]-2-methyl-propionamide, 2-amino-N-{1-(R)-benzyloxymethyl-2-[1,3-dioxo-8a-(R,S)-pyridin-2-ylmethyl-2-(2,2,2-trifluoro-ethyl)-hexahydro-imidazo[1,5-a]pyrazin-7-yl]-2-oxo-ethyl}-2-methyl-propionamide, 2-amino-N-{1-(R)-(2,4-difluoro-benzyloxymethyl)-2-[1,3-dioxo-8a-(R,S)-pyridin-2-ylmethyl-2-(2,2,2-trifluoro-ethyl)-hexahydro-imidazo[1,5-a]pyrazin-7-yl]-2-oxo-ethyl}-2-methyl-propionamide, 2-amino-N-[2-[1,3-dioxo-8a-(R,S)-pyridin-2-ylmethyl-2-(2,2,2-trifluoro-ethyl)-hexahydro-imidazo[1,5-a]pyrazin-7-yl]-2-oxo-1-(R)-(2-trifluoromethyl-benzyloxymethyl)-ethyl]-2-methyl-propionamide or 2-amino-N-{1-(R)-(4-chloro-benzyloxymethyl)-2-[1,3-dioxo-8a-(R,S)-pyridin-2-ylmethyl-2-(2,2,2-trifluoro-ethyl)-hexahydro-imidazo[1,5-a]pyrazin-7-yl]-2-oxo-ethyl}-2-methyl-propionamide.

The following compounds are particularly preferred of the V Group compounds:

2-amino-N-[1-(R)-benzyloxymethyl-2-(2-methyl-1,3-dioxo-8a-(R)-pyridin-2-ylmethyl-hexahydro-imidazo[1,5-a]pyrazin-7-yl)-2-oxo-ethyl]-2-methyl-propionamide;

2-amino-N-[1-(R)-benzyloxymethyl-2-(2-methyl-1,3-dioxo-8a-(S)-pyridin-2-ylmethyl-hexahydro-imidazo[1,5-a]pyrazin-7-yl)-2-oxo-ethyl]-2-methyl-propionamide;

2-amino-N-{1-(R)-benzyloxymethyl-2-[1,3-dioxo-8a-(R)-pyridin-2-ylmethyl-2-(2,2,2-trifluoro-ethyl)-hexahydro-imidazo[1,5-a]pyrazin-7-yl]-2-oxo-ethyl}-2-methyl-propionamide;

2-amino-N-{1-(R)-benzyloxymethyl-2-[1,3-dioxo-8a-(S)-pyridin-2-ylmethyl-2-(2,2,2-trifluoro-ethyl)-hexahydro-imidazo[1,5-a]pyrazin-7-yl]-2-oxo-ethyl}-2-methyl-propionamide;

2-amino-N-{1-(R)-(2,4-difluoro-benzyloxymethyl)-2-[1,3-dioxo-8a-(R)-pyridin-2-ylmethyl-2-(2,2,2-trifluoro-ethyl)-hexahydro-imidazo[1,5-a]pyrazin-7-yl]-2-oxo-ethyl}-2-methyl-propionamide;

2-amino-N-{1-(R)-(2,4-difluoro-benzyloxymethyl)-2-[1,3-dioxo-8a-(S)-pyridin-2-ylmethyl-2-(2,2,2-trifluoro-ethyl)-hexahydro-imidazo[1,5-a]pyrazin-7-yl]-2-oxo-ethyl}-2-methyl-propionamide;

2-amino-N-[2-[1,3-dioxo-8a-(R)-pyridin-2-ylmethyl-2-(2,2,2-trifluoro-ethyl)-hexahydro-imidazo[1,5-a]pyrazin-7-yl]-2-oxo-1-(R)-(2-trifluoromethyl-benzyloxymethyl)-ethyl]-2-methyl-propionamide;

2-amino-N-[2-[1,3-dioxo-8a-(S)-pyridin-2-ylmethyl-2-(2,2,2-trifluoro-ethyl)-hexahydro-imidazo[1,5-a]pyrazin-7-yl]-2-oxo-1-(R)-(2-trifluoromethyl-benzyloxymethyl)-ethyl]-2-methyl-propionamide;

2-amino-N-{1-(R)-(4-chloro-benzyloxymethyl)-2-[1,3-dioxo-8a-(R)-pyridin-2-ylmethyl-2-(2,2,2-trifluoro-ethyl)-hexahydro-imidazo[1,5-a]pyrazin-7-yl]-2-oxo-ethyl}-2-methyl-propionamide; and 2-amino-N-{1-(R)-(4-chloro-benzyloxymethyl)-2-[1,3-dioxo-8a-(S)-pyridin-2-ylmethyl-2-(2,2,2-trifluoro-ethyl)-hexahydro-imidazo[1,5-a]pyrazin-7-yl]-2-oxo-ethyl}-2-methyl-propionamide.

Another group of compounds which is preferred among the E Group compounds, designated the W Group, are those compounds of the E Group wherein Z is C=O; Q is a covalent bond; X is C=O; and Y is $CH_2$.

A group of compounds which is preferred among the W Group compounds, designated the X Group, are those compounds of the W Group wherein $R^1$ is —$CH_2$—$A^1$ where $A^1$ is phenyl, pyridyl or thiazolyl, optionally substituted with one to three substituents, each substituent being independently selected from the group consisting of fluoro, chloro, methyl, $OCH_3$, $OCF_2H$, $OCF_3$ and $CF_3$; and $R^3$ is selected from the group consisting of 3-indolyl-$CH_2$—, phenyl-$(CH_2)_3$—, phenyl-$CH_2$—O—$CH_2$— and thiazolyl-$CH_2$—O—$CH_2$—, where the aryl portion of the groups defined for $R^3$ is optionally substituted with one to three substituents, each substituent being independently selected from the group consisting of methylenedioxy, F, Cl, $CH_3$, $OCH_3$, $OCF_3$, $OCF_2H$ and $CF_3$.

A preferred compound of the X Group is the 1(R),8a(R,S) diastereomeric mixture, the 1(R),8a(R) diastereomer or the 1(R),8a(S) diastereomer of 2-amino-N-{1-benzyloxymethyl-2-[8a-(4-fluoro-benzyl)-6,8-dioxo-hexahydro-pyrrolo[1,2-a]pyrazin-2-yl]-2-oxo-ethyl}-2-methyl-propionamide.

Another group of compounds which is preferred among the D Group compounds, designated the Y Group, are those compounds of the D Group wherein HET is

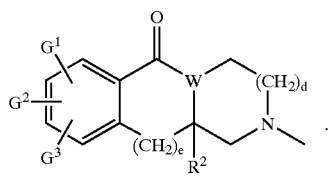

A group of compounds which is preferred among the Y Group compounds, designated the Z Group, are those compounds of the Y Group wherein W is N; d is 1; e is 0 or 1;

$R^2$ is hydrogen, $(C_1-C_5)$alkyl or —$(C_0-C_2)$alkyl-$(C_3-C_8)$ cycloalkyl;

where the alkyl and cycloalkyl groups in the definition of $R^2$ are optionally substituted with 1, 2 or 3 fluoro groups;

$G^1$ is hydrogen, halo, hydroxy, —$(C_1-C_2)$alkyl optionally independently substituted with one to three halo groups or —$(C_1-C_2)$alkoxy optionally independently substituted with one to three halo groups;

$G^2$ is hydrogen, halo, hydroxy, —$(C_1-C_2)$alkyl optionally independently substituted with one to three halo groups or —$(C_1-C_2)$alkoxy optionally independently substituted with one to three halo groups; and $G^3$ is hydrogen.

A group of compounds which is preferred among the Z Group compounds, designated the AA Group, are those compounds of the Z Group wherein $R^2$ is hydrogen or $(C_1-C_3)$alkyl optionally substituted with 1–3 fluoro groups;

$R^3$ is selected from the group consisting of 3-indolyl-$CH_2$—, phenyl-$(CH_2)_3$—, phenyl-$CH_2$—O—$CH_2$— and thiazolyl-$CH_2$—O—$CH_2$—, where the aryl portion of the groups defined for $R^3$ is optionally substituted with one to three substituents, each substituent being independently selected from the group consisting of methylenedioxy, F, Cl, $CH_3$, $OCH_3$, $OCF_3$, $OCF_2H$ and $CF_3$; and $G^1$, $G^2$ and $G^3$ are each independently hydrogen, Cl or F.

A preferred compound of the AA Group is 2-amino-N-[1-(R)-(1H-indol-3-ylmethyl)-2-oxo-2-(9-oxo-1,2,4a,9-tetrahydro-4H-3,9a-diaza-fluoren-3-yl)-ethyl]-2-methyl-propionamide.

Another group of compounds which is preferred among the C Group compounds, designated the AB Group, are those compounds of the C Group wherein HET is

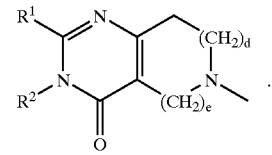

A group of compounds which is preferred among the AB Group compounds, designated the AC Group, are those compounds of the AB Group wherein $X^5$ and $X^{5a}$ are each methyl; d is 1; e is 1;

$R^1$ is —$(CH_2)_t$—$A^1$, —$(CH_2)_q$—$(C_3-C_7)$cycloalkyl or $(C_1-C_{10})$alkyl;

$A^1$ in the definition of $R^1$ is phenyl, pyridyl, thiazolyl or thienyl, optionally substituted with one to three substituents, each substituent being independently selected from the group consisting of F, Cl, $CH_3$, $OCH_3$, $OCF_2H$, $OCF_3$ and $CF_3$;

the cycloalkyl and alkyl groups in the definition of $R^1$ are optionally substituted with $(C_1-C_4)$alkyl, hydroxy, $(C_1-C_4)$alkoxy or 1 to 3 fluoro groups;

t is 1 or 2; q is 1 or 2; and $R^2$ is hydrogen, $(C_1-C_5)$alkyl or —$(C_0-C_2)$alkyl-$(C_3-C_8)$ cycloalkyl;

where the alkyl and cycloalkyl groups in the definition of $R^2$ are optionally substituted with 1, 2 or 3 fluoro groups.

A group of compounds which is preferred among the AC Group compounds, designated the AD Group, are those compounds of the AC Group wherein $R^1$ is $(C_1-C_6)$alkyl optionally substituted with 1–3 fluoro groups;

$R^2$ is hydrogen or $(C_1-C_3)$alkyl optionally substituted with 1–3 fluoro groups; and $R^3$ is selected from the group consisting of 3-indolyl-$CH_2$—, phenyl-$(CH_2)_3$—, phenyl-$CH_2$—O—$CH_2$— and thiazolyl-$CH_2$—O—$CH_2$—, where the aryl portion of the groups defined for $R^3$ is optionally substituted with one to three substituents, each substituent being independently selected from the group consisting of methylenedioxy, F, Cl, $CH_3$, $OCH_3$, $OCF_3$, $OCF_2H$ and $CF_3$.

A preferred compound of the AD Group is 2-amino-N-[2-(2,3-dimethyl-4-oxo-3,5,7,8-tetrahydro-4H-pyrido[4,3-d]pyrimidin-6-yl)-1-(R)-(1H-indol-3-ylmethyl)-2-oxo-ethyl]-2-methyl-propionamide.

Another group of compounds which is preferred among the D Group compounds, designated the AE Group, are those compounds of the D Group wherein HET is

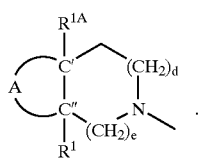

A group of compounds which is preferred among the AE Group compounds, designated the AF Group, are those compounds of the AE Group wherein A is —$NR^2$—C(O)—O—; d is 1; e is 1;

$R^1$ is —$(CH_2)_t$—$A^1$, —$(CH_2)_q$—$(C_3$-$C_7)$cycloalkyl or $(C_1$-$C_{10})$alkyl;

$A^1$ in the definition of $R^1$ is phenyl, pyridyl, thiazolyl or thienyl, optionally substituted with one to three substituents, each substituent being independently selected from the group consisting of F, Cl, $CH_3$, $OCH_3$, $OCF_2H$, $OCF_3$ and $CF_3$;

the cycloalkyl and alkyl groups in the definition of $R^1$ are optionally substituted with $(C_1$-$C_4)$alkyl, hydroxy, $(C_1$-$C_4)$alkoxy or 1–3 fluoro groups;

t is 1 or 2; q is 1 or 2;

$R^{1A}$ is hydrogen or methyl; and $R^2$ is hydrogen, $(C_1$-$C_5)$alkyl, —$(C_0$-$C_2)$alkyl-$(C_3$-$C_8)$ cycloalkyl or $(C_1$-$C_2)$alkyl-$A^1$, where $A^1$ in the definition of $R^2$ is pyridyl;

where the alkyl and cycloalkyl groups in the definition of $R^2$ are optionally substituted with 1–3 fluoro groups.

A group of compounds which is preferred among the AF Group compounds, designated the AG Group, are those compounds of the AF Group wherein $R^1$ is —$CH_2$—$A^1$ where $A^1$ is phenyl, pyridyl or thiazolyl, optionally substituted with one to three substituents, each substituent being independently selected from the group consisting of F, Cl, $CH_3$, $OCH_3$, $OCF_2H$, $OCF_3$ and $CF_3$;

$R^2$ is hydrogen or $(C_1$-$C_3)$alkyl optionally substituted with 1–3 fluoro groups;

$R^3$ is selected from the group consisting of 3-indolyl-$CH_2$—, phenyl-$(CH_2)_3$—, phenyl-$CH_2$—O—$CH_2$— and thiazolyl-$CH_2$—O—$CH_2$—, where the aryl portion of the groups defined for $R^3$ is optionally substituted with one to three substituents, each substituent being independently selected from the group consisting of methylenedioxy, F, Cl, $CH_3$, $OCH_3$, $OCF_3$, $OCF_2H$ and $CF_3$; and $R^{1A}$ is hydrogen.

A group of compounds which is preferred among the AG Group compounds, designated the AH Group, are those compounds of the AG Group where the compound is the 3a(R,S)-7a(R,S) diastereomeric mixture, the 3a(R),7a(R) diastereomer, the 3a(S),7a(S) diastereomer, the 3a(R),7a(S) diastereomer or the 3a(S),7a(R) diastereomer of the compound selected from the group consisting of 3a-7a-2-amino-N-[2-(3a-benzyl-2-oxo-hexahydro-oxazolo[4,5-c]pyridin-5-yl)-1-(R)-benzyloxymethyl-2-oxo-ethyl]-2-methyl-propionamide, 3a-7a-2-amino-N-[1-(R)-benzyloxymethyl-2-(3-methyl-2-oxo-3a-pyridin-3-ylmethyl-hexahydro-oxazolo[4,5-c]pyridin-5-yl)-2-oxo-ethyl]-2-methyl-propionamide, 3a-7a-2-amino-N-[2-(3a-benzyl-3-methyl-2-oxo-hexahydro-oxazolo[4,5-c]pyridin-5-yl)-1-(R)-(1H-indol-3-ylmethyl)-2-oxo-ethyl]-2-methyl-propionamide and 3a-7a-2-amino-N-[1-(R)-benzyloxymethyl-2-oxo-2-(2-oxo-3a-pyridin-2-ylmethyl-hexahydro-oxazolo[4,5-c]pyridin-5-yl)-ethyl]-2-methyl-propionamide.

Another group of compounds which is preferred among the AE Group compounds, designated the AI Group, are those compounds of the AE Group wherein A is —C(O)—$NR^2$—$CH_2$—, —C(O)—O—$CH_2$—, —C(O)—$NR^2$—C(O)—, —$CH_2NR^{12}$—$CH_2$— or —C(O)—$NR^2$—$CH_2$—$CH_2$—;

d is 1; e is 1;

$R^1$ is —$(CH_2)_t$—$A^1$, —$(CH_2)_q$—$(C_3$-$C_7)$cycloalkyl or $(C_1$-$C_{10})$alkyl;

$A^1$ in the definition of $R^1$ is phenyl, pyridyl, thiazolyl or thienyl, optionally substituted with one to three substituents, each substituent being independently selected from the group consisting of F, Cl, $CH_3$, $OCH_3$, $OCF_2H$, $OCF_3$ and $CF_3$;

the cycloalkyl and alkyl groups in the definition of $R^1$ are optionally substituted with $(C_1$-$C_4)$alkyl, hydroxy, $(C_1$-$C_4)$alkoxy or 1–3 fluoro groups;

t is 1 or 2; q is 1 or 2;

$R^{1A}$ is hydrogen or methyl; and $R^2$ is hydrogen, $(C_1$-$C_5)$alkyl, —$(C_0$-$C_2)$alkyl-$(C_3$-$C_8)$ cycloalkyl;

where the alkyl and cycloalkyl groups in the definition of $R^2$ are optionally substituted with 1–3 fluoro groups.

A group of compounds which is preferred among the AI Group compounds, designated the AJ Group, are those compounds of the AI Group wherein $R^1$ is —$CH_2$—$A^1$ where $A^1$ is phenyl, pyridyl or thiazolyl, optionally substituted with one to three substituents, each substituent being independently selected from the group consisting of F, Cl, $CH_3$, $OCH_3$, $OCF_2H$, $OCF_3$ and $CF_3$;

$R^2$ is hydrogen or $(C_1$-$C_3)$alkyl optionally substituted with 1–3 fluoro groups; and $R^3$ is selected from the group consisting of 3-indolyl-$CH_2$—, phenyl-$(CH_2)_3$—, phenyl-$CH_2$—O—$CH_2$— and thiazolyl-$CH_2$—O—$CH_2$—, where the aryl portion of the groups defined for $R^3$ is optionally substituted with one to three substituents, each substituent being independently selected from the group consisting of methylenedioxy, F, Cl, $CH_3$, $OCH_3$, $OCF_3$, $OCF_2H$ and $CF_3$; and $R^{1A}$ is hydrogen.

A group of compounds which is preferred among the AJ Group compounds, designated the AK Group, are those compounds of the AJ Group where the compound is selected from the group consisting of 2-amino-N-[1-(R)-(1H-indol-3-ylmethyl)-2-(2-methyl-1,3-dioxo-octahydro-pyrrolo[3,4-c]pyridin-5-yl)-2-oxo-ethyl]-2-methyl-propionamide, the 3a(R,S),1(R) diastereomeric mixture, the 3a(R),1(R) diastereomer or the 3a(S),1(R) diastereomer of 2-amino-N-[2-(3a-benzyl-3-oxo-octahydro-pyrrolo[3,4-c]pyridin-5-yl)-1-benzyloxymethyl-2-oxo-ethyl]-2-methyl-propionamide, the 3a(R,S),1(R) diastereomeric mixture, the 3a(R),1(R) diastereomer or the 3a(S),1(R) diastereomer of 2-amino-N-[2-(3a-benzyl-3-oxo-hexahydro-furo[3,4-c]pyridin-5-yl)-1-benzyloxymethyl-2-oxo-ethyl]-2-methyl-propionamide, the 3a(R,S),1(R) diastereomeric mixture, the 3a(R),1(R) diastereomer or the 3a(S),1(R) diastereomer of N-[2-(2-acetyl-3a-benzyl-octahydro-pyrrolo[3,4-c]pyridin-5-yl)-(1H-indol-2-ylmethyl)-2-oxo-ethyl]-2-amino-2-methyl-propionamide and the 8a(R,S),1(R) diastereomeric mixture, the 8a(R),1(R) diastereomer or the 8a(S),1(R) diastereomer of 2-amino-N-

[2-(8a-benzyl-7-methyl-8-oxo-octahydro-[2,7]naphthyridin-2-yl)-1-benzyloxymethyl-2-oxo-ethyl]-2-methyl-propionamide.

Another group of compounds which is preferred among the AE Group compounds, designated the AL Group, are those compounds of the AE Group wherein $R^1$ is —$(CH_2)_t$—$A^1$, —$(CH_2)_q$—$(C_3$-$C_7)$cycloalkyl or $(C_1$-$C_{10})$alkyl;

$A^1$ in the definition of $R^1$ is phenyl, pyridyl, thiazolyl or thienyl, optionally substituted with one to three substituents, each substituent being independently selected from the group consisting of F, Cl, $CH_3$, $OCH_3$, $OCF_2H$, $OCF_3$ and $CF_3$;

the cycloalkyl and alkyl groups in the definition of $R^1$ are optionally substituted with $(C_1$-$C_4)$alkyl, hydroxy, $(C_1$-$C_4)$alkoxy, or 1–3 fluoro groups;

t is 1 or 2; q is 1 or 2;

$R^{1A}$ is hydrogen or methyl;

$R^2$ is hydrogen, $(C_1$-$C_5)$alkyl or —$(C_0$-$C_2)$alkyl-$(C_3$-$C_8)$cycloalkyl;

where the alkyl and cycloalkyl groups in the definition of $R^2$ are optionally substituted with 1–3 fluoro groups;

d is 1; e is 1; and $R^9$ and $R^{10}$ are each hydrogen.

A group of compounds which is preferred among the AL Group compounds, designated the AM Group, are those compounds of the AL Group wherein $R^1$ is —$CH_2$—$A^1$ where $A^1$ is phenyl, pyridyl or thiazolyl, optionally substituted with one to three substituents, each substituent being independently selected from the group consisting of F, Cl, $CH_3$, $OCH_3$, $OCF_2H$, $OCF_3$ and $CF_3$;

$R^2$ is hydrogen or $(C_1$-$C_3)$alkyl optionally substituted with 1–3 fluoro groups; and $R^3$ is selected from the group consisting of 3-indolyl-$CH_2$—, phenyl-$(CH_2)_3$—, phenyl-$CH_2$—O—$CH_2$— and thiazolyl-$CH_2$—O—$CH_2$—, where the aryl portion of the groups defined for $R^3$ is optionally substituted with one to three substituents, each substituent being independently selected from the group consisting of methylenedioxy, F, Cl, $CH_3$, $OCH_3$, $OCF_3$, $OCF_2H$ and $CF_3$; and $R^{1A}$ is hydrogen.

Another group of compounds which is preferred among the C Group compounds, designated the AN Group, are those compounds of the C Group wherein

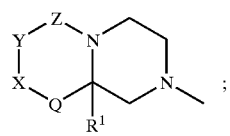

HET is

Z is C=O or $S(O)_2$; Q is a covalent bond; X is C=O; Y is $NR^2$;

$R^2$ is hydrogen, $(C_1$-$C_5)$alkyl or —$(C_0$-$C_2)$alkyl-$(C_3$-$C_8)$cycloalkyl; where the alkyl and cycloalkyl groups in the definition of $R^2$ are optionally substituted with 1, 2 or 3 fluoro groups;

$R^1$ is hydrogen; and $R^3$ is selected from the group consisting of phenyl-$CH_2$—O—$CH_2$—, pyridyl-$CH_2$—O—$CH_2$—, phenyl-$(CH_2)_3$—, 3-indolyl-$CH_2$— and thiazolyl-$CH_2$—O—$CH_2$—, where the aryl portion of the groups defined for $R^3$ is optionally substituted with one to three substituents, each substituent being independently selected from the group consisting of methylenedioxy, F, Cl, $CH_3$, $OCH_3$, $OCF_3$, $OCF_2H$ and $CF_3$.

A group of compounds which is preferred among the AN Group compounds, designated the AO Group, are those compounds of the AN Group wherein Z is C=O; $R^2$ is hydrogen or $(C_1$-$C_3)$alkyl optionally substituted with 1–3 fluoro groups.

A group of compounds which is preferred among the AO Group compounds, designated the AP Group, are those compounds of the AO Group wherein $R^3$ is selected from the group consisting of 3-indolyl-$CH_2$—, phenyl-$(CH_2)_3$—, phenyl-$CH_2$—O—$CH_2$— and thiazolyl-$CH_2$—O—$CH_2$—, where the aryl portion of the groups defined for $R^3$ is optionally substituted with one to three substituents, each substituent being independently selected from the group consisting of methylenedioxy, F, Cl, $CH_3$, $OCH_3$, $OCF_3$, $OCF_2H$ and $CF_3$.

A preferred compound of the AP Group is 8a-(R,S)-2-amino-N-[1-(R)-(1H-indol-3-ylmethyl)-2-(2-methyl-1,3-dioxo-hexahydro-imidazo[1,5-a]pyrazin-7-yl)-2-oxo-ethyl]-2-methyl-propionamide.

An even more preferred compound of the AP Group is 8a-(R)-2-amino-N-[1-(R)-(1H-indol-3-ylmethyl)-2-(2-methyl-1,3-dioxo-hexahydro-imidazo[1,5-a]pyrazin-7-yl)-2-oxo-ethyl]-2-methyl-propionamide.

Another more preferred compound of the AP Group is 8a-(S)-2-amino-N-[1-(R)-(1H-indol-3-ylmethyl)-2-(2-methyl-1,3-dioxo-hexahydro-imidazo[1,5-a]pyrazin-7-yl)-2-oxo-ethyl]-2-methyl-propionamide.

This invention also provides:

methods for increasing levels of endogenous growth hormone in a human or other animal such as especially dogs, cats and horses, which comprise administering to such human or other animal an effective amount of a compound of Formula I;

pharmaceutical compositions which comprise a pharmaceutically acceptable carrier and an effective amount of a compound of Formula I;

pharmaceutical compositions useful for increasing the endogenous production or release of growth hormone in a human or other animal which comprise a pharmaceutically acceptable carrier, an effective amount of a compound of Formula I and a growth hormone secretagogue selected from the group consisting of GHRP-6, Hexarelin, GHRP-1, growth hormone releasing factor (GRF), IGF-1, IGF-2 and B-HT920 or an analog thereof;

methods for treating or preventing osteoporosis and/or frailty which comprise administering to a human or other animal especially dogs, cats and horses, in need of such treatment or prevention an amount of a compound of Formula I which is effective in treating or preventing osteoporosis and/or frailty;

methods for treating or preventing diseases or conditions which may be treated or prevented by growth hormone which comprise administering to a human or other animal in need of such treatment or prevention an amount of a compound of Formula I which is effective in promoting release of endogenous growth hormone;

preferred methods of the immediately foregoing methods is where the disease or condition is congestive heart failure, frailty associated with aging or obesity;

preferred methods of the immediately foregoing methods is where the disease or condition is congestive heart failure or frailty associated with aging;

methods for accelerating bone fracture repair, attenuating protein catabolic response after a major operation, reducing cachexia and protein loss due to chronic illness such as AIDS or cancer, accelerating wound healing, or accelerating the recovery of bum patients or patients having undergone major surgery, which methods comprise administering to a mammal in need of such treatment an amount of a compound of Formula I which is effective in promoting release of endogenous growth hormone;

preferred methods of the immediately foregoing methods is for accelerating the recovery of patients having undergone major surgery or for accelerating bone fracture repair;

methods for improving muscle strength, mobility, maintenance of skin thickness, metabolic homeostasis or renal homeostasis, which methods comprise administering to a human or other animal in need of such treatment an amount of a compound of Formula I which is effective in promoting release of endogenous growth hormone;

methods for the treatment or prevention of osteoporosis and/or frailty which comprises administering to a human or other animal especially dogs, cats and horses, with osteoporosis and/or frailty effective amounts of a bisphosphonate compound and a compound of Formula I;

preferred methods of the immediately foregoing methods is where the bisphosphonate compound is alendronate or ibandronate;

methods for the treatment or prevention of osteoporosis and/or frailty which comprise administering to a human or other animal especially dogs, cats and horses, with osteoporosis and/or frailty effective amounts of estrogen or Premarin® and a compound of Formula I and, optionally, progesterone;

methods for the treatment of osteoporosis and/or frailty which comprise administering to a human or other animal especially dogs, cats and horses, with osteoporosis and/or frailty effective amounts of calcitonin and a compound of Formula I;

methods to increase IGF-1 levels in a human or other animal especially dogs, cats and horses, deficient in IGF-1 which comprise administering to a human or other animal with IGF-1 deficiency a compound of Formula I;

methods for the treatment of osteoporosis and/or frailty which comprises administering to a human or other animal especially dogs, cats and horses, with osteoporosis and/or frailty effective amounts of an estrogen agonist or antagonist and a compound of Formula I;

preferred methods of the immediately foregoing methods is where the estrogen agonist or antagonist is tamoxifen, droloxifene, raloxifene, idoxifene, cis-6-(4-fluoro-phenyl)-5-[4-(2-piperidin-1-yl-ethoxy)-phenyl]-5,6,7,8-tetrahydro-naphthalen-2-ol; (–)-cis-6-phenyl-5-[4-(2-pyrrolidin-1-yl-ethoxy)-phenyl]-5,6,7,8-tetrahydro-naphthalen-2-ol; cis-6-phenyl-5-[4-(2-pyrrolidin-1-yl-ethoxy)-phenyl]-5,6,7,8-tetrahydro-naphthalen-2-ol; cis-1-[6'-pyrrolodinoethoxy-3'-pyridyl]-2-phenyl-6-hydroxy-1,2,3,4-tetrahydro-naphthalene; 1-(4'-pyrrolidinoethoxyphenyl)-2-(4"-fluorophenyl)-6-hydroxy-1,2,3,4-tetrahydroisoquinoline; cis-6-(4-hydroxyphenyl)-5-[4-(2-piperidin-1-yl-ethoxy)-phenyl]-5,6,7,8-tetrahydro-naphthalen-2-ol; or 1-(4'-pyrrolidinolethoxyphenyl)-2-phenyl-6-hydroxy-1,2,3,4-tetrahydro-isoquinoline.

methods for enhancing growth and improving carcass quality of an animal other than humans which comprise administering to said animal an effective amount of a compound of Formula I;

methods for enhancing feed efficiency in an animal other than humans which comprise administering to said animal an effective amount of a compound of Formula I;

methods for increasing milk production in a female mammal which comprise administering to said female mammal an effective amount of a compound of Formula I;

methods for increasing piglet number, increasing pregnancy rate in sows, increasing viability of piglets, increasing weight of piglets or increasing muscle fiber size in piglets which comprise administering to a sow or piglet an effective amount of a compound of Formula I;

methods for increasing muscle mass, which comprise administering to a human or other animal such as dogs, cats, horses, cattle, pigs, chickens, turkeys, sheep and fish, in need of such treatment an amount of a compound of Formula I;

methods for promoting growth in growth hormone deficient children which comprise administering to a growth hormone deficient child a compound of Formula I;

methods for the treatment or prevention of congestive heart failure, obesity or frailty associated with aging, which comprise administering to a human or other animal in need thereof effective amounts of a functional somatostatin antagonist and a compound of Formula I;

preferred methods of the immediately foregoing methods is where the functional somatostatin antagonist is an alpha-2 adrenergic agonist and the other animal is a dog, cat or a horse;

preferred methods of the immediately foregoing methods is where the alpha-2 adrenergic agonist is clonidine, xylazine or medetomidine.

methods for treating insulin resistance in a mammal, which comprises administering to said mammal an effective amount of a compound of Formula I;

preferred methods of the immediately foregoing methods is where the condition associated with insulin resistance is type I diabetes, type II diabetes, hyperglycemia, impaired glucose tolerance or an insulin resistant syndrome; or where the condition associated with insulin resistance is associated with obesity or old age;

methods for increasing the endogenous production or release of growth hormone in a human or other animal especially dogs, cats and horses, which comprise administering effective amounts of a compound of Formula I and a growth hormone secretagogue selected from the group consisting of GHRP-6, Hexarelin, GHRP-1, growth hormone releasing factor (GRF), IGF-1, IGF-2 and B-HT920 or an analog thereof;

pharmaceutical compositions useful for treating or preventing osteoporosis and/or frailty which comprise a pharmaceutically acceptable carrier, an amount of a bisphosphonate compound and an amount of a compound of Formula I;

pharmaceutical compositions useful for treating or preventing osteoporosis and/or frailty which comprises a pharmaceutically acceptable carrier, an amount of estrogen or Premarin®, an amount of a compound of Formula I and, optionally, an amount of progesterone;

pharmaceutical compositions useful for treating osteoporosis and/or frailty which comprise a pharmaceutically acceptable carrier, an amount of calcitonin and an amount of a compound of Formula I;

pharmaceutical compositions useful for treating preventing congestive heart failure, obesity or frailty associated with aging, which comprise a pharmaceutically acceptable carrier, an amount of an alpha-2 adrenergic agonist and an amount of a compound of Formula I;

a preferred pharmaceutical composition of the immediately foregoing compositions is where the alpha-2 adrenergic agonist is clonidine, xylazine or medetomidine; and methods for increasing levels of endogenous growth hormone, which comprise administering to a human or other animal in need thereof effective amounts of a functional somatostatin antagonist and a compound of Formula I.

In yet another aspect, this invention provides methods for improving muscle strength, mobility, maintenance of skin thickness, metabolic homeostasis and renal homeostasis, which comprise administering to a human or other animal especially dogs, cats and horses, in need of such treatment an amount of a compound of claim 1 which is effective in promoting release of endogenous growth hormone.

The instant compounds promote the release of growth hormone which are stable under various physiological conditions and may be administered parenterally, nasally or by the oral route.

Another group of compounds which is preferred within the E Group compounds, designated the EA Group, comprises those compounds, or stereoisomeric mixtures thereof, diastereomerically enriched, diastereomerically pure, enantiomerically enriched or enantiomerically pure isomers thereof, or prodrugs of such compounds, mixtures or isomers thereof, or pharmaceutically acceptable salts of the compounds, mixtures, isomers or prodrugs wherein:

Z is C=O; Q is a covalent bond;

Y is $CR^9R^{10}$ where $R^9$ in the definition of Y is selected from the group consisting of hydrogen, fluoro, hydroxy and $(C_1-C_2)$alkyl optionally substituted with 1–3 fluoro groups; and $R^{10}$ in the definition of Y is selected from the group consisting of hydrogen, fluoro, and $(C_1-C_2)$ alkyl optionally substituted with 1–3 fluoro groups with the proviso that $R^{10}$ cannot be fluoro when $R^9$ is hydroxy;

and X is $CHR^9$ where $R^9$ in the definition of X is selected from the group consisting of hydrogen, fluoro, hydroxy and $(C_1-C_2)$alkyl optionally substituted with 1–3 fluoro groups.

A group of compounds which is preferred within the EA Group compounds, designated the EB Group, comprises those compounds or stereoisomeric mixtures thereof, diastereomerically enriched, diastereomerically pure, enantiomerically enriched or enantiomerically pure isomers thereof, or prodrugs of such compounds, mixtures or isomers thereof, or pharmaceutically acceptable salts of the compounds, mixtures, isomers or prodrugs wherein:

$R^1$ is —$CH_2$—$A^1$ where $A^1$ is phenyl, pyridyl or thiazolyl, optionally substituted with one to three substituents, each substituent being independently selected from the group consisting of F, Cl, $CH_3$, $OCH_3$, $OCF_2H$, $OCF_3$ and $CF_3$; and $R^3$ is selected form the group consisting of 3-indolyl-$CH_2$—, phenyl-$(CH_2)_3$—, phenyl-$CH_2$—O—$CH_2$— and thiazolyl-$CH_2$—O—$CH_2$—, where the aryl portion of the groups defined for $R^3$ is optionally substituted with one to three substituents, each substituent being independently selected from the group consisting of F, Cl, $CH_3$, $OCH_3$, $OCF_2H$, $OCF_3$ and $CF_3$.

A group of compounds which is preferred within the EB Group compounds, designated the EC Group, comprises those compounds or stereoisomeric mixtures thereof, diastereomerically enriched, diastereomerically pure, enantiomerically enriched or enantiomerically pure isomers thereof, or prodrugs of such compounds, mixtures or isomers thereof, or pharmaceutically acceptable salts of the compounds, mixtures, isomers or prodrugs wherein X is $CH_2$;

Y is $CR^9R^{10}$ where $R^9$ and $R^{10}$ in the definition of Y are independently selected from the group consisting of hydrogen, fluoro, and $(C_1-C_2)$alkyl optionally substituted with 1–3 fluoro groups.

A group of compounds which is preferred within the EC Group, designated the ED Group, comprises those compounds or prodrugs of such compounds or pharmaceutically acceptable salts of the compounds or prodrugs wherein the compound is the 8a(R,S),1(R) diastereomeric mixture, the 8a(R),1(R) diastereomer or the 8a(S),1(R) diastereomer of 2-amino-N-[2-(8a-benzyl-6-oxo-hexahydro-pyrrolo[1,2-a]pyrazin-2-yl)-1-benzyloxymethyl-2-oxo-ethyl]-2-methyl-propionamide or 2-amino-N-[1-benzyloxymethyl-2-oxo-2-(6oxo-8a-pyridin-2-ylmethyl-hexahydro-pyrrolo[1,2-a]pyrazin-2-yl)-ethyl]-2-methyl-propionamide.

Another group of compounds which is preferred within the J Group comprises those compounds or prodrugs of such compounds or pharmaceutically acceptable salts of the compounds or prodrugs wherein the compound is the 8a(R,S),1(R) diastereomeric mixture, the 8a(R),1(R) diastereomer or the 8a(S),1(R) diastereomer of 2-amino-N-{1-benzyloxymethyl-2-oxo-2-[3-oxo-8a-pyridin-2-ylmethyl-2-(2,2,2-trifluoro-ethyl)-hexahydro-imidazo[1,5-a]pyrazin-7-yl]-ethyl}-2-methyl-propionamide; 2-amino-N-{-1-benzyloxymethyl-2-[8a-(2,4-difluoro-benzyl)-3-oxo-2-(2,2,2-trifluoro-ethyl)-hexahydro-imidazo[1,5-a]pyrazin-7-yl]-2-oxo-ethyl}-2-methyl-propionamide; 2-amino-N-[1-benzyloxymethyl-2-oxo-2-(3-oxo-8a-pyridin- 2-ylmethyl-hexahydro-imidazo[1,5-a]pyrazin-7-yl)-ethyl]-2-methyl-propionamide; or 2-amino-N-[1-benzyloxymethyl-2-(2-ethyl-3-oxo-8a-pyridin-2-ylmethyl-hexahydro-imidazo[1,5-a]pyrazin-7-yl)-2-oxo-ethyl]-2-methyl-propionamide.

Another group of compounds which is preferred within the Q Group compounds, designated the QA Group, comprises those compounds or stereoisomeric mixtures thereof, diastereomerically enriched, diastereomerically pure, enantiomerically enriched or enantiomerically pure isomers thereof, or prodrugs of such compounds, mixtures or isomers thereof, or pharmaceutically acceptable salts of the compounds, mixtures, isomers or prodrugs wherein:

$R^1$ is —$CH_2$—$A^1$ where $A^1$ is phenyl, 2-pyridyl, or 3-pyridyl, optionally substituted with 1–3 F, 1–3 Cl;

R² is methyl or ethyl where the ethyl group is optionally substituted with 1–3 F; and R³ is phenyl-(CH₂)₃—, where the phenyl is optionally substituted with 1–3 F, 1–3 Cl or 1–2 CF₃;

A group of compounds which is preferred within the QA Group of compounds, designated the QB Group, comprises those compounds or stereoisomeric mixtures thereof, diastereomerically enriched, diastereomerically pure, enantiomerically enriched or enantiomerically pure isomers thereof, or prodrugs of such compounds, mixtures or isomers thereof, or pharmaceutically acceptable salts of the compounds, mixtures, isomers or prodrugs wherein R¹ is —(CH₂)—A¹ where A¹ is 2-pyridyl, optionally substituted with 1–2 Cl; and R² is methyl or —CH₂CF₃.

A group of compounds which is preferred within the QB Group of: compounds, designated the QC Group, comprises those compounds or prodrugs of such compounds or pharmaceutically acceptable salts of the compounds or prodrugs wherein the compound is 2-amino-N-{1-(R)-[1,3-dioxo-8a-(R,S)-pyridin-2-ylmethyl-2-(2,2,2-trifluoro-ethyl)-hexahydro-imidazo[1,5-a]pyrazine-7-carbonyl]-(4-phenyl-butyl)}-2-methyl-propionamide.

An especially preferred compound within the QC Group comprises the compound or prodrugs of such compound or pharmaceutically acceptable salts of the compound or prodrugs where the compound is 2-amino-N-{1-(R)-[1,3-dioxo-8a-(R)-pyridin-2-ylmethyl-2-(2,2,2-trifluoro-ethyl)-hexahydro-imidazo[1,5-a]pyrazine-7-carbonyl]-(4-phenyl-butyl)}-2-methyl-propionamide.

Another especially preferred compound within the QC Group comprises the compound or prodrugs of such compound or pharmaceutically acceptable salts of the compound or prodrugs where the compound is 2-amino-N-{1-(R)-[1,3-dioxo-8a-(S)-pyridin-2-ylmethyl-2-(2,2,2-trifluoro-ethyl)-hexahydro-imidazo[1,5-a]pyrazine-7-carbonyl]-(4-phenyl-butyl)}-2-methyl-propionamide.

Another group of compounds which is preferred within the AI Group of compounds, designated the AI^A Group, comprises those compounds or stereoisomeric mixtures thereof, diastereomerically enriched, diastereomerically pure, enantiomerically enriched or enantiomerically pure isomers thereof, or prodrugs of such compounds, mixtures or isomers thereof, or pharmaceutically acceptable salts of the compounds, mixtures, isomers or prodrugs wherein:

A is —C(O)—NR²—CH₂—;

R¹ is —CH₂—A¹ where A¹ is phenyl, pyridyl or thiazolyl, optionally substituted with one to three substituents, each substituent being independently selected from the group consisting of F, Cl, CH₃, OCH₃, OCF₂H, OCF₃ and CF₃;

R² is hydrogen or —(C₁-C₃)alkyl or —(C₀-C₂)alkyl-(C₃-C₅)cycloalkyl where the alkyl and cycloalkyl groups in the definition of R² are optionally substituted with 1–3 fluoro groups;

R³ is selected form the group consisting of 3-indolyl-CH₂—, phenyl-(CH₂)₃—, phenyl-CH₂—O—CH₂— and thiazolyl-CH₂—O—CH₂—, where the aryl portion of the groups defined for R³ is optionally substituted with one to three substituents, each substituent being independently selected from the group consisting of F, Cl, CH₃, OCH₃, OCF₂H, OCF₃ and CF₃; and R^{1A} is hydrogen.

A group of compounds which is preferred within the AI^A Group of compounds, designated the AI^B Group, comprises those compounds or prodrugs of such compounds or pharmaceutically acceptable salts of the compounds or prodrugs where the compound is the 3a(R,S),7a(R,S) diastereomeric mixture, the 3a(R),7a(R) diastereomer, the 3a(S),7a(S) diastereomer, the 3a(R),7a(S) diastereomer, or the 3a(S),7a (R) diastereomer of 2-amino-N-[2-(3a-benzyl-2-cyclopropyl-3-oxo-octahydro-pyrrolo[3,4-c]pyridin-5-yl)-1(R)-benzyloxymethyl-2-oxo-ethyl]-2-methyl-propionamide; 2-amino-N-[2-(3a-benzyl-2-methyl-3-oxo-octahydro-pyrrolo[3,4-c]pyridin-5-yl)-1(R)-benzyloxymethyl-2-oxo-ethyl]-2-methyl-propionamide; or 2-amino-N-[1(R)-benzyloxymethyl-2-(2-methyl-3-oxo-3a-pyridin-2-ylmethyl-octahydro-pyrrolo[3,4-c]pyridin-5-yl)-2-oxo-ethyl]-2-methyl-propionamide.

This invention also provides compounds of the formula

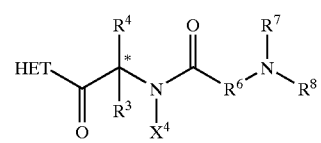

I or a stereoisomeric mixture thereof, diastereomerically enriched, diastereomerically pure, enantiomerically enriched or enantiomerically pure isomer thereof, or a prodrug of such compound, mixture or isomer thereof, or a pharmaceutically acceptable salt of the compound, mixture, isomer or prodrug, wherein HET is a heterocyclic moiety selected from the group consisting of

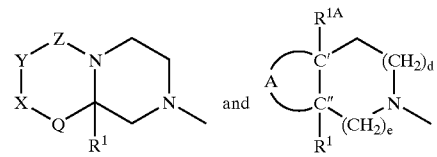

d is 0, 1 or 2;

e is 1 or 2;

A is a divalent radical, where the left hand side of the radical as shown below is connected to C" and the right hand side of the radical as shown below is connected to C', selected from the group consisting of —C(R⁹R¹⁰)—NR²—C(O)—,
—C(R⁹R¹⁰)—C(R⁹R¹⁰)—C(R⁹R¹⁰)—,
—S(O)₂—C(R⁹R¹⁰)—C(R⁹R¹⁰)—,
—C(R⁹R¹⁰)—O—C(O)—,
—C(R⁹R¹⁰)—O—C(R⁹R¹⁰)—,
—NR²—C(O)—C(R⁹R¹⁰)—,
—O—C(O)—C(R⁹R¹⁰)—,
—C(R⁹R¹⁰)—C(O)—NR²—,
—C(R⁹R¹⁰)—C(O)—O—,
—C(O)—NR²—C(R⁹R¹⁰)—C(R⁹R¹⁰)—,
—C(O)—O—C(R⁹R¹⁰)—,
—C(R⁹R¹⁰)—C(R⁹R¹⁰)—C(R⁹R¹⁰)—C(R⁹R¹⁰)—,
—S(O)₂—NR²—C(R⁹R¹⁰)—C(R⁹R¹⁰)—,
—C(R⁹R¹⁰)—C(R⁹R¹⁰)—NR²—C(O)—,
—C(R⁹R¹⁰)—C(R⁹R¹⁰)—O—C(O)—,
—NR²—C(O)—C(R⁹R¹⁰)—C(R⁹R¹⁰)—,
—NR²—S(O)₂—C(R⁹R¹⁰)—C(R⁹R¹⁰)—,
—O—C(O)—C(R⁹R¹⁰)—C(R⁹R¹⁰)—,
—C(R⁹R¹⁰)—C(R⁹R¹⁰)—C(O)—NR²—,
—C(R⁹R¹⁰)—C(R⁹R¹⁰)—C(O)—,
—C(R⁹R¹⁰)—NR²—C(O)—O—,
—C(R⁹R¹⁰)—O—C(O)—NR², —C($R^9R^{10}$)—$NR^2$C(O)—$NR^2$—,
—$NR^2$—C(O)—O—C($R^9R^{10}$)—,
—$NR^2$—C(O)—$NR^2$—C($R^9R^{10}$)—,
—$NR^2$—S(O)$_2$—$NR^2$—C($R^9R^{10}$)—,
—O—C(O)—$NR^2$—C($R^9R^{10}$)—,
—C($R^9R^{10}$)—$NR^2$—C($R^9R^{10}$)—,
—$NR^{12}$—C($R^9R^{10}$)—,
—$NR^{12}$—C($R^9R^{10}$)—C($R^9R^{10}$)—,
—C(O)—O—C($R^9R^{10}$)—C($R^9R^{10}$)—,
—C($R^9R^{10}$)—C($R^9R^{10}$)—N($R^{12}$)—,
—C($R^9R^{10}$)—$NR^{12}$—,
—C($R^9R^{10}$)—C($R^9R^{10}$)$NR^2$—S(O)$_2$—,
—C($R^9R^{10}$)—C($R^9R^{10}$)—S(O)$_2$—$NR^2$—,
—C($R^9R^{10}$)—C($R^9R^{10}$)—C(O)—O—,
—C($R^9R^{10}$)—S(O)$_2$—C($R^9R^{10}$)—,
—C($R^9R^{10}$)—C($R^9R^{10}$)—S(O)$_2$—,
—O—C($R^9R^{10}$)—C($R^9R^{10}$)—,
—C($R^9R^{10}$)—C($R^9R^{10}$)—O—,
—C($R^9R^{10}$)—C(O)—C($R^9R^{10}$)—,
—C(O)—C($R^9R^{10}$)—C($R^9R^{10}$)— and
—C($R^9R^{10}$)—$NR^2$—S(O)$_2$—$NR^2$—;

Q is a covalent bond or CH$_2$;
W is CH or N;
X is C$R^{9a}R^{10a}$, C=CH$_2$ or C=O;
Y is C$R^9R^{10}$, O or $NR^2$;
Z is C=O, C=S or S(O)$_2$;
$R^1$ is hydrogen, —CN, —(CH$_2$)$_q$N(X$^6$)C(O)X$^6$,
—(CH$_2$)$_q$N(X$^6$)C(O)(CH$_2$)$_t$—A$^1$,
—(CH$_2$)$_q$N(X$^6$)S(O)$_2$(CH$_2$)$_t$—A$^1$, —(CH$_2$)$_q$N(X$^6$)S(O)$_2$X$^6$, —(CH$_2$)$_q$N(X$^6$)C(O)N(X$^6$)(CH$_2$)$_t$—A$^1$,
—(CH$_2$)$_q$N(X$^6$)C(O)N(X$^6$)(X$^6$), —(CH$_2$)$_q$C(O)N(X$^6$)(X$^6$), —(CH$_2$)$_q$C(O)N(X$^6$)(CH$_2$)$_t$—A$^1$,
—(CH$_2$)$_q$C(O)OX$^6$, —(CH$_2$)$_q$C(O)O(CH$_2$)$_t$—A$^1$,
—(CH$_2$)$_q$OX$^6$, —(CH$_2$)$_q$OC(O)X$^6$,
—(CH$_2$)$_q$OC(O)(CH$_2$)$_t$—A$^1$, —(CH$_2$)$_q$OC(O)N(X$^6$)(CH$_2$)$_t$—A$^1$, —(CH$_2$)$_q$OC(O)N(X$^6$)(X$^6$),
—(CH$_2$)$_q$C(O)X$^6$, —(CH$_2$)$_q$C(O)(CH$_2$)$_t$—A$^1$,
—(CH$_2$)$_q$N(X$^6$)C(O)OX$^6$,
—(CH$_2$)$_q$N(X$^6$)S(O)$_2$N(X$^6$)(X$^6$), —(CH$_2$)$_q$S(O)$_m$X$^6$,
—(CH$_2$)$_q$S(O)$_m$(CH$_2$)$_t$—A$^1$,
—(C$_1$–C$_{10}$)alkyl, —(CH$_2$)$_t$—A$^1$, —(CH$_2$)$_q$—(C$_3$–C$_7$)cycloalkyl, —(CH$_2$)$_q$—Y$^1$—(C$_1$–C$_6$)alkyl,
(CH$_2$)$_q$—Y$^1$—(CH$_2$)$_t$—A$^1$ or —(CH$_2$)$_q$—Y$^1$—(CH$_2$)$_t$—(C$_3$–C$_7$)cycloalkyl;
where the alkyl and cycloalkyl groups in the definition of $R^1$ are optionally substituted with (C$_1$–C$_4$)alkyl, hydroxy, (C$_1$–C$_4$)alkoxy, carboxyl, —CONH$_2$, —S(O)$_m$(C$_1$–C$_6$)alkyl, —CO$_2$(C$_1$–C$_4$)alkyl ester, 1H-tetrazol-5-yl or 1, 2 or 3 fluoro groups;
$Y^1$ is O, S(O)$_m$, —C(O)NX$^6$—, —CH=CH—, —C≡C—, —N(X$^6$)C(O)—, —C(O)NX$^6$—, —C(O)O—, —OC(O)N(X$^6$)— or —OC(O)—;
q is 0, 1, 2, 3 or 4;
t is 0, 1, 2 or 3;
said (CH$_2$)$_q$ group and (CH$_2$)$_t$ group in the definition of $R^1$ are optionally independently substituted with hydroxy, (C$_1$–C$_4$)alkoxy, carboxyl, —CONH$_2$, —S(O)$_m$(C$_1$–C$_6$)alkyl, —CO$_2$(C$_1$–C$_4$)alkyl ester, 1H-tetrazol-5-yl, 1, 2 or 3 fluoro groups or 1 or 2 (C$_1$–C$_4$)alkyl groups;
$R^{1A}$ is selected from the group consisting of hydrogen, F, Cl, Br, I, (C$_1$–C$_6$)alkyl, phenyl(C$_1$–C$_3$)alkyl, pyridyl(C$_1$–C$_3$)alkyl, thiazolyl(C$_1$–C$_3$)alkyl and thienyl(C$_1$–C$_3$)alkyl, provided that $R^{1A}$ is not F, Cl, Br or I when a heteroatom is vicinal to C";
$R^2$ is hydrogen, (C$_1$–C$_8$)alkyl, —(C$_0$–C$_3$)alkyl-(C$_3$–C$_8$)cycloalkyl, —(C$_1$–C$_4$)alkyl-A$^1$ or A$^1$;

where the alkyl groups and the cycloalkyl groups in the definition of $R^2$ are optionally substituted with hydroxy, —C(O)OX$^6$, —C(O)N(X$^6$)(X$^6$), —N(X$^6$)(X$^6$), —S(O)$_m$(C$_1$–C$_6$)alkyl, —C(O)A$^1$, —C(O)(X$^6$), CF$_3$, CN or 1, 2 or 3 independently selected halo groups;
$R^3$ is selected from the group consisting of A$^1$, (C$_1$–C$_{10}$)alkyl, —(C$_1$–C$_6$)alkyl-A$^1$, —(C$_1$–C$_6$)alkyl-(C$_3$–C$_7$)cycloalkyl, —(C$_1$–C$_5$)alkyl-X$^1$—(C$_1$–C$_5$)alkyl, —(C$_1$–C$_5$)alkyl-X$^1$—(C$_0$–C$_5$)-alkyl-A$^1$ and —(C$_1$–C$_5$)alkyl-X$^1$—(C$_1$–C$_5$)alkyl-(C$_3$–C$_7$)cycloalkyl;
where the alkyl groups in the definition of $R^3$ are optionally substituted with —S(O)$_m$(C$_1$–C$_6$)alkyl, —C(O)OX$^3$, 1, 2, 3, 4 or 5 independently selected halo groups or 1, 2 or 3 independently selected —OX$^3$ groups;
$X^1$ is O, S(O)$_m$, —N(X$^2$)C(O)—, —C(O)N(X$^2$)—, —OC(O)—, —C(O)O—, —CX$^2$=CX$^2$—, —N(X$^2$)C(O)O—, —OC(O)N(X$^2$)— or —C≡C—;
$R^4$ is hydrogen, (C$_1$–C$_6$)alkyl or (C$_3$–C$_7$)cycloalkyl, or $R^4$ is taken together with $R^3$ and a the carbon atom to which they are attached and form (C$_5$–C$_7$)cycloalkyl, (C$_5$–C$_7$)cycloalkenyl, a partially saturated or fully saturated 4- to 8-membered ring having 1 to 4 heteroatoms independently selected from the group consisting of oxygen, sulfur and nitrogen, or is a bicyclic ring system consisting of a partially saturated or fully saturated 5- or 6-membered ring, fused to a partially saturated, fully unsaturated or fully saturated 5- or 6-membered ring, optionally having 1 to 4 heteroatoms independently selected from the group consisting of nitrogen, sulfur and oxygen;
$X^4$ is hydrogen or (C$_1$–C$_6$)alkyl or $X^4$ is taken together with $R^4$ and the nitrogen atom to which $X^4$ is attached and the carbon atom to which $R^4$ is attached and form a five to seven membered ring;
$R^6$ is a bond or is $$\diagdown_{Z^1}\diagdown_{(CH_2)_a}\diagup^{X^5\diagdown \diagup X^{5a}}_{C}\diagdown_{(CH_2)_b}\diagup \ ;$$

where a and b are each independently 0, 1, 2 or 3;
$X^5$ and $X^{5a}$ are each independently selected from the group consisting of hydrogen, CF$_3$, A$^1$ and optionally substituted (C$_1$–C$_6$)alkyl;
the optionally substituted (C$_1$–C$_6$)alkyl in the definition of $X^5$ and $X^{5a}$ is optionally substituted with a substituent selected from the group consisting of A$^1$, OX$^2$, —S(O)$_m$(C$_1$–C$_6$)alkyl, —C(O)OX$^2$, (C$_3$–C$_7$)cycloalkyl, —N(X$^2$)(X$^2$) and —C(O)N(X$^2$)(X$^2$);
or the carbon bearing $X^5$ or $X^{5a}$ forms one or two alkylene bridges with the nitrogen atom bearing $R^7$ and $R^8$ wherein each alkylene bridge contains 1 to 5 carbon atoms, provided that when one alkylene bridge is formed then only one of $X^5$ or $X^{5a}$ is on the carbon atom and only one of $R^7$ or $R^8$ is on the nitrogen atom and further provided that when two alkylene bridges are formed then $X^5$ and $X^{5a}$ cannot be on the carbon atom and $R^7$ and $R^8$ cannot be on the nitrogen atom;
or $X^5$ is taken together with $X^{5a}$ and the carbon atom to which they are attached and form a partially saturated or fully saturated 3- to 7-membered ring, or a partially saturated or fully saturated 4- to 8-membered ring having 1 to 4 heteroatoms independently selected from the group consisting of oxygen, sulfur and nitrogen;
or $X^5$ is taken together with $X^{5a}$ and the carbon atom to which they are attached and form a bicyclic ring system consisting of a partially saturated or fully saturated 5- or 6-membered ring, optionally having 1 or 2 heteroatoms independently selected from the group consisting of nitrogen, sulfur and oxygen, fused to a partially saturated, fully saturated or fully unsaturated 5- or 6-membered ring, optionally having 1 to 4 heteroatoms independently selected from the group consisting of nitrogen, sulfur and oxygen; $Z^1$ is a bond, O or N—$X^2$, provided that when a and b are both 0 then $Z^1$ is not N—$X^2$ or O;
$R^7$ and $R^8$ are each independently hydrogen or optionally substituted $(C_1-C_6)$alkyl;
where the optionally substituted $(C_1-C_6)$alkyl in the definition of $R^7$ and $R^8$ is optionally independently substituted with $A^1$, —C(O)O—$(C_1-C_6)$alkyl, —S(O)$_m$$(C_1-C_6)$alkyl, 1 to 5 halo groups, 1 to 3 hydroxy groups, 1 to 3 —O—C(O)$(C_1-C_{10})$alkyl groups or 1 to 3 $(C_1-C_6)$alkoxy groups; or
$R^7$ and $R^8$ can be taken together to form —(CH$_2$)$_r$—L—(CH$_2$)$_r$—;
where L is C($X^2$)($X^2$), S(O)$_m$ or N($X^2$);
$R^9$, $R^{9a}$, $R^{10}$ and $R^{10a}$ are each independently hydrogen, fluoro, hydroxy, $(C_1-C_4)$alkoxy or $(C_1-C_5)$alkyl optionally substituted with 1 to 5 halogroups, provided that at least one of $R^9$, $R^{9a}$, $R^{10}$ or $R^{10a}$ is present and is $(C_1-C_4)$alkoxy;
$R^{11}$ is selected from the group consisting of $(C_1-C_5)$ alkyl and phenyl optionally substituted with 1–3 substitutents each independently selected from the group consisting of $(C_1-C_5)$alkyl, halo and $(C_1-C_5)$ alkoxy;
$R^{12}$ is selected from the group consisting of $(C_1-C_5)$ alkylsulfonyl, $(C_1-C_5)$alkanoyl and $(C_1-C_5)$alkyl where the alkyl portion is optionally independently substituted by 1–5 halo groups;
$A^1$ for each occurrence is independently selected from the group consisting of $(C_5-C_7)$cycloalkenyl, phenyl, a partially saturated, fully saturated or fully unsaturated 4- to 8-membered ring optionally having 1 to 4 heteroatoms independently selected from the group consisting of oxygen, sulfur and nitrogen and a bicyclic ring system consisting of a partially saturated, fully unsaturated or fully saturated 5- or 6-membered ring, optionally having 1 to 4 heteroatoms independently selected from the group consisting of nitrogen, sulfur and oxygen, fused to a partially saturated, fully saturated or fully unsaturated 5- or 6-membered ring, optionally having 1 to 4 heteroatoms independently selected from the group consisting of nitrogen, sulfur and oxygen;
$A^1$ for each occurrence is independently optionally substituted, on one or optionally both rings if $A^1$ is a bicyclic ring system, with up to three substituents, each substituent independently selected from the group consisting of F, Cl, Br, I, OCF$_3$, OCF$_2$H, CF$_3$, CH$_3$, OCH$_3$, —O$X^6$, —C(O)N($X^6$)($X^6$), —C(O) O$X^6$, oxo, $(C_1-C_6)$alkyl, nitro, cyano, benzyl, —S(O)$_m$$(C_1-C_6)$alkyl, 1H-tetrazol-5-yl, phenyl, phenoxy, phenylalkyloxy, halophenyl, methylenedioxy, —N($X^6$)($X^6$), —N($X^6$)C(O)($X^6$), —S(O)$_2$N($X^6$)($X^6$), —N($X^6$)S(O)$_2$-phenyl, —N($X^6$) S(O)$_2$$X^6$, —CON$X^{11}$$X^{12}$, —S(O)$_2$N$X^{11}$$X^{12}$, —N$X^6$S(O)$_2$$X^{12}$, —N$X^6$CON$X^{11}$$X^{12}$, —N$X^6$S(O)$_2$N$X^{11}$$X^{12}$, —N$X^6$C(O)$X^{12}$, imidazolyl, thiazolyl and tetrazolyl, provided that if $A^1$ is optionally substituted with methylenedioxy then it can only be substituted with one methylenedioxy;
where $X^{11}$ is hydrogen or optionally substituted $(C_1-C_6)$alkyl;
the optionally substituted $(C_1-C_6)$alkyl defined for $X^{11}$ is optionally independently substituted with phenyl, phenoxy, $(C_1-C_6)$alkoxycarbonyl, —S(O)$_m$$(C_1-C_6)$alkyl, 1 to 5 halo groups, 1 to 3 hydroxy groups, 1 to 3 $(C_1-C_{10})$alkanoyloxy groups or 1 to 3 $(C_1-C_6)$alkoxy groups;
$X^{12}$ is hydrogen, $(C_1-C_6)$alkyl, phenyl, thiazolyl, imidazolyl, furyl or thienyl, provided that when $X^{12}$ is not hydrogen, the $X^{12}$ group is optionally substituted with one to three substituents independently selected from the group consisting of Cl, F, CH$_3$, OCH$_3$, OCF$_3$ and CF$_3$;
or $X^{11}$ and $X^{12}$ are taken together to form —(CH$_2$)$_r$—$L^1$—(CH$_2$)$_r$—;
$L^1$ is C($X^2$)($X^2$), O, S(O)$_m$ or N($X^2$);
r for each occurrence is independently 1, 2 or 3;
$X^2$ for each occurrence is independently hydrogen, optionally substituted $(C_1-C_6)$alkyl or optionally substituted $(C_3-C_7)$cycloalkyl, where the optionally substituted $(C_1-C_6)$alkyl and optionally substituted $(C_3-C_7)$cycloalkyl in the definition of $X^2$ are optionally independently substituted with -S(O)$_m$$(C_1-C_6)$ alkyl, —C(O)O$X^3$, 1 to 5 halo groups or 1–3 O$X^3$ groups;
$X^3$ for each occurrence is independently hydrogen or $(C_1-C_6)$alkyl;
$X^6$ for each occurrence is independently hydrogen, optionally substituted $(C_1-C_6)$alkyl, $(C_2-C_6)$ halogenated alkyl, optionally substituted $(C_3-C_7)$ cycloalkyl, $(C_3-C_7)$-halogenated cycloalkyl, where optionally substituted $(C_1-C_6)$alkyl and optionally substituted $(C_3-C_7)$cycloalkyl in the definition of $X^6$ is optionally independently mono- or di-substituted with $(C_1-C_4)$alkyl, hydroxy, $(C_1-C_4)$alkoxy, carboxyl, CONH$_2$, —S(O)$_m$$(C_1-C_6)$alkyl, carboxylate $(C_1-C_4)$alkyl ester or 1H-tetrazol-5-yl; or
when there are two $X^6$ groups on one atom and both $X^6$ are independently $(C_1-C_6)$alkyl, the two $(C_1-C_6)$ alkyl groups may be optionally joined and, together with the atom to which the two $X^6$ groups are attached, form a 4- to 9-membered ring optionally having oxygen, sulfur or N$X^7$ as a ring member,
$X^7$ is hydrogen or $(C_1-C_6)$alkyl optionally substituted with hydroxy;
m for each occurrence is independently 0, 1 or 2;
with the proviso that:
$X^6$ and $X^{12}$ cannot be hydrogen when attached to C(O) or S(O)$_2$ in the form C(O)$X^6$, C(O)$X^{12}$, S(O)$_2$$X^6$ or S(O)$_2$$X^{12}$; and
when $R^6$ is a bond then L is N($X^2$) and each r in the definition —(CH$_2$)$_r$—L—(CH$_2$)$_r$— is independently 2 or 3.

A preferred group of compounds within the scope of the compounds disclosed in the immediately preceding paragraph, designated the ZA Group, comprises those compounds or a stereoisomeric mixtures thereof, diastereomerically enriched, diastereomerically pure, enantiomerically enriched or enantiomerically pure isomers thereof, or prodrugs of such compounds, mixtures or isomers thereof, or pharmaceutically acceptable salts of the compounds, mixtures, isomers or prodrugs wherein:

HET is

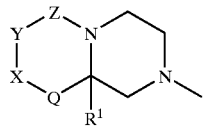

R¹ is —(CH₂)ₜ—A¹, —(CH₂)_q—(C₃–C₇)cycloalkyl or (C₁–C₁₀)alkyl;
  where A¹ in the definition or R¹ is phenyl, pyridyl, thiazolyl or thienyl, optionally substituted with one to three substituents, each substituent being independently selected from the group consisting of F, Cl, CH₃, OCH₃, OCF₂H, OCF₃ and CF₃;
  the cycloalkyl and alkyl groups in the definition of R¹ are optionally substituted with (C₁–C₄)alkyl, hydroxy, (C₁–C₄)alkoxy or 1 to 3 fluoro atoms;
  q is 1 or 2;
  t is 1 or 2;
R³ is selected form the group consisting of phenyl-CH₂—O—CH₂, phenyl-CH₂—S—CH₂—, pyridyl-CH₂—O—CH₂—, thienyl-CH₂—O—CH₂—, 3-indolyl-CH₂—, phenyl-(CH₂)₃— and thiazolyl-CH₂—O—CH₂—; where the carbon atom bearing the substituent R³ is of the (R)-configuration;
  where the aryl portion of the groups defined for R³ is optionally substituted with one to three substituents, each substituent being independently selected from the group consisting of F, Cl, CH₃, OCH₃, OCF₂H, OCF₃ and CF₃
R⁴ is hydrogen;
R⁶ is

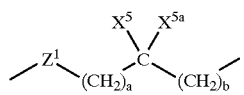

where Z¹ is a bond; X⁵ and X⁵ᵃ are each methyl; a and b are each 0;
  R⁷ and R⁸ or each hydrogen;
  X⁴ is hydrogen.

A group of compounds which is preferred within the ZA Group of compounds, designated the ZB Group, comprises those compounds or stereoisomeric mixtures thereof, diastereomerically enriched, diastereomerically pure, enantiomerically enriched or enantiomerically pure isomers thereof, or prodrugs of such compounds, mixtures or isomers thereof, or pharmaceutically acceptable salts of the compounds, mixtures, isomers or prodrugs wherein:
Z is C=O; Q is a covalent bond;
Y is CR⁹R¹⁰
  where R⁹ in the definition of Y is selected from the group consisting of hydrogen, fluoro, hydroxy, (C₁–C₂) alkoxy and (C₁–C₂)alkyl optionally substituted with 1-3 fluoro groups; and R¹⁰ in the definition of Y is selected from the group consisting of hydrogen, fluoro, and (C₁–C₂)alkyl optionally substituted with 1–3 fluoro groups with the proviso that R¹⁰ cannot be fluoro when R⁹ is hydroxy or (C₁–C₂)alkoxy;
and X is CHR⁹ᵃ
  where R⁹ in the definition of X is selected from the group consisting of hydrogen, fluoro, hydroxy, (C₁–C₂) alkoxy and (C₁–C₂)alkyl optionally substituted with 1-3 fluoro groups.

R¹ is —CH₂—A¹
  where A¹ is phenyl, pyridyl or thiazolyl, optionally substituted with one to three substituents, each substituent being independently selected from the group consisting of F, Cl, CH₃, OCH₃, OCF₂H, OCF₃ and CF₃; and
R³ is selected form the group consisting of 3-indolyl-CH₂—, phenyl-(CH₂)₃—, phenyl-CH₂—O—CH₂— and thiazolyl-CH₂—O—CH₂—,
  where the aryl portion of the groups defined for R³ is optionally substituted with one to three substituents, each substituent being independently selected from the group consisting of F, Cl, CH₃, OCH₃, OCF₂H, OCF₃ and CF₃.

A group of compounds which is preferred within the ZB Group of compounds, designated the ZC Group, comprises those compounds or prodrugs of such compounds or pharmaceutically acceptable salts of the compounds or prodrugs where the compound is the 8(R,S),8a(R,S) diastereomeric mixture, the 8(R),8a(R) diastereomer, the 8(S),8a(S) diastereomer, the 8(R),8a(S) diastereomer, or the 8(S),8a(R) diastereomer of 2-amino-N-[1(R)-benzyloxymethyl-2-(8-methoxy-6-oxo-8a-pyridin-2-ylmethyl-hexahydro-pyrrolo[1,2-a]pyrazin-2-yl)-2-oxo-ethyl]-2-methyl-propionamide.

This invention also provides methods of treating or preventing sleep disorders in a mammal, including humans or other animals such as especially dogs, cats and horses, which comprise administering to such human or other animal an effective amount of a compound of Formula I.

This invention also provides the L-tartrate salt of 2-amino-N-{1-(R)-benzyloxymethyl-2-[1,3-dioxo-8a-(S)-pyridin-2-ylmethyl-2-(2,2,2-trifluoro-ethyl)-hexahydro-imidazo[1,5-a]pyrazin-7-yl]-2-oxo-ethyl}-2-methyl-propionamide.

This invention also provides compounds of the formula

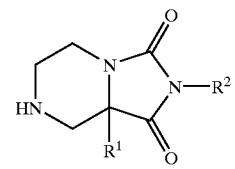

where R¹ is hydrogen, —CN, —(CH₂)_qN(X⁶)C(O)X⁶, —(CH₂)_qN(X⁶)C(O)(CH₂)ₜ—A¹, —(CH₂)_qN(X⁶)S(O)₂(CH₂)ₜ—A¹, —(CH₂)_qN(X⁶)S(O)₂X⁶, —(CH₂)_qN(X⁶)C(O)N(X⁶)(CH₂)ₜ—A¹, —(CH₂)_qN(X⁶)C(O)N(X⁶)(X⁶), —(CH₂)_qC(O)N(X⁶)(X⁶), —(CH₂)_qC(O)N(X⁶)(CH₂)ₜ—A¹, —(CH₂)_qC(O)OX⁶, —(CH₂)_qC(O)O (CH₂)ₜ—A¹, —(CH₂)_qOX⁶, —(CH₂)_qOC(O)X⁶, —(CH₂)_qOC(O)(CH₂)ₜ—A¹, —(CH₂)_qOC(O)N(X⁶)(CH₂)ₜ—A¹, —(CH₂)_qOC(O)N(X⁶)(X⁶), —(CH₂)_qC(O)X⁶, —(CH₂)_qC(O)(CH₂)ₜ—A¹, —(CH₂)_qN(X⁶)C(O)OX⁶, —(CH₂)_qN(X⁶)S(O)₂N(X⁶)(X⁶), —(CH₂)_qS(O)_mX⁶, —(CH₂)_qS(O)_m(CH₂)ₜ—A¹, —(C₁–C₁₀)alkyl, —(CH₂)ₜ—A¹, —(CH₂)_q—(C₃–C₇)cycloalkyl, —(CH₂)_q—Y¹—(C₁–C₆)alkyl, —(CH₂)_q—Y¹—(CH₂)ₜ—A¹ or —(CH₂)_q—Y¹—(CH₂)ₜ—(C₃–C₇)cycloalkyl;
where the alkyl and cycloalkyl groups in the definition of R¹ are optonally substituted with (C₁–C₄)alkyl, hydroxy, (C₁–C₄)alkoxy, carboxyl, —CONH₂, —S(O)_m(C₁–C₆)alkyl, —CO₂(C₁–C₄)alkyl ester, 1H-tetrazol-5-yl or 1, 2 or 3 fluoro groups;
Y¹ is O, S(O)_m, —C(O)NX⁶—, —CH=CH—, —C≡C—, —N(X⁶)C(O)—, —C(O)NX⁶—, —C(O) O—, —OC(O)N(X⁶)— or —OC(O)—;

m for each occurrence is 0, 1 or 2;

q is 0, 1, 2, 3 or 4;

t is 0, 1, 2 or 3;

said $(CH_2)_q$ group and $(CH_2)_t$ group in the definition of $R^1$ are optionally independently substituted with hydroxy, $(C_1–C_4)$alkoxy, carboxyl, —$CONH_2$, —$S(O)_m(C_1–C_6)$alkyl, —$CO_2(C_1–C_4)$alkyl ester, 1H-tetrazol-5-yl, 1, 2 or 3 fluoro groups or 1 or 2 $(C_1–C_4)$alkyl groups;

$A^1$ for each occurrence is independently selected from the group consisting of $(C_5–C_7)$cycloalkenyl, phenyl, a partially saturated, fully saturated or fully unsaturated 4- to 8-membered ring optionally having 1 to 4 heteroatoms independently selected from the group consisting of oxygen, sulfur and nitrogen and a bicyclic ring system consisting of a partially saturated, fully unsaturated or fully saturated 5- or 6-membered ring, optionally having 1 to 4 heteroatoms independently selected from the group consisting of nitrogen, sulfur and oxygen, fused to a partially saturated, fully saturated or fully unsaturated 5- or 6-membered ring, optionally having 1 to 4 heteroatoms independently selected from the group consisting of nitrogen, sulfur and oxygen;

$A^1$ for each occurrence is independently optionally substituted, on one or optionally both rings if $A^1$ is a bicyclic ring system, with up to three substituents, each substituent independently selected from the group consisting of F, Cl, Br, I, $OCF_3$, $OCF_2H$, $CF_3$, $CH_3$, $OCH_3$, —$OX^6$, —$C(O)N(X^6)(X^6)$, —$C(O)OX^6$, oxo, $(C_1–C_6)$ alkyl, nitro, cyano, benzyl, —$S(O)_m(C_1–C_6)$alkyl, 1H-tetrazol-5-yl, phenyl, phenoxy, phenylalkyloxy, halophenyl, methylenedioxy, —$N(X^6)(X^6)$, —$N(X^6)C(O)(X^6)$, —$S(O)_2N(X^6)(X^6)$, —$N(X^6)S(O)_2$-phenyl, —$N(X^6)S(O)_2X^6$, —$CONX^{11}X^{12}$, —$S(O)_2NX^{11}X^{12}$, —$NX^6S(O)_2X^{12}$, —$NX^6CONX^{11}X^{12}$, —$NX^6S(O)_2 NX^{11}X^{12}$, —$NX^6C(O)X^{12}$, imidazolyl, thiazolyl and tetrazolyl, provided that if $A^1$ is optionally substituted with methylenedioxy then it can only be substituted with one methylenedioxy;

where $X^{11}$ is hydrogen or optionally substituted $(C_1–C_6)$alkyl;

the optionally substituted $(C_1–C_6)$alkyl defined for $X^{11}$ is optionally independently substituted with phenyl, phenoxy, $(C_1–C_6)$alkoxycarbonyl, —$S(O)_m$ $(C_1–C_6)$alkyl, 1 to 5 halo groups, 1 to 3 hydroxy groups, 1 to 3 $(C_1–C_{10})$alkanoyloxy groups or 1 to 3 $(C_1–C_6)$alkoxy groups;

$X^{12}$ is hydrogen, $(C_1–C_6)$alkyl, phenyl, thiazolyl, imidazolyl, furyl or thienyl, provided that when $X^{12}$ is not hydrogen, the $X^{12}$ group is optionally substituted with one to three substituents independently selected from the group consisting of Cl, F, $CH_3$, $OCH_3$, $OCF_3$ and $CF_3$;

or $X^{11}$ and $X^{12}$ are taken together to form —$(CH_2)_r$—$L^1$—$(CH_2)_r$—;

$L^1$ is $C(X^2)(X^2)$, O, $S(O)_m$ or $N(X^2)$;

$X^6$ for each occurrence is independently hydrogen, optionally substituted $(C_1–C_6)$alkyl, $(C_2–C_6)$ halogenated alkyl, optionally substituted $(C_3–C_7)$ cycloalkyl, $(C_3–C_7)$-halogenated cycloalkyl, where optionally substituted $(C_1–C_6)$alkyl and optionally substituted $(C_3–C_7)$cycloalkyl in the definition of $X^6$ is optionally independently mono- or di-substituted with $(C_1–C_4)$alkyl, hydroxy, $(C_1–C_4)$alkoxy, carboxyl, $CONH_2$, —$S(O)_m(C_1–C_6)$alkyl, carboxylate $(C_1–C_4)$alkyl ester or 1H-tetrazol-5-yl; or when there are two $X^6$ groups on one atom and both $X^6$ are independently $(C_1–C_6)$ alkyl, the two $(C_1–C_6)$alkyl groups may be optionally joined and, together with the atom to which the two $X^6$ groups are attached, form a 4- to 9-membered ring optionally having oxygen, sulfur or $NX^7$ as a ring member; and $R^2$ is hydrogen, $(C_1–C_8)$alkyl, —$(C_0–C_3)$alkyl-$(C_3–C_8)$ cycloalkyl, —$(C_1–C_4)$alkyl-$A^1$ or $A^1$;

where the alkyl groups and the cycloalkyl groups in the definition of $R^2$ are optionally substituted with hydroxy, —$C(O)OX^6$, —$C(O)N(X^6)(X^6)$, —$N(X^6)$ $(X^6)$, —$S(O)_m(C_1–C_6)$alkyl, —$C(O)A^1$, —$C(O)$ $(X^6)$, $CF_3$, CN or 1, 2 or 3 independently selected halo groups.

A group of compounds which is preferred within the compounds disclosed within the immediately preceding paragraph, designated the XA Group, comprises those compounds wherein $R^1$ is $CH_2$—$A^1$ and $R^2$ is $CF_3CH_2$—.

A group of compounds which is preferred within the XA Group of compounds, designated the XB Group, comprises those compounds wherein $A^1$ is 2-pyridyl.

A compound which is preferred within the XB Group of compounds is 8a-pyridin-2-ylmethyl-2-(2,2,2-trifluoro-ethyl)-tetrahydro-imidazo[1,5-a]pyrazine-1,3-dione.

Another compound which is preferred within the XB group of compounds is the L-tartrate salt of 8a-pyridin-2-ylmethyl-2-(2,2,2-trifluoro-ethyl)-tetrahydro-imidazo[1,5-a]pyrazine-1,3-dione.

This invention also provides a process for preparing 1,3-dioxo-8a(S)-pyridin-2-ylmethyl-2-(2,2,2-trifluoro-ethyl)-hexahydro-imidazo[1,5-a]pyrazine-7-carboxylic acid tert-butyl ester comprising reacting 8a-pyridin-2-ylmethyl-2-(2,2,2-trifluoro-ethyl)-tetrahydro-imidazo[1,5-a]pyrazine-1,3-dione with D-tartaric acid in a reaction inert solvent at 0° C. to about room temperature for about 5 minutes to about 48 hours.

This invention also provides a process for preparing 2-amino-N-(1(R)-benzyloxymethyl-2-(1,3-dioxo-8a(S)-pyridin-2-ylmethyl-2-(2,2,2-trifluoro-ethyl)-hexahydro-imidazo[1,5-a]pyrazin-7-yl)-2-methyl-propionamide hydrochloride comprising (a) reacting 8a-pyridin-2-ylmethyl-2-(2,2,2-trifluoro-ethyl)-tetrahydro-imidazo[1,5-a]pyrazine-1,3-dione with D-tartaric acid in a reaction inert solvent to form 1,3-dioxo-8a(S)-pyridin-2-ylmethyl-2-(2,2,2-trifluoro-ethyl)-hexahydro-imidazo[1,5-a]pyrazine-7-carboxylic acid tert-butyl ester;

(b) reacting said 1,3-dioxo-8a(S)-pyridin-2-ylmethyl-2-(2,2,2-trifluoro-ethyl)-hexahydro-imidazo[1,5-a] pyrazine-7-carboxylic acid tert-butyl ester with 3-benyloxy-2-(2-tert-butoxycarbonylamino-2-methyl-propionylamino)-propionic acid in the presence of a tertiary amine and 1-propanephosphonic acid cyclic anhydride in a reaction inert solvent to form (1-(1(R)-benzyloxymethyl-2-(1,3-dioxo-8a(S)-pyridin-2-ylmethyl-2-(2,2,2-trifluoro-ethyl)-hexahydro-imidazo [1,5-a]pyrazin-7-yl)-2-oxo-ethylcarbamoyl)-1-methyl-ethyl)-carbamic acid tert-butyl ester, and (c) reacting said (1-(1(R)-benzyloxymethyl-2-(1,3-dioxo-8a(S)-pyridin-2-ylmethyl-2-(2,2,2-trifluoro-ethyl)-hexahydro-imidazo[1,5-a]pyrazin-7-yl)-2-oxo-ethylcarbamoyl)-1-methyl-ethyl)-carbamic acid tert-butyl ester with concentrated hydrochloric acid in a reaction inert solvent to form 2-amino-N-(1(R)-benzyloxymethyl-2-(1,3-dioxo-8a(S)-pyridin-2- ylmethyl-2-(2,2,2-trifluoro-ethyl)-hexahydro-imidazo[1,5-a]pyrazin-7-yl)-2-methyl-propionamide hydrochloride.

DETAILED DESCRIPTION OF THE INVENTION

In general the compounds of Formula I can be made by processes known in the chemical arts. Certain processes for the manufacture of Formula I compounds are provided as further features of the invention and are illustrated by the following reaction schemes.

In the above structural formulae and throughout the instant application, the following terms have the indicated meanings unless expressly stated otherwise:

The alkyl groups are intended to include. those alkyl groups of the designated length in either a straight or branched configuration which may optionally contain double or triple bonds. Exemplary of such alkyl groups are methyl, ethyl, propyl, isopropyl, butyl, sec-butyl, tertiary butyl, pentyl, isopentyl, hexyl, isohexyl, allyl, ethynyl, propenyl, butadienyl, hexenyl and the like.

When the definition $C_0$-alkyl occurs in the definition, it means a single covalent bond.

The alkoxy groups specified above are intended to include those alkoxy groups of the designated length in either a straight or branched configuration which may optionally contain double or triple bonds. Exemplary of such alkoxy groups are methoxy, ethoxy, propoxy, isopropoxy, butoxy, isobutoxy, tertiary butoxy, pentoxy, isopentoxy, hexoxy, isohexoxy, allyloxy, 2-propynyloxy, isobutenyloxy, hexenyloxy and the like.

The term "halogen" or "halo" is intended to include the halogen atoms fluorine, chlorine, bromine and iodine.

The term "halogenated alkyl" is intended to include an alkyl group as defined hereinabove substituted by one or more halogen atoms as defined hereinabove.

The term "halogenated cycloalkyl" is intended to include a cycloalkyl group substituted by one or more halogen atoms as defined hereinabove.

The term "aryl" is intended to include phenyl and naphthyl and aromatic 5- and 6-membered rings with 1 to 4 heteroatoms or fused 5- and/or 6-membered bicyclic rings with 1 to 4 heteroatoms of nitrogen, sulfur or oxygen. Examples of such heterocyclic aromatic rings are pyridine, thiophene (also known as thienyl), furan, benzothiophene, tetrazole, indole, N-methylindole, dihydroindole, indazole, N-formylindole, benzimidazole, thiazole, pyrimidine, and thiadiazole.

The expression "prodrug" refers to compounds that are drug precursors which following administration, release the drug in vivo via some chemical or physiological process (e.g., a prodrug on being brought to the physiological pH is converted to the desired drug form). Exemplary prodrugs upon cleavage release the corresponding free acid, and such hydrolyzable ester-forming residues of the compounds of this invention include but are not limited to carboxylic acid substituents (e.g., when $R^1$ is —$(CH_2)_qC(O)OX^6$ where $X^6$ is hydrogen, or when $R^2$ or $A^1$ contains carboxylic acid) wherein the free hydrogen is replaced by ($C_1$–$C_4$)alkyl, ($C_2$–$C_{12}$)alkanoyloxymethyl, ($C_4$–$C_9$)1-(alkanoyloxy)ethyl, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N—($C_1$–$C_2$)alkylamino($C_2$–$C_3$)alkyl (such as β-dimethylaminoethyl), carbamoyl-($C_1$–$C_2$)alkyl, N,N-di($C_1$–$C_2$)-alkylcarbamoyl-($C_1$–$C_2$)alkyl and piperidino-, pyrrolidino- or morpholino($C_2$–$C_3$)alkyl.

Other exemplary prodrugs release an alcohol of Formula I wherein the free hydrogen of the hydroxyl substituent (e.g., when $R^1$ contains hydroxyl) is replaced by ($C_1$–$C_6$)alkanoyloxymethyl, 1-(($C_1$–$C_6$)alkanoyloxy)ethyl, 1-methyl-1-(($C_1$–$C_6$)alka-noyloxy)ethyl, ($C_1$–$C_6$)alkoxycarbonyloxymethyl, N—($C_1$–$C_6$)alkoxycarbonylamino-methyl, succinoyl, ($C_1$–$C_6$)alkanoyl, α-amino($C_1$–$C_4$)alkanoyl, arylacetyl and α-aminoacyl, or α-aminoacyl-α-aminoacyl wherein said α-aminoacyl moieties are independently any of the naturally occurring L-amino acids found in proteins, —$P(O)(OH)_2$, —$P(O)(O(C_1$–$C_6)alkyl)_2$ or glycosyl (the radical resulting from detachment of the hydroxyl of the hemiacetal of a carbohydrate).

Prodrugs of this invention where a carboxyl group in a carboxylic acid of Formula I is replaced by an ester may be prepared by combining the carboxylic acid with the appropriate alkyl halide in the presence of a base such as potassium carbonate in an inert solvent such as DMF at a temperature of about 0° C. to 100° C. for about 1 to about 24 hours. Alternatively, the acid is combined with the appropriate alcohol as solvent in the presence of a catalytic amount of acid such as concentrated sulfuric acid at a temperature of about 20° C. to 120° C., preferably at reflux, for about 1 hour to about 24 hours. Another method is the reaction of the acid in an inert solvent such as THF, with concomitant removal of the water being produced by physical (e.g., Dean Stark trap) or chemical (e.g., molecular sieves) means.

Prodrugs of this invention where an alcohol function has been derivatized as an ether may be prepared by combining the alcohol with the appropriate alkyl bromide or iodide in the presence of a base such as potassium carbonate in an inert solvent such as DMF at a temperature of about 0° C. to 1000° C. for about 1 to about 24 hours. Alkanoylaminomethyl ethers may be obtained by reaction of the alcohol with a bis-(alkanoylamino)methane in the presence of a catalytic amount of acid in an inert solvent such as THF, according to a method described in U.S. Pat. No. 4,997,984. Alternatively, these compounds may be prepared by the methods described by Hoffman et al. in J. Org. Chem. 1994, 59, p. 3530.

Certain of the above defined terms may occur more than once in the above formula and upon such occurrence each term shall be defined independently of the other.

The compounds of the instant invention all have at least one asymmetric center as noted by the asterisk in the structural Formula I. Additional asymmetric centers may be present on the molecule depending upon the nature of the various substituents on the molecule. Each such asymmetric center will produce two optical isomers and it is intended that all such optical isomers, as separated, pure or partially purified optical isomers, racemic mixtures or diastereomeric mixtures thereof, be included within the scope of the instant invention. In the case of the asymmetric center represented by the asterisk, it has been found that the absolute stereochemistry of the more active and thus more preferred isomer is shown in Formula IA. This preferred absolute configuration also applies to Formula I.

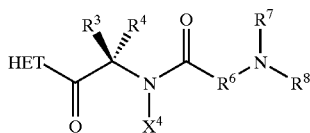

With the $R^4$ substituent as hydrogen, the spatial configuration of the asymmetric center corresponds to that in a D-amino acid. In most cases this is also designated an R-configuration although this will vary according to the values of $R^3$ and $R^4$ used in making R- or S-stereochemical assignments.

The instant compounds are generally isolated in the form of their pharmaceutically acceptable acid addition salts, such as the salts derived from using inorganic and organic acids. Examples of such acids are hydrochloric, nitric, sulfuric, phosphoric, formic, acetic, trifluoroacetic, propionic, maleic, succinic, D-tartaric, L-tartaric, malonic, methane sulfonic and the like. In addition, certain compounds containing an acidic function such as a carboxy can be isolated in the form of their inorganic salt in which the counter-ion can be selected from sodium, potassium, lithium, calcium, magnesium and the like, as well as from organic bases.

The pharmaceutically acceptable salts are formed by taking about 1 equivalent of a compound of Formula I and contacting it with about 1 equivalent of the appropriate corresponding acid of the salt which is desired. Work-up and isolation of the resulting salt is well-known to those of ordinary skill in the art.

The growth hormone releasing compounds of Formula I are useful in vitro as unique tools for understanding how growth hormone secretion is regulated at the pituitary level. This includes use in the evaluation of many factors thought or known to influence growth hormone secretion such as age, sex, nutritional factors, glucose, amino acids, fatty acids, as well as fasting and non-fasting states. In addition, the compounds of this invention can be used in the evaluation of how other hormones modify growth hormone releasing activity. For example, it has already been established that somatostatin inhibits growth hormone release.

The compounds of Formula I can be administered to animals, including humans, to release growth hormone in vivo. The compounds are useful for treating symptoms related to GH deficiency; stimulating pre- and post-natal growth or enhancing feed efficiency and improving carcass quality of animals raised for meat production; increasing milk production in dairy cattle; improving estrous synchronization in livestock such as swine, beef and dairy cattle; improving bone or wound healing and improving vital organ function in animals. The compounds of the present invention, by inducing endogenous GH secretion, will alter body composition and modify other GH-dependent metabolic, immunologic or developmental processes. For example, the compounds of the present invention can be given to chickens, turkeys, livestock animals (such as sheep, pigs, horses, cattle, etc.) and companion animals (e.g., dogs). These compounds may also have utility in aquaculture to accelerate growth and improve the percent lean meat. In addition, these compounds can be administered to humans in vivo as a diagnostic tool to directly determine whether the pituitary is capable of releasing growth hormone. For example, the compounds of Formula I or a pharmaceutically acceptable salt or prodrug thereof can be administered in vivo to children and serum samples taken before and after such administration can be assayed for growth hormone. Comparison of the amounts of growth hormone in each of these samples would be a means for directly determining the ability of the patient's pituitary to release growth hormone.

Accordingly, the present invention includes within its scope pharmaceutical compositions comprising, as an active ingredient, at least one of the compounds of Formula I or a pharmaceutically acceptable salt or prodrug thereof in association with a pharmaceutically acceptable carrier. Optionally, the pharmaceutical compositions can further comprise an anabolic agent in addition to at least one of the compounds of Formula I or a pharmaceutically acceptable salt or prodrug thereof, or another compound which exhibits a different activity, e.g., an antibiotic or coccidiostat (e.g., monensin) growth promotant or an agent to treat osteoporosis or with other pharmaceutically active materials wherein the combination enhances efficacy and minimizes side effects.

Growth promoting and anabolic agents include, but are not limited to, TRH, PTH, diethylstilbesterol, estrogens, β-agonists, theophylline, anabolic steroids, enkephalins, E series prostaglandins, compounds disclosed in U.S. Pat. No. 3,239,345, the disclosure of which is hereby incorporated by reference, e.g., zeranol; compounds disclosed in U.S. Pat. No. 4,036,979, the disclosure of which is hereby incorporated by reference, e.g., sulbenox; and peptides disclosed in U.S. Pat. No. 4,411,890, the disclosure of which is hereby incorporated by reference.

The growth hormone secretagogues of this invention in combination with other growth hormone secretagogues such as the growth hormone releasing peptides GHRP-6 and GHRP-1 as described in U.S. Pat. No. 4,411,890, the disclosure of which is hereby incorporated by reference, and publications WO 89/07110, WO 89/07111 and B-HT920 as well as hexarelin and the newly discovered GHRP-2 as described in WO 93/04081 or growth hormone releasing hormone (GHRH, also designated GRF) and its analogs or growth hormone and its analogs or somatomedins including IGF-1 and IGF-2 or alpha-2-adrenergic agonists such as clonidine, xylazine, detomidine and medetomidine or serotonin 5HTID agonists such as sumitriptan or agents which inhibit somatostatin or its release such as physostigmine and pyridostigmine, are useful for increasing the endogenous levels of GH in mammals. The combination of a GH secretagogue of this invention with GRF results in synergistic increases of endogenous growth hormone.

As is well known to those skilled in the art, the known and potential uses of growth hormone are varied and multitudinous [See "Human Growth Hormone", Strobel and Thomas, Pharmacological Reviews, 46, pg. 1–34 (1994); T. Rosen et al., Horm Res, 1995; 43: pp. 93–99; M. Degerblad et al., European Journal of Endocrinology, 1995, 133: pp.180–188; J. O. Jorgensen, European Journal of Endocrinology, 1994, 130: pp. 224–228; K. C. Copeland et al., Journal of Clinical Endocrinology and Metabolism, Vol. 78 No. 5, pp. 1040–1047; J. A. Aloi et al., Journal of Clinical Endocrinology and Metabolism, Vol. 79 No. 4, pp. 943–949; F. Cordido et al., Metab. Clin. Exp., (1995), 44(6), pp. 745–748; K. M. Fairhall et al., J. Endocrinol., (1995), 145(3), pp. 417–426; R. M. Frieboes et al., Neuroendocrinology, (1995), 61(5), pp. 584–589; and M. Llovera et al., Int. J. Cancer, (1995), 61(1), pp. 138–141]. Thus, the administration of the compounds of this invention for purposes of stimulating the release of endogenous growth hormone can have the same effects or uses as growth hormone itself. These varied uses of growth hormone may be summarized as follows: stimulating growth hormone release in elderly humans or companion animals especially dogs, cats, camels and horses; treating growth hormone deficient adult humans or other animals especially dogs, cats, camels and horses; preventing catabolic side effects of glucocorticoids, treating osteoporosis, stimulating the immune system, accelerating wound healing, accelerating bone fracture repair, treating growth retardation, treating congestive heart failure as disclosed in PCT publications WO 95/28173 and WO 95/28174 (an example of a method for assaying growth hormone secretagogues for efficacy in treating congestive heart failure is disclosed in R. Yang et al., Circulation, Vol. 92, No. 2, p.262, 1995), treating acute or chronic renal failure or insufficiency; treating physiological short stature including growth hormone deficient children, treating short stature associated with chronic illness, treating obesity, treating growth retardation associated with Prader-Willi syndrome and Turners syndrome; accelerating the recovery and reducing hospitalization of bum patients or following major surgery such as gastrointestinal surgery; treating intrauterine growth retardation, skeletal dysplasia, hypercortisonism and Cushings syndrome; replacing growth hormone in stressed patients; treating osteochondrodysplasias, Noonans syndrome, sleep disorders, Alzheimer's disease, delayed wound healing, and psychosocial deprivation; treating pulmonary dysfunction and ventilator dependency; attenuating protein catabolic response after a major operation; treating malabsorption syndromes, reducing cachexia and protein loss due to chronic illness such as cancer or AIDS; accelerating weight gain and protein accretion in patients on TPN (total parenteral nutrition); treating hyperinsulinemia including nesidioblastosis; adjuvant treatment for ovulation induction and to prevent and treat gastric and duodenal ulcers; stimulating thymic development and preventing age-related decline of thymic function; adjunctive therapy for patients on chronic hemodialysis; treating immunosuppressed patients and enhancing antibody response following vaccination; improving muscle strength, increasing muscle mass, mobility, maintenance of skin thickness, metabolic homeostasis, renal hemeostasis in the frail elderly; stimulating osteoblasts, bone remodeling, and cartilage growth; treating neurological diseases such as peripheral and drug induced neuropathy, Guillian-Barre Syndrome, amyotrophic lateral sclerosis, multiple sclerosis, cerebrovascular accidents and demyelinating diseases; and stimulating wool growth in sheep.

Uses of GH in farm animals raised for meat production such as chickens, turkeys, sheep, pigs and cattle include stimulation of pre- and post- natal growth, enhanced feed efficiency in animals raised for meat production, improved carcass quality (increased muscle to fat ratio) (Campbell, R. G. et al., (1989), J. Anim. Sci. 67, 1265; Dave, D. J., Bane, D. P., (1990), The Compendium Food Anual, Vol. 12(1), 117; Holden, P. J., (1990), Agri-Practice, 11(3), 25; Claus, R., Weiber, U., (1994), Livestock Production Science, 37, 245; Roeder, R. et al., (1994), Growth Regulation, 4, 101); increased milk production in dairy cattle (McBride, B. W. et al., (1988), Research and Development in Agriculture 5(1), 1; McDowell, G. H. et al., (1988), Aust. J. Biol. Sci., 41, 279); improved body composition; modification of other GH-dependent metabolic (Claus, R. and Weiber, U., (1994), Livestock Production Science, 37, 245) and immunologic functions such as enhancing antibody response following vaccination or improved developmental processes; and may have utility in aquaculture to accelerate growth and improve the protein-to-fat ratio in fish.

Preferred uses in companion animals include stimulating endogenous growth hormone release in companion animals such as dogs, cats and horses; treating disorders of aging (Detenbeck, L. C., Jowsey, J., Clinical Orthopedics and Related Research, July-August 1969, No. 65, pp. 76–80); stimulating thymic development and preventing age-related decline of thymic function (Goff, B. L. et al., Clinical and Experimental Immunology, 1987, 68:3, pp. 580–587; Morrison, W. B. et al., Am. J. Vet. Res., Jan. 1990, 51:1, pp. 65–70; Roth, J. A. et al., Am. J. Vet. Res., 1984, Vol. 45, pp. 1151–1155); preventing age-related decline of thymic function; preventing age-related decline in cognition; accelerating wound healing (Jacks, T. et al., Vet. Surg. 1996, 25, (5), 430); accelerating bone fracture repair (Pandey, S. K, Udupa, K. N., Indian J. Vet. Surg. 1 (2): 73–78, July 1980); stimulating osteoblasts, bone remodelling and cartilage growth (Harris, W. H. et al., Calc. Tiss. Res., 10, 1972, pp. 1–13; Heaney, R. P. et al., Calc. Tiss. Res. 10, 1972, pp. 14–22; Mankin. H. J. et al., J. of Bone and Joint Surgery, Vol. 60-A, #8, Dec. 1978, pp. 1071–1075); attenuating protein catabolic response after major surgery, accelerating recovery from bum injuries and major surgeries such as gastrointestinal surgery; stimulating the immune system and enhancing antibody response following vaccination; treating congestive heart failure, treating acute or chronic renal failure or insufficiency, treating obesity; treating growth retardation, skeletal dysplasia and osteochondrodysplasias; preventing catabolic side effects of glucocorticoids; treating Cushing's syndrome; treating malabsorption syndromes, reducing cachexia and protein loss due to chronic illness such as cancer, accelerating weight gain and protein accretion in animals receiving total parenteral nutrition; providing adjuvant treatment for ovulation induction and to prevent gastrointestinal ulcers; improving muscle mats, strength and mobility; maintenance of skin thickness, and improving vital organ function and metabolic homeostasis.

The growth hormone secretagogues of this invention, compounds of Formula I, or a pharmaceutically acceptable salt or prodrug thereof in combination with an alpha-2 adrenergic agonist are useful in promoting GH secretion in humans and other animals (See Cella, S. G. et al., Acta Endocrinologica (Copenh.) 1989, 121, pp. 177–184). As such, a combination of a compound of Formula I or a pharmaceutically acceptable salt or prodrug thereof and an alpha-2 adrenergic agonist is useful in the treatment or prevention of frailty associated with aging, congestive heart failure and obesity which comprises administering to a human or another animal, especially dogs, cats and horses, in need of such treatment a combination of an alpha-2 adrenergic agonist and a compound of Formula I or a pharmaceutically acceptable salt or prodrug thereof, defined above. Preferred alpha-2 adrenergic agonists include clonidine, which is disclosed in U.S. Pat. No. 3,202,660 the disclosure of which is hereby incorporated by reference, xylazine, which is disclosed in U.S. Pat. No. 3,235,550 the disclosure of which is hereby incorporated by reference and medetomidine, which is disclosed in U.S. Pat. No. 4,544,664 the disclosure of which is hereby incorporated by reference. In another aspect, this invention provides methods for accelerating bone fracture repair and wound healing, attenuating protein catabolic response after a major operation, and reducing cachexia and protein loss due to chronic illness, which comprise administering to a human or another animal, especially dogs, cats and horses in need of such treatment a combination of an alpha-2 adrenergic agonist such as clonidine, xylazine or medetomidine and a compound of Formula I or a pharmaceutically acceptable salt or prodrug thereof. It has been shown that alpha-2 adrenergic agonists cause release of endogenous growth hormone in human and canine subjects (Cella et al., Life Sciences (1984), 34:447–454; Hampshire J, Altszuler N., American Journal of Veterinary Research (1981), 42:6, 1073–1076; Valcavi et al., Clinical Endocrinology (1988), 29:309–316; Morrison et al., American Journal of Veterinary Research (1990), 51:1, 65–70;), and that the co-administration of an alpha-2 adrenergic agonist with growth hormone-releasing factor restores defective growth hormone secretion in aged dogs (Arce et al., Brain Research (1990), 537:359–362; Cella et. al., Neuroendocrinology (1993), 57:432–438).

This invention also relates to a method of treating insulin resistant conditions such as Non-insulin Dependent Diabetes Mellitus (NIDDM) and reduced glycemic control associated with obesity and aging in a mammal in need thereof which comprises administering to said mammal an effective amount of a compound of the Formula I or a pharmaceutically acceptable salt or prodrug thereof.

This invention is directed to the use of growth hormone secretagogues specifically growth hormone releasing peptides (GHRP) or GHRP mimetics of Formula I or a pharmaceutically acceptable salt or prodrug thereof to improve glycemic control. Agents that increase growth hormone (GH) levels would not be expected to have this effect since it is widely recognized that GH is diabetogenic in animals and in humans. In acromegalics, glucose utilization and suppression of hepatic glucose production are impaired (see Hansen, I., et al., Am J Physiol, 250:E269 (1986)). In this disease of GH excess, impaired glucose handling and hyperinsulinemia have been reversed by pituitary surgery or chemotherapy which reduced GH levels (see Levin S. R., et al., Am J Med. 57:526 (1974), Feek, C. M., et al., J Clin Endocrinol 22:532 (1981)). Furthermore, administration of GH to older subjects caused hyperglycemia, glucose intolerance and hyperinsulinemia in numerous studies (see Aloia, J.F., et al., J Clin Endocrinol Metab, 43:992 (1976); Binnerts et al., J Clin Endocrinol Metab, 67:1312 (1988); Marcus, R., et al., J Clin Endocrinol Metab, 70:519 (1990)). Therefore, GH therapy is contra-indicated for individuals with diabetes or those at risk for diabetes.

It will be known to those skilled in the art that there are numerous compounds now being used in an effort to treat the diseases or therapeutic indications enumerated above. Combinations of these therapeutic agents, some of which have also been mentioned above, with growth promotant, exhibit anabolic and desirable properties of these various therapeutic agents. In these combinations, the therapeutic agents and the growth hormone secretagogues of this invention may be independently and sequentially administered in any order or co-administered in dose ranges from one one-hundredth to one times the dose levels which are effective when these compounds and secretagogues are used singly. Combined therapy to inhibit bone resorption, prevent osteoporosis, reduce skeletal fracture, enhance the healing of bone fractures, stimulate bone formation and increase bone mineral density can be effectuated by combinations of bisphosphonates and the growth hormone secretagogues of this invention. See PCT publication WO 95/11029 for a discussion of combination therapy using bisphosphonates and GH secretagogues. The use of bisphosphonates for these utilities has been reviewed, for example, by Hamdy, N.A.T., Role of Bisphosphonates in Metabolic Bone Diseases, Trends in Endocrinol. Metab., 1993, 4, pages 19–25. Bisphosphonates with these utilities include but are not limited to alendronate, tiludronate, dimethyl-APD, risedronate, etidronate, YM-175, clodronate, pamidronate, and BM-210995 (ibandronate). According to their potency, oral daily dosage levels of the bisphosphonate of between 0.1 mg/kg and 5 g/kg of body weight and daily dosage levels of the growth hormone secretagogues of this invention of between 0.01 mg/kg to 20 mg/kg of body weight are administered to patients to obtain effective treatment of osteoporosis.

The compounds of this invention may be combined with a mammalian estrogen agonist/antagonist. Any estrogen agonist/antagonist may be used as the second compound of this invention. The term estrogen agonist/antagonist refers to compounds which bind with the estrogen receptor, inhibit bone turnover and prevent bone loss. In particular, estrogen agonists are herein defined as chemical compounds capable of binding to the estrogen receptor sites in mammalian tissue, and mimicking the actions of estrogen in one or more tissue. Estrogen antagonists are herein defined as chemical compounds capable of binding to the estrogen receptor sites in mammalian tissue, and blocking the actions of estrogen in one or more tissues. Such activities are readily determined by those skilled in the art according to standard assays including estrogen receptor binding assays, standard bone histomorphometric and densitometer methods (see Eriksen E.F. et al., Bone Histomorphometry, Raven Press, New York, 1994, pages 1–74; Grier S. J. et. al., The Use of Dual-Energy X-Ray Absorptiometry In Animals, Inv. Radiol., 1996, 31(1):50–62; Wahner H. W. and Fogelman I., The Evaluation of Osteoporosis: Dual Energy X-Ray Absorptiometry in Clinical Practice., Martin Dunitz Ltd., London 1994, pages 1–296). A variety of these compounds are described and referenced below,h however, other estrogen agonists/antagonists will be known to those skilled in the art. A preferred estrogen agonist/antagonist is droloxifene: (phenol, 3-[1-[4[2-(dimethylamino)ethoxy]-phenyl]-2-phenyl-1-butenyl]-, (E)-) and associated compounds which are disclosed in U.S. Pat. No. 5,047,431, the disclosure of which is hereby incorporated by reference.

Another preferred estrogen agonist/antagonist is tamoxifen: (ethanamine,2-[-4-(1,2-diphenyl-1-butenyl)phenoxy]-N,N-dimethyl, (Z)-2,2-hydroxy-1,2,3-propanetricarboxylate (1:1)) and associated compounds which are disclosed in U.S. Pat. No. 4,536,516, the disclosure of which is hereby incorporated by reference. Another related compound is 4-hydroxy tamoxifen which is disclosed in U.S. Pat. No. 4,623,660, the disclosure of which is hereby incorporated by reference.

Another preferred estrogen agonist/antagonist is raloxifene: (methanone, [6-hydroxy-2-(4-hydroxyphenyl)benzo[b]thien-3-yl][4-[2-(1-piperidinyl)ethoxy]phenyl]-hydrochloride) and associated compounds which are disclosed in U.S. Pat. No. 4,418,068, the disclosure of which is hereby incorporated by reference.

Another preferred estrogen agonist/antagonist is idoxifene: Pyrrolidine, 1-[-[4-[[1-(4iodophenyl)-2-phenyl-1-Butenyl]phenoxy]ethyl] and associated compounds which are disclosed in U.S. Pat. No. 4,839,155, the disclosure of which is hereby incorporated by reference.

Other preferred estrogen agonist/antagonists include compounds as described in commonly assigned U.S. Pat. No. 5,552,412 the disclosure of which is hereby incorporated by reference. Especially preferred compounds which are described therein are:

cis-6-(4-fluoro-phenyl)-5-[4-(2-piperidin-1-yl-ethoxy)-phenyl]-5,6,7,8-tetrahydro-naphthalene-2-ol;

(−)-cis-6-phenyl-5-[4-(2-pyrrolidin-1-yl-ethoxy)-phenyl]-5,6,7,8-tetrahydro-naphthalene-2-ol;

cis-6-phenyl-5-[4-(2-pyrrolidin-1-yl-ethoxy)-phenyl]-5,6,7,8-tetrahydro-naphthalene-2-ol;

cis-1-[6'-pyrrolodinoethoxy-3'-pyridyl]-2-phenyl-hydroxy-1,2,3,4-tetrahydronaphthalene;

1-(4'-pyrrolidinoethoxyphenyl)-2-(4"-fluorophenyl) hydroxy-1,2,3,4-tetrahydroisoquinoline;

cis-6-(4 hydroxyphenyl)-5-[4-(2-piperidin-1-yl-ethoxy)-phenyl]-5,6,7,8-tetrahydro-naphthalene-2-ol; and 1-(4'-pyrrolidinolethoxyphenyl)-2-phenylhydroxy-1,2,3,4-tetrahydroisoquinoline.

Other estrogen agonist/antagonists are described in U.S. Pat. No. 4,133,814, the disclosure of which is hereby incorporated by reference. U.S. Pat. No. 4,133,814 discloses derivatives of 2-phenyl-3-aroyl-benzothiophene and 2-phenyl-3-aroylbenzothiophene-1-oxide.

The following paragraphs provide preferred dosage ranges for various anti-resorptive agents.

The amount of the anti-resorptive agent to be used is determined by its activity as a bone loss inhibiting agent. This activity is determined by means of an individual compound's pharmacokinetics and its minimal maximal effective dose in inhibition of bone loss using a protocol such as those referenced above.

In general an effective dosage for the activities of this invention, for example the treatment of osteoporosis, for the estrogen agonists/antagonists (when used in combination with a compound of Formula I or a pharmaceutically acceptable salt or prodrug thereof of this invention) is in the range of 0.01 to 200 mg/kg/day, preferably 0.5 to 100 mg/kg/day.

In particular, an effective dosage for droloxifene is in the range of 0.1 to 40 mg/kg/day, preferably 0.1 to 5 mg/kg/day.

In particular, an effective dosage for raloxifene is in the range of 0.1 to 100 mg/kg/day, preferably 0.1 to 10 mg/kg/day.

In particular, an effective dosage for tamoxifen is in the range of 0.1 to 100 mg/kg/day, preferably 0.1 to 5 mg/kg/day.

In particular, an effective dosage for cis-6-(4-fluoro-phenyl)-5-[4-(2-piperidin-1-yl-ethoxy)-phenyl]-5,6,7,8-tetrahydronaphthalene-2-ol;

(−)-cis-6-phenyl-5-[4-(2-pyrrolidin-1-yl-ethoxy)-phenyl]-5,6,7,8-tetrahydro-naphthalene-2-ol;

cis-6-phenyl-5-[4-(2-pyrrolidin-1-yl-ethoxy)-phenyl]-5,6,7,8-tetrahydro-naphthalene-2-ol;

cis-1-[6'-pyrrolodinoethoxy-3'-pyridyl]-2-phenyl-6-hydroxy-1,2,3,4-tetrahydronaphthalene;

1-(4'-pyrrolidinoethoxyphenyl)-2-(4"-fluorophenyl)+ hydroxy-1,2,3,4-tetrahydroisoquinoline;

cis-6-(4-hydroxyphenyl)-5-[4-(2-piperidin-1-yl-ethoxy)-phenyl]-5,6,7,8-tetrahydro-naphthalene-2-ol; or 1-(4'-pyrrolidinolethoxyphenyl)-2-phenyl-6-hydroxy-1,2,3,4-tetrahydroisoquinoline is in the range of 0.0001 to 100 mg/kg/day, preferably 0.001 to 10 mg/kg/day.

In particular, an effective dosage for 4-hydroxy tamoxifen is in the range of 0.0001 to 100 mg/kg/day, preferably 0.001 to 10 mg/kg/day.

Assay for Stimulation of GH Release from Rat Pituicytes

Compounds that have the ability to stimulate GH secretion from cultured rat pituitary cells are identified using the following protocol. This test is also useful for comparison to standards to determine dosage levels. Cells are isolated from pituitaries of 6-week old male Wistar rats. Following decapitation, the anterior pituitary lobes are removed into cold, sterile Hank's balanced salt solution without calcium or magnesium (HBSS). Tissues are finely minced, then subjected to two cycles of mechanically assisted enzymatic dispersion using 10 U/mL bacterial protease (EC 3.4.24.4, Sigma P-6141, St. Louis, Mo.) in HBSS. The tissue-enzyme mixture is stirred in a spinner flask at 30 rpm in a 5% $CO_2$ atmosphere at about 37° C. for about 30 min., with manual trituration after about 15 min. and about 30 min. using a 10-mL pipet. This mixture is centrifuged at 200×g for about 5 min. Horse serum (35% final concentration) is added to the supernatant to neutralize excess protease. The pellet is resuspended in fresh protease (10 U/mL), stirred for about 30 min. more under the previous conditions, and manually triturated, ultimately through a 23-gauge needle. Again, horse serum (35% final concentration) is added, then the cells from both digests are combined, pelleted (200×g for about 15 min.), resuspended in culture medium (Dulbecco's Modified Eagle Medium (D-MEM) supplemented with 4.5 g/L glucose, 10% horse serum, 2.5% fetal bovine serum, 1% non-essential amino acids, 100 U/mL nystatin and 50 mg/mL gentamycin sulfate, Gibco, Grand Island, N.Y.) and counted. Cells are plated at 6.0–6.5×10$^4$ cells per cm$^2$ in 48-well Costar™ (Cambridge, Mass.) dishes and cultured for 3–4 days in culture medium.

Just prior to GH secretion assay, culture wells are rinsed twice with release medium, then equilibrated for about 30 minutes in release medium (DMEM buffered with 25 mM Hepes, pH 7.4 and containing 0.5% bovine serum albumin at 37° C.). Test compounds are dissolved in DMSO, then diluted into pre-warmed release medium. Assays are run in quadruplicate. The assay is initiated by adding 0.5 mL of release medium (with vehicle or test compound) to each culture well. Incubation is carried out at about 37° C. for about 15 minutes, then terminated by removal of the release medium, which is centrifuged at 2000×g for about 15 minutes to remove cellular material. Rat growth hormone concentrations in the supernatants are determined by a standard radioimmunoassay protocol described below.

Measurement of Rat Growth Hormone

Rat growth hormone concentrations were determined by double antibody radioimmunoassay using a rat growth hormone reference preparation (NIDDK-rGH-RP-2) and rat growth hormone antiserum raised in monkey (NIDDK-anti-rGH-5) obtained from Dr. A. Parlow (Harbor-UCLA Medical Center, Torrence, Calif.). Additional rat growth hormone (1.5 U/mg, #G2414, Scripps Labs, San Diego, Calif.) is iodinated to a specific activity of approximately 30 $\mu$Ci/$\mu$g by the chloramine T method for use as tracer. Immune complexes are obtained by adding goat antiserum to monkey IgG (ICN/Cappel, Aurora, Ohio) plus polyethylene glycol, MW 10,000–20,000 to a final concentration of 4.3%; recovery is accomplished by centrifugation. This assay has a working range of 0.08–2.5 $\mu$g rat growth hormone per tube above basal levels.

Assay for Exogenously-Stimulated Growth Hormone Release in the Rat after Intravenous Administration of Test Compounds Twenty-one day old female Sprague-Dawley rats (Charles River Laboratory, Wilmington, Mass.) are allowed to acclimate to local vivarium conditions (24° C., 12 hr light, 12 hr dark cycle) for approximately 1 week before compound testing. All rats are allowed access to water and a pelleted commercial diet (Agway Country Food, Syracuse N.Y.) ad libitum. The experiments are conducted in accordance with the NIH Guide for the Care and Use of Laboratory Animals.

On the day of the experiment, test compounds are dissolved in vehicle containing 1% ethanol, 1 mM acetic acid and 0.1% bovine serum albumin in saline. Each test is conducted in three rats. Rats are weighed and anesthetized via intraperitonèal injection of sodium pentobarbital (Nembutol®, 50 mg/kg body weight). Fourteen minutes after anesthetic administration, a blood sample is taken by nicking the tip of the tail and allowing the blood to drip into a microcentrifuge tube (baseline blood sample, approximately 100 μl). Fifteen minutes after anesthetic administration, test compound is delivered by intravenous injection into the tail vein, with a total injection volume of 1 mL/kg body weight. Additional blood samples are taken from the tail at 5, 10 and 15 minutes after compound administration. Blood samples are kept on ice until serum separation by centrifugation (1430×g for 10 minutes at 10° C.). Serum is stored at −80° C. until serum growth hormone determination by radioimmunoassay as described above.

Assessment of Exogenously-Stimulated Growth Hormone Release in the Dog after Oral Administration On the day of dosing, the test compound is weighed out for the appropriate dose and dissolved in water. Doses are delivered at a volume of 0.5–3 mL/kg by gavage to 2–4 dogs for each dosing regimen. Blood samples (5 mL) are collected from the jugular vein by direct vena puncture pre-dose and at 0.17, 0.33, 0.5, 0.75, 1, 2, 4, 6, 8 and 24 hours post dose using 5 mL vacutainers containing lithium heparin. The prepared plasma is stored at −20° C. until analysis.

Measurement of Canine Growth Hormone

Canine growth hormone concentrations are determined by a standard radioimmunoassay protocol using canine growth hormone (antigen for iodination and reference preparation AFP-1983B) and canine growth hormone antiserum raised in monkey (AFP-21452578) obtained from Dr. A. Parlow (Harbor-UCLA Medical Center, Torrence, Calif.). Tracer is produced by chloramine T-iodination of canine growth hormone to a specific activity of 20–40 μCi/μg. Immune complexes are obtained by adding goat antiserum to monkey IgG (ICN/Cappel, Aurora, Ohio) plus polyethylene glycol, MW 10,000–20,000 to a final concentration of 4.3%; recovery is accomplished by centrifugation. This assay has a working range of 0.08–2.5 μg canine GH/tube.

Assessment of Canine Growth Hormone and Insulin-Like Growth Factor-1 Levels in the Dog after Chronic Oral Administration The dogs receive test compound daily for either 7 or 14 days. Each day of dosing, the test compound is weighed out for the appropriate dose and dissolved in water. Doses are delivered at a volume of 0.5–3 ml/kg by gavage to 5 dogs for each dosing regimen. Blood samples are collected at days 0, 3, 7, 10 and 14. Blood samples (5 ml) are obtained by direct venipuncture of the jugular vein at pre-dose, 0.17, 0.33, 0.5, 0.754, 1, 2, 3, 6, 8, 12 and 24 hours post administration on days 0, 7 and 14 using 5 ml vacutainers containing lithium heparin. In addition, blood is drawn pre-dose and 8 hours on days 3 and 10. The prepared plasma is stored at −20° C. until analysis.

Female Rat Study

This study evaluates the effect of chronic treatment with a GHRP mimetic on weight, body composition and non-fasting plasma concentrations of glucose, insulin, lactate and lipids in estrogen-deficient and estrogen-replete female rats. Acute responsiveness of serum GH levels to i.v. administration of the GH releasing agent was assessed on the last day of dosing. Body weight was monitored weekly throughout the treatment period; additionally, body composition and plasma levels of glucose, insulin, lactate, cholesterol and triglycerides were assessed at the end of treatment.

Virgin female Sprague-Dawley rats were obtained from Charles River Laboratories (Wilmington, Mass.) and underwent bilateral ovariectomy (Ovx) or sham-surgery (Sham) at approximately 12 weeks of age. For sham surgeries, ovaries were exteriorized and replaced into the abdominal cavity. Following surgery the rats were housed individually in 20 cm×32 cm×20 cm cages under standard vivarium conditions (about 24° C. with about 12 hours light/12 hours dark cycle). All rats were allowed free access to water and a pelleted commercial diet (Agway ProLab 3000, Agway Country Food, Inc., Syracuse, N.Y.). The experiment was conducted in accordance with NIH Guidelines for the Care and Use of Laboratory Animals.

Approximately seven months post-surgery, Sham and Ovx rats were weighed and randomly assigned to groups. Rats were dosed daily by oral gavage with 1 mL of either vehicle (1% ethanol in distilled-deionized water), 0.5 mg/kg or 5 mg/kg of a growth hormone releasing agent for 90 days. Rats were weighed at weekly intervals throughout the study. Twenty-four hours after the last oral dose, the acute response of serum growth hormone (GH) to test agent was assessed by the following procedure. Rats were anesthetized with sodium pentobarbital 50 mg/kg. Anesthetized rats were weighed and a baseline blood sample (~100 μl) was collected from the tail vein. Test agent (growth hormone releasing agent or vehicle) was then administered intravenously via the tail vein in 1 mL. Approximately ten minutes after injection, a second 100 μl blood sample was collected from the tail. Blood was allowed to clot at about 4° C., then centrifuged at 2000×g for about 10 minutes. Serum was stored at about −70° C. Serum growth hormone concentrations were determined by radioimmunoassay as previously described. Following this procedure, each anesthetized rat underwent whole body scanning by dual-energy X-ray absorptiometry (DEXA, Hologic QDR 1000/W, Waltham Mass.). A final blood sample was collected by cardiac puncture into heparinized tubes. Plasma was separated by centrifugation and stored frozen as described above.

Plasma insulin is determined by radioimmunoassay using a kit from Binax Corp. (Portland, Me.). The interassay coefficient of variation is ≦10%. Plasma triglycerides, total cholesterol, glucose and lactate levels are measured using Abbott VP™ and VP Super System® Autoanalyzer (Abbott Laboratories, Irving, Tex.), using the A-Gent™ Triglycerides, Cholesterol and Glucose Test reagent systems, and a lactate kit from Sigma, respectively. The plasma insulin, triglycerides, total cholesterol and lactate lowering activity of a growth hormone releasing peptide (GHRP) or GHRP mimetic such as a compound of Formula I, are determined by statistical analysis (unpaired t-test) with the vehicle-treated control group.

The compounds of this invention can be administered by oral, parenteral (e.g., intramuscular, intraperitoneal, intravenous or subcutaneous injection, or implant) nasal, vaginal, rectal, sublingual, or topical routes of administration and can be formulated with pharmaceutically acceptable carriers to provide dosage forms appropriate for each route of administration.

Solid dosage forms for oral administration include capsules, tablets, pills, powders and granules and for companion animals the solid dosage forms include an admixture with food and chewable forms. In such solid dosage forms, the active compound is admixed with at least one inert pharmaceutically acceptable carrier such as sucrose, lactose, or starch. Such dosage forms can also comprise, as is normal practice, additional substances other than such inert diluents, e.g., lubricating agents such as magnesium stearate. In the case of capsules, tablets and pills, the dosage forms may also comprise buffering agents. Tablets and pills can additionally be prepared with enteric coatings. In the case of chewable forms, the dosage form may comprise flavoring agents and perfuming agents.

Liquid dosage forms for oral administration include pharmaceutically acceptable emulsions, solutions, suspensions, syrups, the elixirs containing inert diluents commonly used in the art, such as water. Besides such inert diluents, compositions can also include adjuvants, such as wetting agents, emulsifying and suspending agents, and sweetening, flavoring and perfuming agents.

Preparations according to this invention for parenteral administration include sterile aqueous or non-aqueous solutions, suspensions, or emulsions. Examples of non-aqueous solvents or vehicles are propylene glycol, polyethylene glycol, vegetable oils, such as olive oil and corn oil, gelatin, and injectable organic esters such as ethyl oleate. Such dosage forms may also contain adjuvants such as preserving, wetting, emulsifying, and dispersing agents. They may be sterilized by, for example, filtration through a bacteria-retaining filter, by incorporating sterilizing agents into the compositions, by irradiating the compositions, or by heating the compositions. They can also be manufactured in the form of sterile solid compositions which can be dissolved in sterile water, or some other sterile injectable medium immediately before use.

Compositions for rectal or vaginal administration are preferably suppositories which may contain, in addition to the active substance, excipients such as coca butter or a suppository wax.

Compositions for nasal or sublingual administration are also prepared with standard excipients well known in the art.

The dosage of active ingredient in the compositions of this invention may be varied; however, it is necessary that the amount of the active ingredient be such that a suitable dosage form is obtained. The selected dosage depends upon the desired therapeutic effect, on the route of administration, and on the duration of the treatment. Generally, dosage levels of between 0.0001 to 100 mg/kg of body weight daily are administered to humans and other animals, e.g., mammals, to obtain effective release of growth hormone.

A preferred dosage range in humans is 0.01 to 5.0 mg/kg of body weight daily which can be administered as a single dose or divided into multiple doses.

A preferred dosage range in animals other than humans is 0.01 to 10.0 mg/kg of body weight daily which can be administered as a single dose or divided into multiple doses. A more preferred dosage range in animals other than humans is 0.1 to 5 mg/kg of body weight daily which can be administered as a single dose or divided into multiple doses.

Throughout this disclosure the following abbreviations are used with the following meanings:

BOC t-Butyloxycarbonyl
Bz Benzyl
BOP Benzotriazol-1-yloxy tris(dimethylamino) phosphonium hexafluorophosphate
CBZ Benzyloxycarbonyl
CDI N,N'-Carbonyidiimidazole
DCC Dicyclohexylcarbodiimide
DEC 1,2-Diethylaminoethyl chloride hydrochloride
DMAP 4-Dimethylaminopyridine
DMF Dimethylformamide
DPPA Diphenylphosphoryl azide
EDC 1-(3-Dimethylaminopropyl)-3-ethylcarbodiimide hydrochloride
EtOAc Ethyl acetate
Hex Hexane
HOAT 1-Hydroxy-7-azabenzotriazole
HOBT Hydroxybenzotnazole hydrate
HPLC High pressure liquid chromatography
Hz Hertz
KHMDS Potassium Bis(trimethylsilyl)amide
LHMDS Lithium Bis(trimethylsilyl)amide
MHz Megahertz
MS Mass Spectrum
NaHMDS Sodium Bis(trimethylsilyl)amide
NMR Nuclear Magnetic Resonance
PPAA 1-Propanephosphonic acid cyclic anhydride
PTH Parathyroid hormone
TFA Trifluoroacetic acid
THF Tetrahydrofuran
TLC Thin layer chromatography
TRH Thyrotropin releasing hormone The preparation of the compounds of Formula I of the present invention can be carried out in sequential or convergent synthetic routes. Syntheses detailing the preparation of the compounds of Formula I in a sequential manner are presented in the following reaction schemes.

Many protected amino acid derivatives are commercially available, where the protecting groups, Prt, Prt' or Prt", are, for example, BOC, CBZ, FMOC, benzyl or ethoxycarbonyl groups. Other protected amino acid derivatives can be prepared by literature methods well-known to one skilled in the art. Some substituted piperazines and piperidines are commercially available, and many other piperazines and 4-substituted piperidines are known in the literature. Various heterocyclic substituted piperidines and piperazines can be prepared following literature methods using derivatized heterocyclic intermediates. Alternatively, the heterocyclic rings of such compounds can be derivatized by standard means, such as coupling with CDl, hydrogenation of aromatic heterocycles, etc. as is well-known to those skilled in the art.

Many of the schemes illustrated below describe compounds which contain protecting groups Prt, Prt' or Prt", which can be any suitable protecting group known to those skilled in the art. Benzyloxycarbonyl groups can be removed by a number of methods including, catalytic hydrogenation with hydrogen in the presence of a palladium or platinum catalyst in a protic solvent such as methanol. Preferred catalysts are palladium hydroxide on carbon or palladium on carbon. Hydrogen pressures from 1–1000 psi can be employed; pressures from 10 to 70 psi are preferred. Alternatively, the benzyloxycarbonyl group can be removed by transfer hydrogenation.

Removal of BOC protecting groups can be carried out using a strong acid such as trifluoroacetic acid or hydrochloric acid with or without the presence of a cosolvent such as dichloromethane or methanol at a temperature of about −30° to 70° C., preferably about −5° to about 35° C.

Benzyl groups on amines can be removed by a number of methods including catalytic hydrogenation with hydrogen in the presence of a palladium catalyst in a protic solvent such as methanol. Hydrogen pressures from 1–1000 psi can be employed; pressures from 10 to 70 psi are preferred. The addition and removal of these and other protecting groups are discussed in detail by T. Greene in Protective Groups in Organic Synthesis, John Wiley & Sons, New York, 1981.

The variables shown in the following schemes are as described for compounds of Formula I, above, unless otherwise indicated.

SCHEME 1

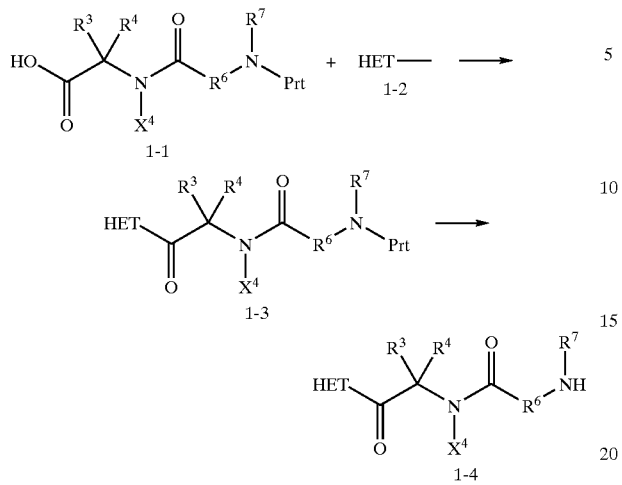

SCHEME 2

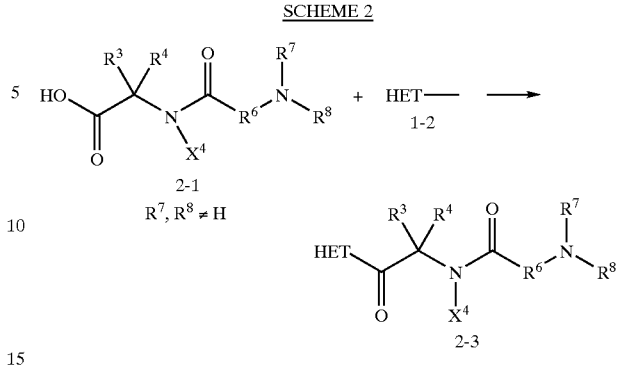

As illustrated in Scheme 2, coupling of a heterocyclic amine of formula 1-2, as defined in claim 1, with an amino acid of formula 2-1, where $R^7$ and $R^8$ are not hydrogen, is conveniently carried out in a manner similar to that described in Scheme 1.

As illustrated in Scheme 1, coupling of a heterocyclic amine (HET at the NH) of formula 1-2, as defined for Formula I, with a protected amino acid of formula 1-1, where Prt is a suitable protecting group, is conveniently carried out in an inert solvent such as dichloromethane or DMF by a coupling reagent such as EDC, DCC or DEC in the presence of HOBT or HOAT. In the case where amine 1–2 is present as the hydrochloride salt, it is preferable to add one equivalent of a suitable base such as triethylamine to the reaction mixture. Alternatively, the coupling can be effected with a coupling reagent such as BOP in an inert solvent such as methanol or with PPAA in a solvent like ethyl acetate. Such coupling reactions are generally conducted at temperatures of about −30° to about 80° C., preferably 0° to about 25° C. For a discussion of other conditions used for coupling peptides see Houben-Weyl, Vol. XV, part II, E. Wunsch, Ed., George Theime Verlag, 1974, Stuttgart. Separation of unwanted side products and purification of intermediates is achieved by chromatography on silica gel, employing flash chromatography (W. C. Still, M. Kahn and A. Mitra, J. Org. Chem. 43 2923 1978), by crystallization, or by trituration. Transformation of 1-3 into an intermediate of formula 1-4 can be carried out by removal of the protecting group Prt as described above.

SCHEME 3

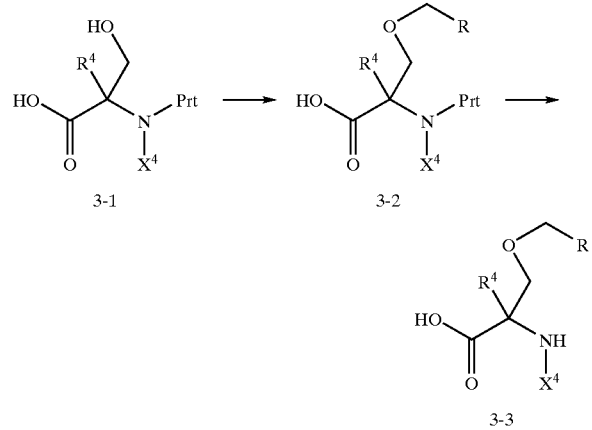

As illustrated in Scheme 3, an intermediate ether of formula 3-2 can be prepared by treating an amino acid of formula 3-1, where Prt is a suitable protecting group, with a base such as potassium carbonate or sodium hydride followed by an alkyl halide, benzyl halide, tosylate or mesylate such as benzylbromide in a suitable solvent such as DMF or THF. Deprotection of the amine transforms 3-2 into 3-3. Alternatively, many amino acids of formula 3-3 are commercially available. R is a group defined for $R^3$ in Formula I, above.

SCHEME 4

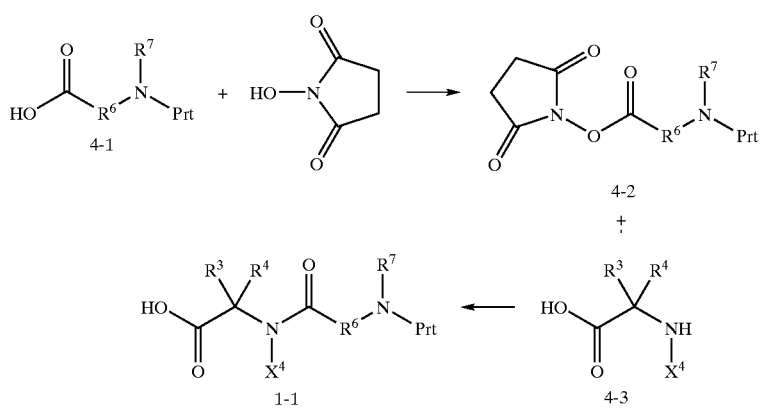

As illustrated in Scheme 4, intermediates of formula 4-2 can be prepared by treating an acid of formula 4-1 with hydroxysuccinimide in the presence of a coupling agent such as EDC in an inert solvent such as methylene chloride. Treating 4-2 with an amino acid of formula 4-3 in a solvent such as DMF in the presence of a base such as diisopropylethylamine produces compounds of formula Bigge, C.F. et al., Tet. Lett., 1989, 30, 5193–5196. Intermediate 6-4 is generated by alkylating ester 6-2 with a reagent such as an alkyl halide, tosylate or mesylate with a base such as NaHMDS in a suitable solvent system such as DMF/THF at a temperature of about −78° C.

Intermediate carbamates of formula 6-5 can be prepared by reacting an intermediate of formula 6-4 with a hydride

SCHEME 5

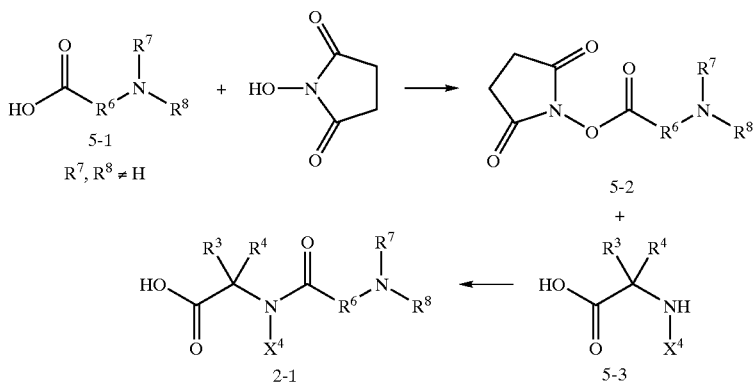

As illustrated in Scheme 5, dipeptides of formula 2-1, where $R^7$ and $R^8$ are not hydrogen, is conveniently synthesized by the procedures described in Scheme such as sodium borohydride or superhydride. Transformation of intermediate 6-5 to 6-6 can be achieved by removal of the protecting group Prt as described above.

SCHEME 6

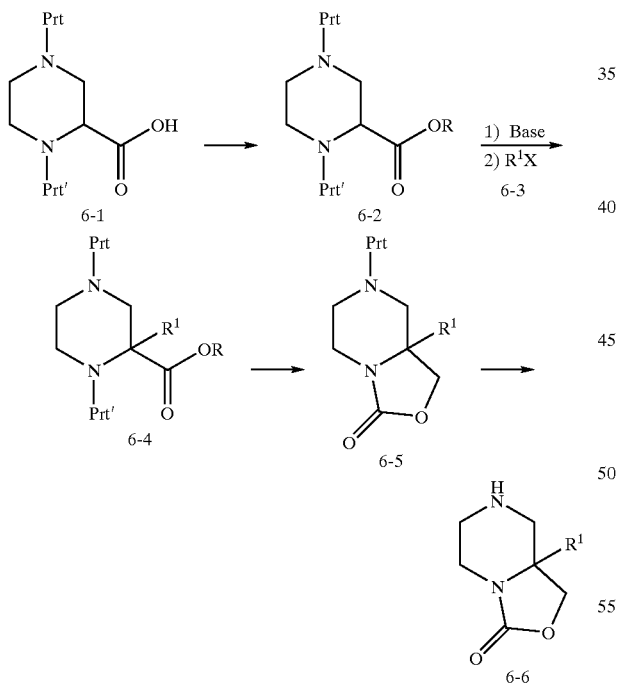

SCHEME 7

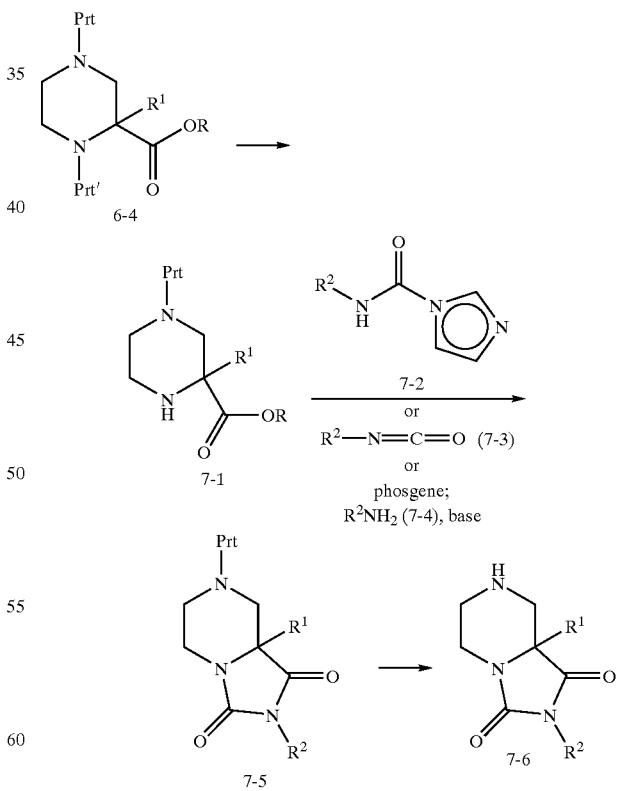

Intermediate esters of formula 6-2, where Prt and Prt' are protecting groups, preferably Prt' is a carbamate protecting group such as CBZ, can be prepared by treating an acid of formula 6-1 with a base such as potassium carbonate followed by an alkyl halide such as iodomethane in a suitable solvent such as DMF. Alternatively, an ester of formula 6-2 can be prepared by reacting an acid of formula 6-1 with diazomethane. For the preparation of compound 6-2 see Transformation of intermediate 6-4 to 7-1 can be achieved by removal of the protecting group Prt' as described above. Intermediateureas of formula 7-5 can be prepared by reacting an intermediate of formula 7-1 with either an acyl imidizolide of formula 7-2, an isocyanate of formula 7-30 or phosgene (or other phosgene equivalent) followed by an amine of formula 7-4 in the presence of a suitable base such as triethylamine. When $R^1$ is —$CH_2$-pyridyl it is preferred to use an isocyanate or acyl imidizolide. Transformation of 7-5 to 7-6 can be achieved by removal of the protecting group Prt as described above.

SCHEME 8

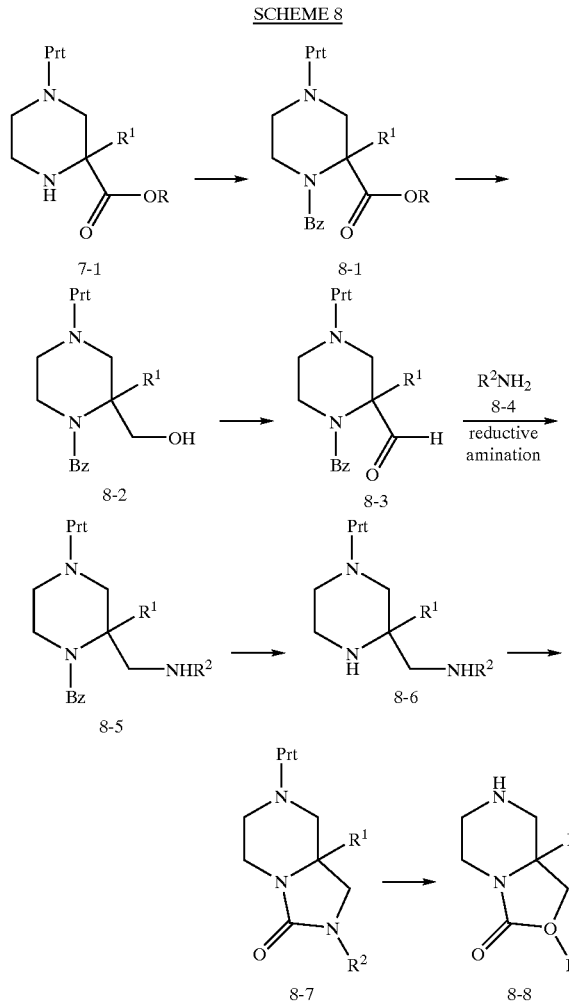

An intermediate benzylamine of formula 8-1 can be prepared by treating an amine of formula 7-1 with a base such as diisopropylethylamine followed by a benzyl halide such as benzyl bromide in a suitable solvent such as acetonitrile. Alternatively, 8-1 can be prepared by treating 7-1 with benzaldehyde and a suitable reducing agent such as $NaCNBH_3$ or $Na(OAc)_3BH$ in a suitable solvent such as methanol or dichloromethane. An alcohol of the formula 8-2 can be prepared by reducing an intermediate of the formula 8-1 with a reducing agent such as superhydride in a suitable solvent such as THF. An alcohol of the formula 8-2 can be oxidized to an aldehyde of the formula 8-3 with an oxidizing agent such as oxalyl chloride/DMSO in a suitable solvent such as dichloromethane at a temperature of about −78° C., with the later addition of a base such as triethylamine to neutralize the reaction mixture (Swem-type oxidabon, see Mancuso, A.J., Swem, D., Syhthesis, 1981, pp. 165–185). Compounds of formula 8-5 can be prepared by treating an aldehyde of formula 8-3 with an amine of formula 84 in the presence of a suitable reducing agent which include alkali metal borohydrides and cyanoborohydrides. The preferred reducing agent is sodium cyanoborohydride. Sodium borohydride and sodium triacetoxyborohydride may also be used. For a general review of reductive aminations see R. F. Borch, Aldrichimica Acta, 8, 3–10 (1975). Removal of the benzyl group to give 8-6 can be accomplished by a number of reductive methods including hydrogenation in the presence of platinum or palladium catalyst in a protic solvent such as methanol. Cyclization of a diamine of formula 8-6 with CDI or other phosgene equivalents generates a compound of formula 8-7. Removal of the protecting group, as described above, transforms 8-7 into 8-8.

SCHEME 9

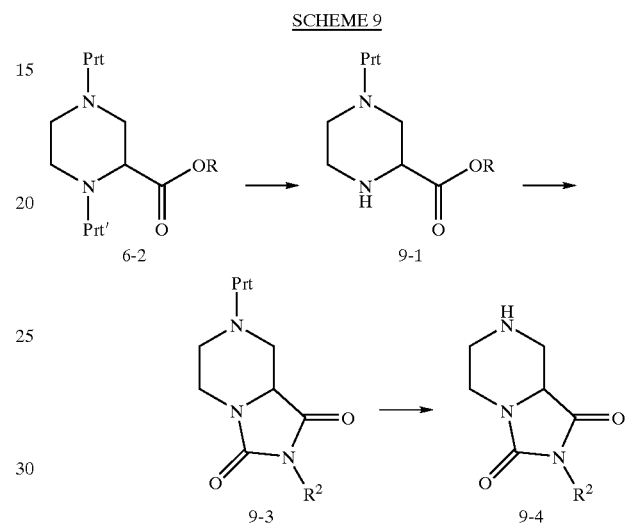

As illustrated in Scheme 9, an intermediate hydantoin of formula 9-4 can be prepared in three steps. An ester of formula 9-1, prepared by cleavage of Prt' from 6-2, can be acylated with an acyl imidizolide of formula 7-2, an isocyanate of formula 7-3, or phosgene (or other phosgene equivalent) followed by an amine of formula 7-4 in the presence of a suitable base such as triethylamine. Transformation of 9-3 to 9-4 can be accomplished by removal of the protecting group Prt as described above.

SCHEME 10

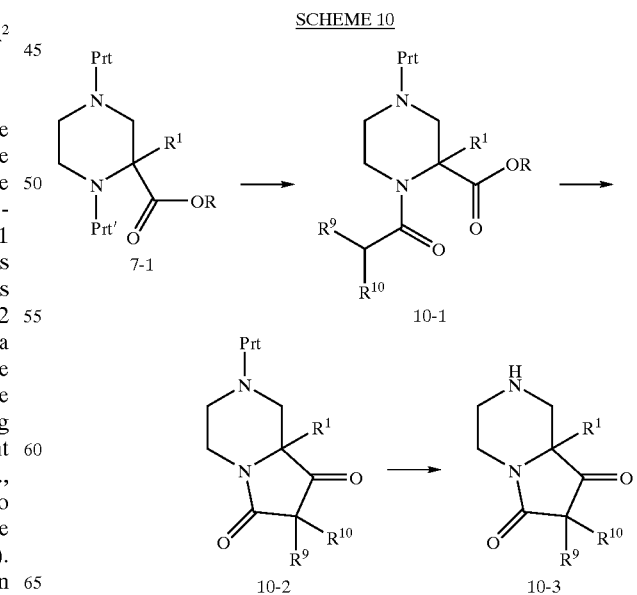

Intermediates of formula 10-1 can be prepared by treating a compound of formula 7-1 with an acyl chloride or other activated carboxylic acid derivative and a suitable base, such as TEA or N,N-diisopropylethylamine. Cyclization of a compound of formula 10-1 occurs upon treating 10-1 with a strong base such as LHMDS at a suitable temperature, about −78° C. to 40° C., to produce an intermediate of formula 10-2. When $R^9$ and/or $R^{10}$ is H, 10-2 may be alkylated with a reagent such as methyl iodide in the presence of a base like NaH to give 10-2 where $R^9$ and $R^{10}$ are not H. Removal of the protecting group, as described above, transforms 10-2 to 10-3.

SCHEME 11

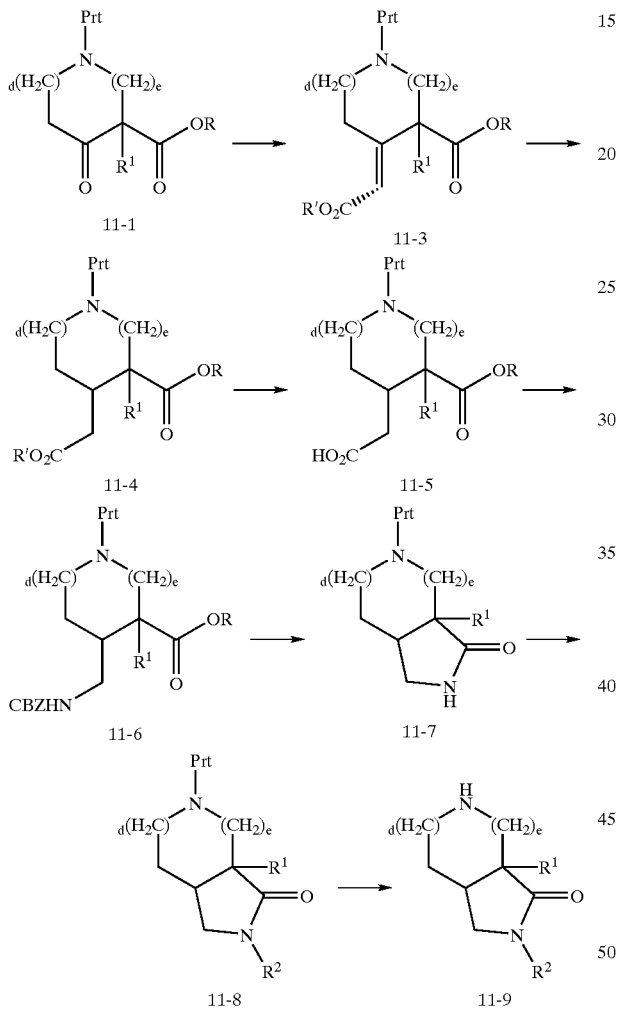

such as with DPPA and TEA in benzene, followed by rearrangement to an isocyanate by heating to reflux in a solvent such as benzene, which is then reacted with benzyl alcohol to form 11-6. A lactam of formula 11-7 can be prepared by removal of the CBZ protecting group from the amine in 11-6, followed by cyclization of the amine with the adjacent ester group. Deprotection of this material provides 11-9, $R^2$=H. Alternatively, amide 11-7 can be alkylated by deprotonation with a strong base such as sodium hydride, LHMDS, or KHMDS in a suitable solvent such as DMF or THF followed by treatment with an alkylating agent such as an alkyl halide, mesylate or tosylate. The product, 11-8, may then be deprotected, as described above, to provide 11-9. One skilled in the art will recognize that substitution next to the lactam nitrogen could have been introduced by alkylating ester 11-4 or by olefinating 11-1 to give a tetra-substituted olefin analogous to 11-3.

SCHEME 12

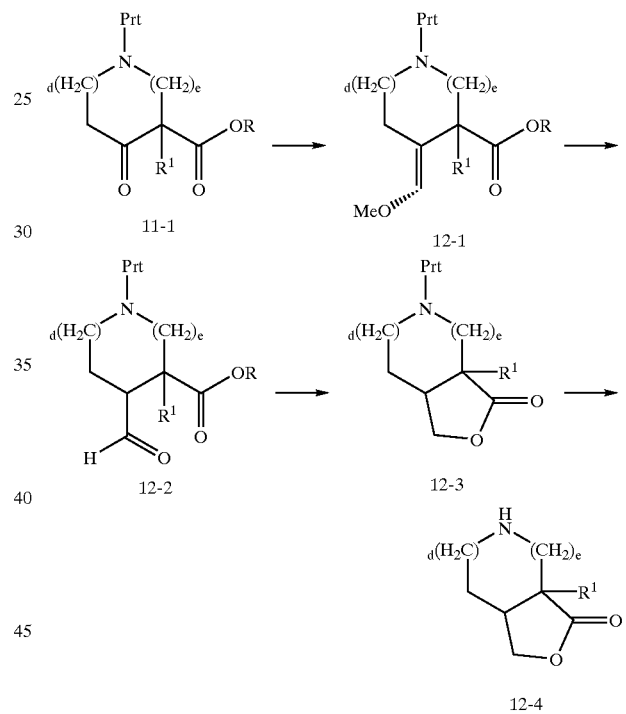

Intermediate α,β-unsaturated esters of formula 11-3 (R is an alkyl group) can be prepared by olefinating 11-1 with a reagent such as the anion generated upon treating trimethylphosphonoacetate with a strong base such as potassium tert-butoxide in a suitable solvent such as THF. Catalytic hydrogenation, such as with Pd on carbon in the presence of hydrogen, preferably at 1–4 atmospheres, in a suitable solvent, such as ethyl acetate or methanol, reduces the double bond of 11-3 to produce 11-4. Selective hydrolysis of the less hindered ester group in 11-4 can be performed with a base such as an alkali metal hydroxide in an appropriate solvent, such as a mixture of water, methanol, and/or dioxane. A carboxylic acid of formula 11-5, thus produced can be transformed to 11-6 by converting 11-5 to an acyl azide, Intermediate enol ethers of formula 12-1 can be prepared by treating 11-1 (R is an alky( group) with a reagent, such as methoxymethyl triphenylphosphonium chloride and a strong base, such as potassium tert-butoxide, in a suitable solvent such as THF. Hydrolysis of an enol ether of formula 12-1 under acidic conditions produces aldehyde 12-2. Reduction of the aldehyde group to an alcohol, for example with sodium borohydride in methanol, followed by cyclization converts 12-2 to a lactone of formula 12-3. Deprotection of the nitrogen, as described above, affords 12-4. One skilled in the art will recognize that an $R^{1A}$ substituent could have been introduced by alkylating aldehyde 12-2. In addition, substitution next to the lactone oxygen ($R^9/R^{10}$) could be introduced by olefinating 11-1 to give a tetra-substituted olefin and by treating the latter ketone or aldehyde (12-2) with an alkyl metal such as a Grignard reagent.

SCHEME 13

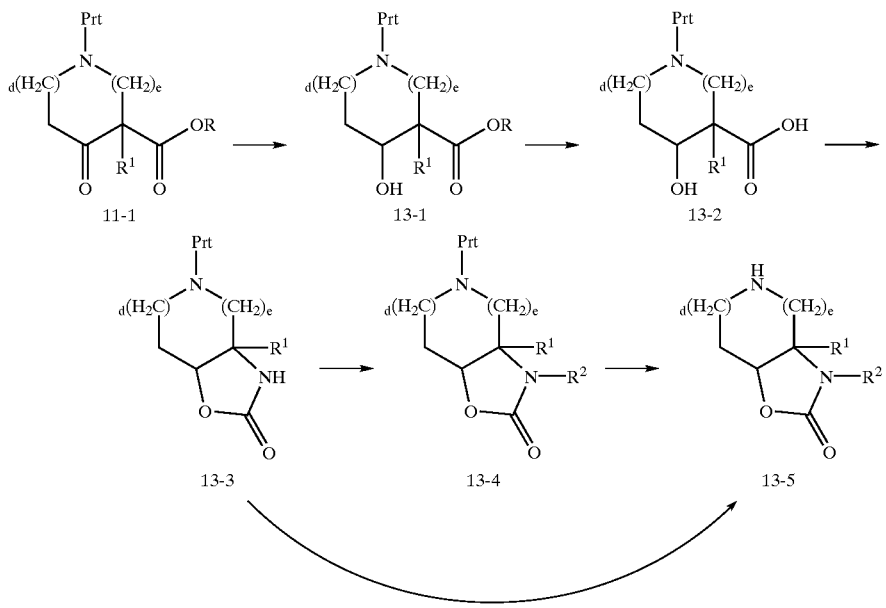

Reduction of the ketone in 11-1 (R is an alkyl group) to an alcohol with a suitable reducing reagent, such as with sodium borohydride in methanol, converts 11-1 to 13-1. Hydrolysis of the ester group in 13-1 according to the method discussed in Scheme 11 produces acid 13-2. Transformation of 13-2 to 13-3 can be achieved by converting 13-2 to acyl azides, for instance with DPPA and TEA in a solvent such as benzene, followed by rearrangement to isocyanates, which then react intramolecularly with the adjacent alcohol to form carbamate 13-3. Deprotection of 13-3 as described above would provides 13-5 where $R^2$ is H.

Alternatively, carbamate 13-3 can be alkylated by deprotonation with a strong base such as sodium hydride, LHMDS, or KHMDS in a suitable solvent such as DMF or THF followed by treatment with an alkylating agent such as an alkyl halide ($R^2$-halide), mesylate or tosylate. Removal of the protecting group, as described above, transforms 13-4 to 13-5. One skilled in the art will recognize that an $R^{1A}$ substituent could have been introduced by treating ketone 11-1 with an alkyl metal reagent, such as methyl magnesium bromide, at a suitable temperature for a Grignard reaction.

SCHEME 14

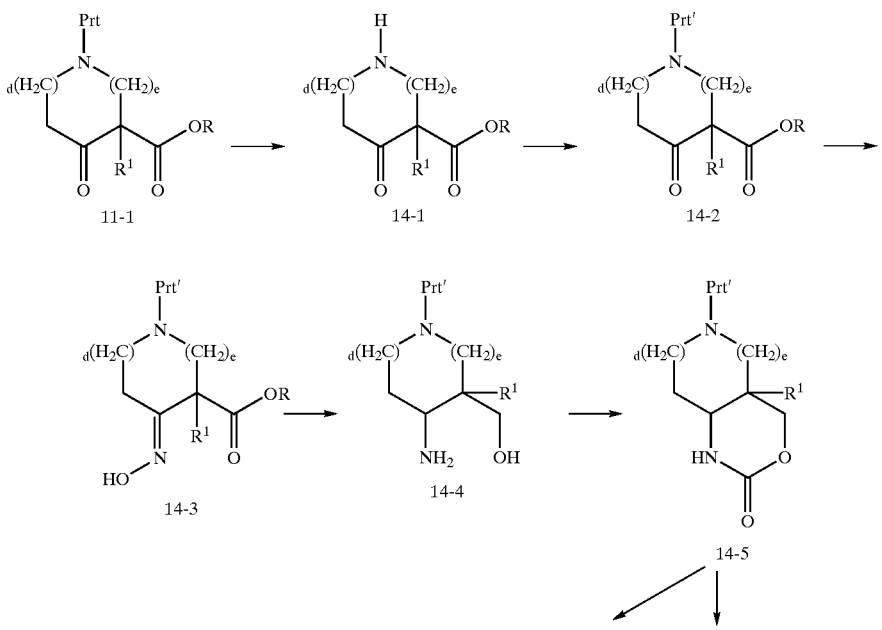

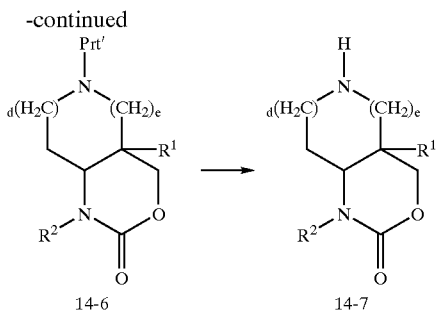

Removal of the carbamate protecting group, Prt, from 11-1 (R is an alkyl group) produces 14-1. Reprotection, such as with a benzyl group gives 14-2. Treating 14-2 with hydroxylamine yields an oxime of formula 14-3. The oxime and ester groups in 14-3 can be reduced to an amine and alcohol, respectively, to form 14-4 with a suitable reducing reagent, such as with LAH in THF. Transformation of 14-4 to a carbamate of formula 14-5 can be achieved by reaction of 14-4 with CDI or another phosgene equivalent in the presence of a base like TEA and solvent such as DME. Deprotecton of 14-5 produces 14-7 where $R^2$ is H. Alternatively, alkylation of the carbamate as described above (Scheme 13) affords 14-6, which can be deprotected, as described above, to give 14-7.

SCHEME 15

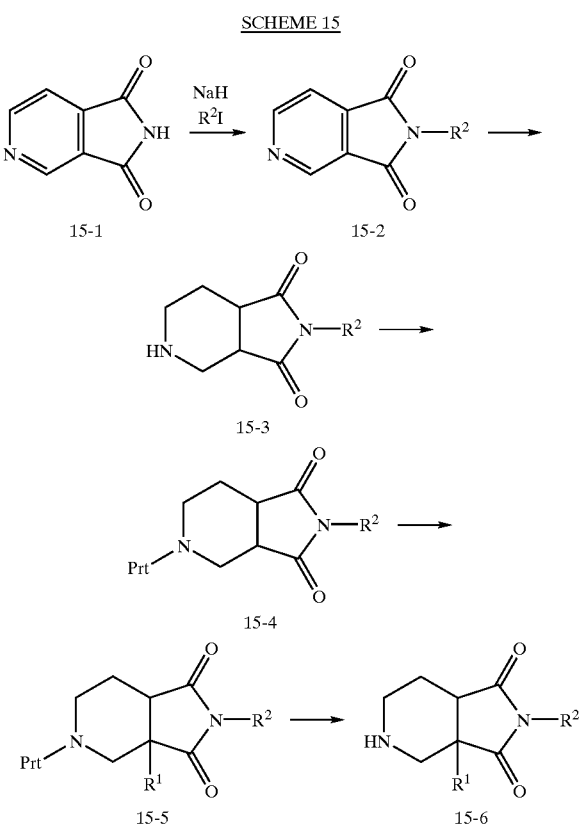

Treating 15-1 with a strong base such as sodium hydride in a suitable solvent such as DMF, followed by treatment with an alkylating agent, such as an alkyl halide, mesylate or tosylate, produces an N-substituted imide of formula 15-2. Reduction of the pyridine ring by catalytic hydrogenation, such as with Pd on carbon in an ethanolic HCl solution converts 15-2 to 15-3. Protection of the nitrogen, such as with a benzyl group, gives 15-4. A compound of the formula 15-5 can be generated upon deprotonation of 154 with a suitable strong base such as LHMDS in a solvent such as THF at a temperature of about −78° C., followed by alkylation with an electrophile such as an alkyl halide such as benzyl bromide. Cleavage of the protecting group, as described above, then gives 15-6.

SCHEME 16

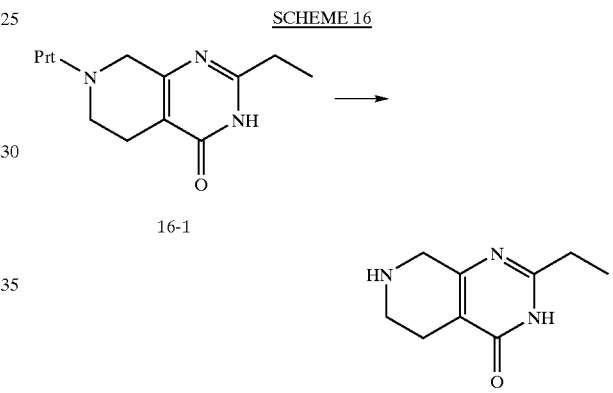

Deprotection of 16-1 as described above produces 16-2.

SCHEME 17

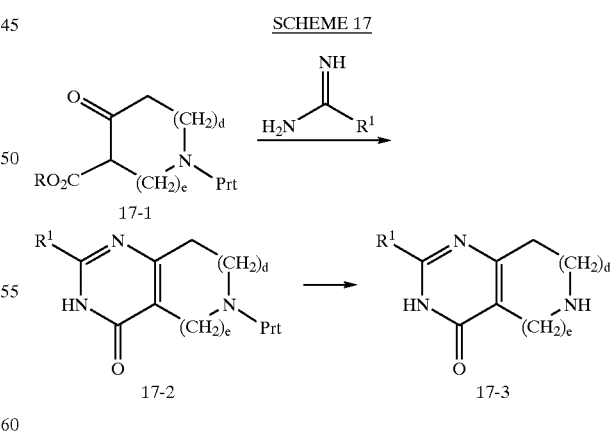

Condensation of 17-1 (R is an alkyl group) with an amidine in a solvent such as ethanol at an elevated temperature, preferably refluxing solvent, produces a heterocyclic intermediate of formula 17-2. Deprotection of 17-2, as described above, gives an intermediate of formula 17-3.

SCHEME 18

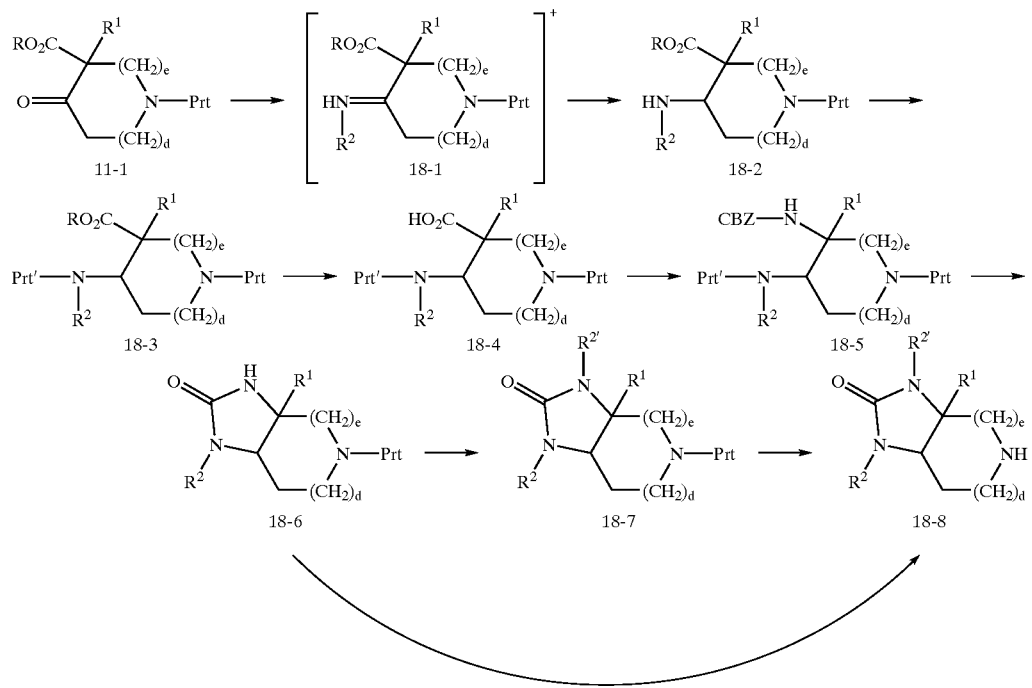

An intermediate amine of formula 18-2 can be prepared from a ketone of formula 11-1 (R is an alkyl group) by reductive amination as described above (see Scheme 8). Protection of the secondary amine in 18-2 produces 18-3. Intermediate carboxylic acids of formula 18-4 can be prepared by hydrolysis of the ester group of formula 18-3 (see Scheme 11). Transformation of 18-4 to 18-5 can be achieved through an intermediate acyl azide as described above (see Scheme 11). Cyclization of an intermediate of formula 18-5 at a suitable temperature after removing Prt' yields an intermediate urea of formula 18-6. Deprotection of 18-6 provides 18-8 where $R^{2'}$ is H. Alternatively, urea 18-6 can be alkylated by deprotonation with a strong base such as sodium hydride, LHMDS, or KHMDS in a suitable solvent such as DMF or THF followed by treatment with an alkylating agent such as an alkyl halide, mesylate or tosylate. Removal of the protecting group transforms 18-7 to 18-8 where $R^2$ and $R^{2'}$ are each alkyl.

SCHEME 19

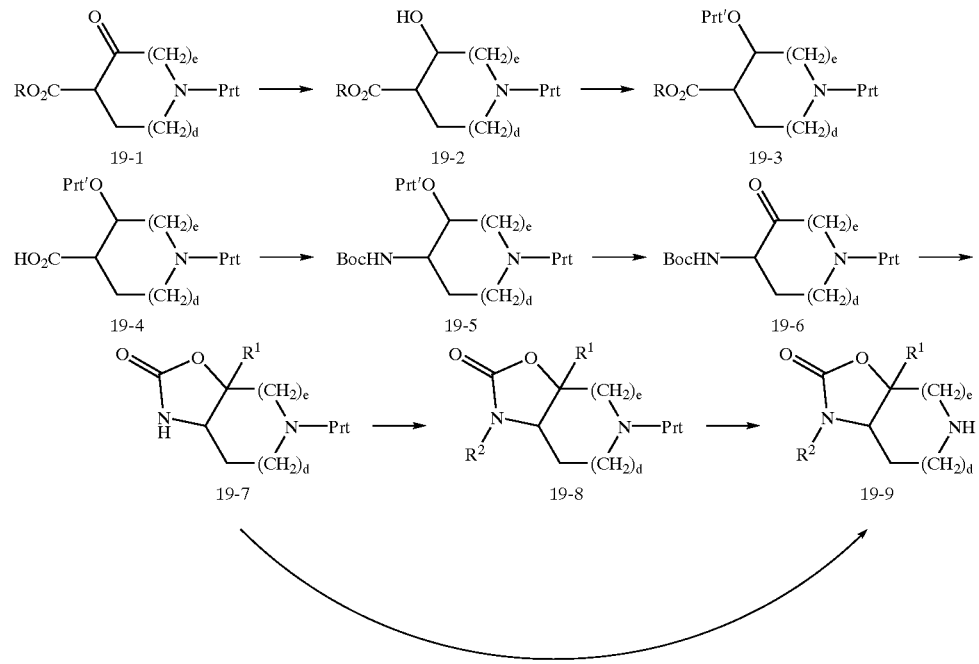

As illustrated in Scheme 19, reduction of a ketoester of formula 19-1, such as with sodium borohydride in methanol, preferably at 0° C., produces an alcohol of formula 19-2. An intermediate of formula 19-3 can be prepared by protection of the hydroxyl group in an intermediate of formula 19-2 with a suitable protecting group, such as forming a tetrahydropyranyl acetal or silyl ether. Transformation of the ester of formula 19-3 to amide 19-5 can be achieved as described above (see Scheme 11). Deprotection of the hydroxy group of 19-5 yields the free alcohol intermediate, which can be oxidized to an intermediate ketone of formula 19 with a suitable oxidizing agent, such as pyridinium chlorochromate or a Swern-type reagent (see Scheme 8). Transformation of 19-6 to a cyclized carbamate of formula 19-7 can be achieved by treating 19-6 with an alkyl metal, such as a Grignard reagent, in a suitable solvent such as THF, followed by cyclization. Removal of the protecting group then yields 19-9 wherein $R^2$ is H. Alternatively, the carbamate of 19-7 may be alkylated as described above (see Scheme 13) to afford 19-8, which can then be deprotected to provide 19-9. Those skilled in the art will recognize that an R1A substituent could have been introduced by alkylating ketoester 19-1.

SCHEME 20

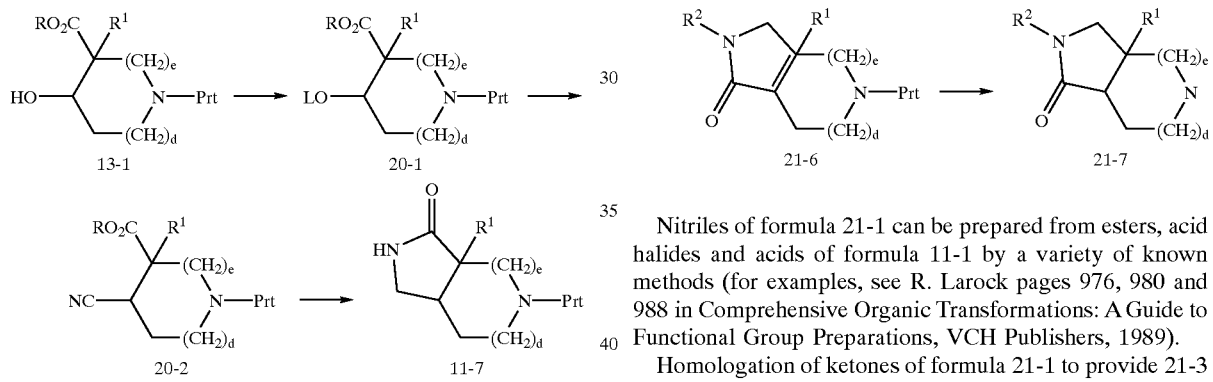

An alternate synthesis of lactam 11-7 is illustrated in Scheme 20. An alcohol of formula 13-1 can be, converted to an intermediate nitrile of formula 20-1 by first activating the hydroxyl of 13-1 (R is an alkyl group), such as with methanesulfonyl chloride or methanesulfonic acid in a suitable solvent, such as methylene chloride in the presence of an amine base. Subsequent reaction of 20-1 (LO- is an activated hydroxyl) with a cyanide salt, such as potassium cyanide, then yields an intermediate nitrile of formula 20-2, which can be transformed to 11-7 by catalytic hydrogenation of the nitrile to amine, which then reacts with the ester group to form lactam (11-7). Those skilled in the art will recognize that an $R^{1A}$ substituent could be introduced by alkylating nitrile 20-2.

SCHEME 21

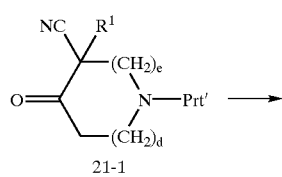

Nitriles of formula 21-1 can be prepared from esters, acid halides and acids of formula 11-1 by a variety of known methods (for examples, see R. Larock pages 976, 980 and 988 in Comprehensive Organic Transformations: A Guide to Functional Group Preparations, VCH Publishers, 1989).

Homologation of ketones of formula 21-1 to provide 21-3 as described above (Scheme 12) yields an aldehyde of formula 21-3. Oxidation of the aldehyde group in 21-3, such as with sodium hypochlorite, provides an acid which can be esterified to give 21-4 by a number of methods described above (Scheme 6). Reduction of the nitrile group in a compound of formula 21-4, such as by catalytic hydrogenation over Pd on carbon, gives an amine which will cyclize to give a lactam of formula 21-5. Deprotection of 21-5 yields 21-7, $R^2$ is H. Alternatively, alkylation of the amide of formula 21-5 as described above (Scheme 11) yields an N-substituted amide of formula 21-6, which can be deprotected to provide 21-7. Those skilled in the art will recognize that an $R^{1A}$ substituent could have been introduced by alkylating ester 21-4.

SCHEME 22

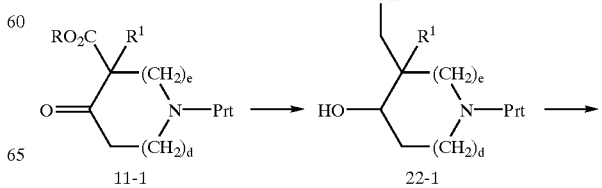

-continued

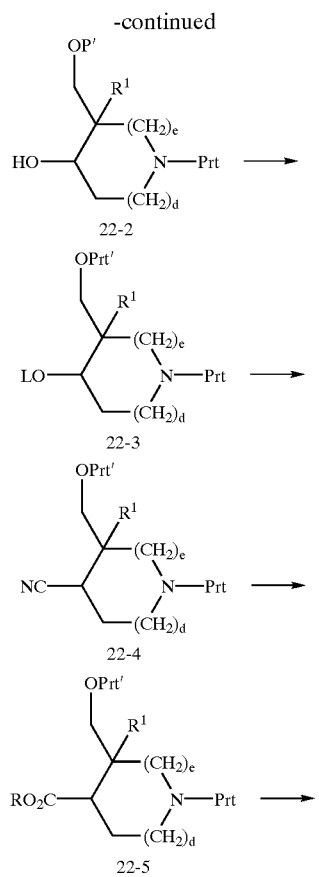

-continued

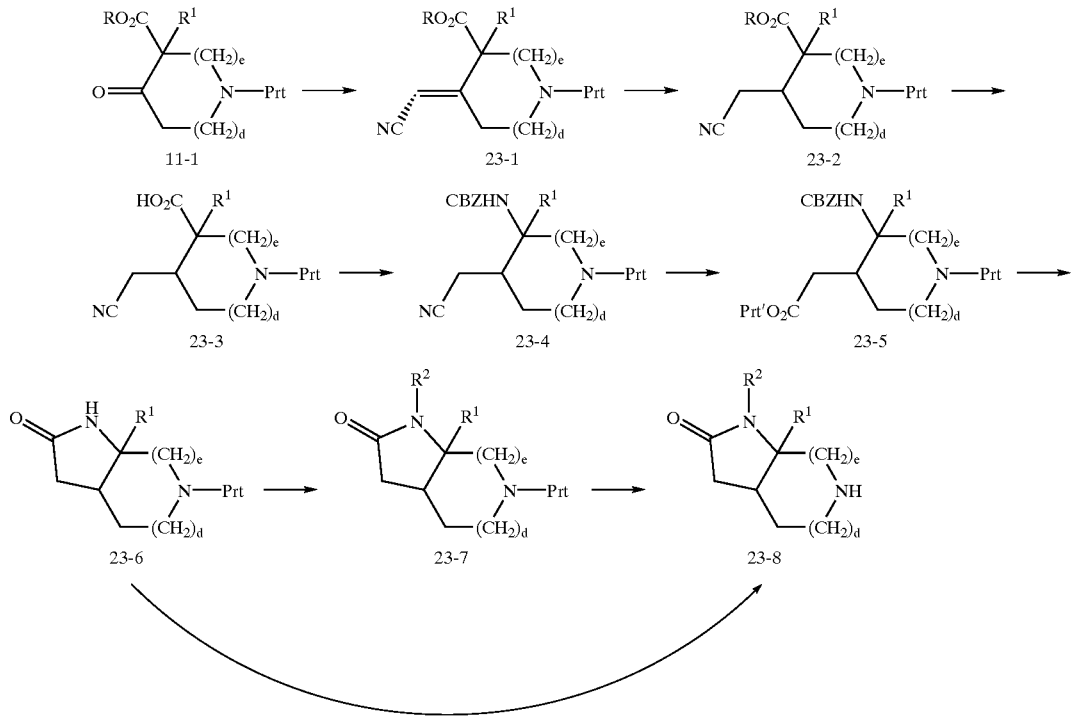

Intermediate alcohols of formula 22-1 can be prepared by reducing the ketone and ester groups of 11-1 (R is an alkyl group), such as with a metal borohydride or lithium aluminum hydride in a suitable solvent such as THF. Selective protection of the primary hydroxyl group of the intermediate of formula 22-1 with a suitable protecting group, such as a trialkylsilyl ether or pivaloyl ester gives a secondary alcohol of formula 22-2. An intermediate nitrile of formula 22-4 can be prepared from the alcohol of formula 22-2 by methods described above (see Scheme 20). An intermediate nitrile of formula 22-4 can be transformed to an ester of formula 22-5 by alcoholysis of nitrile 22-4, for instance with aqueous HCl or sodium hydroxide in ethanol. Removal of the alcohol protecting group and reaction of the hydroxyl group with the adjacent ester group in 22-5 forms a lactone of formula 22-6. Deprotection as described above yields 22-7. Those skilled in the art will recognize that an $R^{1A}$ substituent could have been introduced by treating ketone 11-1 with the appropriate alkyl metal reagent. Substitution ($R^9$, $R^{10}$) adjacent to the lactone oxygen could then be introduced by treating the ester with the appropriate alkyl metal reagent (the ketone would have to be reduced if $R^{1A}$ is not O).

Intermediate α,β-unsaturated nitriles of formula 23-1 can be prepared by olefinating 11-1 (R is an alkyl group) with a reagent such as cyanomethyltriphenylphosphonium chloride and a strong base, such as KHMDS, in a suitable solvent, such as THF. Reduction of the double bond in 23-1, such as with sodium borohydride in pyridine, produces nitrile 23-2. The ester group of formula 23-2 can then be transformed to a carbamate of formula 23-4 by methods described above (see Scheme 11). Alcoholysis of the nitrile of 23-4 in an alcoholic solvent under acidic condition produces an ester of formula 23-5. A lactam of formula 23-6 can be prepared by removal of the CBZ protecting group, followed by cyclization of the amine with the adjacent ester group. Deprotection at this stage provides 23-8, $R^2$ is H. Alternatively, alkylation of the amide (according to Scheme 11) provides an N-subsitituted lactam, which can be converted to 23-8 by deprotection as described above. One skilled in the art will recognize that an $R^{1A}$ substituent could have been introduced by conjugate addition to the unsaturated nitrile (23-1), such as with an alkyl cuprate. In addition, $R^9$, $R^{10}$ substituents can be introduced next to the lactam carbonyl by alkylating nitrile 23-2.

diate of formula 24-4. The cyano group of 24-4 can then be converted to an ester by alcoholysis as described above (Scheme 22). Reaction of the tertiary alcohol with the neighboring ester forms a lactone which can then be deprotected to give 24-5. One skilled in the art will recognize that an $R^{1A}$ substituent could be introduced by alkylating ester 19-3. In addition, $R^9$, $R^{10}$ substituents could be introduced adjacent to the lactone carbonyl by alkylation before final deprotection.

SCHEME 24

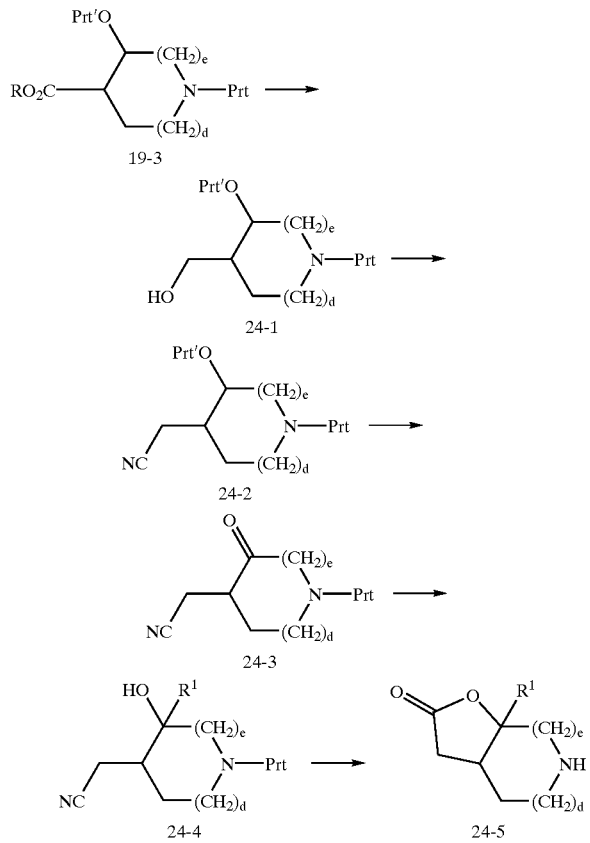

SCHEME 25

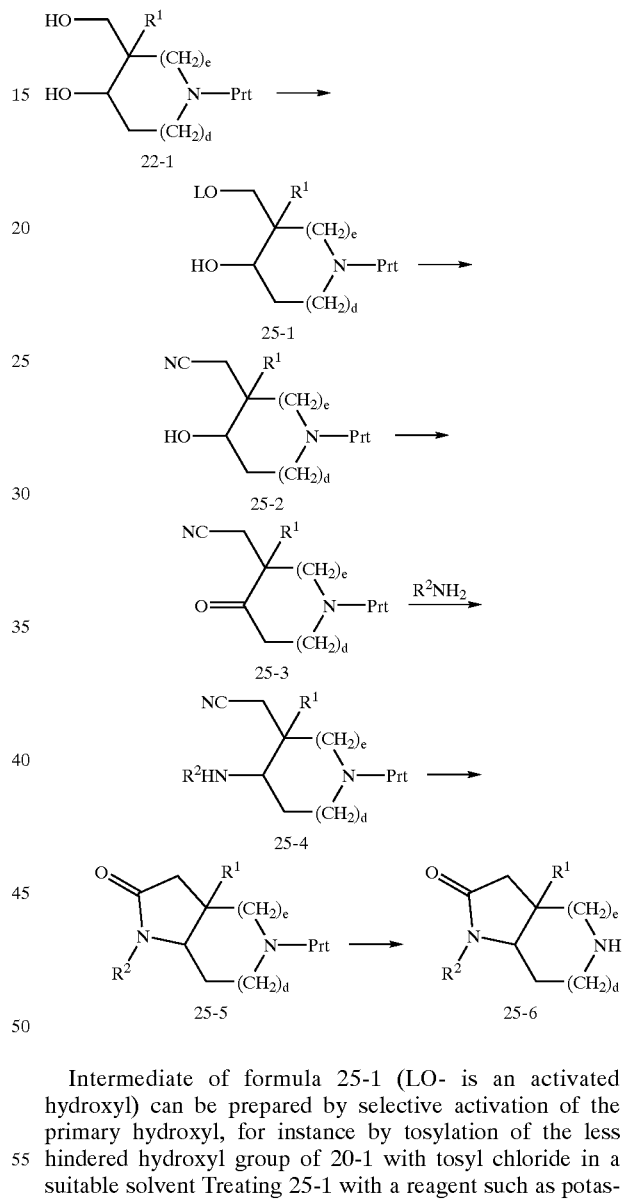

As illustrated in Scheme 24, an alcohol of formula 24-1 can be prepared from 19-3 (R is an alkyl group) by reduction of the ester with a reducing reagent such as lithium borohydride in a solvent such as THF. A nitrile of formula 24-2 can be prepared from the alcohols of formula 24-1 by methods described above (see Scheme 20). Deprotection of the alcohol of 24-2 followed by oxidation of the hydroxyl as previously described (see Scheme 19) produces a ketone 24-3. Treating 24-3 with an alkyl metal such as a Grignard reagent in a suitable solvent such as THF gives an interme- Intermediate of formula 25-1 (LO- is an activated hydroxyl) can be prepared by selective activation of the primary hydroxyl, for instance by tosylation of the less hindered hydroxyl group of 20-1 with tosyl chloride in a suitable solvent Treating 25-1 with a reagent such as potassium cyanide in a suitable solvent produces a nitrile of formula 25-2. Oxidation of the alcohol (see Scheme 19) of formula 25-2 gives a ketone of formula 25-3. Transformation of 25-3 to 25-4 can be achieved by reductive amination as was described above (see Scheme 8). The cyano amine of formula 25-4 can be converted to a lactam of formula 25-5 by treating 25-4 with a strong acid or base in a protic solvent such as ethanol. Removal of the protecting group on the secondary nitrogen can then provide lactam 25-6. One skilled in the art rill recognize that $R^9$, $R^{10}$ substituents could be introduced by alkylation of lactam 25-5.

SCHEME 26

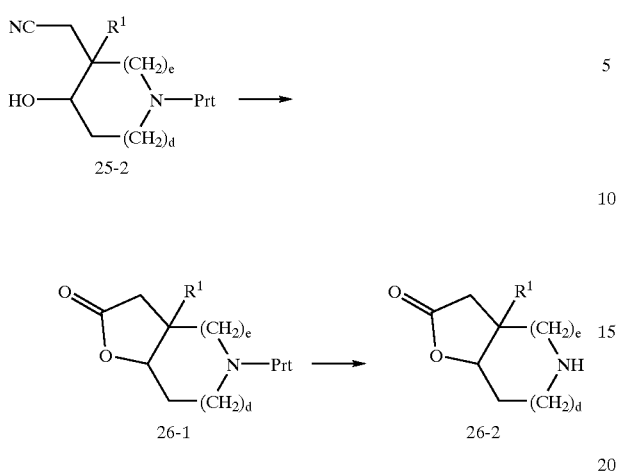

A lactone of formula 26-1 can be prepared by treating a cyano alcohol of formula 25-2 with a strong acid such as HCl, or a strong base such as NaOH, in a protic solvent such as EtOH. Deprotection, as described above, of the secondary amine of formula 26-1 gives 26-2. One skilled in the art will recognize that $R^9$, $R^{10}$ substituents can be introduced by alkylation of lactone 26-1.

SCHEME 27

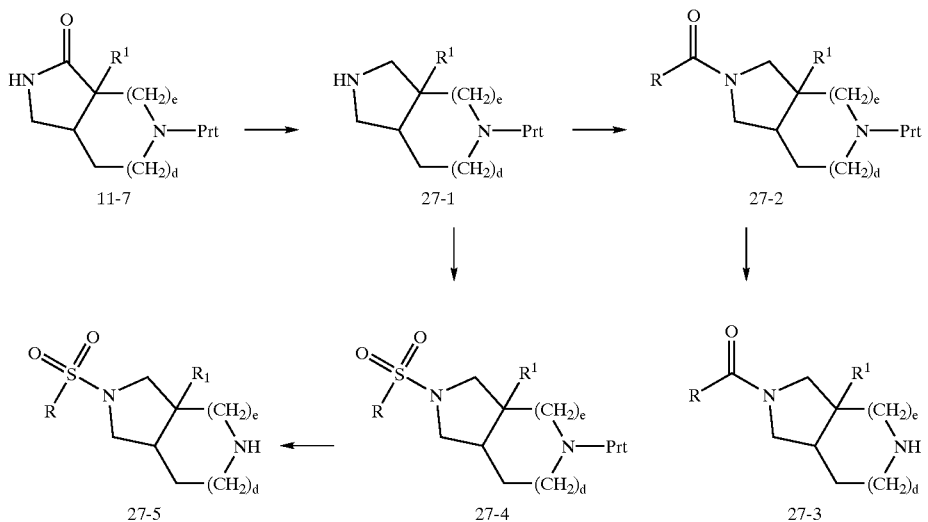

Intermediates of formula 27-1 can be prepared by reducing a lactam of formula 11-7 to a pyrrolidine with a suitable reducing reagent such as borane or lithium aluminum hydride in a suitable solvent such as THF. Treating 27-1 with an acyl chloride of formula RCOCl (where R is an alkyl group) in a suitable solvent produces an intermediate amide of formula 27-2. Removal of the protecting group of the amide of formula 27-2 by the method described previously gives an amide of formula 27-3.

A sulfonamide of formula 27-5 can be prepared by treating 27-1 with a sulfonate such as tosyl chloride in the presence of a base such as pyridine to yield 27-4, followed by removal of the protecting group as previously described.

SCHEME 28

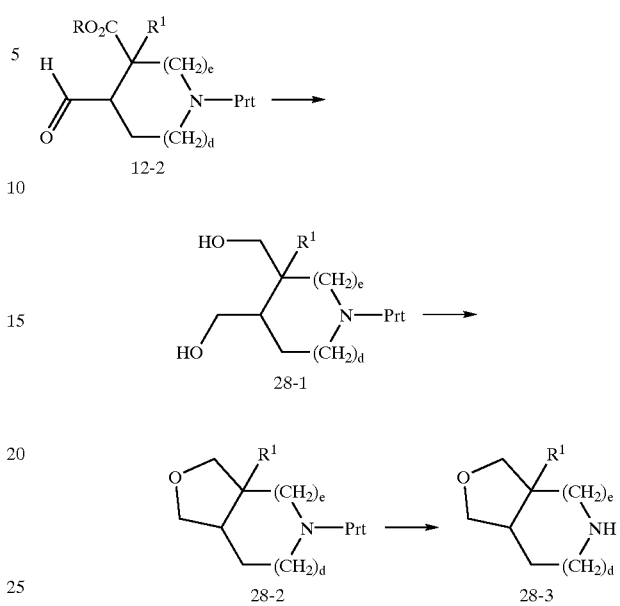

Intermediate diols of formula 28-1 (R is an alkyl group) can be prepared by treating 12-2 with a suitable reducing agent, such as lithium borohydride, in an appropriate solvent, such as THF. Methods for converting diol 28-1 to furan 28-2 include dehydration under acidic conditions, dehydration with a reagent such as $Ph_3P(OEt)_2$, or reaction with a reagent such as toluenesulfonylchloride in the presence of a base followed by displacement of the activated alcohol with the remaining hydroxyl group. Removal of the protecting group from 28-2 subsequently forms a compound of formula 28-3. One skilled in the art will recognize that an $R^{14}$ substituent can be added by alkylating aldehyde 12-2. In addition, $R^9$, $R^{10}$ substituents can be introduced by treating 12-2 with an alkyl metal reagent.

SCHEME 29

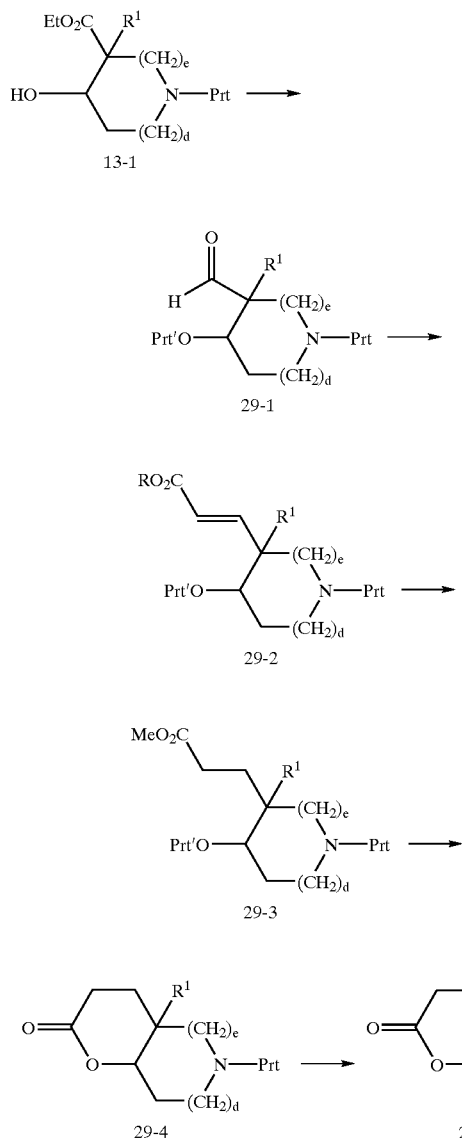

Intermediate aldehydes of formula 29-1 can be prepared by protecting the secondary alcohol of 13-1 such as with a silyl ether, followed by reduction of the ester with a reducing reagent such as diisobutylaluminum hydride at −78° C. in a suitable solvent Alternatively, 13-1 can be reduced to the primary alcohol with a reagent such as lithium borohydride, and then oxidized to the aldehyde with a variety of reagents described above (see Scheme 8). Homologation of aldehydes of formula 29-1 to saturated esters of formula 29-3 can be performed as previously described (see similar homologation of ketones in Scheme 11). Deprotection of the secondary alcohol of 29-3, followed by cyclization produces lactones of formula 29-4. Deprotection of 294 will then give 29-5. An $R^9$ substituent β to the lactone carbonyl may be introduced by conjugate addition to unsaturated ester 29-2, such as with an alkyl cuprate. In addition, $R^9$, $R^{10}$ substituents could be introduced next to the lactone carbonyl by alkylating lactone 294.

SCHEME 30

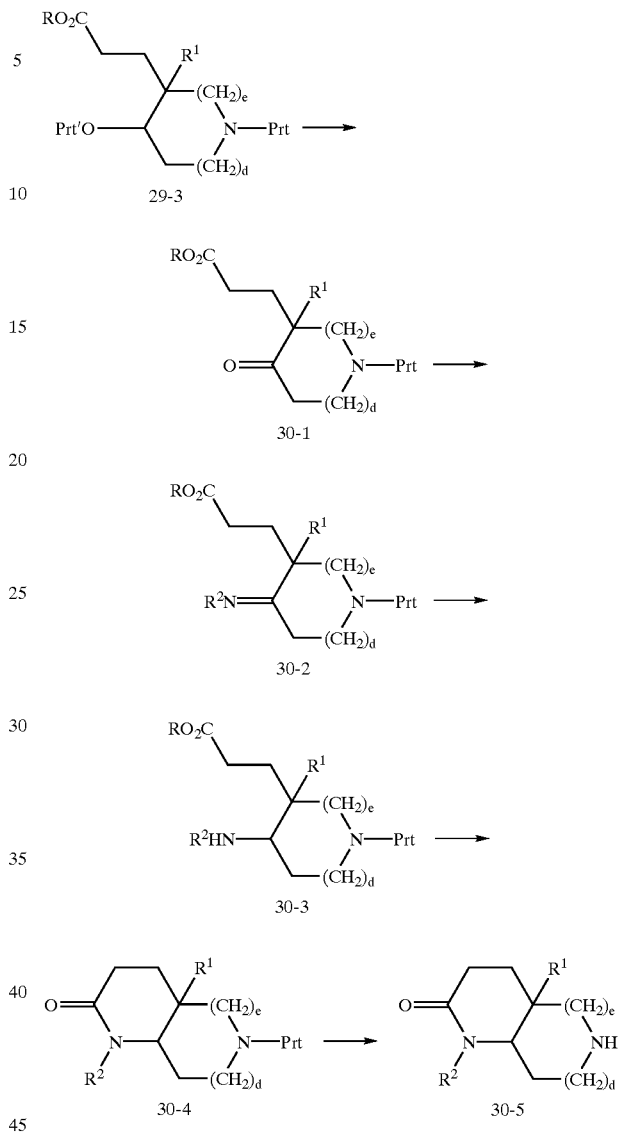

Intermediate ketones of formula 30-1 can be prepared by deprotecting the secondary hydroxyl of 29-3 (R is an alkyl group), followed by oxidation of the alcohol to a ketone (see Scheme 19). Reductive amination of 30-1 with a primary amine as previously described (see Scheme 8) produces intermediate 30-3. Cyclization of 30-3 at a suitable temperature yields a lactam of formula 304, which can be deprotected to give 30-5. One skilled in the art will recognize that $R^9$, $R^{10}$ substituents can be introduced by alkylation of lactam 304.

SCHEME 31

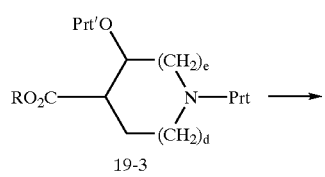

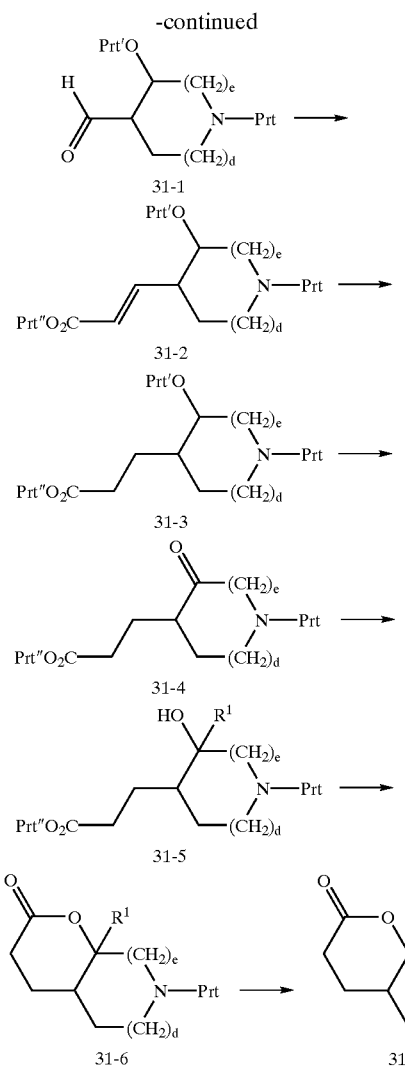

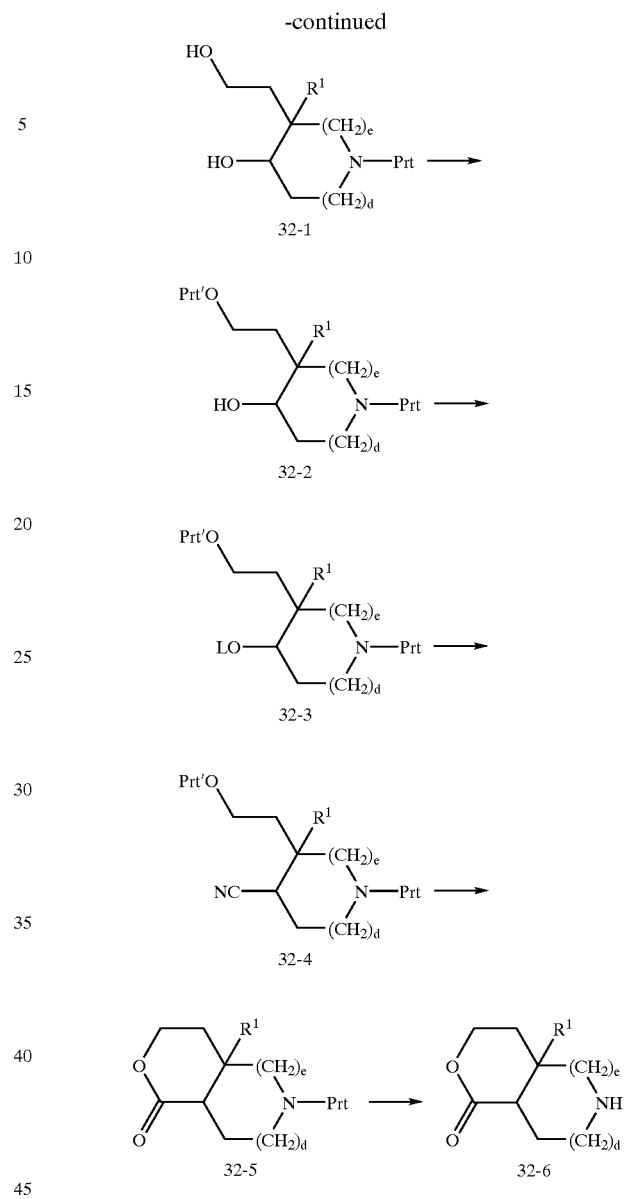

Homologation of 19-3 (R is an alkyl group) to an ester of formula 31-3 can be performed analogously to routes described above (see Scheme 29). Removal of Prt' of 31-3 gives a secondary alcohol which can be oxidized as was previously described (see Scheme 19) to produce a ketone of formula 31-4. Treating 31-4 with an alkyl metal reagent, such as a Grignard reagent, in a suitable solvent produces intermediate 31-5, which can be cyclized to form lactone 316. Removal of the protecting group then produces 31-7. One skilled in the art will recognize that an $R^{1A}$ substituent may be introduced by alkylation of ester 19-3. A substituent β to the lactone carbonyl may be introduced by conjugate addition to unsaturated ester 31-2, such as with an alkyl cuprate. Also, $R^9$, $R^{10}$ substituents can be introduced next to the lactone by alkylation of 316.

SCHEME 32

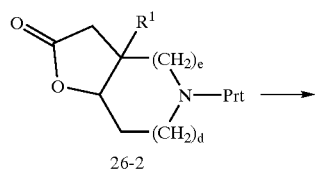

Intermediate diols of formula 32-1 can be prepared by reducing the lactone group of 26-2 with a reagent such as lithium aluminum hydride in a suitable solvent such as THF at a suitable temperature. Selective protection at the less hindered hydroxy group of 32-1, such as with t-butyldimethylsilyl chloride using triethylamine in the presence of DMAP in a solvent such as dichloromethane, produces alcohol 32-2. Conversion of alcohol 32-2 to a nitrile of formula 324 may be accomplished as described above (LO— is an activated hydroxyl group) (see Scheme 20). Alcoholysis of the cyano group of formula 32-4 (see Scheme 22), deprotection of the alcohol, and subsequent lactonization forms lactones of formula 32-5. Deprotection of an amine of formula 32-5 gives a lactone of formula 326. One skilled in the art will recognize that $R^9$, $R^{10}$ substituents can be introduced β- to the ring oxygen in lactone 32-6 by alkylating lactone 26-2. Substitution α to the lactone ring oxygen may be introduced by treating 26-2 with an alkyl metal reagent.

SCHEME 33

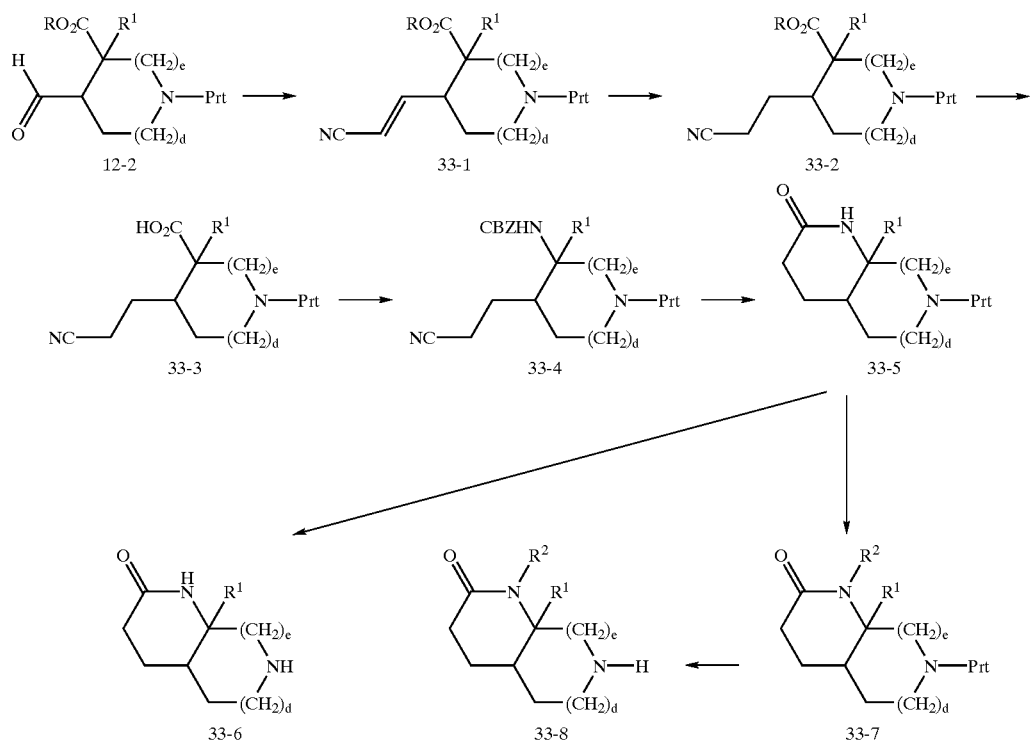

Intermediate nitriles of formula 33-2 can be prepared by homologating 12-2 (R is an alkyl group), analogous to the ketone homologation described in Scheme 23. Conversion of ester 33-2 to carbamates of formula 33-4 can be accomplished as described above (see Scheme 11). Alcoholysis of the cyano group of 33-4 as described above (see Scheme 22) and removal of the CBZ protecting group, followed by cyclization of the amine with the adjacent ester group produces a lactam of formula 33-5. Deprotection of 33-5 gives the lactam of formula 33-6.

Alternatively, alkylation of 33-5 in the usual fashion (see Scheme 11) gives 33-7, which can be deprotected to give 33-8. One skilled in the art will recognize that an $R^{1A}$ substituent may be introduced by alkylating aldehyde 12-2. An $R^9$ substituent may be introduced by conjugate addition to the unsaturated nitrile (33-1). $R^9$, $R^{10}$ substitution can be introduced next to the lactam by alkylation of 33-7.

SCHEME 34

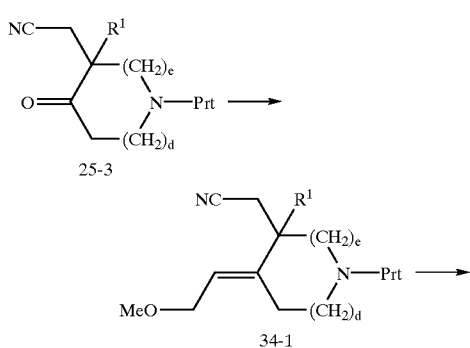

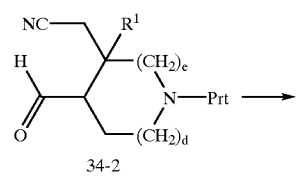

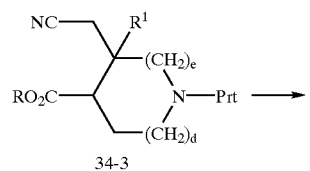

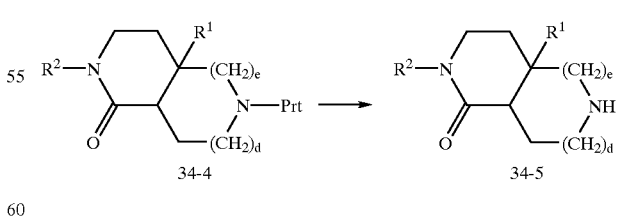

The homologation of 25-3 to give a lactam of formula 34-5 can be analogously performed according to the procedures described in Scheme 21. One skilled in the art will recognize that an $R^{1A}$ substituent may be introduced by alkylating 34-4 (R is an alkyl group). $R^9$, $R^{10}$ substitution may be introduced by alkylating nitrile 341.

SCHEME 35

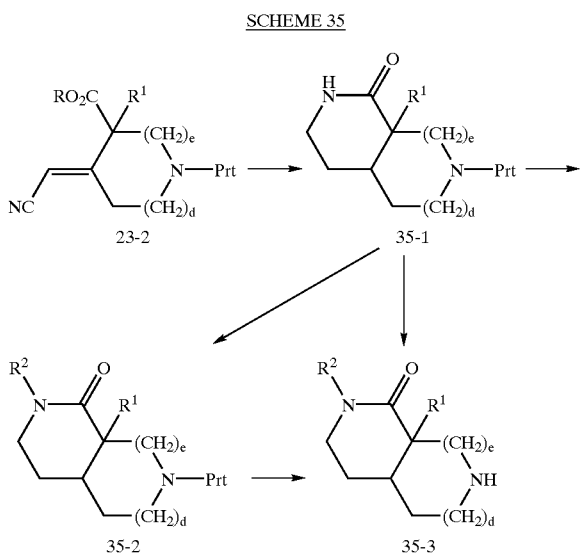

As illustrated in Scheme 35, catalytic hydrogenation of a nitrile of formula 23-2 (R is an alkyl group) gives an amine, followed by cyclization of the amine with the adjacent ester group to give lactams of formula 35-1. Deprotection of 35-1 gives 35-3, $R^2$ is H. Alternatively, alkylation of lactam 35-1 as described above (see Scheme 11) provides N-substituted amides of formula 35-2. Deprotection of 35-2 affords 35-3. One skilled in the art will recognize that an $R^{1A}$ substituent may be introduced by conjugate, addition to the unsaturated nitrile.

SCHEME 36

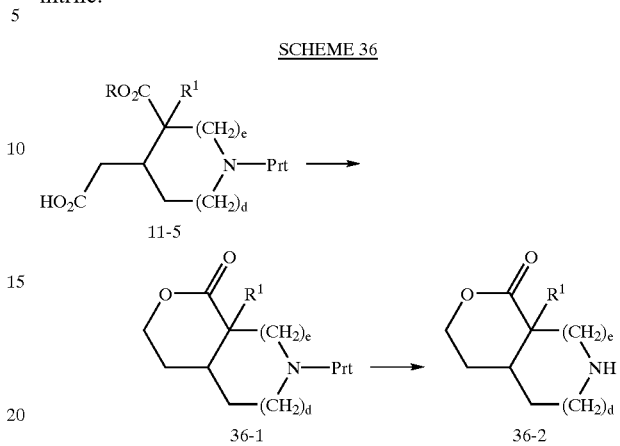

As illustrated in Scheme 36, selective reduction of the carboxylic acid group of 11-5 to an alcohol, such as by treating 11-5 (R is an alkyl group) with borane in a suitable solvent, followed by cyclization of the alcohol and ester produces a lactone of the formula 36-1. Deprotection of 36-1 then gives 36-2.

SCHEME 37

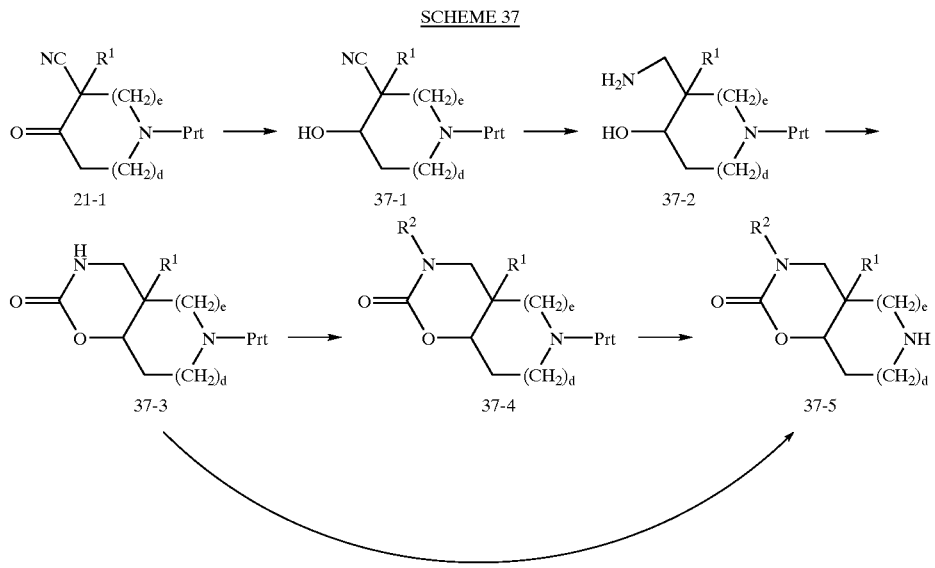

Intermediate alcohols of formula 37-1 can be prepared by reducing the ketone of 21-1, such as with sodium borohydride in a solvent such as methanol at a temperature of about 0° C. Reduction of the cyano group to an amine, such as by catalytic hydrogenation, affords aminoalcohol 37-2. Treating 37-2 with a reagent like CDI or other phosgene equivilent in the presence of a base like TEA (see Scheme 14) produces a cyclized carbamate of formula 37-3. Deprotection of 37-3 then gives 37-5, $R^2$ is H. Alternatively, 37-3 may be alkylated as described above (see Scheme 13) to give an N-substituted carbamate of formula 374, which is deprotected to give 37-5. One skilled in the art will recognize that an $R^{1A}$ substituent may be introduced by addition to ketone 21-1.

SCHEME 38

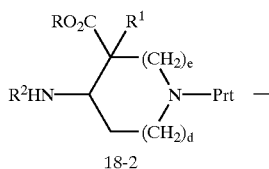

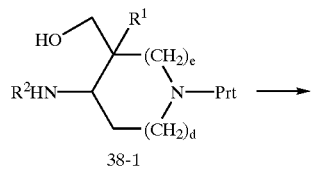

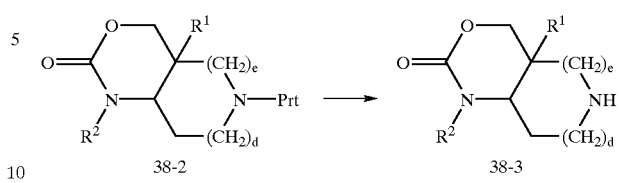

Intermediate aminoalcohols of formula 38-1 can be prepared by reducing an ester of formula 18-2 (R is an alkyl group), such as with lithium borohydride. Treating 38-1 with a phosgene equivalent as described in Scheme 14 produces a cyclized carbamate of formula 38-2. Deprotection subsequently provides 38-3.

SCHEME 39

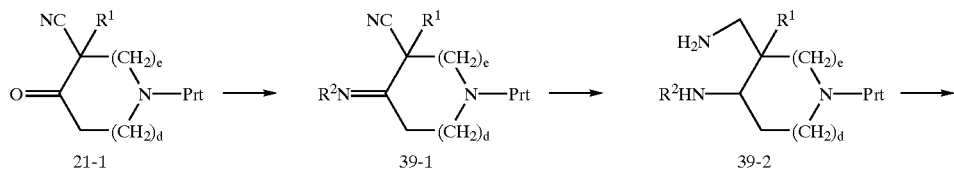

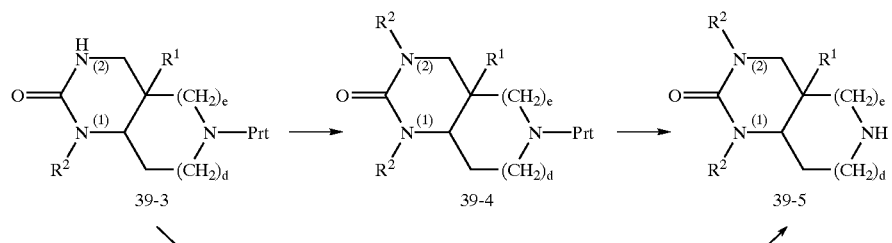

Intermediate imines of formula 39-1 can be prepared by condensing the ketone of 21-1 with a primary amine under dehydrating conditions, such as azeotropic distillation using a solvent like benzene. Catalytic hydrogenation to reduce the nitrile and imine converts 39-1 to 39-2. Treating 39-2 with a reagent like CDI, phosgene, or triphosgene in the presence of a base like TEA produces the cyclized and N-substituted ureas of formula 39-3. Deprotection of this material provides 39-5 where the $R^2$ attached to the (2)-nitrogen is H. Alkylation of 39-3, such as with sodium hydride and an alkyl halide produces the N,N'-substituted ureas of formula 39-4, which can be deprotected to provide 39-5 where the $R^2$ attached to the (2)-nitrogen is an alkyl group.

SCHEME 40

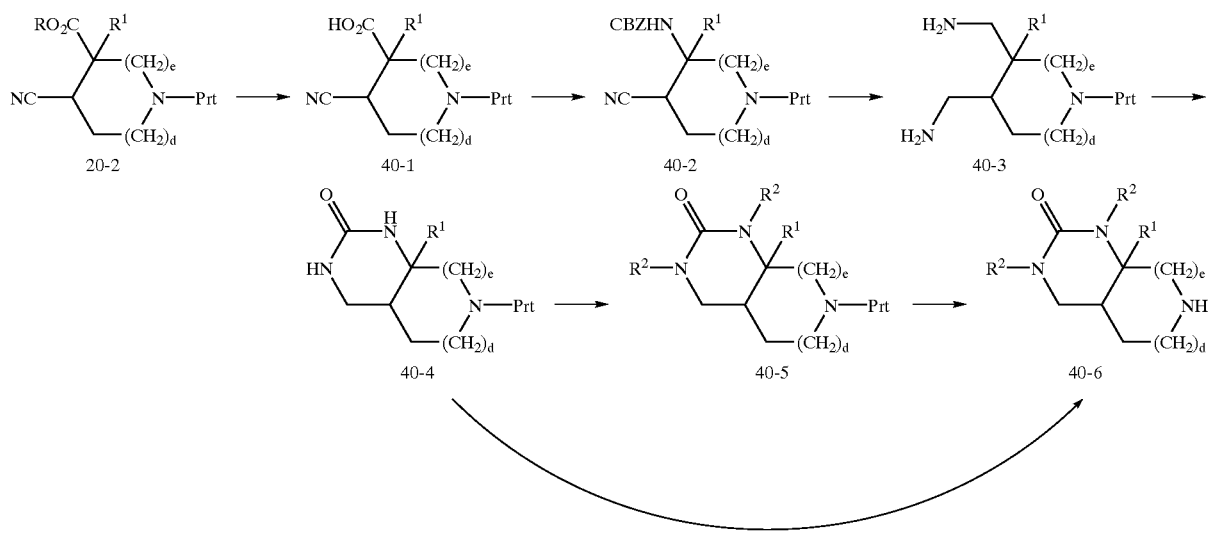

As illustrated in Scheme 40, ester 20-2 (R is an alkyl group) can be converted to carbamate 40-2 as described above (see Scheme 11). Catalytic hydrogenation of 40-2 will reduce the nitrile and cleave the CBZ group to provide a diamine of formula 40-3. Acylating 40-3 with a reagent such as CDI, phosgene, or triphosgene in the presence of a base like TEA produces the cyclized ureas of formula 40-4. Deprotection at this stage provides 40-6 where each $R^2$ is H. Alternatively, alkylation of 40-4, such as by deprotonation with a strong base like sodium hydride followed by reaction with an alkylating reagent like an alkyl halide, tosylate or mesylate produces the N,N'-substituted ureas of formula 40-5. Deprotection then provides 40-6 where each $R^2$ is alkyl. One skilled in the art will recognize that an $R^{1A}$ substituent may be introduced by alkylation of nitrile 20-2.

Intermediate esters of formula 41-1 (R is an alkyl group) can be prepared by alcoholysis of the cyano group in 40-2 with ethanolic HCl. Reducing the ester group in 41-1, such as with lithium borohydride in THF produces an alcohol of formula 41-2. Catalytic hydrogenation to remove the CBZ group to yield an amine as previously described converts 41-2 to 41-3. Treating 41-3 with a reagent like CDI or other phosgene equivalent in the presence of a base like TEA produces a carbamate of formula 41-4. Deprotection at this stage provides 416 where $R^2$ is H. Alternatively, transformation of 41-4 to N-substituted carbamates of formula 41-5 can be achieved by deprotonating 41-4 with a stong base such as sodium hydride in a solvent like DMF, followed by alkylation with a reagent such as an alkyl halide, tosylate or mesylate. Deprotection then converts 41-5 to 416 where $R^2$ is alkyl.

SCHEME 41

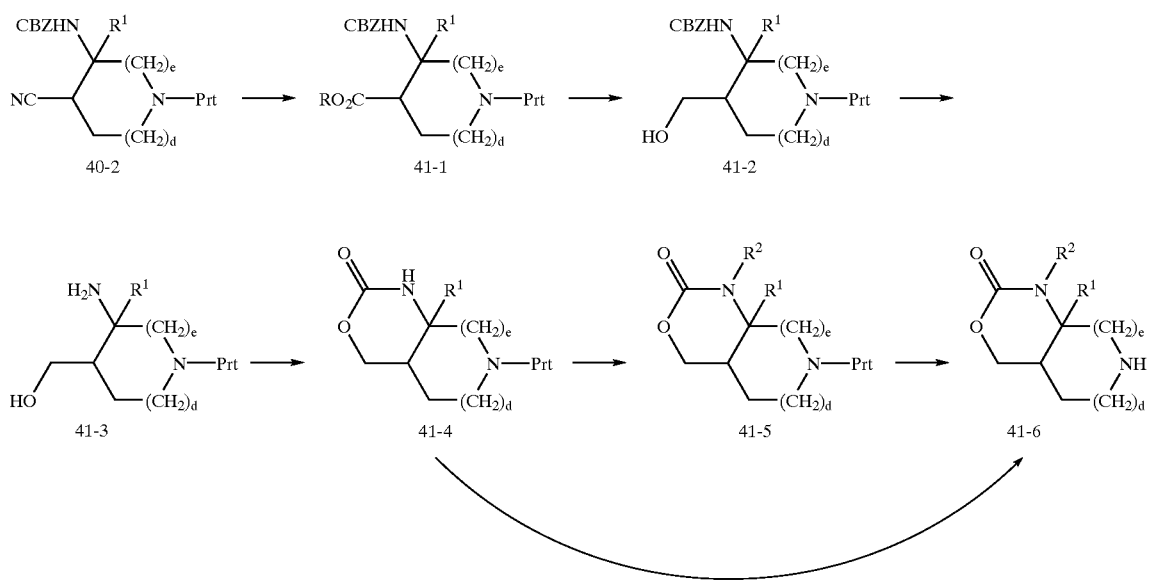

SCHEME 42

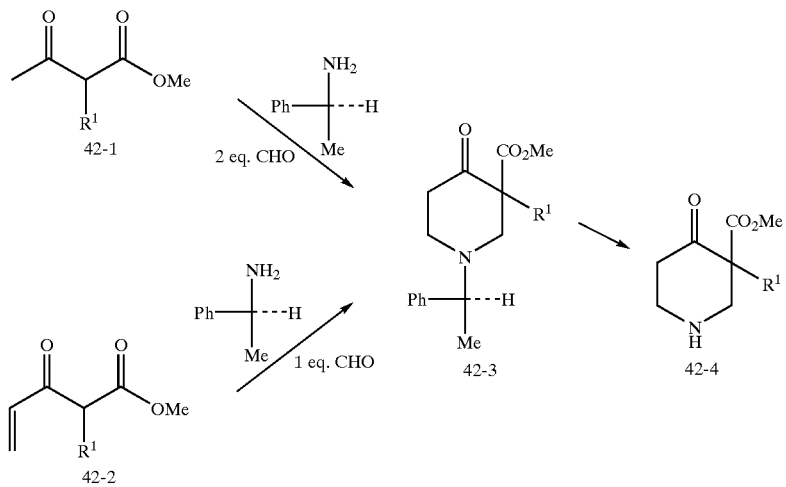

Reaction of a ketoester of formula 42-1 with a chiral amine such as alpha-methylbenzylamine with a suitable aldehyde such as formaldehyde, or reaction of a vinyl ketoester of formula 42-2 with a chiral amine such as alpha-methylbenzylamine with a suitable aldehyde such as formaldehyde, affords a compound of formula 42-3 via a double Mannich reaction. Compound 42-3 is equivalent to 11-1 where d and e are 1, and may be deprotected with a suitable catalyst such as palladium in the presence of hydrogen to give 42-4. In addition, 42-3 could be isolated as a single diastereomer (by selective cyclization or separation of diastereomers), thereby providing 424 as a single enantiomer.

SCHEME 43

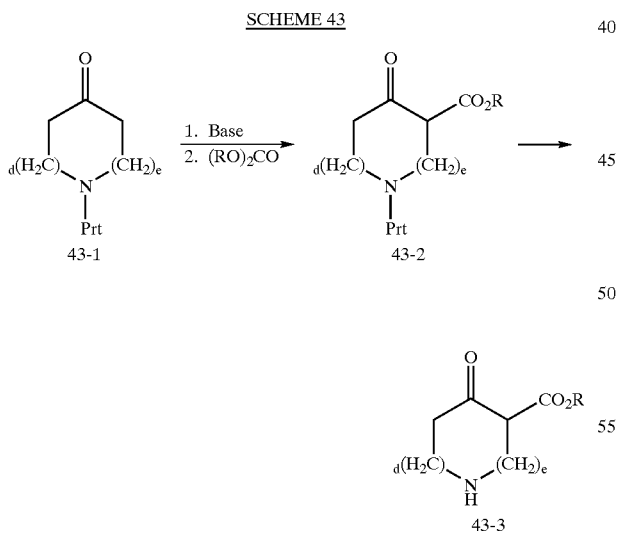

Treatment of a compound of formula 43-1 with a base such as sodium hydride in a solvent such as DMF followed by treatment with diethylcarbonate generates the ethyl ester of compound 43-2 (R is an alkyl group). Deprotection of the amine transforms 43-2 into 43-3. It will be recognized by one skilled in the art that 191 is equivalent to 43-3.

SCHEME 44

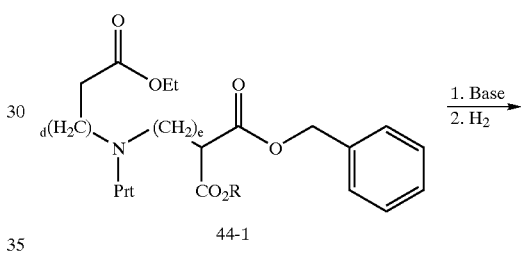

Treatment of a malonic ester of formula 44-1 (R is an alkyl group) with a base such as sodium hydride in a solvent such as DMF and subsequent hydrogenolysis of the benzyl group with hydrogen and a catalyst such as palladium in a suitable solvent such as methanol produces the ester of formula 43-2. Deprotection of the amine generates compounds of formula 43-3. It will be recognized by one skilled in the art that 19-1 is equivalent to 43-3.

SCHEME 45

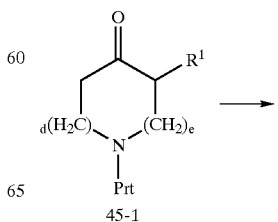

-continued

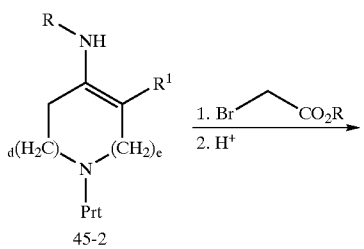
45-2

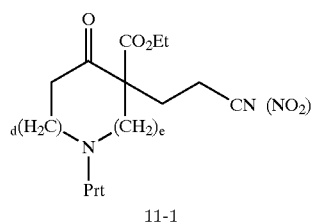
11-1

Treatment of a ketoester of formula 43-3 with an olefin such as acrylonitrile or nitroethylene generates a ketoester of formula 11-1 where $R^1$ is $CH_2CH_2CN$ or $R^1$ is $CH_2CH_2NO_2$.

SCHEME 48

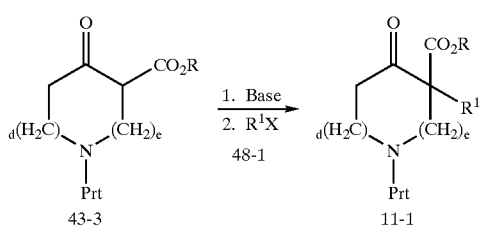

Treatment of an ester of formula 43-3 (R is an alkyl group) with a base such as sodium hydride in a solvent such as DMF followed by an alkyl halide 48-1 generates a compound of formula 11-1 as illustrated in Scheme 48.

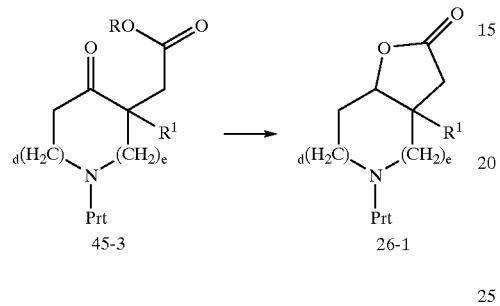

Treatment of a ketone of formula 45-1 with a secondary amine such as piperidine in a suitable solvent such as benzene with removal of water affords an enamine of formula 45-2 (each R is an alkyl group). Alkylation of the enamine with an alpha-haloester such as ethylbromoacetate in a suitable solvent such as benzene or THF using a suitable base such as LDA or $NaN(SiMe_3)_2$ affords a ketoester of formula 45-3. Reduction with a mild reducing agent such as sodium borohydride in methanol and subsequent cyclization then affords 26-1.

SCHEME 46

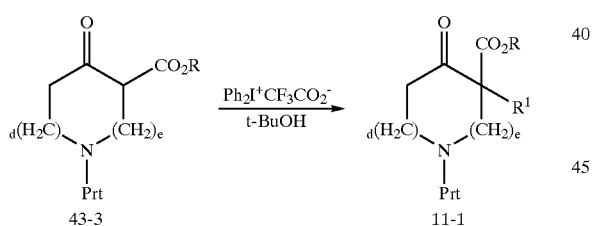

Treatment of a ketoester of formula 43-3 (R is an alkyl group) with an iodonium salt such as diphenyliodonium trifluoroacetate in a suitable solvent such as t-butanol generates a ketoester of formula 11-1 where $R^1$ is phenyl. See Synthesis, (9), 1984 p. 709 for a detailed description.

SCHEME 47

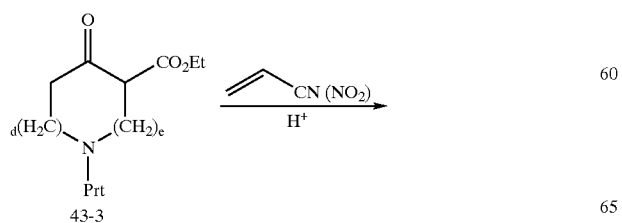

SCHEME 49

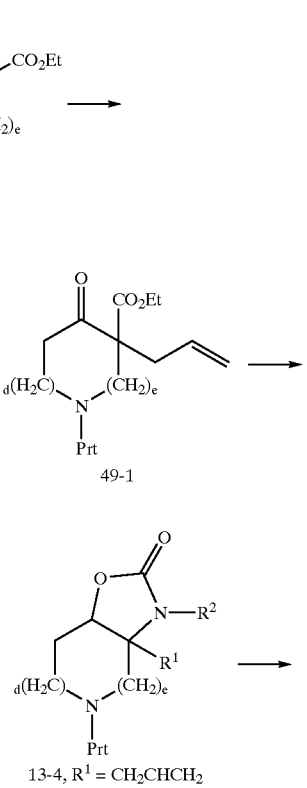

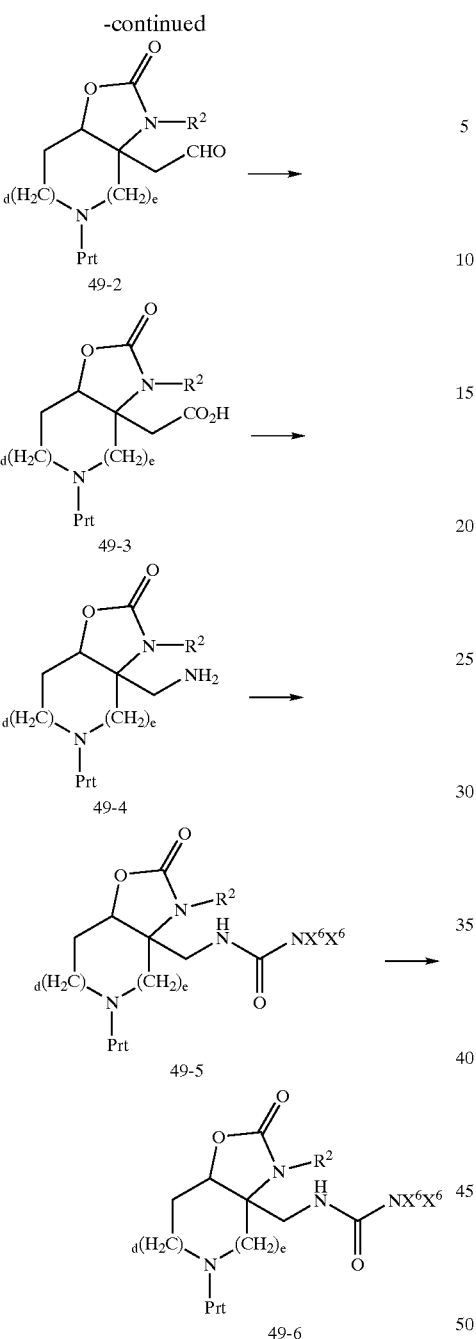

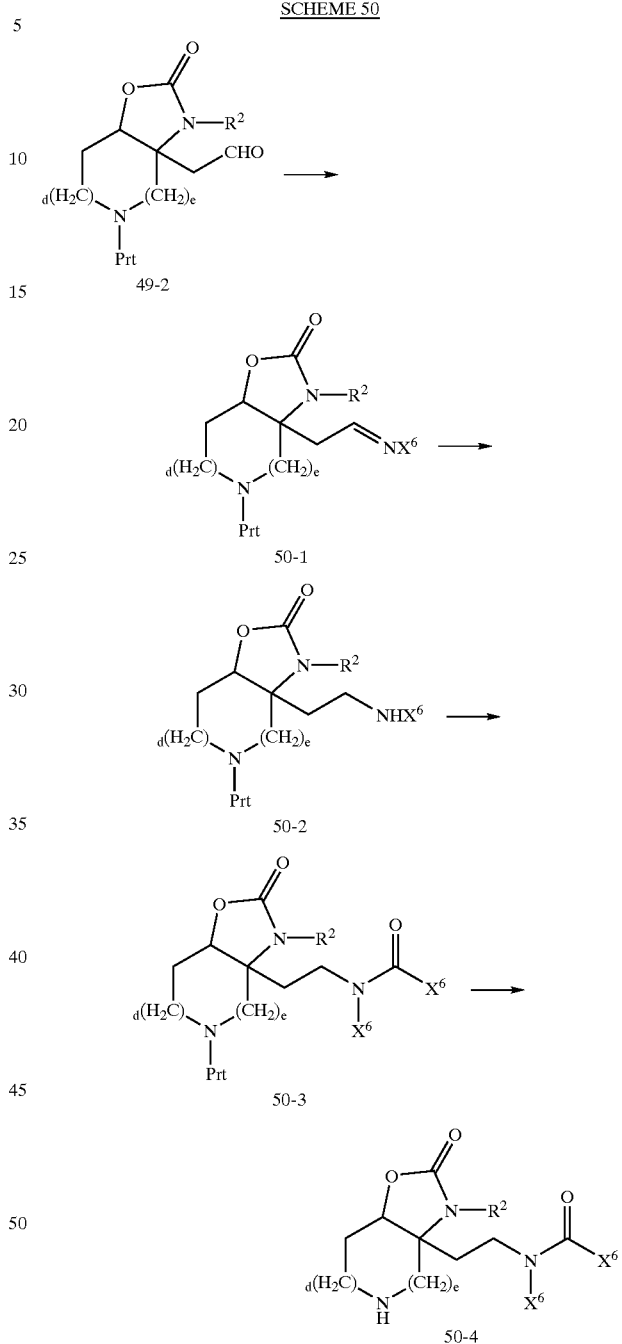

SCHEME 50

Treatment of a ketoester of formula 43-2 with allyl bromide and a suitable base such as sodium hydride in a suitable solvent such as DMF affords a ketoester of formula 49-1 (11-1, $R^2$ is allyl). Compound 49-1 may then be converted to 13-4 as described in Scheme 13. Ozonolysis of 13-4 in a suitable solvent such as methylene chloride followed by treatment with a reducing agent such as dimethylsulfide affords an aldehyde of formula 49-2. Oxidation of 49-2 affords a carboxylic acid of formula 49-3. Curtius rearrangement of 49-3, followed by hydrolysis of the intermediate isocyanate affords a primary amine of formula 49-4. Treatment of a compound of formula 49-4 with an isocyanate or carbamate affords a urea of formula 49-5. Deprotection of the nitrogen affords compounds of formula. 496 (13-5, $R^1$ is $CH_2NHCONX^6X^6$). Those skilled in the art will recognize that other heterocycles, prepared in previous schemes, could be transformed analogously to the conversion of 13-4 to 49-6.

Treatment of a compound of formula 49-2 with a primary amine of formula $HNX^6$ affords an imine of formula 50-1. Reduction of a compound of formula 50-1 affords a compound of formula 50-2. Treatment of a compound of formula 50-2 with an acylating agent affords a compound of formula 50-3. Deprotection of the nitrogen affords compounds of formula 50-4 (13-5, $R^1$ is $CH_2CH_2NX^6COX^6$). Those skilled in the art will recognize that other heterocycles, prepared in previous schemes, could be transformed in a manner analogous to the conversion of 49-2 to 50-4.

SCHEME 51

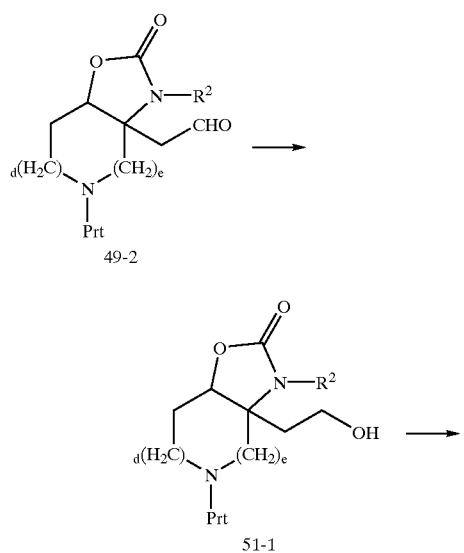

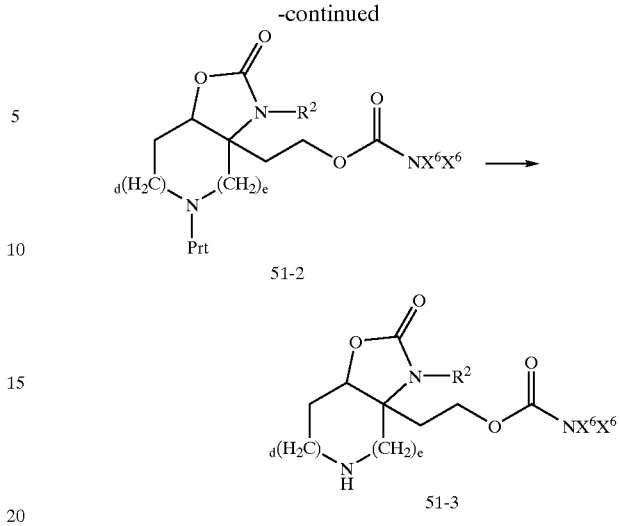

Treatment of a compound of formula 49-2 with a reducing agent such as sodium borohydride affords a compound of formula 51-1. Reaction of 51-1 with an acylating agent such as an isocyanate or carbamate affords compounds of formula 51-2. Deprotection of the nitrogen affords compounds of formula 51-3. Those skilled in the art will, recognize that other heterocycles, prepared in previous schemes, could be transformed in a manner analogous to the conversion of 49-2 to 51-3.

SCHEME 52

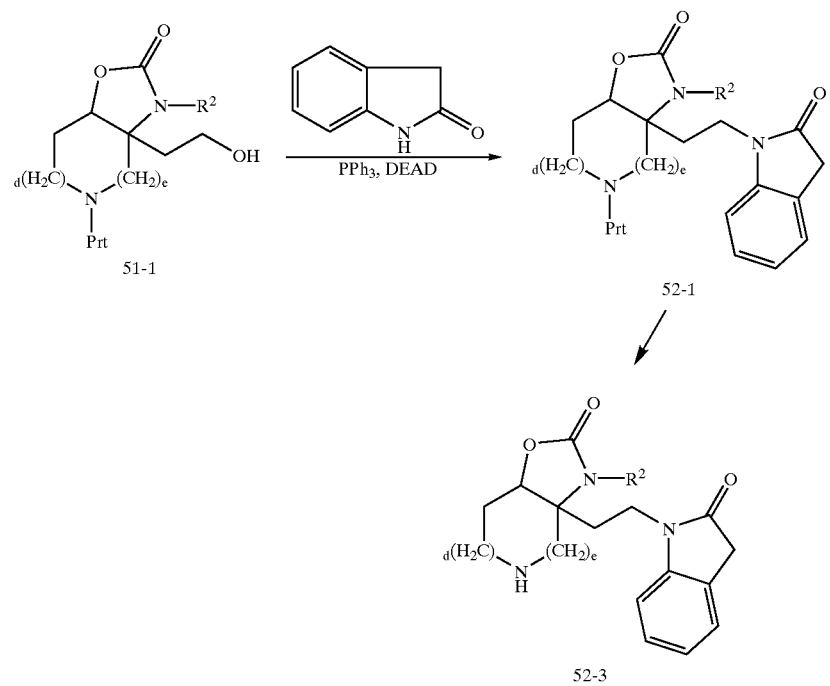

Treatment of a compound of formula 51-1 with a phosphine such as triphenyl phosphine and an azo compound such as diethylazodicarboxylate and an oxindole affords a compound of formula 52-1. Deprotection of the nitrogen affords the compound of formula 52-3. Those skilled in the art will recognize that other heterocycles, prepared in previous schemes, could be transformed in a manner analogous to the conversion of 49-2 to 52-3.

SCHEME 53

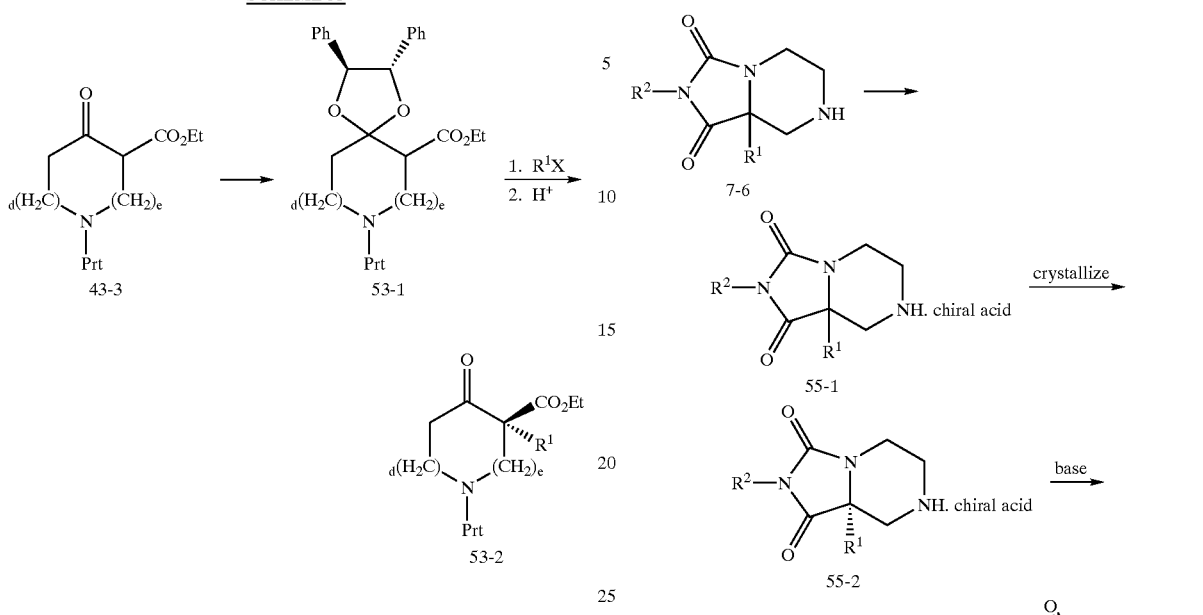

Treatment of a ketoester of formula 43-3 with a chiral diol and add catalyst with removal of water in a suitable solvent such as benzene affords a chiral ketal like formula 53-1. Alkylation of 53-1 with an alkyl halide in the presence of a base such as LDA followed by acid-catalyzed hydrolysis of the ketal affords chiral ketoesters of formula 53-2. Ketoester 53-2 is a single enantiomer of 11-1 and may homologated in a similar fashion to give various heterocycles.

SCHEME 54

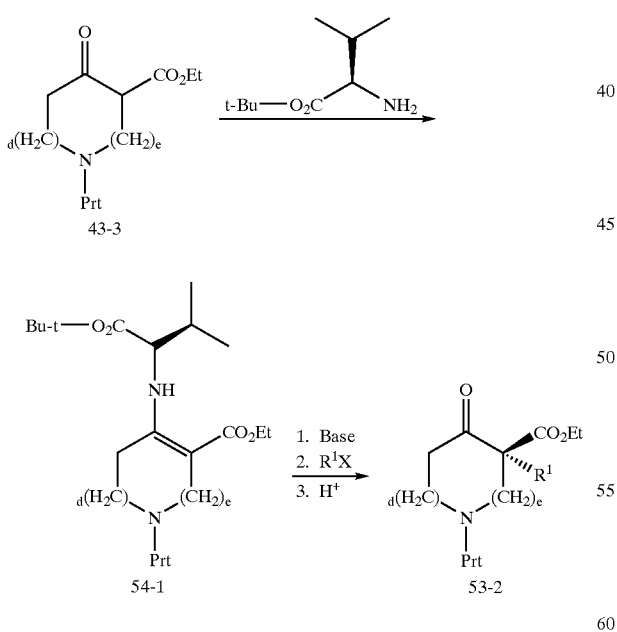

Treatment of a ketoester of formula 43-3 with a chiral amino acid ester such as valine t-butyl ester affords a chiral enamine of formula 54-1. Alkylation of 54-1 with an alkyl halide in the presence of a base such as LDA followed by acid-catalyzed hydrolysis of the enamine affords chiral ketoesters of formula 53-2.

SCHEME 55

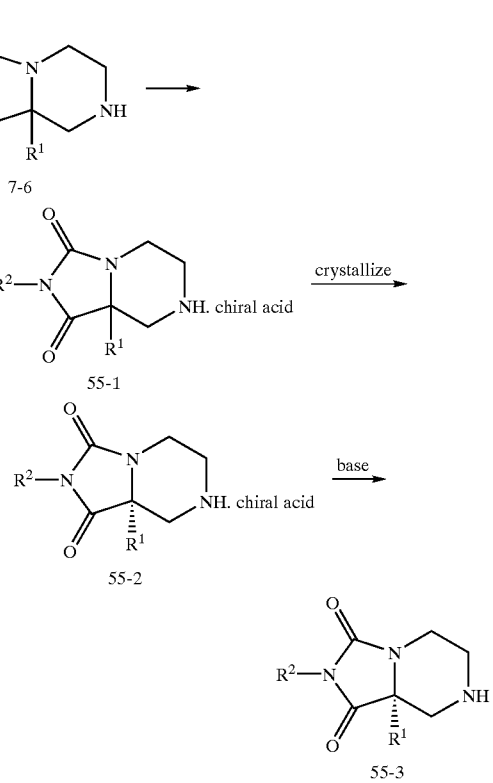

Salt formation of 7-6 with a chiral acid affords a mixture of diastereomeric salts of formula 55-1. Crystallization of the diastereomeric salts affords the acid salt of chiral compounds of formula 55-2. Decomposition of the salt 55-2 with base liberates chiral compounds of formula 55-3. This resolution scheme could be applied to the resolution of other HET-bicyclic compounds described above.

SCHEME 56

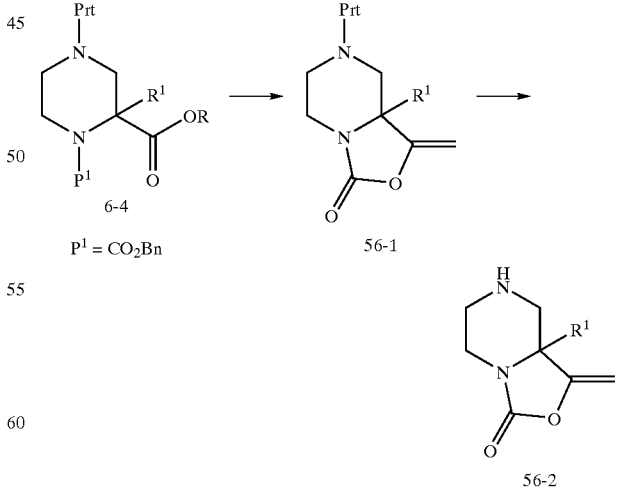

As illustrated in Scheme 56, treatment of 6-4 ($P^1$ is $CO_2Bn$) with an alkyl metal reagent like methyl magnesium bromide affords 56-1. Deprotection as usual then affords 56-2.

SCHEME 57

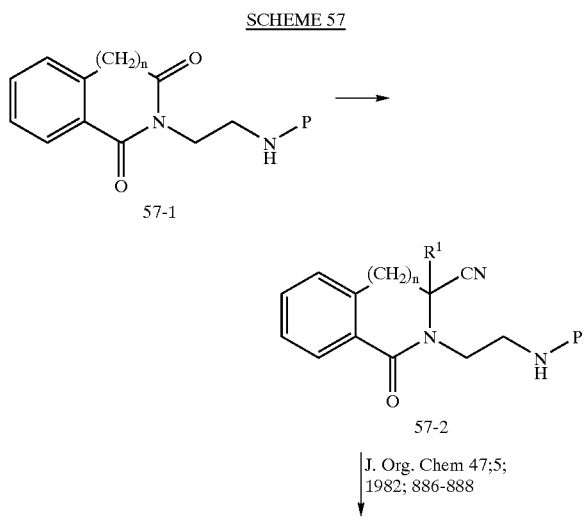

J. Org. Chem 47;5; 1982; 886-888

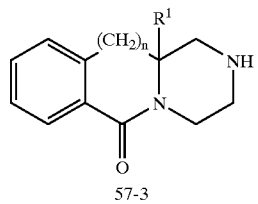
57-3

Compounds of formula 57-3 can be prepared from known phthalic or homophthalic anhydrides by methods previously described by Welch, Willard M. (J.Org.Chem 47; 5; 1982; 886–888. J.Org.Chem.; 47; 5; 1982; 886–888) or Machida, Minoru et al. (Heterocycles; 14; 9; 1980; 1255–1258). Alternatively, the analogous phthalimides or homophthalimides of formula 57-1 can be treated with the appropriate hydride reagent (e.g., $NaBH_4$) or organometallic reagent (e.g., methyl Grignard), followed by treatment with sodium or potassium cyanide to produce an intermediate of the formula 57-2. Compounds of formula 57-2 can be converted to compounds of formula 57-3 as previously described by Welch, Willard M. (J.Org.Chem 47; 5; 1982; 886–888).

SCHEME 58

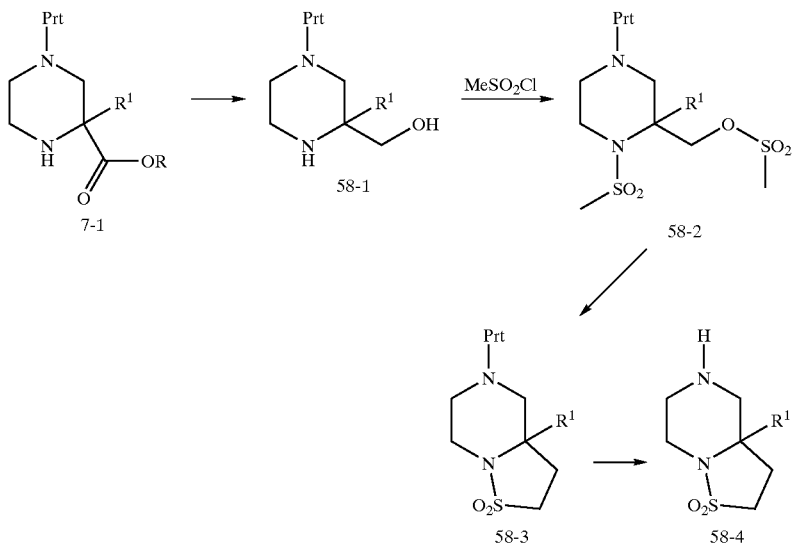

As illustrated in Scheme 58, intermediates of formula 58-4 can be prepared in four steps from compounds of formula 7-1. Compounds of formula 7-1 are treated with a suitable reducing agent such as Super Hydride® in a suitable solvent, preferably THF at a temperature of −20 to 50° C., preferably at around 25° C. to give compounds of formula 58-1. Amino alcohols of formula 58-1 are then treated with at least two equivalents of methanesulfonyl chloride and at least two equivalents of a suitable base, preferably pyridine in a suitable solvent, preferably pyridine at a temperature of −20 to 50° C. preferably around 25° C. to give intermediates of formula 58-2. Treatment of 58-2 with a strong base, preferably sec-butyllithium at a temperature of around −78° C. followed by warming to a temperature of around 25° C. affords intermediates of formula 58-3. Removal of the protecting group as described above, transforms 58-3 into 58-4.

SCHEME 59

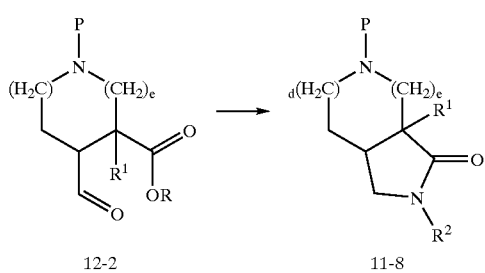

An alternative synthesis of lactam 11-8 is illustrated in Scheme 59. An aldehyde of formula 12-2 can be employed in a reductive amination with an amine and reducing agent, for example sodium triacetoxyborohydride. Subsequent cyclization of the amine with the adjacent ester group affords 11-8. One skilled in the art will recognize that an $R^{1A}$ substituent could have been introduced adjacent to the aldehyde by alkylating aldehyde 12-2 according to well known procedures.

SCHEME 60

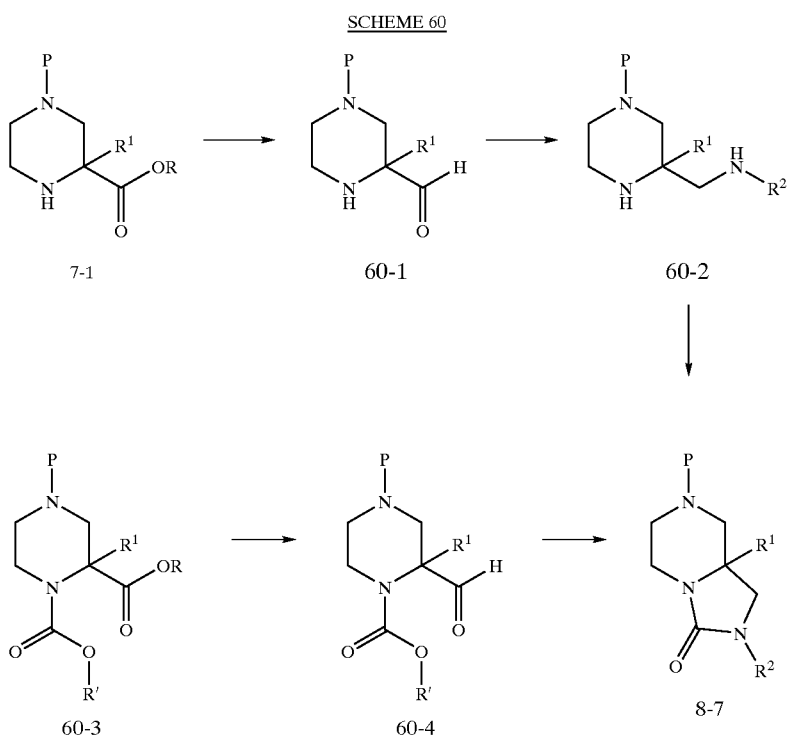

Aldehydes of formula 60-1 can be prepared by reducing 7-1 with an agent like diisobutylaluminum hydride at a suitable temperature, preferably −78° C. to 0° C. in a suitable solvent, such as THF, methylene chloride, toluene or ether. This aldehyde may then be converted to amines of the formula 60-2 by the methods described in Scheme 8 to convert 8-3 to 8-5. In addition, an oxime may be formed by treating the aldehyde with hydroxylamine hydrochloride. Reduction of this oxime, such as with Raney-nickel provides 60-2 where $R^2$ is hydrogen. Treatment of this material with phosgene, triphosgene, carbonyl diimidazole, or other equivalent in the presence of a base, preferably a tertiary amine base, provides a route to ureas of formula 8-7. Those skilled in the art will recognize that $R^2$ may have been a group, such as a benzyl or allyl group, which could be cleaved to give 8-7 where $R^2$ is hydrogen.

Alternatively, compounds of the formula 8-7 may be prepared by reducing carbamate protected ester 60-3, for example when $R^1=CH_2$-2-Pyr, according to well known reduction techniques to afford aldehyde 60-4 which may then be converted to an amine, as described above, which is then reacted with the carbamate at a suitable temperature to provide 8-7.

SCHEME 61

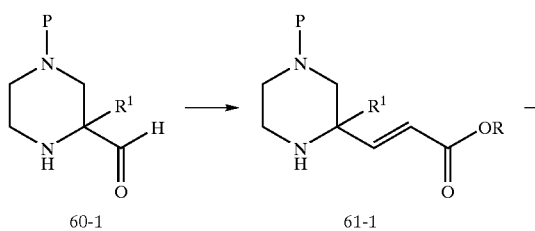

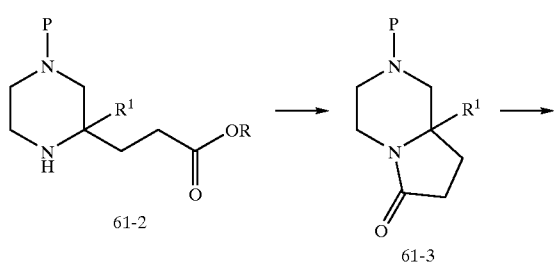

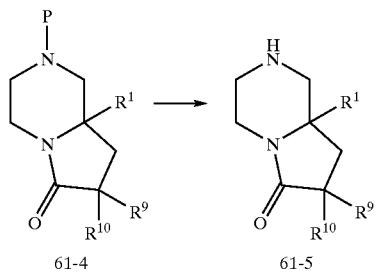

Olefin 61-1 may be prepared by olefinating aldehyde 60-1 with a reagent such as the anion generated upon treating a trialkylphosphono acetate with an appropriate base, such as NaHMDS in a suitable solvent, such as THF. Reduction of the olefin, by methods such as catalytic hydrogenation (see Scheme 11) or conjugate reduction with an agent such as the alkali metal salt of a trialkylborohydride, such as lithium tri-sec-butylborohydride, provides the compounds of formula 61-2. This material is cyclized at elevated temperatures in a reaction inert solvent using cyclization conditions well known to those skilled in the art. Those skilled in the art will recognize that the cyclization reaction may require the addition of a base such as potassium carbonate. Generally the reaction is carried out at reflux in a solvent such as methanol. Deprotection of 61-3 affords compounds of formula 61-5 where $R^9$ and $R^{10}$=H. Those skilled in the art will recognize that 61-3 can be alkylated under a variety of conditions, such as by treating 61-3 with a strong base, e.g., lithium diisopropylamide or LHMDS in a reaction inert solvent such as THF at a suitable temperature, preferably −78° C. The anion generated is treated with alkylating reagents such as alkyl halides or alkyl tosylates, such as methyl iodide, to give 61-4. This process may be repeated to introduce a second substituent. Deprotection affords compounds of formula 61-5. Those skilled in the art will recognize that a $R^9$ substituent can be introduced β to the lactam by conjugate addition to 61-1, such as would be afforded by the use of an alkyl cuprate reagent.

SCHEME 62

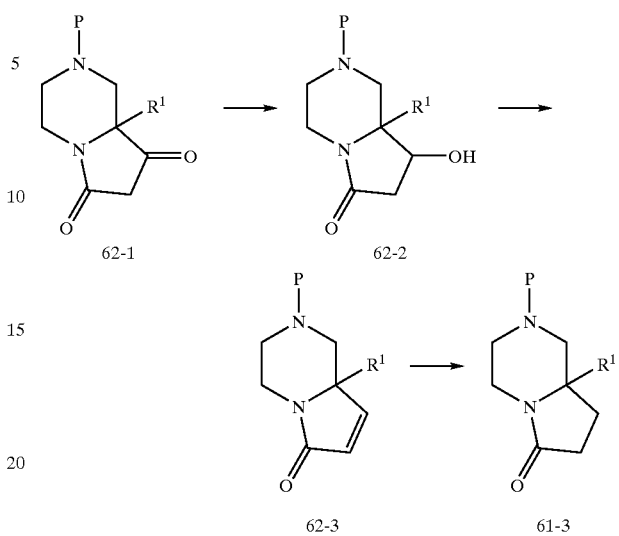

An alternate synthesis of 61-3 is shown above. Reduction of ketoamide 62-1, which is equivalent to 10-2 where $R^9$ and $R^{10}$ are hydrogen, with a reducing agent such sodium borohydride, in an reaction inert solvent such as methanol at a suitable temperature such as 0° C. affords alcohol 62-2. The alcohol is reacted under standard elimination conditions well known to those skilled in the art to provide unsaturated lactam 61-3. Suitable elimination conditions include activating the alcohol, such as by converting it to the corresponding tosylate or mesylate, and then treating the activated alcohol with base at a suitable temperature, for instance with 1,8-diazabicyclo[5.4.0]undec-7-ene in refluxing toluene, or by deprotonating the amide with a strong base such as LHMDS. The alcohol may also be eliminated at suitable temperatures in the presence of a strong base or strong acid. Those skilled in the art will recognize that these conditions may also cleave the protecting group (P). Reduction of 62-3, by methods such as catalytic hydrogenation (see Scheme 11) or conjugate reduction with an agent such as the alkali metal salt of a trialklyborohydride, like lithium tri-sec-butylborohydride, will then provide 61-3. Those skilled in the art will recognize that a $R^9$ substituent could have been introduced β to the lactam by conjugate addition of a reagent, such as a cuprate, to the unsaturated lactam.

SCHEME 63

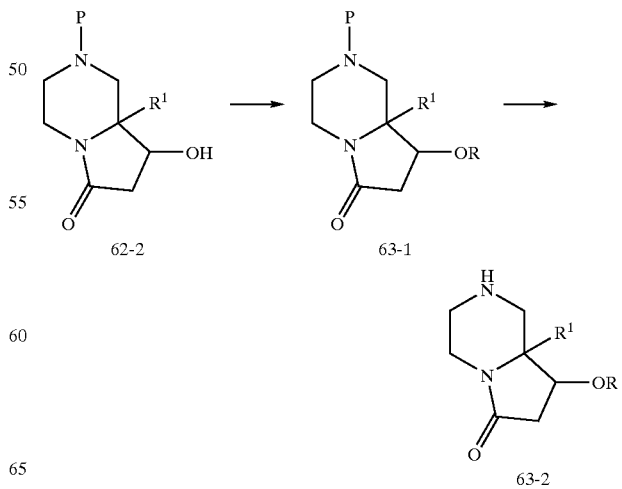

Compounds of formula 63-1 are prepared by deprotonating the alcohol with a strong base such as sodium hydride, LHMDS, KHMS or NaHMDS in a suitable solvent such as DMF or THF followed by treatment with an alkylating agent such as an alkyl halide, mesylate or tosylate, for instance, methyl iodide. The product is then deprotected according to methods well known to those skilled in the art to provide 63-2.

General Experimental Procedures

Silica gel was used for column chromatography. Melting points were taken on a Buchi 510 apparatus and are uncorrected. Proton and carbon NMR spectra were recorded on a Varian XL-300, UNITYPlus-400, Bruker AC-300, or Bruker AC-250 at 25° C. Chemical shifts are expressed in parts per million downfield from trimethylsilane. Particle beam mass spectra (PBMS) were obtained on a Hewlett-Packard 5989A spectrometer using ammonia as the source of chemical ionization. The protonated parent ion is reported as $(M+1)^+$. For initial sample dissolution chloroform or methanol was employed. Atmospheric Pressure Chemical Ionization mass spectra (APcl MS) were obtained on a Platform II by Fisons (now called Micromass Inc.) instrument. They are either run via +APcl (basic method) or +APcl (acid method). The mobile phase is 50:50H$_2$O:acetonitrile. Either a protonated parent $(+APcl)$ or deprotonated parent ion $(-APcl)$ is observed (reported as $(M+1)^+$ or $(M-1)^-$). For initial sample dissolution, chloroform or methanol was employed. Thermospray mass spectra (TSMS) were obtained on a Trio-1000 by Fisions spectrometer using 0.1 M ammonium acetate in 1/4 water/methanol. The protonated parent ion is reported as $(M+1)^+$. For initial sample dissolution chloroform or methanol were employed. TLC analyses were performed using E. Merck Kieselgel 60 F254 silica plates visualized (after elution with the indicated solvent(s)) by UV, iodine or by staining with 15% ethanolic phosphomolybdic acid or ceric sulfate/ammonium molybdate and heating on a hot plate. The terms "concentrated" and "coevaporated" refer to removal of solvent at water aspirator pressure on a rotary evaporator with a bath temperature of less than 40° C.

The following examples are provided for the purpose of further illustration only and are not intended to be limitations on the disclosed invention.

General Procedure A (Peptide coupling using DEC). A 0.2–0.5 M solution of the primary amine (about 1.0 equivalent) in dichloromethane (or a primary amine hydrochloride and about 1.0–1.3 equivalents of triethylamine) was treated sequentially with about 1.0–1.2 equivalents of the carboxylic acid coupling partner, about 1.5–1.8 equivalents of 1-hydroxy-7-azabenzotriazole (HOAT) and about 1.0–1.2 equivalents 1,2-diethylaminoethyl chloride hydrochloride (DEC) and the mixture was stirred for about 18–48 hours in an ice bath (the ice bath was allowed to warm, thus the reaction mixture was typically held at about 0–20° C. for about 4–6 hours and about 20–25° C. for the remaining period). The mixture was diluted with ethyl acetate or other solvent as specified, and the resulting mixture washed 1–2 times with 1 N NaOH or saturated sodium bicarbonate (the aqueous phase being sometimes back-washed with ethyl acetate), once with brine, dried over Na$_2$SO$_4$, and concentrated giving the crude product which was purified as specified. The carboxylic acid component could be used as the dicyclohexylamine salt in coupling to the primary amine or hydrochloride of the latter, in which case no triethylamine was employed.

General Procedure B (Peptide coupling using EDC). A 0.04–0.5 M solution of the primary amine (about 1.0 equivalent) in dichloromethane (or a primary amine hydrochloride and about 1.0–1.3 equivalents of triethylamine) was treated sequentially with about 1.0–1.2 equivalents of the carboxylic acid coupling partner, about 1.5–1.8 equivalents of 1-hydroxy-7-azabenzotriazole (HOAT), and about 1.0–1.2 equivalents of (stoichiometrically equivalent to the quantity of carboxylic acid) 1-(3-dimethylaminopropyl)-3-ethylcarbodiimide hydrochloride (EDC) and the mixture was stirred for about 18–48 hours in an ice bath (the ice bath was allowed to warm, thus the reaction mixture was typically held at about 0–20° C. for about 4–6 hours and about 20–25° C. for the remaining period). The mixture was diluted with chloroform or other solvent as specified, and the resulting mixture washed twice with 10% HCl (if the product does not contain a basic functionality that would make the compound soluble in aqueous acidic solution), twice with saturated sodium bicarbonate solution, 1–2 times with brine, dried over anhydrous magnesium sulfate, and concentrated giving the crude product which was purified as specified. The carboxylic acid component could be used as the dicyclohexylamine salt in coupling to the primary amine or hydrochloride of the latter, in which case no triethylamine was employed.

General Procedure C. (Cleavage of a t-BOC-protected amine using concentrated HCl). The t-Boc amine was dissolved in a minimum volume of ethanol and the resulting solution was cooled to about 0° C. and concentrated HCl (typically about 1–4 mL per mmol amine) was added and the reaction was warmed to room temperature and stirred for about 1–2.5 hours (the time required for complete disappearance of the starting material to a more polar product as judged by TLC). The resulting solution or suspension was concentrated, and the residue coevaporated several times with added ethanol to give the free amine which was used without further purification or purified as specified.

General Procedure D. (Cleavage of a t-BOC-protected amine using TFA). Trifluoroacetic acid (usually at about 0–25° C.) was added to the t-Boc amine (typically about 10 mL per mmol amine) neat or dissolved in a minimum volume of dichloromethane and the resulting solution was stirred at about 0° C. or at room temperature for 0.25–2 hours (the time required for complete disappearance of the starting material to a more polar product as judged by TLC). The resulting solution or suspension was concentrated, and the residue coevaporated several times with added methylene chloride. The residue was then dissolved in ethyl acetate and washed twice with 1 N NaOH and once with brine. The organic phase was then dried over Na$_2$SO$_4$ and evaporated to give the free amine which was used without further purification or purified as specified.

General Procedure E. (Cleavage of a benzyl-protected amine using 10% palladium on carbon). The benzyl amine, ethanol (typically about 1 mL per every 0.03–0.08 mmol of amine), and 10% palladium on carbon (typically about 20–100% of the weight of the amine used) were combined and hydrogenated at about 40–50 psi hydrogen on a Parr® shaker overnight. The mixture was then filtered through a bed of Celite®. The Celite® was washed with ethanol, and the filtrate was concentrated in vacuo to give the de-benzylated amine which was used without further purification or purified as specified.

General Procedure F. (Cleavage of a CBZ-protected amine using 10% palladium on carbon) The CBZ amine, ethanol (typically about 1 mL per every 0.03–0.08 mmol of amine), and 10% palladium on carbon (typically about 20–100% of the weight of the amine used) were combined and hydrogenated at about 40–50 psi hydrogen on a Parr® shaker overnight. The mixture was then filtered through a bed of Celite®. The Celite® was washed with ethanol, and the filtrate was concentrated in vacuo to give the de-benzylated amine which was used without further purification or purified as specified.

EXAMPLE 1

2-Amino-N-[2-(8a(S)-benzyl-3-oxo-tetrahydro-oxazolo[3,4-a]pyrazin-7-yl)-1(R)-(3,5-dichloro-benzyloxymethyl)-2-oxo-ethyl]-2-methyl-propionamide, Hydrochloride

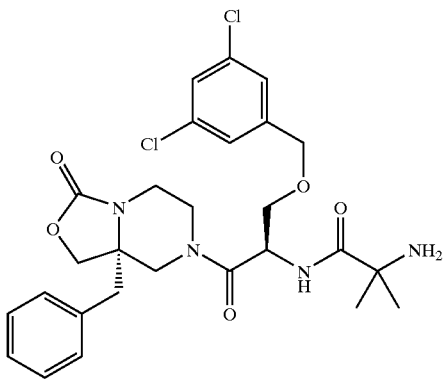

A. 2-Benzyl-piperazine-1,2,4-tricarboxylic Acid 1-Benzyl Ester 4-tert-Butyl Ester 2-Methyl Ester To a stirred solution of piperazine-1,2,4-tricarboxylic acid 1-benzyl ester 4-tert-butyl ester 2-methyl ester (20.0 g, 53 mmol), prepared as described by Bigge et al. (Tetrahedron Let. 1989, 30, 5193), in tetrahydrofuran (500 mL) was added N,N-dimethylformamide (50 mL). The reaction was cooled to about −78° C., and a 1M solution of sodium bis(trimethylsilyl)amide in tetrahydrofuran (80 mL) was added. The reaction was stirred at about −78° C. for about 1 hour, and then benzyl bromide (9.4 mL, 79 mmol) was added. The reaction was stirred for about 30 minutes more at about −78° C., then warmed to room temperature and stirred overnight. The reaction was quenched with saturated sodium bicarbonate solution, and the mixture was extracted three times with ethyl acetate. The combined organic layers were extracted twice with water, brine, dried over anhydrous magnesium sulfate, filtered and concentrated in vacuo to give 31 g of crude product. Purification by silica gel chromatography using 10–20% ethyl acetate/hexanes as eluent afforded the title compound of part 1-A (20.33 g, 82%): +APcl MS (M−55)$^+$ 413, (M−99)$^+$ 369; $^1$H NMR=400 MHz (CDCl$_3$) δ: 7.37 (arom, m, 5H), 7.22 (arom, m, 3H), 7.00 (arom, m, 2H), 1.41 (BOC, d, 9H).

B. 8a-Benzyl-3-oxo-tetrahydro-oxazolo[3,4-a] pyrazine-7-carboxylic Acid tert-Butyl Ester To a stirred solution of the title compound of part 1-A (18.06 g, 38.5 mmol) in tetrahydrofuran (180 mL) cooled to about 0° C. was added a 1M solution of lithium triethylborohydride in tetrahydrofuran (86.8 mL) over about 10 min. The reaction was allowed to warm to room temperature for about 1 hour, after which an additional 5 mL of the 1M solution of lithium triethylborohydride was added. The reaction was stirred for about 30 minutes at room temperature, then quenched with saturated sodium bicarbonate solution followed by the addition of 1 N HCl solution. The mixture was then extracted three times with ethyl acetate. The combined organic layers were extracted with brine, dried over sodium sulfate, filtered and concentrated in vacuo to give 20.4 g of a clear oil. Purification by silica gel chromatography using 5% methanol/ethyl acetate as eluent afforded 13 g of a solid. Trituration of the solid with ethyl ether afforded the title compound of part 1-B (9.50 g, 74%): +APcl MS (M−55)$^+$ 277, (M−99)$^+$ 233; $^1$H NMR=400 MHz (methanol-d$_4$) δ: 7.30–7.23 arom, m, 5H), 4.11 (—CO$_2$C$\underline{H}_2$13 , d of d, 2H), 1.50 (BOC, s, 9H).

C. 8a-Benzyl-hexahydro-oxazolo[3,4-a]pyrazin-3-one, Hydrochloride

The title compound of part 1-B (9.5 g, 28.6 mmol) was deprotected according to the method described in General Procedure C to give the title compound of part 1-C (7.90 g, ca 100%): +APcl MS (M+1)$^+$ 233; $^1$H NMR=400 MHz (methanol-d$_4$) δ: 7.32–7.23 (arom, m, 5H), 4.22 (—CO$_2$C$\underline{H}^2$—, d of d, 2H).

D. 2-tert-Butoxycarbonylamino-2-methyl-propionic Acid 2,5-Dioxo-pyrrolidin-1-yl Ester A stirred solution of N-hydroxysuccinimide (112 g, 0.973 mol), N-t-butoxycarbonyl-α-methylalanine (197 g, 0.969 mol), and 1-(3-dimethylaminopropyl)-3-ethyl-carbodiimide (186 g, 0.970 mol) in anhydrous dichloromethane (1.4 L) was stirred at room temperature for about 18 hours under nitrogen atmosphere. The reaction mixture was washed three times each with saturated sodium bicarbonate solution and then brine. The organic layer was dried over sodium sulfate, filtered and concentrated in vacuo to give the title compound of part 1-D as a white solid (256 g, 88%): PBMS (M+18)$^+$ 318; $^1$H NMR=250 MHz (CDCl$_3$) δ: 4.91 (N$\underline{H}$, br s, 1H), 2.84 (—CO(C$\underline{H}_2$)$_2$CO—, s, 4H), 1.67 (Me, s, 6H), 1.48 (BOC, s, 9H).

E. 2-tert-Butoxycarbonylamino-3-(3,5-dichloro-benzyloxy)-propionic Acid

To a stirred solution of N-t-butoxycarbonyl-D-serine (10.0 g, 48.7 mol) in N,N-dimethylformamide (150 mL) at about 0° C. was added sodium hydride (4.0 g, 60% dispersion in mineral oil, 99.84 mmol) portionwise. The mixture was stirred for about 30 minutes, and then a solution of 1,3-dichloro-5-chloromethyl-benzene (9.5 mL, 48.7 mmol) in ethyl ether (40 mL) was added. The reaction was allowed to slowly warm to room temperature overnight. The reaction was then quenched with 1 N NaOH, the mixture extracted three times with dichloromethane. The combined organic layers were then washed three times with water, 1 N HCl, dried over anhydrous magnesium sulfate, filtered and concentrated in vacuo to give crude product. The original basic aqueous layer was then acidified to about pH 4 with 1 N HCl, and the mixture was extracted three times with dichloromethane. These three organic layers were combined and washed three times each with water and brine then dried over anhydrous magnesium sulfate, filtered and concentrated in vacuo to give an additional 620 mg of crude product. Both product fractions were combined and purified by silica gel chromatography using 5% methanol/chloroform as eluent and yielded the title compound of part 1-E (12.39 g, 70%): −APcl MS (M−1)$^-$363, (M−3)$^-$361; $^1$H NMR=400 MHz (CDCl$_3$) δ: 7.13 (arom, s, 3H), 5.42 (N$\underline{H}$, d, 1H), 4.50 (C$\underline{H}$CO$_2$H, m, 1H), 4.45 (PhC$\underline{H}_2$O, s, 2H), 3.82 (C$\underline{H}_2$OBz, d of d, 2H), 1.43 (BOC, s, 9H).

F. 2-Amino-3-(3,5-dichloro-benzyloxy)-propionic Acid, Hydrochloride

The title compound of part 1-E (12.39 g, 34.02 mmol) was deprotected according to the method described in General Procedure C to give the title compound of part 1-F (9.52 g, 93%): −APcl MS (M−1)⁻ 263; ¹H NMR=400 MHz (methanol-d₄) δ: 7.35 (arom, m, 3H), 4.59 (PhC$\underline{H}_2$O, s, 2H), 4.17 (C$\underline{H}$CO₂H, m, 1H), 3.93 (C$\underline{H}_2$OBz, m, 2H).

G. 2-(2-tert-Butoxycarbonylamino-2-methyl-propionylamino)-3-(3,5-dichloro-benzyloxy)-propionic Acid A stirred solution of the title compound of part 1-F (9.52 g, 31.67 mmol), the title compound of part 1-D (9.5 g, 31.67 mmol), and triethylamine (13.24 mL, 95.01 mmol) in dioxane/water (100 mL/25 mL) was heated to about 50° C. for about 3 days. The reaction mixture was then concentrated in vacuo, diluted with 1 N HCl, and then extracted three times with aqueous 10% HCl until the mixture was at pH 2.

The organic layer was washed with ethyl acetate. The combined organic layers were washed with brine, dried over anhydrous magnesium sulfate, filtered and concentrated in vacuo to give the title compound of part 1-G: −APcl MS (M−1)⁻ 448, (M−2)⁻ 447; ¹H NMR=400 MHz (CDCl₃) δ: 7.15 (arom, m, 3H), 5.12 (N$\underline{H}$, br s, 1H), 4.64 (C$\underline{H}$CO₂H, m, 1H), 4.45 (PhC$\underline{H}_2$O, s, 2H), 3.70 (C$\underline{H}_2$OBz, d of d, 2H), 1.49 (Me, s, 3H), 1.48 (Me, s, 3H), 1.38 (BOC, s, 9H).

H. {1-[2-(8a(S)-Benzyl-3-oxo-tetrahydro-oxazolo[3,4-a]pyrazin-7-yl)-1(R)-(3,5-dichloro-benzyloxymethyl)-2-oxo-ethylcarbamoyl]-1-methyl-ethyl}-carbamic Acid tert-Butyl Ester According to General Procedure A, the title compound of part 1-C (0.15 g, 0.56 mmol) was coupled to the title compound of part 1-G (0.25 g, 0.56 mmol), and the product was purified by silica gel chromatography using ethanol/ethyl acetate/hexanes (1:50:40) as eluent to give the less polar isomer the title compound of part 1-H (153 mg, 41%): +APcl MS (M)⁺ 663, (M+2)⁺ 665, (M−98)⁺ 565, (M−100)⁺ 563; ¹H NMR=400 MHz (CDCl₃) δ: 7.23–7.10 (arom, m, 8H), 4.41 (PhC$\underline{H}_2$O, AB, 2H), 1.42 (Me, s, 3H), 1.38 (Me, s, 3H), 1.29 (BOC, s, 9H).

I. 2-Amino-N-[2-(8a(S)-benzyl-3-oxo-tetrahydro-oxazolo[3,4-a]pyrazin-7-yl)-1(R)-(3,5-dichloro-benzyloxymethyl)-2-oxo-ethyl]-2-methyl-propionamide, Hydrochloride The title compound of part 1-H (153 mg, 0.230 mmol) was deprotected according to the method described in General Procedure C to give the title compound of this Example 1 (128 mg, 93%): +APcl MS (M)⁺ 563, (M+2)⁺ 565; ¹H NMR=400 MHz (methanol-d₄) δ: 7.30–7.24 (arom, m, 8H), 4.54 (PhC$\underline{H}_2$O, s, 2H), 1.58 (Me, s, 3H), 1.57 (Me, s, 3H).

EXAMPLE 2

2-Amino-N-[2-(8a(S)-benzyl-2-methyl-3-oxo-hexahydro-imidazo[1,5-a]pyrazin-7-yl)-1(R)-benzyloxymethyl-2-oxo-ethyl]-2-methyl-propionamide, Hydrochloride

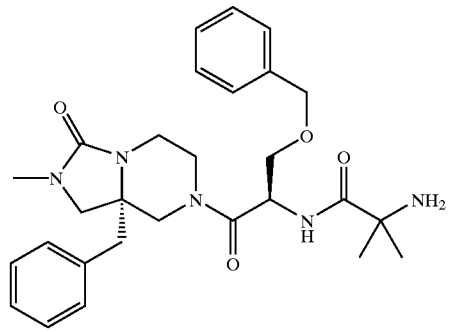

A. 3-Benzyl-piperazine-1,3-dicarboxylic Acid 1-tert-butyl Ester 3-Methyl Ester The title compound of part 1-A (2.80 g, 5.98 mmol) was deprotected according to the method described in General Procedure F to give the title compound of part 2-A as a white foam (1.89 g, 95%): +APcl MS (M+1)⁺ 335, (M−55)⁺ 279, (M−99)⁺ 235; ¹H NMR=400 MHz (CDCl₃) δ: 7.28–7.18 (arom, m, 5H), 3.66 (Me, s, 3H), 1.40 (BOC, s, 9H).

B. 3,4-Dibenzyl-piperazine-1,3-dicarboxylic Acid 1-tert-Butyl Ester 3-Methyl Ester To a solution of the title compound of part 2-A (1.22 g, 3.65 mmol) and diisopropylamine (0.63 mL, 3.65 mmol) in acetonitrile (18 mL) was added benzyl bromide (0.45 mL, 3.83 mmol), and the reaction was stirred at room temperature overnight. The reaction was then heated to reflux for about 5 hours. The solvent was then removed in vacuo, and ether was added to the residue. The solid precipitate was removed by filtration, and the filtrate was concentrated in vacuo to give the title compound of part 2-B as a colorless oil (0.87 g, 56%): ¹H NMR=400 MHz (CDCl₃) δ: 7.32–7.13 (arom, m, 10H), 3.65 (Me, s, 3H), 1.37 (BOC, s, 9H).

C. 3,4-Dibenzyl-3-hydroxymethyl-piperazine-1-carboxylic Acid tert-Butyl Ester To a solution of the title compound of part 2-B (0.87 g, 2.05 mmol) in tetrahydrofuran (10 mL) was added a 1M solution of lithium triethylborohydride in tetrahydrofuran (4.1 mL), with immediate effervescence observed. The reaction was stirred for about 30 minutes, after which an additional 0.5 mL of the 1M solution of lithium triethylborohydride was added. The reaction was then quenched with a 1 N HCl solution (0.5 mL). The mixture was stirred for about 5 minutes, then basified with 1 N NaOH. The mixture was extracted three times with ethyl acetate. The combined organic layers were extracted with brine, dried over sodium sulfate, filtered and concentrated in vacuo to give the title compound of part 2-C as a clear oil (0.80 g, 99%): +APcl MS (M+1)⁺ 397, (M−55)⁺ 341, (M−99)⁺ 297; ¹H NMR=300 MHz (CDCl₃) δ: 7.31–7.25 (arom, m, 10H), 1.50 (BOC, s, 9H).

D. 3,4-Dibenzyl-3-formyl-piperazine-1-carboxylic Acid tert-Butyl Ester

To a stirred solution of DMSO (0.312 mL, 4.44 mmol) in dichloromethane (10 mL) cooled to about −78° C. was slowly added oxalyl chloride (0.193 mL, 2.22 mmol), followed by a solution of the title compound of part 2-C (0.80 g, 2.0 mmol) in dichloromethane (3 mL). The reaction was then allowed to warm to about −30° C. and was stirred for about 30 minutes. The reaction was re-cooled to about −78° C., and triethylamine (1.40 mL, 10.1 mmol) was slowly added. The reaction was stirred for about 5 minutes at about −78° C., then was allowed to warm to room temperature. The reaction was quenched with water and the mixture was extracted several times with dichloromethane. The combined organic layers were washed with brine, dried over sodium sulfate, filtered and concentrated in vacuo to give the title compound of part 2-D as a clear oil (777 mg, 97%): +APcl MS (M)$^+$ 394, (M−56)$^+$ 338, (M−100)$^+$ 294; $^1$H NMR=300 MHz (CDCl$_3$) δ: 9.72 (aldehyde, s, 1H), 7.30–7.22 (arom, m, 10H), 1.40 (BOC, s, 9H).

E. 3,4-Dibenzyl-3-methylaminomethyl-piperazine-1-carboxylic Acid tert-Butyl Ester To a stirred solution of the title compound of part 2-D (0.34 g, 0.86 mmol) in methanol (4 mL) cooled to about 0° C. was slowly added methylamine hydrochloride (0.29 g, 4.3 mmol), followed by sodium acetate (0.707 g, 8.63 mmol), 3 Å molecular sieves (0.34 g), and sodium cyanoborohydride (0.064 g, 1.03 mmol). The reaction was allowed to warm to room temperature and was stirred overnight. The mixture was then filtered through a bed of Celite®. The Celite® was washed with methanol, and the filtrate was concentrated in vacuo. The residue was diluted with ethyl acetate, and the mixture was extracted twice with 1 N NaOH, brine, dried over sodium sulfate, filtered and concentrated in vacuo to give 340 mg of a clear oil. Purification by silica gel chromatography using 4% methanol/dichloromethane as eluent afforded the title compound of part 2-E as a clear oil (214 mg, 61%): +APcl MS (M+1)$^+$ 410, (M−55)$^+$ 354, (M−99)$^+$ 310; $^1$H NMR=400 MHz (CDCl$_3$) δ: 7.32–7.24 (arom, m, 10H), 2.30 (NMe, s, 3H), 1.50 (BOC, s, 9H).

F. 3-Benzyl-3-methylaminomethyl-piperazine-1-carboxylic Acid tert-Butyl Ester The title compound of part 2-E (0.21 g, 0.51 mmol), methanol (15 mL), and palladium hydroxide on carbon (0.187 g) were combined and hydrogenated at 45 psi H$_2$ on a Parr® shaker for approximately 2 days. The mixture was then filtered through a bed of Celite®. The Celite® was washed with ethanol, and the filtrate was concentrated in vacuo to give 180 g of a clear oil. Purification by silica gel chromatography using ammonium hydroxide/methanol/chloroform (0.25:5:95) as eluent yielded the title compound of part 2-F as a dear oil (102 mg, 65%): +APcl MS (M+1)$^+$ 320, (M−55)$^+$ 264, (M−99)$^+$ 220; $^1$H NMR=400 MHz (CDCl$_3$) δ: 7.24–7.17 (arom, m, 5H), 2.42 (NMe, s, 3H), 1.40 (BOC, s, 9H).

G. 8a-Benzyl-2-methyl-3-oxo-hexahydro-imidazo[1,5-a]pyrazine-7-carboxylic Acid tert-Butyl Ester A stirred solution of the title compound of part 2-F (100 mg, 0.31 mmol) and 1,1'-carbonyldiimidazole (54 mg, 0.34 mmol) in tetrahydrofuran (3 mL) was heated to reflux for about 2.5 hours, and then allowed to sit at room temperature overnight. The reaction was quenched with saturated sodium bicarbonate solution, and extracted three times with ethyl acetate. The combined organic layers were extracted with brine, dried over sodium sulfate, filtered and concentrated in vacuo to give 142 mg of crude product. Purification by silica gel chromatography using 67% ethyl acetate/hexanes as eluent yielded the title compound of part 2-G as a white solid (93 mg, 87%): +APcl MS (M−55)$^+$ 290, (M−99)$^+$ 246; $^1$H NMR=400 MHz (CDCl$_3$) δ: 7.29–7.21 (arom, m, 5H), 2.68 (NMe, s, 3H), 1.48 (BOC, s, 9H).

H. 8a-Benzyl-2-methyl-hexahydro-imidazo[1,5-a]pyrazin-3-one, Hydrochloride

The title compound of part 2-G (89 mg, 0.258 mmol) was deprotected according to the method described in General Procedure C to give the title compound of part 2-H (77 mg, 77%): +APcl MS (M+1)$^+$ 246; $^1$H NMR=400 MHz (CDCl$_3$) δ: 7.28 (arom, m, 5H), 4.40–2.82 (series of m, 10H), 2.70 (NMe, s, 3H).

I. 3-Benzyloxy-2-(2-tert-butoxycarbonylamino-2-methyl-propionylamino)-propionic Acid To a solution of D-O-benzylserine (106 g, 0.532 mol) and the title compound of part 1-D (160 g, 0.532 mol) in water/dioxane (250/1000 mL) was slowly added triethylamine (223 mL, 1.60 mol) at room temperature. The reaction was heated to about 50° C. and stirred for about 15 hours under nitrogen atmosphere. The solvent was then removed in vacuo, ethyl acetate was added, and the stirred mixture was acidified with 10% aqueous HCl solution to pH 2–3. The organic layer was dried over sodium sulfate, filtered and concentrated in vacuo to give the title compound of part 2-I (200 g, 99%): −APcl MS (M−1)$^-$ 379; $^1$H NMR=300 MHz (methanol-d$_4$) δ: 7.69 (NH, d, 1H), 7.32 (Ph, m, 5H), 4.60 (CHCO$_2$H, m, 1H), 4.51 (CHH$_2$Ph, s, 2H), 3.81 (CHH$_2$OBz, m, 2H), 1.41 (Me, s, 6H), 1.40 (BOC, s, 9H).

J. {1-[2-(8a(S)-Benzyl-2-methyl-3-oxo-hexahydro-imidazo[1,5-a]pyrazin-7-yl)-1(R)-benzyloxymethyl-2-oxo-ethylcarbamoyl]-1-methyl-ethyl}-carbamic Acid tert-Butyl Ester According to General Procedure A, the title compound of part 2-H (39 mg, 0.14 mmol) was coupled to D-O-benzylserine-N-t-butoxycarbonyl-a-methylalanine (53 mg, 0.14 mmol), and the product was purified by silica gel chromatography using ethyl acetate as eluent to give the title compound of part 2-J (23 mg, 27%): +APcl MS (M+1)$^+$ 608, (M−99)$^+$ 508; $^1$H NMR=400 MHz (CDCl$_3$) δ: 7.28–7.12 (arom, m, 10H), 5.28 (PhCHH$_2$O, s, 2H), 2.65 (NMe, s, 3H), 1.44 (Me, s, 3H), 1.42 (Me, s, 3H), 1.32 (BOC, s, 9H).

K. 2-Amino-N-[2-(8a(S)benzyl-2-methyl-3-oxo-hexahydro-imidazo[1,5-a]pyrazin-7-yl)-1(R)-benzyloxymethyl-2-oxo-ethyl]-2-methyl-propionamide Hydrochloride The title compound of part 2-J (23 mg, 0.038 mmol) was deprotected according to the method described in General Procedure C to give the title compound of this Example 2 as a clear glass (206 mg, 92%): +APcl MS (M+1)$^+$ 508; $^1$H-NMR=400 MHz (methanol-d$_4$) δ: 7.23 (arom, m, 10H), 4.52 (PhCHH$_2$O, s, 2H), 2.58 (NMe, s, 3H), 1.57 (Me, s, 6H).

EXAMPLE 3

2-Amino-N-{1(R)-benzyloxymethyl-2-[1,3-dioxo-8a(S)-pyridin-2-ylmethyl-2-(2,2,2-trifluoro-ethyl)-hexahydro-imidazo[1,5-a]pyrazin-7-yl]-2-oxo-ethyl}-2-methyl-propionamide, Hydrochloride

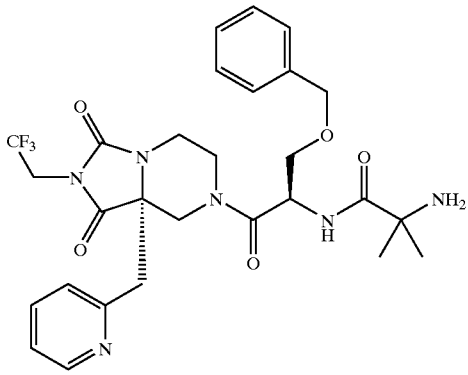

A. 2-Pyridin-2-ylmethyl-piperazine-1,2,4-tricarboxylic Acid 1-Benzyl Ester 4-tert-Butyl Ester 2-Methyl Ester A stirred solution of piperazine-1,2,4-tricarboxylic acid 1-benzyl ester 4-tert-butyl ester 2-methyl ester (200 g, 529 mol), prepared as described by Bigge et al. (Tetrahedron Let. 1989, 30, 5193), in tetrahydrofuran (200 mL) and DMF (1.5 L) was cooled to about −78° C., and a 0.5 M solution of potassium bis(trimethylsilyl)amide in THF (1.27 L) was added. After the above solution had stirred for about one hour, the free base of 2-picolyl chloride was generated by extracting the corresponding hydrochloride salt (217 g, 1.32 mol) from saturated sodium bicarbonate solution with methylene chloride. The combined organic extracts were dried ($MgSO_4$), concentrated, immediately dissolved in DMF (100 mL), and then added dropwise to the enolate containing solution. The reaction was stirred for about 4 hours at about −78° C., then slowly warmed to room temperature and stirred overnight. The toluene and THF were removed under reduced pressure. The residue was extracted from water (1.5 L) with ethyl acetate (3×1 L), the combined extracts were then washed with water (1.5 L), dried ($MgSO_4$) and then concentrated in vacuo to give 240 g of crude product of the title compound of part 3-A which was carried on to the next step: +APcl MS $(M+H)^+$ 470, $(M-^tBu+H)$ 436; $^1$H NMR= 400 MHz (methanol-$d_4$) δ: 8.4 (arom, m, 1H), 7.65–7.2 (arom, m, 7H), 6.94 (arom, m, 1H), 5.18 (CbzNC$\underline{H}$H, m, 1H), 5.05 (CbzNCH$\underline{H}$, m, 1H), 2.54 (m, 1H), 1.41 (Boc, s, 9H).

B. 3-Pyridin-2-ylmethyl-piperazine-1,3-dicarboxylic Acid 1-tert-Butyl Ester 3-Methyl Ester The crude Cbz amine, the title compound of part 3-A, (240 g) in methanol (1 L), and 10% palladium on carbon (10 g, added in 100 mL water) were combined and hydrogenated at about 40–50 psi hydrogen on a Parr® shaker for about 2 days. The mixture was then filtered through a bed of diatomaceous earth. The diatomaceous earth was washed with ethanol, and the filtrate was concentrated in vacuo to give the de-benzylated amine. Two of the above alkylation/reductions were combined and purified by silica gel chromatography using 1:1 ethyl acetate/hexanes to ethyl acetate to 1:9 methanol/ethyl acetate as eluent and yielded the title compound of part 3-B (217 g, 61%): +APcl $(M+1)^+$ 336; $^1$H NMR=400 MHz (methanol-$d_4$) δ: 8.45 (arom, d, 1H), 7.72 (arom, t, 1H), 7.26–7.11 (arom, m, 2H), 4.38 (br s, 1H), 3.57 (MeO, s, 3H), 1.41 (Boc, s, 9H).

C. 1,3-Dioxo-8a-pyridin-2-ylmethyl-2-(2,2,2-trifluoro-ethyl)-hexahydro-imidazo[1,5-a]pyrazine-7-carboxylic Acid tert-Butyl Ester To a suspension of N,N'-carbonyldiimidazole (69 g, 426 mmol) and 2,2,2-trifluoro-ethylamine hydrochloride (71 g, 527 mmol) in dichloromethane (500 mL) was added triethylamine (76 mL, 544 mmol) at about 0° C. dropwise. The reaction was then warmed to room temperature and stirred at room temperature for about 30 minutes. A solution of the title compound of part 3-B (57 g, 170 mmol) in dichloromethane (100 mL) was then added, and the reaction was heated to about 40° C. and then stirred for approximately 2 days. The reaction was quenched with saturated sodium bicarbonate solution, and the mixture was then extracted twice with dichloromethane. The combined organic layers were extracted twice with water, dried over anhydrous magnesium sulfate, filtered and concentrated in vacuo to give crude product. Purification by silica gel chromatography using 1:9 to 1:2 to 1:1 ethyl acetate/hexanes as eluent afforded the title compound of part 3-C (68.3 g, 94%) as an amorphous solid: +APcl MS $(M+H)^+$ 429; $^1$H NMR=400 MHz ($CDCl_3$) δ: 8.4 (arom, d, 1H), 7.54 (arom, t, 1H), 7.12 (arom, t, 1H), 7.04 (arom, d, 1H), 4.16–4.00 ($CF_3C\underline{H}_2$, m, 2H), 3.41 (PyrC$\underline{H}_2$, Ab$_q$, 2H), 1.50 (Boc, s, 9H).

D. 8a-Pyridin-2-ylmethyl-2-(2,2,2-trifluoro-ethyl)-tetrahydro-imidazo[1,5-a]pyrazine-1,3-dione The title compound of part 3-C (22.8 g, 53.2 mmol) was deprotected according to he method described in General Procedure C to give a pink solid. The residue was extracted from saturated aqueous $NaHCO_3$ with methylene chloride, the combined organic layers were washed with brine, dried ($MgSO_4$) and concentrated to give the title compound of part 3-D as a light yellow solid (13.7 g, 78%): +APcl MS $(M+H)^+$ 329; $^1$H NMR=400 MHz ($CDCl_3$) δ: 8.42 (arom, ddd, 1H), 7.55 (arom, td, 1H), 7.37–7.07 (arom, m, 2H); 4.15–3.98 ($CF_3C\underline{H}_2$, m, 2H), 3.87 (NC$\underline{H}$HC$H_2$, m, 1H), 3.79 (CC$\underline{H}$HNH, d, 1H), 3.40 (CCH$\underline{H}$NH, d, 1H), 3.25 (PyrC$\underline{H}$H, d, 1H), 3.13 (NCH$\underline{H}$C$H_2$, ddd, 1H), 3.02 (NC$H_2$C$\underline{H}$HNH, dd, 1H), 2.74 (PyrCH$\underline{H}$, d, 1H), 2.66 (NC$H_2$CH$\underline{H}$NH, td, 1H).

E. (1-{1(R)-Benzyloxymethyl-2-[1,3-dioxo-8a-pyridin-2-ylmethyl-2-(2,2,2-trifluoro-ethyl)-hexahydro-imidazo[1,5-a]pyrazin-7-yl]-2-oxo-ethylcarbamoyl}-1-methyl-ethyl)-carbamic Acid tert-Butyl Ester According to General Procedure B, 3-D (5.6 g, 15.4 mmol) was coupled to the title compound of part 2-I (5.84 g, 15.4 mmol), and the product was purified by silica gel chromatography using 2:1 ethyl acetate/hexanes as eluent to give the title compound of part 3-E (34513-284-1) as a colorless solid (7.3 g, 69%): +APcl MS $(M+H)^+$ 691; $^1$H NMR 400 MHz ($CDCl_3$) δ: 8.35 (arom, m, 1H), 5.23–5.10 (m, 2H), 2.60 (t, 1H).

F. 2-Amino-N-{1(R)-benzyloxymethyl-2-[1,3-dioxo-8a(S)-pyridin-2-ylmethyl-2-(2,2,2-trifluoro-ethyl)-hexahydro-imidazo[1,5-a]pyrazin-7-yl]-2-oxo-ethyl}-2-methyl-propionamide, Hydrochloride The title compound of part 3-E (410 mg, 0.59 mmol) was deprotected according to the method described in General Procedure C to give a colorless solid (6.23 g, 94%).

HPLC separation of the isomers provided the shorter retained isomer (2.65 g, 85%): A 70×500 mm Inertsil 15 micron C-8 column (Phenomenex Inc, 2320 W. 205th St., Torrance, Calif. 90501) was equilibrated with 100% 0.050M $KH_2PO_4$ adjusted pH 2.20 with $H_3PO_4$. The sample was dissolved in 20 ml mobile phase along with a few drops of $H_3PO_4$ and was injected onto the column. The column was eluted at 237.5 ml/min., 100% buffer for 1 min., ramped to 75% buffer 25% $CH_3CN$ in 12.5 min., and then held for 21.5 min. (total run time 35 min.). The column was then rinsed off with 50% water 50% $CH_3CN$. The product was observed at 254 nm, and was found in fractions 7–11 (24–29 min.). These fractions were combined, adjusted to a pH of about 7.5 with $NaHCO_3$ and then extracted with $CHCl_3$ (2×1000 ml). The organics were combined, dried ($Na_2SO_4$) and concentrated to a colorless foam (86.5% diastereomer excess).

HPLC analysis was performed on an Hewlett-Packard 1050 system with a 1050 DAD, autosampler and solvent delivery system (Hewlett-Packard Company, Analytical Business Center, 2850 Centerville Road, Wilmington, Del. 19808-1610). Data was imported into a HP Vectra XM series 3 running HP Chemstation ver A.4.02. A 10 μL sample dissolved in the mobile phase at 1 mg/ml was injected for analysis. A Prodigy 3.2×250 mm 5 micron C-8 column (Phenomenex Inc, 2320 W. 205th St., Torrance, Calif. 90501) was employed with the following solvents: A=0.050 M $KH_2PO_4$ adjusted to pH 2.20 with $H_3PO_4$; C=acetonitrile. An isocratic elution was employed using 65% A and 35% C with a flow rate of 0.5 ml/min. detecting at uv, 254 nm. The desired enantiomer eluted at 5.7 min., while the less desired enantiomer eluted at 6.3 min.

The desired enantiomer was taken up in ethanol (150 mL), slowly treated with concentrated aqueous HCl (75 mL) at about 0° C., and the solvent then removed under reduced pressure. The residue was then concentrated from ethanol (4x) to remove residual, water. The product was triturated with ethyl ether to give the title compound of this Example 3 (2.72 g, 97%): +APcI MS (M+H)$^+$ 591; $^1$H NMR=400 MHz (methanol-$d_4$) δ: 8.83–6.90 (NH and arom, series of m, 10H), 5.18–2.90 (aliphatic, series of m, 15H), 1.59 (Me, s, 6H); $^{13}$C NMR=100 MHz (methanol-$d_4$) δ: 172.4, 148.1, 143.4, 130.3, 129.5, 129.0, 127.7, 74.4, 69.7, 64.6, 58.2, 52.3, 47.9, 46.9, 40.8, 40.5, 39.2, 36.0, 24.2, 24.1.

EXAMPLE 3a

2-Amino-N-{1(R)-benzyloxymethyl-2-[1,3-dioxo-8a (S)-pyridin-2-ylmethyl-2-(2,2,2-trifluoro-ethyl)-hexahydro-imidazo[1,5-a]pyrazin-7-yl]-2-oxo-ethyl}-2-methyl-propionamide, Hydrochloride

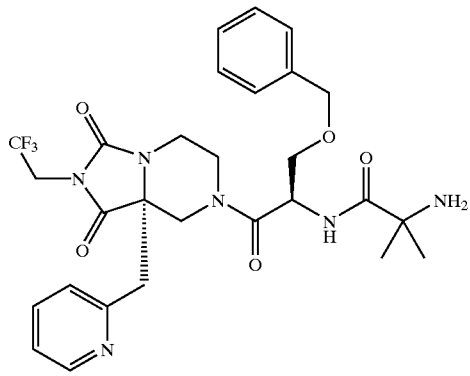

8a(S)-Pyridin-2-ylmethyl-2-(2,2,2-trifluoro-ethyl)-tetrahydro-imidazo[1,5-a]pyrazine-1,3-dione To a solution of the title compound of part 3-D (206 g, 628 mmol) in 10:1 acetone/water (4.5 L) was added D-tartaric acid (94.2 g, 628 mmol). After several minutes a colorless precipitate formed. After stirring for about 2 days the solid was collected by filtration (144 g, 80% ee). The precipitate was then placed in acetone (2 L) and was heated for about 15 hours at about 55° C. The mixture was cooled and the solid collected by filtration (117 g, 94% ee). The tartrate salt was then extracted from aqueous sodium bicarbonate with 3:1 chloroform/isopropanol to give the free base 3a-A (81.7 g, 78% ee) as an off-white solid. HPLC analysis of the title compound of part 3a-A indicated that the material had an enantiomeric excess of 96%: +APcI MS (M+H)$^+$ 329.

HPLC analysis was performed on an Hewlett-Packard 1050 system with a 1050 DAD, autosampler and solvent delivery system. Data was imported into a HP Vectra XM series 3 running HP Chemstation ver A.4.02. When possible, samples were dissolved in the mobile phase at 1 mg/ml. A Chiracel AD 4.6×250 mm column (Chiral Technologies, 730 Springfield Drive, P.O. Box 564, Exton Pa. 19341) was employed with the following solvents: A=hexane+0.1% diethylamine (v/v); C=isopropanol+0.1% diethylamine (v/v). An isocratic elution was employed using 85% A and 15% C with a flow rate of 1 ml/min, detecting at uv, 254 nm. The desired enantiomer eluted at 11.8 min., while the less desired enantiomer eluted at 15.6 min.

B. (1-{1(R)-Benzyloxymethyl-2-[1,3-dioxo-8a(S)-Pyridin-2-ylmethyl-2-(2,2,2-trifluoro-ethyl)-hexahydro-imidazo[1,5-a]pyrazin-7-yl]-2-oxo-ethylcarbamoyl}-1-methyl-ethyl)-carbamic Acid tert-Butyl Ester To a solution of the title compound of part 3a-A at about 0° C. (10.0 g, 30.5 mmol) and the title compound of part 2-I (13.9 g, 36.6 mmol) in ethyl acetate (200 mL) was added triethylamine (17 mL, 122 mmol), followed by slow addition of a 50% solution of 1-propanephosphonic acid cyclic anhydride in ethyl acetate (18.1 mL, 30.5 mmol) and the reaction was allowed to warm to room temperature. After about 15 hours, the reaction was extracted from saturated aqueous sodium bicarbonate with ethyl acetate, the combined organics were washed with water and then brine, dried ($MgSO_4$), concentrated in vacuo, and the product then purified by silica gel chromatography using 0% to 1% to 5% methanol in chloroform as eluent to give the title compound of part 3a-B (19.5 g, 92%) as a colorless foam.

C. 2-Amino-N-{1(R)-benzyloxymethyl-2-[1,3-dioxo-8a(S)-pyridin-2-ylmethyl-2-(2,2,2-trifluoro-ethyl)-hexahydro-imidazo[1,5-a]pyrazin-7-yl]-2-oxo-ethyl}-2-methyl-)propionamide, Hydrochloride The title compound of part 3-E (17.5 g, 25.3 mmol) was deprotected according to the method described in General Procedure C to give a colorless solid. The product was triturated with ethyl ether to give the title compound of this Example 3a (13.6 g, 90%): +APcI MS (M+H)$^+$ 591.

EXAMPLE 4

2-Amino-N-[2-(8a(S)-benzyl-2-methyl-1,3-dioxo-hexahydro-imidazo[1,5-a]pyrazin-7-yl)-1(R)-benzyloxymethyl-2-oxo-ethyl]-2-methyl-propionamide

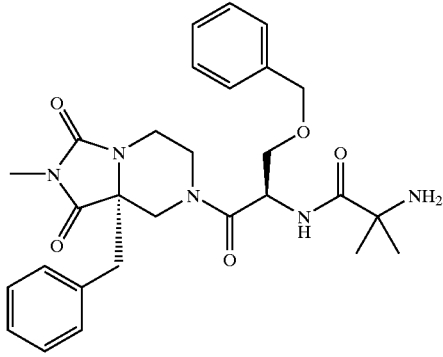

A. 8a-Benzyl-2-methyl-1,3-dioxo-hexahydro-imidazo[1,5-a]pyrazine-7-carboxylic Acid tert-Butyl Ester To a solution of the title compound of part 2-A (676 mg, 2.02 mmol) in acetone (3 mL) was added methyl isocyanate (0.300 mL, 5.09 mmol). The reaction was heated to a gentle reflux and stirred overnight under nitrogen atmosphere. The reaction was quenched with methanol (1 mL), and the mixture was concentrated in vacuo. Purification by silica gel chromatography using 50% ethyl acetate/hexanes as eluent afforded 607 mg of crude product, which was recrystallized in ethanol (0.5 mL) to give the title compound of part 4-A: +APcI MS (M+1)$^+$ 360; $^1$H NMR=300 MHz (CDCl$_3$) δ: 7.20 (arom., m, 3H), 7.04 (arom., m, 2H), 1.52 (BOC, s, 9H).

B. 8a-Benzyl-2-methyl-tetrahydro-imidazo[1,5-a]pyrazine-1,3-dione

The title compound of part 4-A (150 mg, 0.416 mmol) was deprotected according to the method described in General Procedure C to give the title compound of part 4-B (113 mg, 92%), MS (APCI) 260.2.

C. {1-[2-(8a(S)-Benzyl-2-methyl-1,3-dioxo-hexahydro-imidazo[1,5-a]pyrazin-7-yl)-1(R)-benzyloxymethyl-2-oxo-ethylcarbamoyl]-1-methyl-ethyl}-carbamic Acid tert-Butyl Ester According to General Procedure A, the title compound of part 4-B (101 mg, 0.342 mmol) was coupled to the title compound of part 2-I (130 mg, 0.342 mmol), and the product was purified by silica gel chromatography using methylene chloride with a 0–10% methanol gradient as eluent to give the title compound of part 4-C (88 mg, 41%), MS (PB) 622.

D. 2-Amino-N-[2-(8a(S)-benzyl-2-methyl-1,3-dioxo-hexahydro-imidazo[1,5-a]pyrazin-7-yl)-1(R)-benzyloxymethyl-2-oxo-ethyl]-2-methyl-propionamide The title compound of part 4-C (82 mg, 0.132 mmol) was deprotected according to the method described in General Procedure C, and the product was triturated with ethyl ether to give the title compound of this Example 4 (61 mg, 89%). +APcI MS (M+1)$^+$ 522.3.

EXAMPLE 5

2-Amino-N-[1-benzyloxymethyl-2-(2-methyl-1,3-dioxo-hexahydro-imidazo[1,5-a]pyrazin-7-yl)-2-oxo-ethyl]-2-methyl-propionamide, Hydrochloride

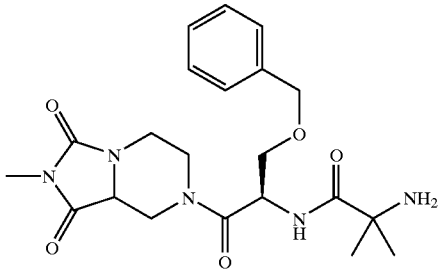

A. Piperazine-1,3-dicarboxylic Acid 1-tert-Butyl Ester 3-Methyl Ester

According to General Procedure F, piperazine-1,2,4-tricarboxylic acid 1-benzyl ester 4-tert-butyl ester 2-methyl ester (3.0 g, 7.9 mmol) was deprotected to give the title compound of part 5-A (1.8 g, 94%): +APcI MS (M+H)$^+$ 245; $^1$H NMR=400 MHz (CDCl$_3$) δ: 3.73 (Me, s, 3H), 3.43 (dd, 1H), 2.73 (t, 1H), 1.45 (BOC, s, 9H).

B. 2-Methyl-tetrahydro-imidazo[1,5-a]pyrazine-1,3-dione, Trifluoroacetic Acid Salt To a pre-dried flask was added the title compound of part 5-A (1.0 g, 4.1 mmol), triethylamine (3.99 mL, 28.7 mmol) and anhydrous dichloromethane (30 mL). The mixture was cooled to about 0° C., and then a 1.93 M solution of phosgene in toluene (3.18 mL, 6.10 mmol) was added, and the reaction was stirred at about 0° C. for about 30 minutes. A 2 M solution of methylamine in methanol (3.07 mL, 6.10 mmol) was added, and the reaction was stirred for about 30 minutes at about 0° C., and then allowed to warm to room temperature and stirred overnight. The reaction was quenched with saturated sodium bicarbonate solution, and the mixture was then extracted three times with dichloromethane. The combined organic layers were washed with brine, dried over anhydrous magnesium sulfate, filtered and concentrated in vacuo to give 0.85 g of t-BOC-protected amine product. The above t-BOC-protected amine product was deprotected according to the method described in General Procedure D to give the title compound of part 5-B as the trifluoroacetic acid salt: +APcI MS (M+H)$^+$ 170; $^1$H NMR=400 MHz (CDCl$_3$) δ: 4.45 (dd, 1H), 4.36 (dd, 1H), 3.07 (Me, s, 3H).

C. {1-[1(R)-Benzyloxymethyl-2-(2-methyl-1,3-dioxo-hexahydro-imidazo[1,5-a]pyrazin-7-yl)-2-oxo-ethylcarbamoyl]-1-methyl-ethyl}-carbamic Acid tert-Butyl Ester According to General Procedure B. the title compound of part 5-B (50 mg, 0.18 mmol) was coupled to the title compound of part 2-I (60 mg, 0.16 mmol), and the product was purified by silica gel chromatography using chloroform to 3% methanol/chloroform as eluent to give the title compound of part 5-C (46 mg, 42%) as a colorless foam: +APcI MS (M+H)$^+$ 532; $^1$H NMR=400 MHz (CDCl$_3$) δ: 7.37–7.20 (arom, m, 5H), 7.02 (CHN$\underline{H}$, d, 1H), 3.00 (Me, s, 1H), 2.96 (Me, s, 2H).

D. 2-Amino-N-[1(R)-benzyloxymethyl-2-(2-methyl-1,3-dioxo-hexahydro-imidazo[1,5-a]pyrazin-7-yl)-2-oxo-ethyl]-2-methyl-propionamide, Hydrochloride The title compound of part 5-C (46 mg, 0.090 mmol) was deprotected according to the method described in General Procedure C, and the product was triturated with ethyl ether to give the title compound of this Example 5 (33 mg, 82%): +APcI MS (M+1)$^+$ 432; $^1$H NMR=400 MHz (CDCl$_3$) δ: 8.70–8.60 (NH, br m, 1H), 2.99 (Me, s, 1H), 2.97 (Me, s, 2H).

EXAMPLE 6

2-Amino-N-{1-benzyloxymethyl-2-[8a(S)-(4-fluoro-benzyl)-6,8-dioxo-hexahydro-pyrrolo[1,2-a]pyrazin-2-yl]-2-oxo-ethyl}-2-methyl-propionamide, Hydrochloride

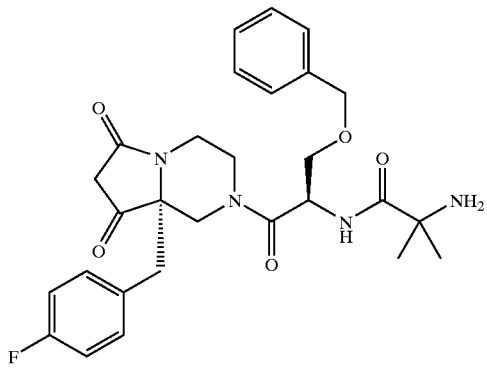

A. 2-(4-Fluoro-benzyl)-piperazine-1,2,4-tricarboxylic Acid 1-Benzyl Ester 4-tert-Butyl Ester 2-Methyl Ester Alkylation of piperazine-1,2,4-tricarboxylic acid 1-benzyl ester 4-tert-butyl ester 2-methyl ester (10.2 g, 27.0 mmol) with 2-fluorobenzyl bromide (5.11 g, 27.0 mmol) was performed analogously to the preparation of the title compound of part 1-A to afford the title compound of part 6-A (2.78 g, 21%): +APcI MS (M–Boc+H)$^+$ 387; $^1$H NMR= 400 MHz (CDCl$_3$) δ: 7.45–7.30 (arom, br s, 5H), 7.00–6.80 (arom, br m, 4H), 5.35–5.05 (br m, 2H), 2.53 (br t, 1H), 1.40 (Boc, s, 9H).

B. 3-(4-Fluoro-benzyl)-piperazine-1,3-dicarboxylic Acid 1-tert-Butyl Ester 3-Methyl Ester According to General Procedure F, the title compound of part 6-A (0.249 g, 0.72 mmol) was deprotected to give the title compound of part 6-B (0.230 g, 91%): +APcI MS (M+H)$^+$ 353, (M–$^t$Bu+H)$^+$ 297, (M–Boc+H)$^+$ 253; $^1$H NMR=400 MHz (CDCl$_3$) δ: 7.08–6.90 (arom, m, 4H), 3.62 (Me, s, 3H), 1.41 (Boc, s, 9H).

C. 4-Acetyl-3-(4-fluoro-benzyl)-piperazine-1,3-dicarboxylic Acid 1-tert-Butyl Ester 3-Methyl Ester To a solution of the title compound of part 6-B (77 mg, 0.22 mmol) and diisopropylethylamine (0.15 mL, 0.87 mmol) in dichloromethane (1 mL) was added acetyl chloride (0.031 mL, 0.44 mmol). The reaction was stirred for about 1.5 hours, then quenched with saturated aqueous NaHCO$_3$. Additional methylene chloride was added and the mixture was washed twice with saturated NaHCO$_3$, then brine, dried over anhydrous magnesium sulfate, filtered and concentrated in vacuo to give the crude product the title compound of part 6-C (86 mg, quantitative): +APcI MS (M–$^t$Bu+H)$^+$ 339, (M–Boc+H)$^+$ 295; $^1$H NMR=400 MHz (CDCl$_3$) δ: 7.10–7.69 (arom., m, 4H), 3.70 (MeO, d, 3H), 2.10 (MeCO, d, 2H), 1.42 (BOC, d, 9H).

D. 8a-(4Fluoro-benzyl)-6,8-dioxo-hexahydro-pyrrolo[1,2-a]pyrazine-2-carboxylic Acid tert-Butyl Ester To a stirred solution of the title compound of part 6-C (86 mg, 0.22 mmol) in anhydrous tetrahydrofuran (1.5 mL) cooled to about –78° C. under nitrogen atmosphere was added a 1M solution of lithium bis(trimethylsilyl)amide in tetrahydrofuran (0.66 mL, 0.66 mmol) dropwise. The reaction was stirred at –78° C. for about 10 minutes, then the reaction was quenched with methanol and concentrated in vacuo. Ethyl acetate was added, and the mixture was extracted with saturated ammonium chloride solution, brine, dried over anhydrous magnesium sulfate, filtered and concentrated in vacuo to give crude product. Purification by silica gel chromatography using 0–50% ethyl acetate/hexanes as eluent yielded the title compound of part 6-D (53 mg, 67%): –APcI MS (M–H)$^-$ 361; $^1$H NMR=400 MHz (CDCl$_3$) δ: 6.94 (arom., d, 4H), 2.66 (CHHPh, d, 1H), 2.01 (CHHPh, d, 1H), 1.47 (BOC, s, 9H).

E. 8a-(4-Fluoro-benzyl)-tetrahydro-pyrrolo[1,2-a]pyrazine-6,8-dione, Hydrochloride The title compound of part 6-D (53 mg, 0.15 mmol) was deprotected according to the method described in General Procedure C, and the product was triturated with ethyl ether to give the title compound of part 6-E (44 mg, quantitative): +APcI MS (M+1)$^+$ 263; $^1$H NMR=400 MHz (methanol-d$_4$) δ: 7.15–6.90 (arom., series of m, 4H), 4.34 (CHHNCO, 1H), 2.93 (td, 1H).

F. (1-{1(R)-Benzyloxymethyl-2-[8a(S)-(4-fluoro-benzyl)-6,8-dioxo-hexahydro-pyrrolo[1,2-a]pyrazin-2-yl]-2-oxo-ethylcarbamoyl}-methyl-ethyl)-carbamic Acid tert-Butyl Ester According to General Procedure B, the title compound of part 6-E (44 mg, 0.15 mmol) was coupled to the title compound of part 2-1 (56 mg, 0.15 mmol), and the product was purified by silica gel chromatography (0–80% ethyl acetate/hexanes) to give desired isomer of the title compound of part 6-F (26 mg, 28%), fractions which contained a mixture of the two diastereomers (20 mg, 22%), followed by the more polar isomer (6 mg, 7%): –APcI MS (M–H)$^-$ 623; For 6-F: $^1$H NMR=400 MHz (CDCl$_3$) δ: 7.35–6.85 (arom., series of m, 9H), 5.16 (br m, 1H), 2.03 (d, 1H). For isomer $^1$H NMR=400 MHz (CDCl$_3$) δ: 7.35–6.55 (arom., series of m, 9H), 5.24 (br m, 1H), 1.91 (d, 1H), 1.40 (Boc, s, 9H).

G. 2-Amino-N-{1(R)-benzyloxymethyl-2-[8a(S)-(4-fluoro-benzyl)-6,8-dioxo-hexahydro-pyrrolo[1,2-a]pyrazin-2-yl]-2-oxo-ethyl}-2-methyl-propionamide, Hydrochloride The title compound of part 6-F (26 mg, 0.042 mmol) was deprotected according to the method described in General Procedure C, and the product was triturated with ethyl ether to give the title compound of this Example 6 (22 mg, 96%): +APcI MS (M+1)$^+$ 525; $^1$H NMR=400 MHz (methanol-d$_4$) δ: 7.40–6.85 (arom., series of m, 9H), 5.15 (t, 1H), 4.54 (s, 2H), 2.68 (d, 1H), 1.58 (Me, m, 6H).

EXAMPLE 7

2-Amino-N-[2-(3a-benzyl-2-methyl-3-oxo-octahydro-pyrrolo[3,4-c]pyridin-5-yl)-1(R)-benzyloxymethyl-2-oxo-ethyl]-2-methyl-propionamide, Hydrochloride

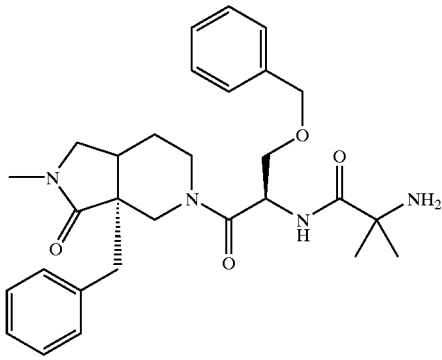

A. 4-Oxo-piperidine-1,3-dicarboxylic Acid 1-tert-Butyl Ester 3-Methyl Ester

To a mixture of 7.00 g (36.2 mmol) of 4-oxo-piperidine-3-carboxylic acid methyl ester and 8.82 g (72.3 mmol) of 4,4-dimethylaminopyridine in 200 mL of methylene chloride at about 0° C. was added a solution of 7.88 g (36.2 mmol) of di-tert-butyldicarbonate in 150 mL of methylene chloride over about 30 min. The mixture was warmed to room temperature and then stirred for about 17 h. The mixture was concentrated and the residue was diluted with chloroform and washed three times each with 10% aqueous HCl, saturated aqueous sodium bicarbonate solution and brine, dried over $MgSO_4$ and concentrated to give 9.18 g of the title compound of part 7-A as a dear yellow oil.

B. 3-(R,S)-Benzyl-4-oxo-piperidine-1,3-dicarboxylic Acid 1-tert-Butyl Ester 3-Methyl Ester To a solution of 5.00 g (19.4 mmol) the title compound of part 7-A in 10 mL of DMF was added 745 mg (7.4 mmol) of sodium hydride (60% oil dispersion) and the mixture was stirred at room temperature for about 15 min. A solution of 3.32 g (19.4 mmol) benzylbromide in 15 mL of DMF was added to the stirring solution by cannula and the mixture was stirred for about 42 h at room temperature. The mixture was diluted with ethyl acetate and washed once with water and four times with brine, dried over $MgSO_4$, and concentrated to give 6.0 g of the title compound of part 7-B as a yellow oil. MS (Cl, $NH_3$) 348 ($MH^+$).

C. 3-Benzyl-4-methoxycarbonylmethylene-piperidine-1,3-dicarboxylic Acid 1-tert-Butyl Ester 3-Methyl Ester In a pre-dried flask under nitrogen atmosphere was placed trimethyl phosphonoacetate (0.97 mL, 6.0 mmol) and anhydrous tetrahydrofuran (5 mL). The mixture was cooled to about 0° C., and t-butoxide was added dropwise over about 5 minutes, and the reaction was stirred about 1 hour at about 0° C. A solution of the title compound of part 7-B (1.058 g, 3.049 mmol) in anhydrous tetrahydrofuran (5 mL) was added via syringe, and the reaction was stirred at room temperature overnight. The solvent was removed in vacuo, and aqueous 2N HCl was added and the mixture was extracted twice with ethyl acetate. The combined organic layers were washed with saturated sodium bicarbonate and brine and dried over anhydrous magnesium sulfate, filtered, and concentrated in vacuo to give the title compound of part 7-C as a colorless liquid (1.407 g, ca 100%): PBMS $(M+1)^+$ 404, $(M+18)^+$ 421, $(M-55)^+$ 348, $(M-99)^+$ 304; $^1$H NMR= 400 MHz ($CDCl_3$) δ: 7.25 m, 3H), 7.10 (arom, m, 2H), 5.99 (=C$\underline{H}$, br s, 1H), 3.70 (Me, s, 3H), 3.60 (Me, s, 3H), 1.40 (BOC, br s, 9H).

D. 3-Benzyl-4-methoxycarbonylmethyl-piperidine-1,3-dicarboxylic Acid 1-tert-Butyl Ester 3-Methyl Ester The title compound of part 7-C (1.4 g, 3.5 mmol), ethyl acetate (25 mL) and 10% palladium on carbon (280 mg) were combined and hydrogenated at 50 psi $H_2$ on a Parr® shaker for about 21 hours. The mixture was then filtered through a bed of diatomaceous earth. The diatomaceous earth was washed with ethyl acetate, and the filtrate was concentrated in vacuo. Purification by silica gel chromatography using 25% ethyl acetate/hexanes as eluent afforded the title compound of part 7-D as a colorless liquid (1.09 g, 79%): PBMS $(M+1)^+$ 406, $(M+18)^+$ 423, $(M-99)^+$ 306; $^1$H NMR=400 MHz ($CDCl_3$) δ: 7.24 (arom, m, 3H), 7.12 (arom, m, 2H), 3.69 (Me, s, 3H), 3.57 (Me, s, 3H), 1.42 (BOC, s, 9H).

E. 3-Benzyl-4-carboxymethyl-piperidine-1,3-dicarboxylic Acid 1-tert-Butyl Ester 3-Methyl Ester To a stirred solution of the title compound of part 7-D (1.07 g, 2.64 mmol) in methanol (15 mL) at about 0° C. was added a 1M aqueous solution of lithium hydroxide (3 mL, 3 mmol). The reaction was stirred at room temperature overnight, then additional 1M aqueous lithium hydroxide solution (1.0 mL, 1 mmol) was added.

The reaction was stirred about another 3 hours, then another 1.0 mL of the lithium hydroxide solution was added. The reaction was stirred for about 5 hours more, then concentrated in vacuo. The residue was quenched with 2N HCl and extracted four times with ethyl acetate. The combined organic layers dried over anhydrous magnesium sulfate, filtered and concentrated in vacuo to give the title compound of part 7-E as a viscous oil (951 mg, 92%): –APcl MS $(M-1)^-$ 390; $^1$H NMR=400 MHz ($CDCl_3$) δ: 7.25 (arom, m, 3H), 7.12 (arom, m, 2H), 3.58 (Me, s, 3H), 1.42 (BOC, s, 9H).

F. 3-Benzyl-4-(benzyloxycarbonylamino-methyl)-piperidine-1,3-dicarboxylic Acid 1-tert-Butyl Ester 3-Methyl Ester A solution of the title compound of part 7-E (951 mg, 2.43 mmol), triethylamine (0.341 mL, 2.46 mmol) and diphenylphosphoryl azide (0.593 mL, 2.67 mmol) in benzene under nitrogen atmosphere was heated to reflux for about 45 minutes. Benzyl alcohol (0.503 mL, 4.86 mmol) was added and the reaction was refluxed overnight. The reaction was cooled to room temperature and the solvent was removed in vacuo. Ethyl acetate was added, and the mixture was extracted with water, saturated sodium bicarbonate solution, brine, dried over anhydrous magnesium sulfate, filtered and concentrated in vacuo to give the title compound of part 7-F as a yellow liquid (1.44 g, ca 100%): +APcl MS $(M-100)^+$ 397; $^1$H NMR=400 MHz ($CDCl_3$) δ: 7.34–7.12 (arom, m, 10H), 5.09 (N$\underline{H}$H, s, 1H), 3.68 (PhC$\underline{H}_2$—O, s, 2H), 3.52 (Me, s, 3H), 1,.42 (BOC, br s, 9H).

G. 4-Aminomethyl-3-benzyl-piperidine-1,3-dicarboxylic Acid 1-tert-Butyl Ester 3-Methyl Ester The title compound of part 7-F (1.4 g, 2.8 mmol), ethyl acetate (20 mL) and 10% palladium on carbon (280 mg)

were combined and hydrogenated at about 50 psi H$_2$ on a Parr® shaker for about 20 hours. The mixture was then filtered through a bed of diatomaceous earth. The diatomaceous earth was washed with ethyl acetate, and the filtrate was concentrated in vacuo. The residue was then dissolved in toluene, and a catalytic amount of triethylamine was added. The reaction was refluxed for about 5 days to form the lactam, with an additional 2–3 drops of triethylamine added after the first day. The filtrate was then concentrated in vacuo. Ethyl acetate was added, and the mixture was washed with saturated sodium bicarbonate solution, 2N HCl, brine, dried over anhydrous magnesium sulfate, filtered and concentrated in vacuo to give 944 mg of a yellow oil. Purification by silica gel chromatography on a chromatotron using 75% ethyl acetate/hexanes as eluent afforded the title compound of part 7-G as a white foam (338 mg, 33%): +APcl MS (M+1)$^+$ 331, (M−55)$^+$ 275, (M−99)$^+$ 231; $^1$H NMR=400 MHz (CDCl$_3$) δ: 7.26–7.10 (arom, m, 5H), 5.69 (NH, br s, 1H), 3.75 (—NHCH$_2$—, br d, 2H), 1.47 (BOC, s, 9H).

H. 3a-Benzyl-2-methyl-3-oxo-octahydro-pyrrolo[3,4-c]pyridine-5-carboxylic Acid tert-Butyl Ester To the title compound of part 7-G (168 mg, 0.508 mmol) in tetrahydrofuran (3 mL) under nitrogen atmosphere was added sodium hydride (22 mg, 60% dispersion in oil, 0.55 mmol), and the mixture was stirred for about 30 minutes at room temperature. Methyl iodide (0.315 mL, 5.06 mmol) was added, and the reaction was stirred for about 3 hours at room temperature. Additional methyl iodide (0.315 mL, 5.06 mmol) was added, and the reaction was stirred for about another 3 hours at room temperature. The reaction mixture was then concentrated in vacuo. Ethyl acetate was added, and the mixture was washed with saturated sodium thiosulfate solution, brine, dried over anhydrous magnesium sulfate, filtered and concentrated in vacuo to give the title compound of part 7-H as a colorless oil (187 mg, ca 100%): +APcl MS (M+1)$^+$ 345, (M−55)$^+$ 289; $^1$H NMR=400 MHz (CDCl$_3$) δ: 7.25–7.15 (arom, m, 5H), 3.64 (—NMeCH$_2$—, br, 2H), 2.70 (NMe, s, 3H), 1.47 (BOC, s, 9H).

I. 3a-Benzyl-2-methyl-octahydro-pyrrolo[3,4-c]pyridin-3-one, Hydrochloride

The title compound of part 7-H (185 mg, 0.537 mmol) in a solution of 4M HCl/dioxane (10 mL) was stirred at room temperature for about 4 hours. The reaction mixture was concentrated in vacuo to a gummy solid, which was triturated with ethyl ether to give a white solid. The ether was decanted off and the solid was dried in vacuo to give the title compound of part 7-I (150 mg, 100%): +APcl MS (M+1)$^+$ 245; $^1$H NMR=400 MHz (methanol-d$_4$) δ: 7.29 (arom, m, 3H), 7.18 (arom, m, 2H), 2.70 (NMe, s, 3H).

J. {1-[2-(3a-Benzyl-2-methyl-3-oxo-octahydro-pyrrolo[3,4-c]pyridin-5-yl)-1(R)-benzyloxymethyl-2-oxo-ethylcarbamoyl]-1-methyl-ethyl}-carbamic Acid tert-Butyl Ester To a stirred solution of the title compound of part 2-I (190 mg, 0.500 mmol), the title compound of part 7-I (150 mg, 0.534 mmol), 1-hydroxy-7-azabenzotriazole (75 mg, 0.55 mmol), and NMM (118 μL, 1.05 mmol) in dichloromethane at about 0° C. under nitrogen atmosphere was slowly added 1-(3-dimethylaminopropyl)-3-ethylcarbodiimide hydrochloride (106 mg, 0.55 mmol). The reaction was allowed to warm to room temperature overnight. The reaction was then concentrated in vacuo. Ethyl acetate was added, and the mixture was extracted with 2N HCl, saturated sodium bicarbonate solution, brine, dried over anhydrous magnesium sulfate, filtered and concentrated in vacuo to give 257 mg of a colorless oil. Purification by silica gel chromatography on a chromatotron using 0–2% methanol/ethyl acetate as eluent afforded the title compound of part 7-J as a colorless oil (205 mg, 68%): +APcl MS (M+1)$^+$ 607, (M−99)$^+$ 507; $^1$H NMR= 400 MHz (methanol-d$_4$) δ: 7.30–7.02. (arom, m, 10H), 5.13 (NCHCO, br m, 1H), 4.50 (OCH$_2$Ph, m, 2H), 1.43 (Me, m, 6H), 1.38 (BOC, m, 9H).

K. 2-Amino-N-[2-(3a-benzyl-2-methyl-3-oxo-octahydro-pyrrolo[3,4-c]pyridin-5-yl)-1(R)-benzyloxymethyl-2-oxo-ethyl]-2-methyl-propionamide, Hydrochloride A solution of the title compound of part 7-J (195 mg, 0.321 mmol) in 4M HCl/dioxane (10 mL) was stirred at room temperature overnight. The reaction was concentrated in vacuo to a gummy solid, which was triturated with ethyl ether to give a solid. The solid was collected by filtration to give the title compound of this Example 7 as a white solid (118 mg, 70%): +APcl MS (M+1)$^+$ 507; $^1$H NMR=400 MHz (methanol-d$_4$) δ: 7.32–7.10 (arom, m, 10H), 5.12 (NCHCO, br m, 1H), 4.55 (OCHH$_2$Ph, m, 2H), 1.60 (Me, m, 6H).

EXAMPLE 8

2-Amino-N-[2-(3a-benzyl-3-oxo-hexahydro-fluoro[3,4-c]pyridin-5-yl)-1(R)-benzyloxymethyl-2-oxo-ethyl]-2-methyl-propionamide, Hydrochloride

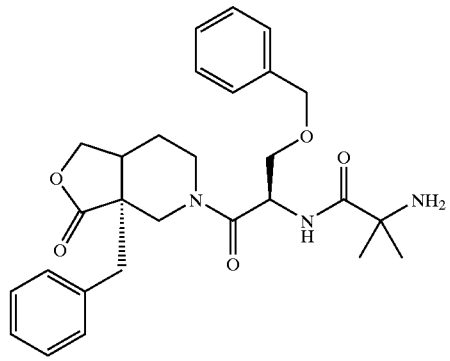

A. 3-Benzyl-4-methoxymethylene-piperidine-1,3-dicarboxylic Acid 1-tert-Butyl Ester 3-Methyl Ester To a suspension of methoxymethyl triphenylphosphonium chloride (9.87 g, 28.8 mmol) in anhydrous tetrahydrofuran (20 mL) was added a 1 M solution of potassium tert-butoxide in tetrahydrofuran (31.7 mL, 31.7 mmol) at room temperature for about 2 hours. The title compound of part 7-B (10 g, 28.8 mmol) was then added, and the reaction was stirred at room temperature overnight. The reaction mixture was diluted with ethyl acetate, and washed twice with 10% aqueous HCl solution, saturated sodium bicarbonate solution, brine, dried over anhydrous magnesium sulfate, filtered, and concentrated in vacuo to give crude product the title compound of part 8-A: +APcl MS (M−56)$^+$ 319, (M−100)$^+$ 275; $^1$H NMR=300 MHz (CDCl$_3$) δ: 7.28–7.11 (arom, series of m, 5H), 6.61 (C=CH—, s, 1H), 3.60 (OMe, s, 3H), 3.55 (OMe, s, 3H), 1.40 (BOC, s, 9H).

B. 3-Benzyl-4-formyl-piperidine-1,3-dicarboxylic Acid 1-tert-Butyl Ester 3-Methyl Ester A solution of the title compound of part 8-A (430 mg, 1.15 mmol) and sodium iodide (343 mg, 2.29 mmol) in tetrahydrofuran (3 mL) was stirred at room temperature for about 2 days. The reaction mixture was diluted with ethyl acetate, and washed twice with saturated sodium bicarbonate solution, brine, dried over anhydrous magnesium sulfate, filtered, and concentrated in vacuo to give the title compound of part 8-B as a yellow oil (410 mg, 99%): PB MS (M+1)⁺ 362, (M+18)⁺ 379, (M–55) 306, (M–99) 262; ¹H NMR 250 MHz (CDCl₃) δ: 9.72 (aldehyde, d, 1H), 7.26–7.08 (arom, series of m, 5H), 3.60 (OMe, s, 3H), 1.48 (BOC, s, 9H).

C. 3a-Benzyl-3-oxo-hexahydro-furo[3,4-c]pyridine-5-carboxylic Acid tert-Butyl Ester To a solution of the title compound of part 8-B (410 mg, 1.14 mmol) in methanol (5 mL) at about 0° C. was added sodium borohydride (86 mg, 2.3 mmol). The reaction was warmed to room temperature and stirred for about 2.5 hours. The reaction mixture was cooled to about 0° C., and quenched with saturated ammonium chloride solution. The mixture was then diluted with ethyl acetate, and washed three times with saturated sodium bicarbonate solution, twice with brine, dried over anhydrous magnesium sulfate, filtered, and concentrated in vacuo to give crude product. Purification by silica gel chromatography using 20–60% ethyl acetate/hexanes as eluent afforded the title compound of part 8-C (90 mg, 24%): +APcl MS (M–55)⁺ 276, (M–99)⁺ 232; ¹H NMR=250 MHz (CDCl₃) δ: 7.28–7.17 (arom, series of m, 5H), 1.50 (BOC, s, 9H).

D. 3a-Benzyl-hexahydro-furo[3,4-c]pyridine-3-one

The title compound of part 8-C (90 mg, 0.27 mmol) was deprotected according to the method described in General Procedure C to give the crude product as an HCl salt. This crude product was then diluted with chloroform, washed with saturated sodium bicarbonate solution, dried over anhydrous magnesium sulfate, filtered, and concentrated in vacuo to give crude product of the title compound of part 8-D as the free amine (50 mg, 81%): +APcl MS (M+1)⁺ 231; ¹H NMR=250 MHz (methanol-d₄) δ: 7.20 (arom, m, 5H), 4.08 (CH₂OCO—, m, 2H).

E. {1-[2-(3a-Benzyl-3-oxo-hexahydro-furo[3,4-c]pyridin-5-yl)-1(R)-benzyloxymethyl-2-oxo-ethylcarbamoyl]-1-methyl-ethyl}-carbamic Acid tert-Butyl Ester According to General Procedure B, the title compound of part 8-D (50 mg, 0.22 mmol) was coupled to the title compound of part 2-I (82 mg, 0.22 mmol), and the product was purified by silica gel chromatography using 50–80% ethyl acetate/hexanes as eluent to give the title compound of part 8-E (100 mg, 77%): PB MS (M+1)⁺ 594, (M+18)⁺ 611; ¹H NMR=250 MHz (CDCl₃) δ: 7.30–6.98 (arom series of m, 10H), 1.45 (Me, d, 6H), 1.40 (BOC, s, 9H).

F. 2-Amino-N-[2-(3a-benzyl-3-oxo-hexahydro-furo[3,4-c]pyridin-5-yl)-1(R)-benzyloxymethyl-2-oxo-ethyl]-2-methyl-propionamide, Hydrochloride The title compound of part 8-E (100 mg, 0.170 mmol) was deprotected according to the method described in General Procedure C to give the title compound of this Example 8 (50 mg, 55%): PB MS (M+1)⁺ 494; ¹H NMR=250 MHz (methanol-d₄) δ: 7.31–7.10 (arom, series of m, 10H), 1.57 (Me, d, 6H).

EXAMPLE 9

2-Amino-N-[1(R)-benzyloxymethyl-2-(3-methyl-2-oxo-3a-pyridin-2-ylmethyl-hexahydro-oxazolo[4,5-c]pyridin-5-yl)-2-oxo-ethyl]-2-methyl-propionamide Hydrochloride

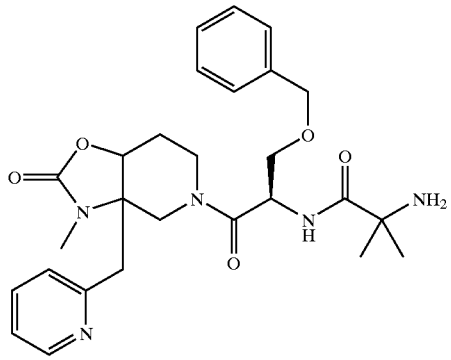

A. 4-Oxo-3-(R,S)-Pyridin-2-ylmethyl-piperidine-1,3-dicarboxylic Acid 1-tert-Butyl Ester 3-Methyl Ester To a solution of 2.00 g (7.8 mmol) of 3-benzyl-4-oxo-piperidine-1,3-dicarboxylic acid 1-tert-butyl ester 3-butyl ester, prepared analogously to the preparation of the methyl ester analog (the title compound of part 7-A), in 32 mL of THF was added 468 mg (11.7 mmol) of sodium hydride (60% oil dispersion) at about 0° C. and the mixture was stirred for about 30 min. A solution of 762 mg (6.0 mmol) 2-picolyl chloride in 5 mL of THF was added to the stirring solution over about 5 min, followed by the addition of 432 mg (2.6 mmol) of potassium iodide. The ice bath was removed and the mixture was heated for about 17 h at reflux. The mixture was diluted with ethyl acetate and washed once with water and once with brine, dried over MgSO₄, and concentrated. The residue was purified by silica gel chromatography using (6:4 v/v ether:hexane) followed by (6:4 v/v ethyl acetate:hexane) to give 1.2 g of the title compound of part 9-A. MS (Cl, NH₃) 349 (MH⁺).

B. 4-Hydroxy-3-pyridin-2-ylmethyl-piperidine-1,3-dicarboxylic Acid 1-tert-Butyl Ester 3-Ethyl Ester To a stirred solution of the title compound of part 9-A (8.0 g, 0.022 mmol) in methanol (80 mL) at 0° C. was added sodium borohydride (0.836, 0.022 mmol) portionwise. The reaction was stirred for about 3 hours at room temperature. The reaction was quenched with saturated ammonium chloride solution, the methanol was removed in vacuo, and the aqueous mixture was extracted several times with ethyl acetate. The combined organic layers were dried over anhydrous magnesium sulfate, filtered, and concentrated in vacuo to give 10 g of crude product. Purification by silica gel chromatography using 50–80% ethyl acetate/hexanes as eluent afforded the title compound of part 9-B (7.3 g, 91%): +APcl MS (M+1)⁺ 365, (M–55)⁺ 309, (M–99)⁺ 265; ¹H NMR=300 MHz (CDCl₃) δ: 8.48 (arom, d, 1H), 7.67 (arom, t, 1H), 7.20 (arom, m, 1H), 7.00 (arom, br, 1H), 1.44 (BOC, s, 9H), 1.20 (CH₂CH₃, t, 3H).

C. 4-Hydroxy-3-pyridin-2-ylmethyl-piperidine-1,3-dicarboxylic Acid 1-tert-Butyl Ester A solution of the title compound of part 9-B (2.3 g, 6.3 mmol) and aqueous 1 N NaOH (32 mL) in ethanol (30 mL)

was stirred overnight at room temperature. The reaction was then stirred overnight at about 35° C. The solvent was removed in vacuo, the aqueous mixture was diluted with water and dichloromethane, and then acidified to about pH 4.0–4.8 with glacial acetic acid. The organic layer was removed, and the aqueous layer was extracted several times with dichloromethane. All of the organic layers were combined and dried over anhydrous magnesium sulfate, filtered, and concentrated in vacuo to give the title compound of part 9-C (2.2 g, 100%): –APcI MS (M–1)$^-$ 335; $^1$H NMR=300 MHz (methanol-d$_4$) δ: 8.44 (arom, d, 1H), 7.75 (arom, t, 1H), 7.29 (arom, m, 2H), 1.40 (BOC, s, 9H).

D. 2-Oxo-3a-pyridin-2-ylmethyl-hexahydro-oxazolo[4,5-c]pyridine-5-carboxylic Acid tert-Butyl Ester A solution of the title compound of part 9-C (2.2 g, 6.5 mmol), diphenylphosphoryl azide(1.8 g, 6.5 mmol), and triethylamine (661 mg, 6.5 mmol) in benzene (25 mL) was heated to reflux for about 14 hours, then stirred at room temperature for about 2 days. The reaction was then concentrated in vacuo. Purification by silica gel chromatography using ethyl acetate/pentane as eluent afforded the title compound of part 9-D (492 mg, 22%): +APcI MS (M+1)$^+$ 334, (M–55)$^+$ 278; $^1$H NMR=300 MHz (CDCl$_3$) δ: 8.50 (arom, d, 1H), 7.64 (arom, t, 1H), 7.16 (arom, m, 2H), 7.08 (NH, br s, 1H), 1.17 (BOC, s, 9H).

E. 3-Methyl-2-oxo-3a-pyridin-2-ylmethyl-hexahydro-oxazolo[4,5-c]pyridine-5-carboxylic Acid tert-Butyl Ester To a stirred solution of the title compound of part 9-D (494 mg, 1.48 mmol) in N,N-dimethylformamide was added sodium hydride (43 mg, 60% dispersion in mineral oil, 1.8 mmol) at room temperature. The mixture was stirred for about 10 minutes, then methyl iodide (256 mg, 1.80 mmol) was added, and the reaction was stirred overnight. Water was added to the reaction mixture, and the mixture was extracted several times with ethyl acetate. The combined organic layers were then back-extracted several times with water. The organic layer was dried over magnesium sulfate, filtered and concentrated in vacuo to give 494 mg of crude product. Purification by silica gel chromatography using 60% ethyl acetate/hexanes as eluent afforded the title compound of part 9-E as a crystalline solid (273 mg, 53%): +APcI MS (M+1)$^+$ 348, (M–55)$^+$ 292, (M–99)$^+$ 248; $^1$H NMR=400 MHz (CDCl$_3$) δ: 8.51 (arom, br, 1H), 7.60 (arom, br, 1H), 7.18 (arom, br m, 2H), 2.85 (NMe, br, 3H), 1.46 (BOC, s, 9H).

F. 3-Methyl-3a-pyridin-2-ylmethyl-hexahydro-oxazolo[4,5-c]pyridin-2-one Dihydrochloride To the title compound of part 9-E (270 mg, 0.778 mmol) in anhydrous dichloromethane (1 mL) was added a solution of 4M HCl/dioxane (1 mL, 4 mmol), and the mixture was stirred for about 4 hours. The reaction mixture was then concentrated in vacuo to give the title compound of part 9-F (220 mg, 89%): +APcI MS (M+1)$^+$ 248; $^1$H NMR=300 MHz (methanol-d$_4$) δ: 8.78 (arom, d, 1H), 8.43 (arom, t, 1H), 8.00 (arom, d, 1H), 7.91 (arom, t, 1H), 2.57 (NMe, s, 3H).

G. {1-[1(R)-Benzyloxymethyl-2-(3-methyl-2-oxo-3a-pyridin-2-ylmethyl-hexahydro-oxazolo[4,5-c]pyridin-5-yl)-2-oxo-ethylcarbamoyl]1-1-methyl-ethyl}-carbamic Acid tert-Butyl Ester To a stirred solution of the title compound of part 9-F (115 mg, 0.360 mmol), the title compound of part 2-I (116 mg, 0.360 mmol), triethylamine (101 μL, 0.72 mmol), and 1-hydroxy-7-azabenzotriazole (61 mg, 0.45 mmol) in dichloromethane (2 mL) cooled to about –30° C. was added 1,2-diethylaminoethyl chloride hydrochloride (69 mg, 0.36 mmol). The reaction was stirred at about –30° C. for about 2 hours, then allowed to warm slowly to room temperature overnight. The reaction was then concentrated in vacuo. Purification by silica gel chromatography using ethyl acetate as eluent afforded the title compound of part 9-G (129 mg, 59%): +APcI MS (M+1)$^+$ 610, (M–99)$^+$ 510; $^1$H NMR=300 MHz (CDCl$_3$) δ: 8.51 (arom, br d, 1H), 7.57 (arom, br, 1H), 7.25–7.15 (arom, m, 7H), 1.42 (Me, s, 6H), 1.38 (BOC, br, 9H).

H. 2-Amino-N-[1(R)-benzyloxymethyl-2-(3-methyl-2-oxo-3a-pyridin-2-ylmethyl-hexahydro-oxazolo[4,5c]pyridin-5-yl)-2-oxo-ethyl]-2-methyl-propionamide, Hydrochloride To the title compound of part 9-G (125 mg, 0.205 mmol) in anhydrous dichloromethane (1 mL) was added 4M HCl/dioxane (1 mL), and the reaction was stirred at room temperature overnight. The reaction was concentrated in vacuo to give the title compound of this Example 9 (133 mg, ca 100%): +APcI MS (M+1)$^+$ 510; $^1$H NMR=300 MHz (CDCl$_3$) δ: 8.80 (arom, m, 1H), 8.52 (arom, m, 1H), 8.10 (arom, m, 1H), 8.02 (arom, m 1H), 7.35–7.27 (arom, series of m, 5H), 1.62 (Me, s, 3H), 1.59 (Me, s, 3H).

EXAMPLE 10

2-Amino-N-[2-(4a-benzyl-2-oxo-hexahydro-3-oxa-1,6-diaza-naphthalen-6-yl)-1(R)-benzyloxymethyl-2-oxo-ethyl]-2-methyl-propionamide, Hydrochloride

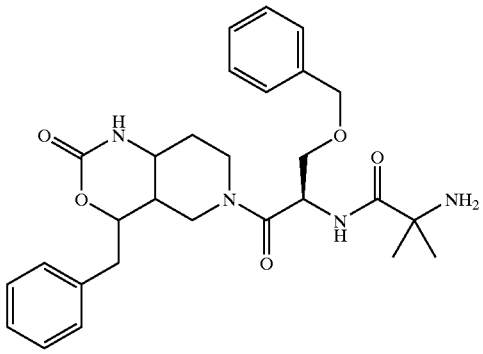

A. 3-Benzyl-4-oxo-piperidine-3-carboxylic Acid Methyl Ester, Hydrochloride

To a stirred solution of the title compound of part 7-A (98.1 g, 282 mmol) in ethyl ether/ethyl acetate (800 mL/200 mL) at room temperature under nitrogen atmosphere was bubbled in HCl gas for about 30 minutes. The reaction was stirred for about 1 hour, then HCl gas was bubbled in for about an additional 30 minutes and the reaction was stirred for about another 1 hour. HCl gas was bubbled in for about an additional 1 hour, and then the solid product was collected by filtration, rinsed with ethyl ether, and dried in vacuo to give the title compound of part 10-A as a white powder. (72 g, 90%); $^1$H NMR=250 MHz (methanol-d$_4$) δ: 7.29 (arom, m, 3H), 7.09 (arom, m, 2H), 3.81 (Me, s, 3H), 3.74–2.66 (series of m, 8H).

B. 3-Benzyl-4-oxo-piperidine-3-carboxylic Acid Methyl Ester

The title compound of part 10-A was suspended in chloroform and washed twice with saturated sodium bicarbonate solution, dried over sodium sulfate, filtered and concentrated in vacuo to give a waxy solid. This solid was stirred in isopropyl ether (250 mL) overnight, and then the solid product was collected by filtration and dried in vacuo to give the title compound of part 10-B as a white powder (23 g, 76%): TSMS (M+1)$^+$ 248; $^1$H NMR=250 MHz (methanol-d$_4$) δ: 7.22 (arom, m, 3H), 7.10 (arom, m, 2H), 3.65 (Me, s, 3H), 3.54–2.35 (series of m, 8H).

C. 1,3-Dibenzyl-4-oxo-piperidine-3-carboxylic Acid Methyl Ester

A solution of the title compound of part 10-B (17.0 g, 68.7 mmol), potassium carbonate (19.0 g, 138 mmol), and benzyl bromide (11.8 g, 68.7 mmol) in N,N-dimethylformamide (100 mL) was stirred at room temperature overnight. The mixture was diluted with ethyl acetate and washed twice with water, brine, dried over sodium sulfate and filtered. The N,N-dimethylformamide was azeotroped off with heptane, and the product was concentrated in vacuo to give the title compound of part 10-C as a yellow oil (19 g, 82%): PBMS (M+1)$^+$ 338; $^1$H NMR=250 MHz (CDCl$_3$) δ: 7.31 (Ph, m, 5H), 7.21 (Ph, m, 5H), 3.64 (Me, s, 3H), 3.60 (s, 2H), 3.41–2.90 (series of m, 8H).

D. 1,3-Dibenzyl-4-hydroxyimino-piperidine-3-carboxylic Acid Methyl Ester

To a stirred solution of the title compound of part 10-C (2.1 g, 6.2 mmol) and triethylamine (0.90 mL, 6.2 mmol) in methanol (30 mL) was added hydroxylamine hydrochloride (433 mg, 6.22 mmol). The reaction was stirred at room temperature for about 16 hours under nitrogen atmosphere. The reaction mixture was then concentrated in vacuo, diluted with dichloromethane, and then quenched with aqueous 10% HCl until the mixture was at about pH 2. The organic layer was washed with saturated sodium bicarbonate solution, brine, dried over sodium sulfate, filtered and concentrated in vacuo to give the title compound of part 10-D as a yellow, hygroscopic solid (1.7 g, 78%): +APcl MS (M+1)$^+$ 353; $^1$H NMR=300 MHz (methanol-d$_4$) δ: 7.28–7.17 (arom, m, 10H), 5.47 (NOH, s, 1H), 3.52 (Me, s, 3H), 3.48–2.20 (series of multiplets, 10H).

E. (4-Amino-1,3-dibenzyl-piperidin-3-yl)-methanol

To a stirred solution of the title compound of part 10-D (1.59 g, 4.51 mmol) in tetrahydrofuran at about 0° C. under nitrogen atmosphere was slowly added a 1M solution of lithium aluminum hydride (11.28 mL). The reaction was slowly warmed to room temperature and then heated at reflux for about 17 hours. The reaction was then cooled to about 0° C. and quenched with water (8 mL), then aqueous 15% NaOH (24 mL) was slowly added, followed by additional water (8 mL). The mixture was filtered, and the solid precipitate was rinsed with ethyl acetate (40 mL). The organic layer in the filtrate was separated and washed twice with brine, dried over sodium sulfate, filtered and concentrated in vacuo to give the title compound of part 10-E as a yellow, hygroscopic solid (1.35 g, 57%): +APcl MS (M+1)$^+$ 311; $^1$H NMR=250 MHz (methanol-d$_4$) δ: 7.18 (arom, m, 10H), 3.31–1.40 (series of m, 12H).

F. 4a,6-Dibenzyl-octahydro-3-oxa-1,6-diaza-naphthalen-2-one

A solution of the title compound of part 10-E (980 mg, 3.16 mmol), 1,1'-carbonyldiimidazole (2.560 mg, 15.78 mmol), and triethylamine (0.90 mL, 6.3 mmol) in ethylene glycol dimethyl ether was heated at reflux for about 2 days under nitrogen atmosphere. The reaction was then cooled to room temperature, and concentrated in vacuo. The mixture was diluted with chloroform (150 mL), and washed with water (30 mL) and then brine (30 mL). The organic layer was dried over sodium sulfate, filtered and concentrated in vacuo. Purification by silica gel chromatography using 75% ethyl acetate/hexanes as eluent afforded the title compound of part 10-F (410 mg, 39%): +APcl MS (M+1)$^+$ 337; $^1$H NMR=300 MHz (CDCl$_3$) δ: 7.40–7.00 (arom, series of m, 10H), 6.34 (NH, br s, 1H), 3.75 (d of d, 2H), 3.51 (s, 2H), 3.39 (m, 2H), 3.11 (br d, 1H), 2.68 (d of d, 2H), 2.14–1.50 (series of m, 4H).

G. 4a-Benzyl-octahydro-3-oxa-1,6-diaza-naphthalen-2-one

The title compound of part 10-F (347 mg, 1.03 mmol), ethanol (50 mL), water (10 mL), and 10% palladium on carbon (347 mg) were combined and hydrogenated at 45 psi H$_2$ on a Parr® shaker overnight. The mixture was then filtered through a bed of diatomaceous earth. The diatomaceous earth was washed with ethanol (200 mL), and the filtrate was concentrated in vacuo. Purification by silica gel chromatography using 75–100% ethyl acetate/hexanes as eluent afforded the title compound of part 10-G as a white solid (130 mg, 53%): +APcl MS (M+1)$^+$ 247; $^1$H NMR=250 MHz (methanol-d$_4$) δ: 7.29 (Ph, m, 5H), 3.78 (s, 1H), 3.35 (s, 2H), 3.22–1.68 (series of m, 8H).

H. {1-[2-(4a-Benzyl-2-oxo-hexahydro-3-oxa-1,6-diaza-naphthalen-6-yl)-1-benzyloxymethyl-2-oxo-ethylcarbamoyl]-1-methyl-ethyl}-carbamic Acid tert-Butyl Ester A solution of the title compound of part 10-G (125 mg, 0.507 mmol), 1-hydroxy-7-azabenzotriazole (103 mg, 0.762 mmol), the title compound of part 2-I (290 mg, 0.762 mmol), and 1-(3-dimethylaminopropyl)-3-ethylcarbodiimide (107 mg, 0.558 mmol) in anhydrous dichloromethane (20 mL) was stirred at room temperature overnight under nitrogen atmosphere. The reaction mixture was diluted with dichloromethane, and the solution was extracted with saturated sodium bicarbonate solution and then brine. The organic layer was dried over sodium sulfate, filtered and concentrated in vacuo. Purification by silica gel chromatography using 5% methanol/dichloromethane as eluent afforded the title compound of part 10-H as a white solid (93 mg, 30%): +APcl MS (M+1)$^+$ 609, (M−99)$^+$ 509; $^1$H NMR=250 MHz (CDCl$_3$) δ: 7.25 (arom, m, 10H), 1.50–1.40 (Me, BOC, 15H).

I. 2-Amino-N-[2-(4a-benzyl-2-oxo-hexahydro-3-oxa-1,6-diaza-naphthalen-6-yl)-1-benzyloxymethyl-2-oxo-ethyl]-2-methyl-propionamide, Hydrochloride To a stirred solution of the title compound of part 10-H (89 mg, 0.15 mmol) in ethanol (30 mL) was added concentrated hydrochloric acid (8 mL) at room temperature. The reaction was stirred for about 30 minutes, then concentrated in vacuo. The residue was dissolved in methanol (1 mL), ethyl acetate was added, and the product precipitated out as a solid. The solvent was removed in vacuo to give the title compound of this Example 10 as a white solid (83 mg, 100%): +APcl MS (M+1)$^+$ 509; $^1$H NMR=250 MHz (methanol-d$_4$) δ: 7.20 (arom, m, 10H), 1.58 (Me, br s, 3H) 1.50 (Me, br s, 3H).

EXAMPLE 11

2-Amino-N-[2-(3a-benzyl-2-methyl-1,3-dioxo-octahydro-pyrrolo[3,4-c]pyridin-5-yl)-1-(R)-benzyloxymethyl-2-oxo-ethyl]-2-methyl-propionamide, Hydrochloride

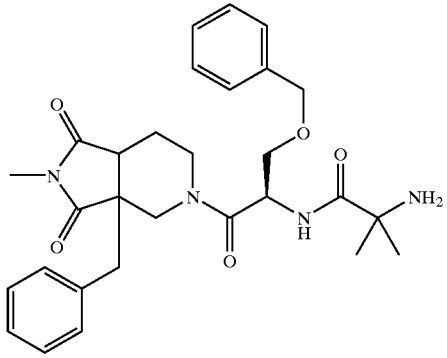

A. 2-Methyl-pyrrolo[3,4-c]pyridine-1,3-dione

To a stirred solution of 3,4-pyridinedicarboximide (10.0 g, 67.5 mmol) in N,N-dimethylformamide was added sodium hydride (1.55 g, 60% dispersion in mineral oil, 67.5 mmol) at room temperature. The mixture was stirred for about 30 minutes, then methyl iodide (9.58 g, 67.5 mmol) was added, and the reaction was stirred overnight. Ethyl acetate was added to the reaction mixture, and the mixture was extracted once with water, twice with brine. The organic layer was dried over anhydrous magnesium sulfate, filtered and concentrated in vacuo (azeotroping excess N,N-dimethylformamide with heptanes) to give crude product. Purification by silica gel chromatography using 0–5% methanol/dichloromethane as eluent afforded the title compound of part 11-A as an off-white solid (5 g, 46%): PB MS (M+1)$^+$ 163; $^1$H NMR=250 MHz (CDCl$_3$) δ: 9.11 (arom, s, 1H), 9.08 (arom, d, 1H), 7.75 (arom, d, 1H), 3.20 (Me, s, 3H).

B. 2-Methyl-hexahydro-pyrrolo[3,4-c]pyridine-1,3-dione, Hydrochloride

The title compound of part 11-A (1.00 g, 6.17 mmol), ethanol (20 mL), 3N HCl (5 mL), and 10% palladium on carbon (1.0 g) were combined and hydrogenated at about 45 psi H$_2$ on a Parr shaker overnight. The mixture was then filtered through a bed of diatomaceous earth. The diatomaceous earth was washed with ethanol, and the filtrate was concentrated in vacuo to give the title compound of part 11-B as a white solid (1.35 g, 100%): PB MS (M+1)$^+$ 169; $^1$H NMR=300 MHz (methanol-d$_4$) δ: 2.98 (Me, s, 3H).

C. 2-Methyl-1,3-dioxo-octahydro-pyrrolo[3,4-c]pyridine-5-carboxylic Acid tert-Butyl Ester To a stirred solution of the title compound of part 11-B (1.27 g, 6.20 mmol) and 4-dimethylaminopyridine (1.51 g, 12.4 mmol) in dichloromethane (100 mL) cooled to about 0° C. was added a solution of di-tert-butyl dicarbonate (1.35 g, 6.20 mmol) in dichloromethane dropwise. The reaction was then allowed to warm slowly to room temperature overnight. The reaction was concentrated in vacuo. Ethyl acetate was added to the reaction mixture, and the mixture was extracted twice with 10% HCl, twice saturated sodium bicarbonate solution, and twice with brine. The organic layer was dried over anhydrous magnesium sulfate, filtered and concentrated in vacuo to give the title compound of part 11-C as a light yellow oil (1.2 g, 72%): PB MS (M+1)$^+$ 269, (M+18)$^+$ 286; $^1$H NMR=300 MHz (CDCl$_3$) δ: 2.85 (Me, s, 3H), 1.34 (BOC, s, 9H).

D. 3a-Benzyl-2-methyl-1,3-dioxo-octahydro-pyrrolo[3,4-c]pyridine-5-carboxylic Acid tert-Butyl Ester To a stirred solution of the title compound of part 11-C (600 mg, 2.24 mmol) in tetrahydrofuran (10 mL) cooled to about −78° C. was added a 1M solution of lithium bis(trimethylsilyl)amide in tetrahydrofuran (2.33 mL) was slowly added over about 10 minutes. The reaction was stirred at about −78° C. for about 30 minutes, and then benzyl bromide (0.28 mL, 2.3 mmol) was added. The reaction was allowed to slowly warm to room temperature and was stirred for about 3 days. The reaction was concentrated in vacuo, and water was added. The mixture was extracted twice with ethyl acetate. The combined organic layers were dried over anhydrous magnesium sulfate, filtered and concentrated in vacuo to give crude product. Purification by silica gel chromatography using 15–100% ethyl acetate/hexanes as eluent afforded the title compound of part 11-D (470 mg, 59%): PB MS (M+1)$^+$ 359, (M+18)$^+$ 376; $^1$H NMR=300 MHz (CDCl$_3$) δ: 7.20 (arom., m, 3H), 7.06 (arom., m, 2H), 2.80 (Me, s, 3H), 1.40 (BOC, s, 9H).

E. 3a-Benzyl-2-methyl-hexahydro-pyrrolo[3,4-c]pyridine-1,3-dione, Hydrochloride The title compound of part 11-D (450 mg, 1.26 mmol) was deprotected according to the method described in General Procedure C to give the title compound of part 11-E (370 mg, 99%): PB MS (M+1)$^+$ 259; $^1$H NMR=250 MHz (methanol-d$_4$) δ: 7.28 (arom., m, 3H), 7.14 (arom., m, 2H), 2.70 (Me, s, 3H).

F. {1-[2-(3a-Benzyl-2-methyl-1,3-dioxo-octahydro-pyrrolo[3,4-c]pyridin-5-yl)-1(R)-benzyloxymethyl-2-oxo-ethylcarbamoyl]-1-methyl-ethyl}-carbamic acid tert-Butyl Ester According to General Procedure B, the title compound of part 11-E (150 mg, 0.51 mmol) was coupled to the title compound of part 2-I (193 mg, 0.51 mmol), and the product was purified by silica gel chromatography using 50–100% ethyl acetate/hexanes as eluent to give the title compound of part 11-F (180 mg, 57%): PB MS (M+1)$^+$ 621, (M+18)$^+$ 638; $^1$H NMR=250 MHz (CDCl$_3$) δ: 7.30–6.90 (arom., series of m, 10H), 1.44 (Me, s, 6H), 1.40 (BOC, s, 9H).

G. 2-Amino-N-[2-(3a-benzyl-2-methyl-1,3-dioxo-octahydro-pyrrolo[3,4-c]pyridin-5-yl)-1(R)-benzyloxymethyl-2-oxo-ethyl]-2-methyl-propionamide, Hydrochloride The title compound of part 11-F (180 mg, 0.29 mmol) was deprotected according to the method described in General Procedure C to give the title compound of this Example 11 (120 mg, 74%): PB MS (M+1)$^+$ 521; $^1$H NMR=300 MHz (methanol-d$_4$) δ: 7.30–7.10 (arom., series of m, 10H), 1.55 (Me, br s, 6H).

EXAMPLE 12

2-Amino-N-[1(R)-benzyloxymethyl-2-(2-ethyl-4-oxo-4,5,6,8-tetrahydro-3H-pyrido[3,4-d]pyrimidin-7-yl)-2-oxo-ethyl]-2-methyl-propionamide, hydrochloride

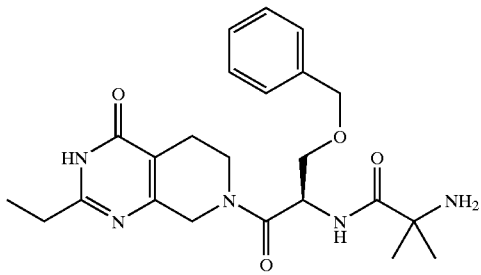

A. 2-Ethyl-5,6,7,8-tetrahydro-3H-pyrido[3,4-d]pyrimidin-4one

7-Benzyl-2-ethyl-5,6,7,8-tetrahydro-3H-pyrido[3,4-d]pyrimidin-4-one (270 mg, 1.00 mmol), prepared by the method of Lazar et al. (J. Heterocycl. Chem. 1990, 27, 1885), was de-benzylated according to the method described in General Procedure D to give the title compound of part 12-A as a white powder (160 mg, 89%): PB MS (M+1)$^+$ 180; $^1$H NMR=300 MHz (methanol-d$_4$) δ: 3.70 (—NC$\underline{H}_2$—, s, 2H), 3.20 (—NC$\underline{H}_2$—, t, 2H), 2.58 (C$\underline{H}_2$Me, t, 2H), 2.48 (—C$\underline{H}_2$—C—CO, br t, 2H), 1.25 (Me, t, 3H).

B. {1-[1-Benzyloxmethyl-2-(2-ethyl-4-oxo-4,5,6,8-tetrahydro-3H-pyrido[3,4-d]pyrimidin-7-yl)-2-oxo-ethylcarbamoyl]-1-methyl-ethyl}-carbamic Acid tert-Butyl Ester According to General Procedure B, the title compound of part 12-A (80 mg, 0.45 mmol) was coupled to the title compound of part 2-I (170 mg, 0.450 mmol), and the product was purified by silica gel chromatography using 0–8% methanol/dichloromethane as eluent to give the title compound of part 12-B (160 mg, 66%): PB MS (M+1)$^+$ 542, (M−99)$^+$ 442; $^1$H NMR=250 MHz (CDCl$_3$) δ: 7.21 (arom., m, 5H), 1.50 (Me, d, 6H), 1.40 (BOC, d, 9H), 1.25 (—CH$_2$C$\underline{H}_3$, d of t, 3H).

C. 2-Amino-N-[1(R)-benzyloxymethyl-2-(2-ethyl-4-oxo-4,5,6,8-tetrahydro-3H-Pyrido[3,4-d]pyrimidin-7-yl)-2-oxo-ethyl]-2-methyl-propionamide, Hydrochloride The title compound of part 12-B (160 mg, 0.300 mmol) was deprotected according to the method described in General Procedure C to give the title compound of this Example 12 as an off-white powder (100 mg, 70%): PB MS (M+1)$^+$ 442; $^1$H NMR=250 MHz (methanol-d$_4$) δ: 7.30 (arom., m, 5H), 1.58 (Me, s, 6H), 1.40 (CH$_2$C$\underline{H}_3$, t, 3H).

EXAMPLE 13

2-Amino-N-[1(R)-benzyloxymethyl-2-(2-ethyl-4-oxo-3,5,7,8-tetrahydro-4H-pyrido[4,3-d]pyrimidin-6-yl)-2-oxo-ethyl]-2-methyl-propionamide, Hydrochloride

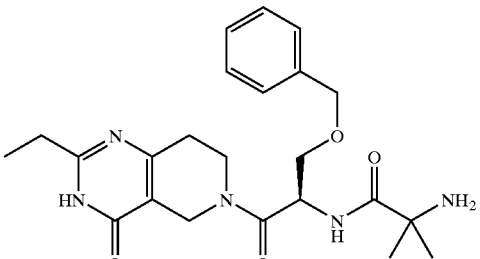

A. 6-Benzyl-2-ethyl-5,6,7,8-tetrahydro-3H-pyrido[4,3-d]pyrimidin-4-one

To a stirred solution of 1-benzyl-3-carboethoxy-4-piperidone hydrochloride (10 g, 34 mmol), prepared by the method of Lazar et al. (J. Heterocycl. Chem. 1990, 27, 1885), in ethanol (200 mL) was added propylamidine hydrochloride (4.01 mg, 36.9 mmol), followed by sodium hydride (2.32 mg, 60% dispersion in mineral oil, 101 mmol). The reaction was heated to about 100° C. and stirred for about 2 days, then cooled to room temperature and stirred for about 1 day. The reaction was concentrated in vacuo, and ethyl acetate was added. The mixture was extracted once with water, twice with brine, dried over anhydrous magnesium sulfate, filtered and concentrated in vacuo to give crude product. Purification by silica gel chromatography using 2–10% methanol/dichloromethane as eluent afforded the title compound of part 13-A (1.9 g, 21%): PB MS (M+1)$^+$ 270; $^1$H NMR=250 MHz (methanol-d$_4$) δ: 7.32 (arom., m, 5H), 2.60 (C$\underline{H}_2$CH$_3$, q, 2H), 1.28 (CH$_2$C$\underline{H}_3$, t, 3H).

B. 2-Ethyl-5,6,7,8-tetrahydro-3H-pyrido[4,3-d]pyrimidin-4-one

The title compound of part 13-A (1.0 g, 3.7 mmol) was de-benzylated according to the method described in General Procedure D to give the title compound of part 13-B (640 mg, 97%): PB MS (M+1)$^+$ 180; $^1$H NMR=300 MHz (methanol-d$_4$) δ: 2.60 (C$\underline{H}_2$CH$_3$, q, 2H), 1.28 (CH$_2$C$\underline{H}_3$, t, 3H).

C. {1-[1-Benzyloxymethyl-2-(2-ethyl-4-oxo-3,5,7,8-tetrahydro-4H-pyrido[4,3-d]pyrimidin-6-yl)-2-oxo-ethylcarbamoyl]-1-methyl-ethyl}-carbamic Acid tert-Butyl Ester According to General Procedure B, the title compound of part 13-B (140 mg, 0.78 mmol) was coupled to the title compound of part 2-I (298 mg, 0.78 mmol), and the product was purified by silica gel chromatography using 2–10% methanol/dichloromethane as eluent to give the title compound of part 13-C (270 mg, 64%): PB MS (M+1)$^+$ 542, (M−99)$^+$ 442; $^1$H NMR=300 MHz (methanol-d$_4$) δ: 7.20 (arom., m, 5H), 1.38 (BOC, s, 9H), 1.31 (Me, s, 6H), 1.27 (—CH$_2$C$\underline{H}_3$, m, 3H).

D. 2-Amino-N-[1(R)-benzyloxymethyl-2-(2-ethyl-4-oxo-3,5,7,8tetrahydro-4H-pyrido[4,3-d]pyrimidin-6-yl)-2-oxo-ethyl]-2-methyl-propionamide, Hydrochloride The title compound of part 13-C (250 mg, 0.46 mmol) was deprotected according to the method described in General Procedure C to give the title compound of this Example 13 (200 mg, 91%): PB MS (M+1)+ 442; $^1$H NMR=250 MHz (methanol-$d_4$) δ: 7.28 (arom., m, 5H), 1.60 (Me, s, 6H), 1.40 (CH$_2$C$\underline{H}_3$, t, 3H).

The following abbreviations and notations are used in the Tables below. Abbreviation:

Me—methyl
Et—ethyl
Ph—phenyl
Pyr—pyridyl
A=Mass Spec. Method is $^-$AP$_c$l
B=Mass Spec. Method is PB
C=Mass Spec. Method is $^+$AP$_c$l

EXAMPLES 14–58

The compounds of examples 14–58 were synthesized in a manner analogous to the procedures described for Examples 3, 3a, 4 and 5, using the appropriate starting materials.

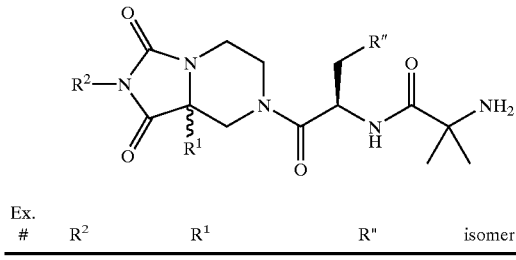

| Ex. # | R² | R¹ | R" | isomer | MS |
|---|---|---|---|---|---|
| 14 | Me | CH₂Ph | OCH₂Ph | d2 | 523$^C$ |
| 15 | Me | CH₂Ph | OCH₂Ph | d1 | 522$^B$ |
| 16 | Me | CH₂-4-F—Ph | OCH₂Ph | d2 | 540$^C$ |
| 17 | Me | CH₂-4-F—Ph | OCH₂Ph | d1 | 523$^C$ |
| 18 | Me | CH₂Ph | OCH₂-2-Pyr | d1,2 | 523$^B$ |
| 19 | Me | CH₂-3-Pyr | OCH₂Ph | d1,2 | 523$^B$ |
| 20 | Me | CH₂Ph | OCH₂-3-Pyr | d1,2 | 523$^C$ |
| 21 | Me | CH₂-2-Pyr | OCH₂Ph | d1,2 | 523$^C$ |
| 22 | Me | CH₂Ph | 2-Indole | d1,2 | 531$^C$ |
| 23 | Me | CH₂Ph | OCH₂-4-Thiazole | d1,2 | 529$^C$ |
| 24 | Et | CH₂Ph | OCH₂-3,4-di-F—Ph | d1,2 | 572$^C$ |
| 25 | Me | CH₂Ph | OCH₂-2,4-di(CF₃)Ph | d2 | 658$^C$ |
| 26 | CF₃CH₂ | CH₂-4-CF₃—Ph | OCH₂Ph | d1,2 | 657$^C$ |
| 27 | CF₃CH₂ | CH₂-4-CF₃—Ph | 2-Indole | d1,2 | 667$^C$ |
| 28 | CF₃CH₂ | CH₂-4-F—Ph | OCH₂Ph | d1,2 | 608$^C$ |
| 29 | CF₃CH₂ | CH₂-4-F—Ph | OCH₂-2,4-di-F—Ph | d1,2 | 644$^C$ |
| 30 | Me | CH₂-4-F—Ph | 3-Indole | d1,2 | 549$^C$ |
| 31 | Me | CH₂-4-F—Ph | OCH₂-2,4-di-F—Ph | d1,2 | 576$^C$ |
| 32 | Me | H | 3-Indole | d1,2 | 441$^C$ |
| 33 | CF₃CH₂ | H | OCH₂-2,4-di-F—Ph | d1,2 | 468$^C$ |
| 34 | Me | H | OCH₂-2,4-di-F—Ph | d1,2 | 536$^C$ |
| 35 | CF₃CH₂ | CH₂-3,4-di-F—Ph | 3-Indole | d1,2 | 635$^C$ |
| 36 | CF₃CH₂ | CH₂-3,4-di-F—Ph | OCH₂Ph | d1,2 | 626$^C$ |
| 37 | CF₃CH₂ | CH₂-3,4-di-F—Ph | OCH₂-2,4-di-F—Ph | d1,2 | 662$^C$ |
| 38 | Me | CH₂Ph | OCH₂-3,4-di-F—Ph | d2 | 558$^C$ |
| 39 | CF₃CH₂ | CH₂-3-F—Ph | 3-Indole | d2 | 617$^C$ |
| 40 | CF₃CH₂ | CH₂-3-F—Ph | 3-Indole | d1 | 617$^C$ |
| 41 | CF₃CH₂ | —CH₂-2-F—Ph | OCH₂Ph | d1,2 | 591$^C$ |
| 42 | Me | CH₂-2-Pyr | OCH₂Ph | d2 | 523$^C$ |
| 43 | Me | H | OCH₂Ph | d1,2 | 432$^C$ |
| 44 | CF₃CH₂ | CH₂Ph | OCH₂Ph | d2 | 590$^C$ |
| 45 | CF₃CH₂ | CH₂Ph | OCH₂Ph | d1 | 590$^C$ |
| 46 | CF₃CH₂ | CH₂-2-Pyr | OCH₂Ph | d1 | 591$^C$ |
| 47 | CF₃CH₂ | CH₂-2-Pyr | OCH₂Ph | d2 | 591$^C$ |
| 48 | CF₃CH₂ | CH₂-3-Pyr | OCH₂-2,4-di-F—Ph | d1,2 | 627$^C$ |
| 49 | CF₃CH₂ | CH₂-3-Pyr | OCH₂-2-CF₃—Ph | d1,2 | 659$^C$ |
| 50 | CF₃CH₂ | CH₂-3-Pyr | OCH₂-4-Cl—Ph | d1,2 | 625$^C$ |
| 51 | CF₃CH₂ | CH₂-3-Pyr | OCH₂-2-Pyr | d1,2 | 592$^C$ |
| 52 | CF₃CH₂ | CH₂-3-Pyr | OCH₂-4-F—Ph | d1,2 | 609$^C$ |
| 53 | CF₃CH₂ | CH₂-3-Pyr | OCH₂-2,3-di-F—Ph | d1,2 | 626$^C$ |

-continued

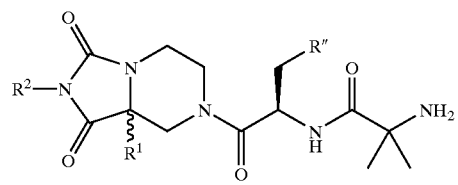

| Ex. # | R² | R¹ | R" | isomer | MS |
|---|---|---|---|---|---|
| 54 | CF₃CH₂ | CH₂-3-Pyr | OCH₂-3-Pyr | d1,2 | 592$^C$ |
| 55 | CF₃CH₂ | CH₂-2-Pyr | OCH₂-2,4-di-F—Ph | d2 | 627$^C$ |
| 56 | CF₃CH₂ | CH₂-2-Pyr | OCH₂-2-CF₃—Ph | d2 | 659$^C$ |
| 57 | CF₃CH₂ | CH₂-2-Pyr | OCH₂-2-Pyr | d2 | 592$^C$ |
| 58 | CF₃CH₂ | CH₂-2-Pyr | OCH₂-4-Cl—Ph | d2 | 625$^C$ |

EXAMPLES 59–60

The compounds of examples 59–60 were synthesized in a manner analogous to the procedures described for Examples 3, 3a, 4 and 5, using the appropriate starting materials.

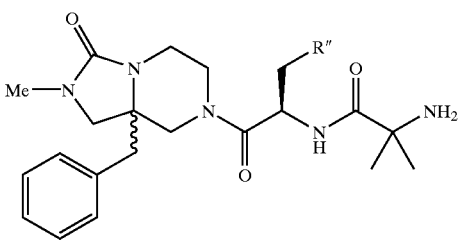

| Ex. # | R² | R¹ | R" | MS |
|---|---|---|---|---|
| 59 | Me | CH₂-4-F—Ph | 1-Naphthalene | 586$^C$ |
| 60 | CF₃CH₂ | CH₂-3,4-di-F—Ph | 1-Naphthalene | 672$^C$ |

EXAMPLES 61–63

The compounds of examples 61–63 were synthesized in a manner analogous to the procedures described for Example 2, using the appropriate starting materials.

| CP# | R" | isomer | MS |
|---|---|---|---|
| 61 | OCH₂Ph | d2 | 508$^C$ |
| 62 | OCH₂Ph | d1 | 508$^C$ |
| 63 | 3-Indole | d1,2 | 517$^C$ |

EXAMPLES 64–95

The compounds of examples 64–95 were synthesized in a manner to the procedures described for Example 1, using the appropriate starting materials.

| Ex. # | R¹ | R" | isomer | MS |
|---|---|---|---|---|
| 64 | CH₂Ph | OCH₂Ph | d2 | 495$^C$ |
| 65 | CH₂Ph | OCH₂Ph | d1 | 495$^C$ |
| 66 | CH₂-2-Pyr | OCH₂Ph | d1,2 | 495$^C$ |
| 67 | CH₂-4-Thiazole | OCH₂Ph | d1,2 | 501$^C$ |
| 68 | CH₂-5-Thiazole | OCH₂Ph | d1,2 | 502$^C$ |
| 69 | CH₂Ph | OCH₂-2-Pyr | d2 | 496$^C$ |
| 70 | CH₂Ph | OCH₂-2-Pyr | d1 | 496$^C$ |
| 71 | CH₂-4-Pyr | OCH₂Ph | d1,2 | 496$^C$ |
| 72 | CH₂Ph | OCH₂-4-Pyr | d1,2 | 496$^C$ |
| 73 | CH₂Ph | OCH₂-2-(Me)Ph | d2 | 509$^C$ |
| 74 | CH₂Ph | OCH₂-2-(Me)Ph | d1 | 509$^C$ |
| 75 | CH₂Ph | OCH₂-2,4-di-F—Ph | d2 | 531$^C$ |
| 76 | CH₂Ph | OCH₂-2,4-di-F—Ph | d1 | 531$^C$ |
| 77 | CH₂Ph | OCH₂-3-Pyr | d1,2 | 496$^C$ |
| 78 | CH₂Ph | OCH₂-3-(Me)Ph | d2 | 509$^C$ |
| 79 | CH₂Ph | OCH₂-3-(Me)Ph | d1 | 509$^C$ |
| 80 | CH₂-3-Pyr | OCH₂Ph | d1,2 | 496$^C$ |
| 81 | CH₂Ph | 3-Indole | d1,2 | 504$^C$ |
| 82 | CH₂Ph | OCH₂-4-Thiazole | d1,2 | 502$^C$ |
| 83 | CH₂-4-(CF₃)—Ph | 3-Indole | d1,2 | 572$^C$ |
| 84 | CH₂-4-(CF₃)—Ph | OCH₂Ph | d1,2 | 563$^C$ |
| 85 | CH₂Ph | OCH₂-3,5-di(CF₃)—Ph | d2 | 631$^C$ |
| 86 | CH₂Ph | OCH₂-3,5-di(CF₃)—Ph | d1 | 631$^C$ |
| 87 | CH₂Ph | OCH₂-3,5-di-Cl—Ph | d2 | 563$^C$ |
| 88 | CH₂Ph | OCH₂-3,5-di-Cl—Ph | d1 | 559$^C$ |
| 89 | CH₂-4-F—Ph | 3-Indole | d1,2 | 522$^C$ |
| 90 | CH₂-4-F—Ph | OCH₂Ph | d1,2 | 513$^C$ |
| 91 | CH₂-3,4-di-F—Ph | OCH₂-2,4-di-F—Ph | d1,2 | 567$^C$ |
| 92 | CH₂-3,4-di-F—Ph | OCH₂Ph | d1,2 | 531$^C$ |
| 93 | CH₂-3,5-di(CF₃)—Ph | 3-Indole | d1,2 | 640$^C$ |
| 94 | CH₂-3,5-di(CF₃)—Ph | OCH₂Ph | d1,2 | 641$^C$ |
| 95 | CH₂-3,5-di(CF₃)—Ph | OCH₂-2,4-di-F—Ph | d1,2 | 667$^C$ |

EXAMPLES 96–97

The compounds of examples 96–97 were synthesized in a manner analogous to the procedures described for Example 1, using the appropriate starting materials.

| Ex. # | R¹ | R" | MS |
|---|---|---|---|
| 96 | CH₂-4-(CF₃)Ph | 1-Naphthalene | 609$^C$ |
| 97 | CH₂-4-F—Ph | 1-Naphthalene | 559$^C$ |

EXAMPLES 98–150

The compounds of examples 98–150 were synthesized in a manner analogous to the procedures described for Example 9, using the appropriate starting materials.

| Ex. # | R² | R¹ | R" | isomer | MS |
|---|---|---|---|---|---|
| 98 | H | CH₂Ph | OCH₂Ph | d2 | 510 |
| 99 | H | CH₂Ph | OCH₂Ph | d1 | 495 |
| 100 | H | CH₂Ph | OCH₂Ph | d3 | 495 |
| 101 | H | CH₂Ph | 3-Indole | d1 | 504$^C$ |
| 102 | Me | CH₂Ph | 3-Indole | d1 | 518$^C$ |
| 103 | H | CH₂Ph | 3-Indole | d3 | 503$^C$ |
| 104 | Me | CH₂Ph | 3-Indole | d3 | 517$^C$ |
| 105 | H | H | OCH₂Ph | d1,2 | 405$^C$ |
| 106 | H | CH₂Ph | 3-(N-Me)Indole | d2 | 518$^C$ |
| 107 | H | CH₂Ph | OCH₂-2-Pyr | d2 | 496$^C$ |
| 108 | H | CH₂Ph | 5-Thiazole | d3 | 502$^C$ |
| 109 | H | CH₂Ph | SCH₂Ph | d3 | 511$^C$ |
| 110 | H | CH₂-4-Pyr | OCH₂Ph | d1,2,3,4 | 496$^C$ |
| 111 | H | CH₂Ph | SCH₂Ph | d2 | 511$^C$ |
| 112 | Me | CH₂-4-Pyr | OCH₂Ph | d1 | 510$^B$ |
| 113 | Me | CH₂-4-Pyr | OCH₂Ph | d2 | 510$^B$ |
| 114 | H | CH₂-3-Pyr | OCH₂Ph | d1,2 | 496$^B$ |
| 115 | H | CH₂-3-Pyr | OCH₂Ph | d3,4 | 496$^B$ |
| 116 | H | CH₂-2-Pyr | OCH₂Ph | d2 | 496$^C$ |
| 117 | H | CH₂-2-Pyr | OCH₂Ph | d3 | 496$^C$ |
| 118 | Me | CH₂-4-Pyr | OCH₂Ph | d3 | 510$^B$ |
| 119 | Me | CH₂-4-Pyr | OCH₂Ph | d4 | 510$^B$ |
| 120 | Me | CH₂-4-Pyr | OCH₂-2-Pyr | d1,2,3,4 | 511$^B$ |
| 121 | Me | CH₂-3-Pyr | OCH₂Ph | d1,2,3,4 | 510$^B$ |
| 122 | Me | CH₂-3-Pyr | OCH₂Ph | d1,2,3,4 | 510$^B$ |
| 123 | Me | CH₂-3-Pyr | OCH₂Ph | d1,2,3,4 | 510$^B$ |
| 124 | Me | CH₂-4-Pyr | 3-Indole | d1,2,3,4 | 519$^B$ |
| 125 | H | CH₂-4-Pyr | 3-Indole | d1,2,3,4 | 505$^B$ |
| 126 | H | CH₂-5-Thiazole | OCH₂Ph | d1,2,3,4 | 502$^B$ |
| 127 | H | CH₂CH₂Ph | OCH₂Ph | d1,2,3,4 | 523$^B$ |
| 128 | Me | CH₂CH₂Ph | OCH₂Ph | d1,2,3,4 | 537$^B$ |
| 129 | Me | CH₂-3-Pyr | OCH₂-2-CF₃—Ph | d1,2 | 578$^B$ |
| 130 | Me | CH₂-3-Pyr | OCH₂-2-CF₃—Ph | d3 | 578$^B$ |
| 131 | Me | CH₂-3-Pyr | OCH₂-2-CF₃—Ph | d4 | 578$^B$ |
| 132 | Me | CH₂-2-Pyr | OCH₂Ph | d2 | 510$^C$ |
| 133 | Me | CH₂-2-Pyr | OCH₂-2,4-di-F—Ph | d2 | 546$^C$ |
| 134 | H | CH₂-3-Pyr | OCH₂-2,4-di-F—Ph | d1,2 | 532$^C$ |
| 135 | Me | CH₂-3-Pyr | OCH₂-2,4-di-F—Ph | d1,2 | 546$^C$ |
| 136 | Me | CH₂-3-Pyr | OCH₂-4-Cl—Ph | d1,2 | 544$^C$ |
| 137 | Et | CH₂-3-Pyr | OCH₂Ph | d1,2 | 524$^C$ |
| 138 | Et | CH₂-3-Pyr | OCH₂-2,4-di-F—Ph | d1,2 | 560$^C$ |
| 139 | Et | CH₂-3-Pyr | OCH₂-4-Cl—Ph | d1,2 | 558$^C$ |
| 140 | CH₂Ph | H | OCH₂Ph | d1,2 | 495$^C$ |
| 141 | CH₂Ph | H | OCH₂-2-Pyr | d1,2 | 496$^C$ |
| 142 | CH₂-2-Pyr | H | OCH₂Ph | d2 | 496$^C$ |
| 143 | CH₂-2-Pyr | H | OCH₂Ph | d1 | 496$^C$ |
| 144 | CH₂-2-Pyr | H | OCH₂-2,4-di-F—Ph | d2 | 532$^C$ |
| 145 | CH₂-2-Pyr | H | OCH₂-2,4-di-F—Ph | d1 | 532$^C$ |
| 146 | CH₂-2-Pyr | H | OCH₂-2-CF₃—Ph | d2 | 564$^C$ |
| 147 | CH₂-2-Pyr | H | OCH₂-2-CF₃—Ph | d1 | 564$^C$ |
| 148 | H | CH₂-3,5-di-Cl-4-Pyr | OCH₂—Ph | d1,2 | 564$^C$ |
| 149 | H | CH₂-3,5-di-Cl-4-Pyr | OCH₂—Ph | d3,4 | 564$^C$ |
| 150 | CH₂-2-Pyr | H | OCH₂-2-Pyr | d1,2 | 497$^C$ |

EXAMPLES 151–163

The compounds of examples 151–163 were synthesized in a manner analogous to the procedures described for Example 11, using the appropriate starting materials.

| Ex. # | R² | R¹ | R" | MS |
|---|---|---|---|---|
| 152 | Me | H | OCH₂Ph | 431$^B$ |
| 153 | Me | H | 3-Indole | 440$^B$ |
| 154 | H | H | 3-Indole | 426$^B$ |
| 155 | Me | CH₂Ph | OCH₂Ph | 521$^B$ |
| 156 | Me | CH₂Ph | 2-Indole | 530$^B$ |
| 157 | Me | CH₂Ph | OCH₂-2-Pyr | 522$^B$ |
| 158 | Me | CH₂-2-Pyr | OCH₂Ph | 522$^B$ |
| 159 | Me | CH₂Ph | OCH₂-2,4-di-F—Ph | 557$^B$ |
| 160 | Me | CH₂-2-Pyr | OCH₂-2,4-di-F—Ph | 558$^B$ |
| 161 | Me | CH₂Ph | OCH₂-4-Thiazole | 528$^B$ |
| 162 | Me | CH₂Ph | OCH₂-4-Thiazole | 528$^B$ |
| 163 | Me | CH₂-2-Pyr | OCH₂-2-(Me)Ph | 536$^B$ |

EXAMPLES 164–171

The compounds of examples 164–171 were synthesized in a manner analogous to the procedures described for Example 13, using the appropriate starting materials.

| Ex # | R¹ | R² | R" | MS |
|---|---|---|---|---|
| 164 | Ph | H | OCH₂Ph | 490$^B$ |
| 165 | Et | H | OCH₂Ph | 442$^B$ |
| 166 | Me | Me | OCH₂Ph | 442$^B$ |
| 167 | Me | Me | 3-Indole | 451$^B$ |
| 168 | Et | Me | OCH₂Ph | 456$^B$ |
| 169 | Et | Me | 3-Indole | 465$^B$ |
| 170 | Et | CH₂Ph | OCH₂Ph | 532$^B$ |
| 171 | Et | CH₂Ph | 3-Indole | 541$^C$ |

EXAMPLES 172–176

The compounds of examples 172–176 were synthesized in a manner analogous to the procedures described for Example 7, using the appropriate starting materials.

| Ex. # | R² | R¹ | R" | MS |
|---|---|---|---|---|
| 172 | Me | CH₂Ph | OCH₂Ph | 507$^C$ |
| 173 | H | CH₂Ph | OCH₂Ph | 493$^C$ |
| 174 | H | CH₂Ph | OCH₂-3-Pyr | 494$^B$ |
| 175 | H | CH₂Ph | OCH₂-2-Pyr | 494$^B$ |
| 176 | H | CH₂Ph | CH₂CH₂Ph | 491$^C$ |

EXAMPLES 177–178

The compounds of examples 177–178 were synthesized in a manner analogous to the procedures described for Example 8, using the appropriate starting materials.

| Ex. # | R¹ | R" | MS |
|---|---|---|---|
| 177 | CH₂Ph | OCH₂Ph | 494$^B$ |
| 178 | CH₂Ph | OCH₂-2-Pyr | 495$^C$ |

EXAMPLE 179–187

The compounds of examples 179–187 were synthesized in a manner analogous to the procedures described for Example 6, using the appropriate starting materials.

| Ex. # | R¹ | X | R" | isomer | MS |
|---|---|---|---|---|---|
| 179 | CH₂-2-F—Ph | O | OCH₂Ph | d2 | 525$^C$ |
| 180 | CH₂-2-F—Ph | O | OCH₂Ph | d1 | 525$^C$ |
| 181 | CH₂-4-F—Ph | O | OCH₂Ph | d2 | 525$^C$ |
| 182 | CH₂-4-F—Ph | O | OCH₂Ph | d1 | 525$^C$ |
| 183 | CH₂-4-F—Ph | O | OCH₂-2,4-di-F—Ph | d2 | 561$^C$ |
| 184 | CH₂-4-F—Ph | O | OCH₂-2,4-di-F—Ph | d1 | 561$^C$ |
| 185 | CH₂-4-F—Ph | S | OCH₂Ph | d1, 2 | 541$^C$ |
| 186 | CH₂-2-Pyr | O | OCH₂-2,4-di-F—Ph | d1, 2 | 544$^C$ |
| 187 | CH₂-2-Pyr | O | OCH₂Ph | d1, 2 | 508$^C$ |

EXAMPLES 188–196

The compounds of examples 188–196 were synthesized by coupling the HET portion to the dipeptidyl portion in a manner analogous to the procedures described in General Procedure B or Example part 3a-B; the HET portion was synthesized in a manner analogous to the method indicated, using the appropriate materials.

| Ex. # | HET | R" | Method of Preparation of HET | MS |
|---|---|---|---|---|
| 188 | 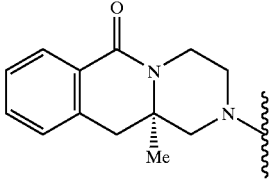 | 3-Indole | Scheme 57 | 474 (TSMS) |
| 189 | 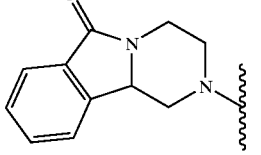 | 3-Indole | Scheme 57 | 460[B] |
| 190 | 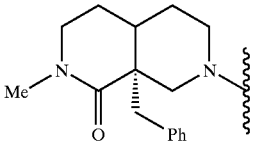 | OCH$_2$Ph | Scheme 35 | 521[B] |
| 191 | 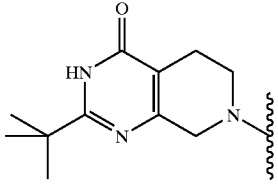 | OCH$_2$-2-Pyr | Example 12 | 471[B] |
| 192 | 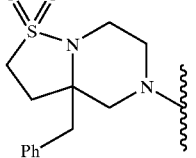 | OCH$_2$Ph | Scheme 58 | 529[B] |
| 193 | 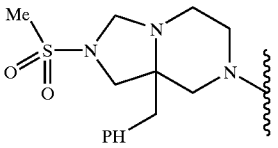 | OCH$_2$Ph | Scheme 27 | 557[C] |
| 194 | 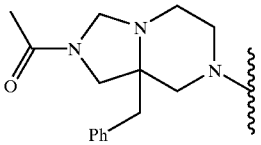 | 3-Indole | Scheme 27 | 530[C] |

-continued

| Ex. # | HET | R" | Method of Preparation of HET | MS |
|---|---|---|---|---|
| 195 | (oxazolidinone-fused piperazine with 2-fluorobenzyl, R-config) | OCH₂Ph | Scheme 56 | 525ᶜ |
| 196 | (oxazolidinone-fused piperazine with 2-fluorobenzyl, S-config) | OCH₂Ph | Scheme 56 | 525ᶜ |

EXAMPLE 197

2-Amino-N-[1(R)-benzyloxymethyl-2-oxo-2-(3-oxo-8a(R,S)-pyridin-2-pyridin-2-ylmethyl-hexahydro-imidazo[1,5-a]pyrazin-7-yl)-ethyl]-2-methyl-propionamide, Hydrochloride

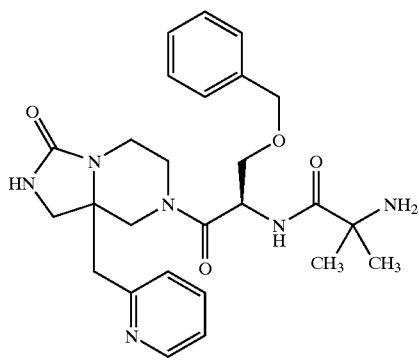

A. 2-Formyl-2-pyridin-2-ylmethyl-piperazine-1,4-dicarboxylic Acid 1-Benzyl Ester 4tert-Butyl Ester A solution of the ester of Example 3, Step A (1.4 g, 3 mmol) in CH₂Cl₂ (10 mL) was cooled to −50° C. and a 1.0 M solution of DIBAL in CH₂Cl₂ (18 mL 18 mmol) was slowly added. Once the DIBAL addition was complete the solution was stirred at −50° C. for 1 h. The reaction was quenched with MEOH (2 mL) and 1 N NaOH (25 mL) was added. The aldehyde was extracted with CH₂Cl₂ (3×25 mL). The extracts were combined, washed with brine, dried over MgSO₄ and concentrated to give the aldehyde of Example 197, Step A as a yellow oil (1.0 g, 76%) which was carried on without further purification: +APcI MS (M+1)⁺ 440, (M−ᵗBu+1)⁺ 384, (M−Boc+1)⁺ 340; ¹H NMR=400 MHz (CDCl₃) δ: 9.51 (br s, 1H), 4.55 (m, 2H), 1.38 (s, 9H).

B. 2-(Hydroxyimino-methyl)-2-pyridin-2-ylmethyl-piperazine-1,4-dicarboxylic Acid 1-Benzyl Ester 4-tert-Butyl Ester A solution of the aldehyde of Example 197, Step A (439 mg, 1 mmol) and hydroxylamine hydrochloride (278 mg, 4 mmol) in pyridine (5 mL) was stirred for 12 h at rt. Solvent was removed under reduced pressure and the resulting residue was dissolved into chloroform (20 mL), washed with saturated NaHCO₃ and brine solutions, dried over MgSO₄ and concentrated to give 462 mg of a crude yellow oil. Purification by flash chromatography (SiO₂ gel, 3:1 EtOAc:hexane) delivered 342 mg (75%) of the oxime of Example 197, Step B as a colorless oil: +APcI MS (M+1)⁺ 455, (M−Bu+1)⁺ 399, (M−Boc+1)⁺ 355; ¹H NMR=400 MHz (CDCl₃) δ: 8.55 (m, 1H), 5.27 (m, 1H), 4.98 (m, 1H), 1.42 (s, 9H).

C. 3-Oxo-8a-pyridin-2-ylmethyl-hexahydro-imidazo [1,5-a]pyrazine-7-carboxylic Acid tert-Butyl Ester To a solution of the oxime of Example 197, Step B (342 mg, 0.75 mmol) in EtOH (10 mL) was added Raney nickel (1 mL of a suspension in water), followed by NaOH (150 mg, 3.75 mmol). The mixture was stirred at room temperature for 2 h and filtered through Celite®. The filtrate was concentrated to afford the urea of Example 197, Step C as a white solid (534 mg, quantitative crude) which was carried on without further purification: +APcl MS (M+1)+ 333, (M−$^t$Bu+1)+ 277, (M−Boc+1)+ 233.

D. {1-[1(R)-Benzyloxymethyl-2-oxo-2-(3-oxo-8a(R,S)-pyridin-2-ylmethyl-hexahydro-imidazo[1,5-a]pyrazin-7-yl)-ethylcarbamoyl]-1-methyl-ethyl}-carbamic Acid tert-Butyl Ester To a solution of the crude urea of Example 197, Step C (534 mg) in EtOH (15 mL, 0° C.) was added conc. HCl (1.5 mL). The solution was stirred at 0° C. for 1 h and concentrated down to provide the deprotected piperazine as a viscous, colorless oil: +Apcl MS (M+1)+ 333.

The residue was dissolved into 15 mL EtOAc and triethylamine (0.2 mL, 1.5 mmol) was added. After stirring for 15 min, the acid of Example 2, Step 1 (380 mg, 1 mmol), PPAA (0.32 mL, 1 mmol) and triethylamine (0.4 mL, 4 mmol) were added and the mixture was stirred at room temperature for 4 h. Water (20 ml) was added and the product was extracted with EtOAc (3×25 mL). The combined extracts were washed with brine, dried over MgSO4 and concentrated to give 612 mg of a crude yellow oil. Purification by flash chromatography (SiO₂ gel, 9:1 EtOAc:EtOH) delivered 72 mg (16% yield from the oxime) of the compound of Example 197, Step D as a 1:1 mixture of diastereomers: +APcl MS (M+1)+ 595, (M−Boc+1)+ 495; $^1$H NMR=400 MHz (CDCl₃) δ: 8.47 (br m, 1H), 5.18 (br m, 1H), 4.85 (br, m, 1H), 1.45 (s, 0.5×3H), 1.44 (s, 0.5×3H), 1.42 (br s, 3H) 1.39 (br s, 9H).

E. 2-Amino-N-[1(R)-benzyloxymethyl-2-oxo-2-(3-oxo-8a(R,S)-pyridin-2-ylmethyl-hexahydro-imidazo[1,5-a]pyrazin-7-yl)-ethyl-2-methyl-propionamide, Hydrochloride To a solution of the compound of Example 197, Step D (30 mg) in EtOH (5 mL), at 0° C. was added conc. HCl (0.5 mL). The solution was stirred at 0° C. for 1 h and concentrated down to deliver 28 mg of the compound of Example 197, Step E: +APcl MS (M+1)+ 495; $^1$H NMR=400 MHz (CD₃OD) δ; 8.58 (br m, 1 H), 4.58 (br m, 2H), 1.61 (br s, 6H).

EXAMPLE 198

2-Amino-N-{1(R)-benzyloxymethyl-2-[8a(S)-(2,4-difluoro-benzyl)-2-methyl-3-oxo-hexahydro-imidazo[1,5-a]pyrazin-7-yl]-2-oxo-ethyl}-2-methyl-propionamide, Hydrochloride

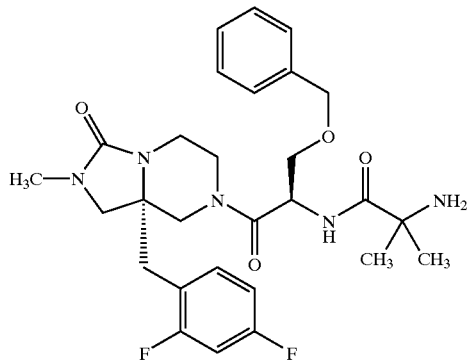

A. 3-(2,4-Difluoro-benzyl)-3-formyl-piperazine-1-carboxylic Acid tert-Butyl Ester A solution of ester 3-(2,4-difluoro-benzyl)-piperazine-1,3-dicarboxylic acid 1-tert-butyl ester 3-methyl ester, prepared analogously to the compound of Example 2, Step A, (1.11 g, 3 mmol) in CH₂Cl₂ (10 mL) was cooled to −40° C. and a 1.0 M solution of DIBAL in CH₂Cl₂ (9 mL, 9 mmol) was slowly added. Once the DIBAL addition was complete the solution was allowed to stir at −40° C. for 1 h. The reaction was quenched with MeOH (2 mL) and 1 N NaOH (25 mL) was added. The aldehyde was extracted with CH₂Cl₂(3×20 mL). The extracts were combined, washed with brine, dried over MgSO₄ and concentrated to give the compound of Example 198, Step A as a yellow oil (647 mg, 64%) which was carried on without further purification: +APcl MS (M+1)+ 341, (M−$^t$Bu+1)+ 285, (M−Boc+1)+ 241; $^1$H NMR=400 MHz (CDCl₃) δ: 9.60 (br s, 1H), 7.10 (m, 1H), 6.78 (m, 2H), 1.41 (s, 9H).

B. 3-(2,4-Difluoro-benzyl)-3-methylaminomethyl-piperazine-1-carboxylic Acid tert-Butyl Ester To a solution of the aldehyde of Example 198, Step A (340 mg, 1 mmol) in dry DME (10 mL) was added about 250 mg MgSO₄ followed by methyl amine (1 mL of a 2.0 M solution in MeOH, 2 equiv). The reaction was monitored by MS for the consumption of aldehyde and formation of the corresponding imine (+APcl (M+1)+ 354). Once imine formation was complete, NaOAc (820 mg, 10 mmol) and NaCNBH₃ (248 mg, 4 mmol) were added and the mixture was stirred at room temperature for 1 h. The mixture was filtered through Celite® and the filtrate was concentrated. The resulting residue was taken up in EtOAc (25 mL) and washed with 1 N NaOH and brine solutions, respectively. The organic phase was dried over MgSO₄ and concentrated to deliver the crude amine (306 mg). Purification by flash chromatography (SiO₂ gel, 3:1:0.2 EtOAc:Hexane:EtOH) delivered 210 mg (59%) of the diamine of Example 198, Step B: +APcl MS (M+1)+ 356, (M−$^t$Bu+1)+ 300, (M−Boc+1)+ 256; $^1$H NMR=400 MHz (CDCl₃) δ: 7.21 (m, 1H), 6.81 (m, 2H), 2.51 (br s, 3H), 1.42 (s, 9H).

C. 8a-(2,4-Difluoro-benzyl)-2-methyl-3-oxo-hexahydro-imidazo[1,5-a]pyrazine-7-carboxylic Acid tert-Butyl Ester To a solution of the diamine of Example 198, Step B (178 mg, 0.5 mmol) in CH₂Cl₂ (5 mL) was added triethylamine (0.13 mL, 1 mmol) and triphosgene (148 mg, 0.5 mmol). The resulting solution was stirred at room temperature for 1 h and then quenched with water (10 mL). The urea was extracted with CH₂Cl₂, dried over MgSO₄ and concentrated to deliver the crude product (187 mg). Purification by flash chromatography (SiO₂ gel, 1:1, EtOAc:Hexane) delivered 156 mg (82%) of the urea of Example 198, Step C: +APcl MS (M+1)+ 382, (M−$^t$Bu+1)+ 326, (M−Boc+1)+ 282.3; $^1$H NMR=400 MHz (CDCl₃) δ: 7.24 (m,1H), 6.81 (m, 2H), 2.67 (br s, 3H), 1.48 (s, 9H).

D. (1-{1(R)-Benzyloxmethyl-2-[8a(S)-(2,4-difluoro-benzyl)-2-methyl-3-oxo-hexahydro-imidazo[1,5-a]pyrazin-7-yl]-2-oxo-ethylcarbamoyl}-1-methyl-ethyl)-carbamic Acid tert-Butyl Ester To a solution of the compound of Example 198, Step C (38 mg, 0.1 mmol) in EtOH (2 mL) was added 0.5 mL of conc. HCl at 0° C. The solution was stirred for 1 h. Water (10 mL) was added and the resulting solution was basified to pH 14 with 1 N NaOH. The amine was extracted with CH₂Cl₂ (3×10 mL) and the combined extracts were dried over MgSO₄ and concentrated to deliver 27 mg of the urea: +APcl MS (M+1)+ 282. To a solution of the above urea (27 mg, 0.1 mmol) in EtOAc (5 mL) was added triethylamine (0.07 mL, 0.5 mmol), PPAA (0.035 mL, 0.1 mmol) and the acid of Example 2, Step 1 (38 mg, 0.1 mmol). The solution was stirred at room temperature for 3 h. Water (10 mL) was added and the product was extracted with EtOAc (3×15 mL). The combined extracts were dried over $MgSO_4$ and concentrated to provide a pale yellow oil. Purification by flash chromatography ($SiO_2$ gel, 3:1, EtOAc:hexanes) delivered 12 mg (19%) of the compound of Example 198, Step D (less polar diastereomer): +APcl MS (M+1)$^+$ 644, (M–Boc+1)$^+$ 544; $^1$H NMR=400 MHz (CDCl$_3$) δ: 7.26 (m, 6H), 6.91 (m, 2H), 2.63 (s, 3H), 1.38 (s, 9H).

E. 2-Amino-N-{1(R)-benzyloxymethyl-2-[8a(S)-(2,4-difluoro-benzyl)-2-methyl-3-oxo-hexahydro-imidazo[1,5-a]pyrazin-7-yl]-2-oxo-ethyl}-2-methyl-propionamide, Hydrochloride To a solution of the compound of Example 198, Step D (12 mg) in EtOH (2 mL, 0° C.) was added conc. HCl (0.2 mL). The solution was stirred at 0° C. for 1 h and concentrated down to deliver 10 mg of Example 198, Step E: +APcl MS (M+1)$^+$ 544; $^1$H NMR=400 MHz (CD$_3$O) δ: 7.31 (br m, 6H), 6.83 (m, 2H), 2.59 (br s, 3H), 1.56 (br s, 6H).

EXAMPLE 199

2-Amino-N-{1(R)-1,3-dioxo-8a(S)-pyridin-2-ylmethyl-2-(2,2,2-trifluoro-ethyl)-hexahydro-imidazo[1,5-a]pyrazine-7-carbonyl]-4-phenyl-butyl}-2-methyl-propionamide, Hydrochloride

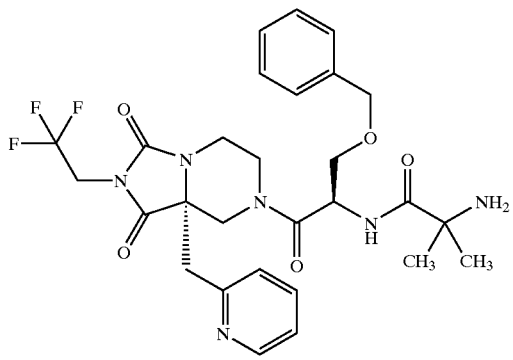

A. 2(R)-Amino-5-phenyl-pentanoic acid (2(S)-hydroxy-1(S)-methyl-2-phenyl-ethyl)-methyl-amide A solution of pseudoephedrine glycinamide (1.5 g, 6.75 mmol), prepared and used by the method of Myers et al. (J. Am. Chem. Soc. 1997, 119, 656), and LiCl(1.71 g, 40.5 mmol) in THF (30 mL) was cooled to –78° C. and n-BuLi was added (13.16 mmol, 5.25 mL of a 2.5 M solution). After stirring for 20 min at –78° C., the reaction was warmed to 0° C. and stirred an additional 20 minutes. 3-Phenyl-1-bromopropane (1.3 mL, 7.42 mmol) was added and the reaction was stirred for 2 h at 0° C. Aqueous 1 N HCl (50 mL) and EtOAc (50 mL) were added, the organic phase was separated and extracted with 1 N HCl (50 mL). The aqueous extracts were combined, cooled in an ice bath and slowly basified to pH 14 with 6 N NaOH. The product was extracted with CH$_2$Cl$_2$ (4×50 mL) and the combined extracts were dried over MgSO$_4$ and concentrated to give a yellow oil. Purification by flash chromatography (SiO$_2$ gel, 92:4:4, CH$_2$Cl$_2$:MeOH:triethylamine) delivered 400 mg (78%) of the Product of Example 199, Step A: +APcl MS (M+1)$^+$ 341; $^1$H NMR=400 MHz (CDCl$_3$) δ: 7.38 (m, 10H), 5.26 (m, 1H), 4.15 (m, 1H), 3.86 (m, 1H), 2.36 (s, 3H).

B. 2(R)-Amino-5-phenyl-pentanoic Acid

A solution of the compound of Example 199, Step A (400 mg, 1.18 mmol) in water (10 mL) was heated to reflux for 20 h. The reaction was diluted with water (20 mL) and extracted with CH$_2$Cl$_2$ (2×20 mL). The combined organic extracts were back extracted with water (2×20 mL) and the combined aqueous extracts were concentrated down to a white solid. The solid was triturated with EtOH to remove residual pseudoephedrine and deliver Example 199, Step B (135 mg, 60%): +APcl MS (M+1)$^+$ 194.

C. 2(R)-(2-tert-Butoxycarbonylamino-2-methyl-propionylamino)-5-phenyl-pentanoic Acid To a solution of the compound of Example 199, Step B (130 mg, 0.67 mmol) in dioxane: water (4:1, 5 mL) was added triethylamine (0.28 mL, 2 mmol) and Example 1, Step D (201 mg, 0.67 mmol). The mixture was stirred at 45° C. for 16 h, diluted with EtOAc (20 mL) and water (10 mL) and acidified to pH 2 with HOAc. The organic phase was collected, washed with saturated NaHCO$_3$ and brine solutions, dried over MgSO$_4$ and concentrated to quantitatively give crude Example 199, Step C (298 mg): +APcl MS (M+1)$^+$ 379, (M–$^t$Bu+1)$^+$ 323, (M–Boc+1)$^+$ 279; $^1$H NMR= 400 MHz (CDCl$_3$) δ: 7.21 (m, 2H), 7.14 (m, 3H), 4.51(m, 1H), 1.38 (s, 9H).

D. (1-{1(R)-[1,3-Dioxo-8a(S)-pyridin-2-ylmethyl-2-(2,2,2-trifluoro-ethyl)-hexahydro-imidazo[1,5-a]pyrazine-7-carbonyl]-4-phenyl-butylcarbamoyl}-1-methyl-ethyl)-carbamic Acid tert-Butyl Ester To a solution of the hydantoin of the Example 3a, Step A (164 mg, 0.5 mmol) in EtOAc (5 mL) was added triethylamine (0.35 mL, 2.5 mmol), PPAA (0.16 mL, 0.5 mmol) and 16-C (189 mg, 0.5 mmol). The solution was stirred at room temperature for 2 h. Water (10 mL) was added and the product was extracted with EtOAc (3×15 mL). The combined extracts were dried over MgSO$_4$ and concentrated to provide 382 mg of a pale yellow oil. Purification by flash chromatography (SiO$_2$ gel, 3:1, EtOAc:hexanes) delivered 73 mg of the compound of Example 199, Step D (diastereomerically pure): +APcl MS (M+1)$^+$ 689, (M–$^t$Bu+ 1)$^{30}$ 633, (M–Boc+1)$^+$ 589; $^1$H NMR=400 MHz (CDCl$_3$) δ: 8.37 (m, 1H), 4.90 (br m, 3H), 1.50 (s, 3H), 1.48 (s, 3H), 1.38 (s, 9H).

E. 2-Amino-N-{1(R)-[1,3-dioxo-8a(S)-pyridin-2-ylmethyl-2-(2,2,2-trifluoro-ethyl)-hexahydro-imidazo[1,5-a]pyrazine-7-carbonyl]-4-phenyl-butyl}-2-methyl-propionamide, Hydrochloride To a solution of the compound of Example 199, Step D (73 mg) in EtOH (5 mL, 0° C.) was added conc. HCl (0.5 mL). The solution was stirred at 0° C. for 1 h and concentrated down to deliver 68 mg of Example 199, Step E: +APcl MS (M+1)$^+$ 589; $^1$H NMR=400 MHz (CD$_3$OD) δ: 8.36 (d, 1H), 4.86 (br m, 3H), 1.44 (s, 3H), 1.42 (s, 3H).

EXAMPLE 200

2-Amino-[2-(7a(R)-3a(S)-benzyl-2-methyl-3-oxo-octahydro-pyrrolo[3,4-c]pyridin-5-yl)-1-benzyloxymethyl-2-oxo-ethyl]-2-methyl-propionamide, Hydrochloride

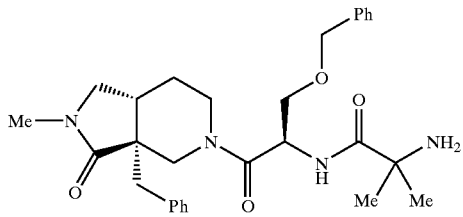

A. 1,3-Dibenzyl-4-oxo-piperidine-3-carboxylic Acid Methyl Ester

To a solution of 1-benzyl-4oxo-piperidine-3-carboxylic acid methyl ester (5.14 g, 20.8 mmol) in DMF (130 mL) at 0° C. was added sodium hydride (60% by weight in mineral oil, 0.874 g, 21.8 mmol) in four portions over 0.5 h. After stirring at 0° C. for an additional 0.5 h, benzyl chloride (2.87 mL, 25.0 mmol) was added and the reaction mixture was allowed to stir for 14 h while warming to room temperature. The reaction mixture was partitioned between EtOAc and saturated aqueous sodium bicarbonate solution, the organic layer was removed and the aqueous layer was washed four times with EtOAc. The combined organic layers were dried over sodium sulfate, filtered and concentrated under vacuum. Purification by silica gel chromatography employing 0.5% MeOH/0.2% NH$_4$OH/CH$_2$Cl$_2$ as the eluant afforded the compound of Example 200, Step A as a pale yellow oil (5.89 g): +APcl MS (M+1)$^+$ 338; $^1$H NMR (400 MHz, CDCl$_3$) δ: 7.09–7.39 (arom, series of m, 10H), 3.60 (s, 3H), 3.56 (d, 2H), 3.38 (m, 1H), 3.20 (d, 1H), 2.93 (m, 2H), 2.78 (m, 1H), 2.42 (m, 2H), 2.31 (m, 1H).

B. 1,3-Dibenzyl-4-methoxymethylene-piperidine-3-carboxylic Acid Methyl Ester The material was prepared from the compound of Example 200, Step A (3.56 9, 11.0 mmol) as described in Example 8, Step A, affording the compound of Example 200, Step B as a pale yellow oil after purification via silica gel chromatography with 2–8% EtOAc/CH$_2$Cl$_2$ as the eluant (4.02 g): +APcl MS (M+1)$^+$ 366; $^1$H NMR (400 MHz, CDCl$_3$) d: 7.08–7.35 (arom, series of m, 10H), 5.94 (s, 1H), 3.61 (s, 3H), 3.57 (s, 3H), 3.05 (d, 1H).

C. 1,3-Dibenzyl-4-formyl-piperidine-3-carboxylic Acid Methyl Ester

A solution of the compound of Example 200, Step B (3.02 g, 8.26 mmol) in THF (40 mL) and 10% aqueous HCl solution (40 mL) was allowed to stir at room temperature for 14 h. The solution was adjusted to pH 9 with 5N NaOH and extracted twice with CH$_2$Cl$_2$. The combined organic layers were washed with a saturated aqueous brine solution, dried over Na$_2$SO$_4$, filtered and concentrated under vacuum. Purification by silica gel chromatography employing 3–5% EtOAc/CH$_2$Cl$_2$ as the eluant afforded the compound of Example 200, Step C as a mixture of isomers (1.89 g): +APcl MS (M+1)$^{30}$ 352; $^1$H NMR (400 MHz, CDCl$_3$) δ: 9.82 and 9.81 (s, 1H), 7.02–7.45 (arom, series of m, 10H), 3.64 and 3.60 (s, 3H).

D. 3a,5-Dibenzyl-2-methyl-octahydro-pyrrolo[3,4-c]pyridin-3-one

To a solution of the compound of Example 200, Step C (0.210 g, 0.60 mmol) in dichloroethane (5 mL) in a resealable tube was added acetic acid (0.188 mL, 3.28 mmol), methyl amine (2.0 M in MeOH, 1.64 mL, 3.28 mmol) and NaB(OAc)$_3$H (0.951 g, 4.48 mmol), the tube was sealed and the reaction mixture was heated to 70° C. for 30 h. The reaction mixture was partitioned between CH$_2$Cl$_2$ and saturated aqueous sodium bicarbonate solution. The organic layer was removed and the aqueous layer was washed twice with CH$_2$Cl$_2$, the combined organic layers were washed with a saturated aqueous brine solution, dried over Na$_2$SO$_4$, filtered and concentrated under vacuum. Purification by silica gel chromatography employing 5–30 20% EtOAc/CH$_2$Cl$_2$ as the eluant afforded the less polar isomer of Example 200, Step D (0.034 g) as well as the more polar isomer (0.046 g). Example 200, Step D less polar isomer: +APcl MS (M+1)$^+$ 335; $^1$H NMR (400 MHz, CDCl$_3$) δ: 7.03–7.37 (arom, series of m, 10H), 3.54 (m, 2H), 3.24 (m, 1H), 2.70 (s, 3H). More polar isomer: +APcl MS (M+1)$^+$ 335; $^1$H NMR (400 MHz, CDCl$_3$) δ: 7.15–7.33 (arom, series of m, 10H), 3.59 (d, 1H), 3.43 (d, 1H), 2.74 (s, 3H).

E. 3a-Benzyl-2-methyl-octahydro-pyrrolo[3,4-c]pyridin-3-one

To a solution of the compound of Example 200, Step D (0.034 g, 0.10 mmol) in acetic acid (18 mL) was added a slurry of palladium on carbon (10% by weight, 0.030 g) in H$_2$O (2 mL). The reaction mixture was shaken under 50 psig hydrogen for 24 h, an additional aliquot of palladium on carbon (0.030 g) was introduced and the reaction was continued under 50 psig hydrogen for another 24 h. The reaction mixture was filtered through a bed of Celite® with the aid of MeOH, concentrated under vacuum, and the residue was partitioned between CH$_2$Cl$_2$ and H$_2$O at pH 9. The organic layer was removed and the aqueous layer was washed twice with CH$_2$Cl$_2$, the organic layers were combined and washed with a saturated aqueous brine solution, dried over Na$_2$SO$_4$, filtered and concentrated under vacuum. Purification by silica gel chromatography employing 3% MeOH/0.2% NH$_4$OH/CH$_2$Cl$_2$ as the eluant afforded the compound of Example 200, Step E (0.019 g): +APcl MS (M+1)$^+$ 245; $^1$H NMR (400 MHz, CDCl$_3$) δ: 7.10–7.24 (arom, series of m, 5H), 3.21 (m, 1H), 2.71 (s, 3H).

F. {1-[2-(7a(R)-3a(S)-Benzyl-2-methyl-3-oxo-octahydro-pyrrolo[3,4-c]pyridin-5-yl)-1(R)-benzyloxymethyl-2-oxo-ethylcarbamoyl]-1-methyl-ethyl}-carbamic Acid tert-Butyl Ester To a solution of the compound of Example 200, Step E (0.019 g, 0.078 mmol), the acid of Example 2, Step 1 (0.045 g, 0.12 mmol) and Et$_3$N (0.045 mL, 0.31 mmol) in EtOAc (1 mL) at 0° C. was added PPAA (50% solution in EtOAc, 0.093 mL, 0.16 mmol). After 24 h of stirring at room temperature, additional 2-I (0.015 g, 0.039 mmol) and PPAA (0.045 mL, 0.078 mmol) were added and stirring was continued at room temperature for 24 h. The reaction mixture was partitioned between EtOAc and saturated aqueous sodium bicarbonate solution, the organic layer was removed and the aqueous layer was washed twice with EtOAc. The combined organic layers were washed with brine, dried over sodium sulfate, filtered and concentrated under vacuum. Purification by silica gel chromatography employing EtOAc as the eluant afforded the less polar isomer of Example 200, Step F (0.005 g), as well as a mixture of the two isomers (0.028 g). Example 200, Step F less polar isomer: +APcl MS (M+1)$^+$ 607; $^1$H NMR (400 MHz, CDCl$_3$) δ: 7.03–7.32 (arom, series of m, 10H), 5.27 (m, 1H), 4.48 (m, 2H), 2.69 (s, 3H), 1.35 (s, 9H).

G. 2-Amino-N-[2-(7a(R)-3a(S)-benzyl-2-methyl-3-oxo-octahydro-pyrrolo[3,4-c]pyridin-5-yl)-1(R)-benzyloxymethyl-2-oxo-ethyl]-2-methyl-propionamide, Hydrochloride The compound of Example 200, Step F (0.005 g, 0.009 mmol) was deprotected as described in General Procedure C to provide the compound of Example 200, Step G as the HCl salt (0.004 g). Example 200, Step G: +APcI MS (M+1)$^+$ 507; $^1$H NMR (400 MHz, CD$_3$OD) δ: 7.10–7.32 (arom, series of m, 10H), 5.23 (m, 1H), 2.73 (s, 3H), 1.56 (m, 6H).

EXAMPLE 201

2-Amino-N-[2-(8a(S*)-benzyl-7(S*)-methyl-6-oxo-hexahydro-pyrrolo[1,2-a]pyrazin-2-yl)-1(R)-benzyloxymethyl-2-oxo-ethyl]-2-methyl-propionamide

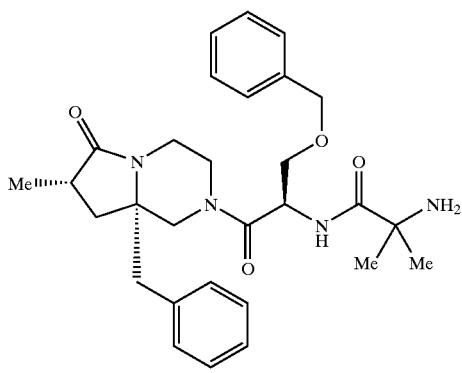

A. 3-Benzyl-3-(2-methoxycarbonyl-vinyl)-piperazine-1-carboxylic Acid tert-Butyl Ester To a THF (1 mL) solution of NaHMDS at 0° C. was added trimethyl phosphonoacetate (0.18 mL, 1.1 mmol), dropwise. After stirring for 1 hour, a THF (1 mL) solution of crude 3-benzyl-3-formyl-piperazine-1-carboxylic acid tert-butyl ester (0.34 mg, 0.92 mmol), prepared analogous to the compound of Example 198, Step A, was added and the reaction was allowed to warm to room temperature. After stirring for 16 hours, the product was isolated by extraction from water with EtOAc (2×) and methylene chloride (2×). The combined extracts were washed with brine, dried (MgSO$_4$) and concentrated. The product was then purified by silica gel chromatography using methylene chloride, then 5% MeOH in methylene chloride as eluents to afford a 7:3 E:Z mixture of olefins of the compound of Example 201, Step A (0.38 g, 81%), where the Z isomer had lactamized: +APcI MS (M+1, ester)$^+$ 361, (M–$^t$Bu+1, ester)$^+$ 305, (M–$^t$Bu+1, lactam)$^+$ 273, (M–BOC+1, ester)$^+$ 261, (M–BOC+1, lactam)$^+$ 229; $^1$H NMR (400 MHz, CDCl$_3$) δ: 7.30–7.05 (arom, series of m, 5H), 6.91 (lactam olefin, d, 0.3H), 6.75 (ester olefin, d, 0.7H), 6.09 (lactam olefin, d, 0.3H), 5.88 (ester olefin, d, 0.7H), 3.71 (ester Me, s, 2.1H), 1.47 (BOC, s, 9H).

B. 3-Benzyl-3-(2-methoxycarbonyl-ethyl)-piperazine-1-carboxylic Acid tert-Butyl Ester A methanolic solution of the compound of Example 201, Step A was hydrogenated (40 psi) in a Parr shaker over 10% Pd-C (35 mg). After 17 hours, the reaction was filtered through a pad of Celite® and then concentrated to give yellowish solid of the compound of the compound of Example 201, Step B (153 mg, 90%) which was a 1:2 mixture of ester and lactam: +APcI MS (M+1, ester)$^+$ 363, (M+1, lactam)$^+$ 331; $^1$H NMR (400 MHz, CDCl$_3$) δ: 7.25–7.05 (arom, series of m, 5H), 3.54 (ester Me, s, 1H), 1.44 (lactam BOC, s, 6H),1.37 (ester BOC, s, 3H).

C. 8a-Benzyl-6-oxo-hexahydro-pyrrolo[1,2-a]pyrazine-2-carboxylic Acid tert-Butyl Ester To a methanolic (4 mL) solution of the compound of Example 201, Step B was added solid K$_2$CO$_3$. The mixture was refluxed for 30 minutes, then concentrated and extracted from saturated aqueous NH$_4$Cl with methylene chloride to give lactam of Example 201, Step C as a yellowish solid (70.6 mg, 50%): +APcI MS (M+1)$^+$ 331, (M–$^t$Bu+1)$^+$ 275, (M–BOC+1)$^+$ 231; $^1$H NMR (400 MHz, CDCl$_3$) δ: 7.30–7.05 (arom, series of m, 5H), 4.06 (d, 1H) , 3.06 (d, 1H), 2.67 (d, 1H), 2.07 (m, 2H), 1.49 (BOC, s, 6H).

D. 8a(S*)-Benzyl-7(S*)-methyl-6-oxo-hexahydro-pyrrolo[1,2-a]pyrazine-2-carboxylic Acid tert-Butyl Ester To a THF (0.4 mL) solution of lithium diisopropylamide (2.0 mmol) at −78° C. was added the compound of Example 201, Step C (192 mg, 0.58 mmol) in 1,2-dimethoxyethane (3 mL). After 20 minutes, methyl iodide (0.36 mL, 5.8 mmol) was added dropwise and the reaction was stirred an additional 1 hour. The reaction was quenched at −78° C. with brine, and the reaction was then extracted with EtOAc (3×), dried (MgSO$_4$), and concentrated. The product was then purified by silica gel chromatography using 7:3 to 1:1 hexanes/EtOAc as eluents to afford the dimethyl lactam (78 mg, 37%), 8a-benzyl-7,7-dimethyl-6-oxo-hexahydro-pyrrolo[1,2-a]pyrazine-2-carboxylic acid tert-butyl ester, the (R*,S*) methyl lactam (68 mg, 34%), followed by the (S*,S*) methyl lactam of Example 201, Step D (58 mg, 29%). Dimethyl lactam: +APcI MS (M+1)$^+$ 359, (M–$^t$Bu+1)$^{30}$ 303, (M–BOC+1)$^+$ 259; $^1$H NMR (400 MHz, CDCl$_3$) δ: 7.30–7.10 (arom, series of m, 5H), 3.18 (td, 1H), 3.0 (d, 1H), 2.0 (d, 1H), 1.49 (BOC, s, 9H), 1.13 (Me, s, 3H), 0.66 (Me, br s, 3H). (R*,S*) lactam: +APcI MS (M+1)$^{30}$ 345, (M–$^t$Bu+1)$^+$ 289, (M–BOC+1)$^+$ 245; $^1$H NMR (400 MHz, CDCl$_3$) δ: 7.30–7.05 (arom, series of m, 5H), 3.04 (d, 1H), 2.66 (d, 1H), 2.31 (dd, 1H), 1.49 (BOC, s, 9H), 1.99 (Me, d, 3H). The (S*, S*) lactam of Example 201, Step D: +APcI MS (M+1)$^{30}$ 345, (M–$^t$Bu+1)$^+$ 289, (M–BOC+1)$^+$ 245; $^1$H NMR (400 MHz, CDCl$_3$) δ: 7.30–7.05 (arom, series of m, 5H), 2.97 (d, 1H), 2.81 (d, 1H), 2.40 (m, 1H), 1.48 (BOC, s, 9H), 0.73 (Me, br s, 3H).

E. {1-[2-(8a(S*)-Benzyl-7(S*)-methyl-6-oxo-hexahydro-pyrrolo[1,2-a]pyrazin-2-yl)-1(R)-benzyloxymethyl-2-oxo-ethylcarbamoyl]-1-methyl-ethyl}-carbamic Acid tert-Butyl Ester The compound of Example 201, Step D (58 mg, 0.17 mmol) was deprotected as described in General Procedure C to provide the secondary amine as the HCl salt: +APcI MS (M+1)$^+$ 245; $^1$H NMR (400 MHz, CD$_3$OD) d: 7.15–7.35 (arom, series of m, 5H), 4.26 (dd, 1H), 3.17 (d, 1H), 2.78 (d, 1H), 2.02 (dd, 1H), 1.76 (dd, 1H), 0.46 (Me, d, 3H).

To a solution of the crude amine, the acid of Example 2, Step 1 (96 mg, 0.25 mmol) and Et$_3$N (0.16 mL, 1.2 mmol) in EtOAc (1 mL) at 0° C. was added PPAA (50% solution in EtOAc, 0.16 mL, 0.27 mmol). After 16 h of stirring at room temperature, the reaction mixture was extracted from saturated aqueous sodium bicarbonate with EtOAc, and the combined extracts dried (MgSO$_4$) and concentrated. Purification by silica gel chromatography employing 7:3 EtOAc/hexanes, then EtOAc, then 19:1 EtOAc/MeOH as eluants afforded the less polar isomer of Example 201, Step E (29 mg, 28%), the more polar isomer (41 mg, 40%), as well as some mixed fractions. Less polar isomer of Example 201, Step E: +APcl MS (M+1)$^+$ 607, (M–BOC+1)$^+$ 507; $^1$H NMR (400 MHz, CDCl$_3$) δ: 7.35–6.80 (arom, series of m, 10H), 4.68 (d, 1H), 4.47 (AB$_q$, 2H), 2.63 (d, 1H), 0.91 (Me, m, 1.5H), 0.63 (Me, d, 1.5H). More polar isomer: +APcl MS (M+1)$^{30}$ 607, (M–BOC+1)$^+$ 507; $^1$H NMR (400 MHz, CDCl$_3$) δ: 7.70–6.85 (arom, series of m, 10H), 4.65 (d, 1H), 4.50 (½Ab$_q$, 1H), 4.41 (½Ab$_q$, 1H) 1H), 2.59 (d, 1H), 0.87 (Me, m, 1.5H), 0.63 (Me, d, 1.5H).

F. 2-Amino-N-[2-(8a(S*)-benzyl-7(S*)-methyl-6-oxo-hexahydro-pyrrolo[1,2-a]pyrazin-2-yl)-1(R)-benzyloxymethyl-2-oxo-ethyl]-2-methyl-propionamide The compound of Example 201, Step E (29 mg, 0.048 mmol) was deprotected as described in General Procedure C to provide, after trituration with ether, the compound of Example 201, Step F as its HCl salt (23 mg, 88%): +APcl MS (M+1)$^+$ 507; $^1$H NMR (400 MHz, CD$_3$OD) δ: 7.40–6.90 (arom, series of m, 10H), 4.59 (d, 1H), 4.54 (s, 2H), 4.04 (d, 1H), 2.71 (d, 1H), 2.57 (d, 1H).

EXAMPLE 202

2-Amino-N-[1(R)-benzyloxymethyl-2-oxo-2-(6-oxo-8a-pyridin-2-ylmethyl-hexahydro-pyrrolo[1,2-a]pyrazin-2-yl)-ethyl]-2-methyl-propionamide

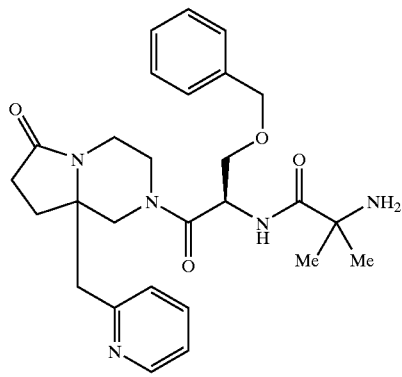

A. 8-Hydroxy-6-oxo-8a-pyridin-2-ylmethyl-hexahydro-pyrrolo[1,2-a]pyrazine-2-carboxylic Acid tert-Butyl Ester To a 0° C. methanolic (5 mL) solution of 6,8-dioxo-8a-pyridin-2ylmethyl-hexahydro-pyrrolo[1,2-a]pyrazine-2-carboxylic acid tert-butyl ester (203 mg, 0.59 mmol), prepared analogously to the compound of Example 6, Step D but used crude, small portions of sodium borohydride were added until TLC indicated starting material was consumed. The reaction was then quenched with water, and then extracted from saturated aqueous NaHCO$_3$ with EtOAc. The combined extracts were washed with brine, dried (MgSO$_4$), and concentrated. Purification by silica gel chromatography employing 3:7 then 2:1 EtOAc/hexanes as eluants afforded the alcohol of Example 202, Step A (95 mg, 38%): +APcl MS (M+1)$^+$ 348, (M–$^t$Bu+1)$^+$ 292; $^1$H NMR (400 MHz, CDCl$_3$) δ: 8.45 (arom, d, 1H), 7.70–7.07 (arom, series of m, 3H), 4.00, (dd, 1H), 3.28 (AB$_q$, 2H), 2.64 (dd, 1H), 1.40 (BOC, s, 9H).

B. 6-Oxo-8a-pyridin-2-ylmethyl-3,4,6,8a-tetrahydro-1H-pyrrolo[1,2-a]pyrazine-2-carboxylic Acid tert-Butyl Ester To a solution of the compound of Example 202, Step A (240 mg, 0.69 mmol) and triethylamine (0.29 mL, 2.1 mmol) at 0° C. in methylene chloride (10 mL) was added methanesulfonyl chloride (0.11 mL, 1.4 mmol), dropwise. After stirring 18 hours, the solvent was removed under vacuum and was replaced with toluene (15 mL), 1,8-diazabicyclo[5.4.0]undec-7-ene (0.5 mL, 3.3 mmol) was added, and the reaction was heated for 4 hours at 100° C. The material was extracted from water with EtOAc, and the combined extracts were dried (MgSO$_4$) and concentrated. Purification by silica gel chromatography employing chloroform then 19:1 chloroform/MeOH as eluants afforded the compound of Example 202, Step B (147 mg, 65%): +APcl MS (M+1)$^+$ 330, (M–$^t$Bu+1)$^+$ 274; $^1$H NMR (400 MHz, CDCl$_3$) δ: 8.43 (arom, d, 1H), 7.55–6.90 (series of m, 4H), 6.00, (olefin, d, 1H), 3.09 (d, 1H), 1.42 (BOC, s, 9H).

C. 6-Oxo-8a-pyridin-2-ylmethyl-hexahydro-pyrrolo[1,2-a]pyrazine-2-carboxylic Acid tert-Butyl Ester To a –78° C. solution of the compound of Example 202, Step B in THF (15 mL) was added lithium tri-sec-butylborohydride (1 M in THF, 1.44 mL), the reaction was stirred 10 minutes and then allowed to warm to room temperature. After 4 hours, the reaction was extracted from saturated aqueous NaHCO$_3$ with EtOAc. The combined extracts were washed with brine, dried (MgSO$_4$), and concentrated to afford the compound of Example 202, Step C (320 mg, quantitative): +APcl MS (M+1)$^+$ 332, (M–$^t$Bu+1)$^+$ 276; $^1$H NMR (400 MHz, CDCl$_3$) δ: 8.40 (arom, m, 1H), 7.55 (arom, m, 1H), 7.15–7.00 (series of m, 2H), 3.99 (br d, 1H), 2.85 (d, 1H), 1.43 (BOC, s, 9H).

D. 8a-Pyridin-2-ylmethyl-hexahydro-pyrrolo[1,2-a]pyrazin-6-one

The compound of Example 202, Step C (11 mg, 0.033 mmol) was deprotected as described in General Procedure C to provide the secondary amine of Example 202, Step D as the HCl salt (9 mg, quantitative): +APcl MS (M+1)$^+$ 232; $^1$H NMR (400 MHz, CD$_3$OD) δ: 8.87 (arom, d, 1H), 8.59 (arom, t, 1H), 8.06 (arom, t, 1H), 7.96 (arom, d, 1H), 4.32 (dd, 1H), 3.94 (d, 1H), 3.74 (d, 1H), 1.59 (m, 1H).

E. {1-[1(R)-Benzyloxmethyl-2-oxo-2-(6-oxo-8a-pyridin-2-ylmethyl-hexahydro-pyrrolo[1,2-a]pyrazin-2-yl)-ethylcarbamoyl]-1-methyl-ethyl}-carbamic Acid tert-Butyl Ester To a solution of the compound of Example 202, Step D (330 mg, 1.54 mmol), the acid of Example 2, Step 1 (785 mg, 2.1 mmol) and Et$_3$N (1.1 mL, 7.7 mmol) in EtOAc (10 mL) at 0° C. was added PPAA (50% solution in EtOAc, 0.88 mL, 2.10 mmol). After 2 h, the reaction mixture was extracted from saturated aqueous sodium bicarbonate with EtOAc, and the combined extracts washed with brine, dried (MgSO$_4$) and concentrated. Purification by silica gel chromatography employing EtOAc, then 19:1 EtOAc/MeOH as eluants afforded the compound of Example 202, Step E (250 mg, 29%) as a 1:1 mixture of diastereomers: +APcl MS (M+1)$^+$ 594, (M–BOC+1)$^+$ 494.

F. 2-Amino-N-[1(R)-benzyloxymethyl-2-oxo-2-(6-oxo-8a-pyridin-2-ylmethyl-hexahydro-pyrrolo[1,2-a]pyrazin-2-yl)-ethyl]-2-methyl-propionamide Compound of Example 202, Step E (12 mg, 0.020 mmol) was deprotected as described in General Procedure C to provide, after trituration with ether, Example 202, Step F as its HCl salt (5 mg, 50%): +APcl MS (M+1)+ 494; $^1$H NMR (400 MHz, CD$_3$OD) δ: 8.90–7.15 (arom, series of m, 9H), 5.31 (m, 0.5H), 5.15 (m, 0.5H), 2.86 (d, 0.5H), 2.77 (d, 0.5H), 1.60 (Me, m, 6H).

EXAMPLE 203

2-Amino-N-{1(R)-benzyloxymethyl-2-[8a(S)-(4-fluoro-benzyl)-7,7-dimethyl-6,8-dioxo-hexahydro-pyrrolo[1,2-a]pyrazin-2-yl]-2-oxo-ethyl}-2-methyl-propionamide

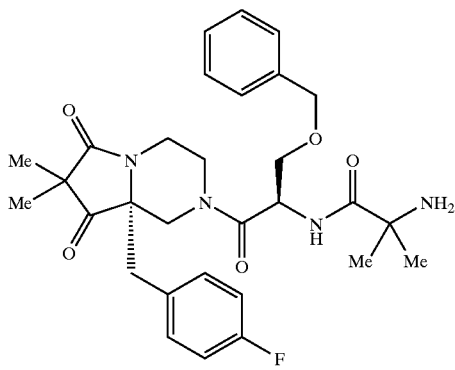

A. 8a-(4-Fluoro-benzyl)-7,7-dimethyl-6,8-dioxo-hexahydro-pyrrolo[1,2-a]pyrazine-2-carboxylic Acid tert-Butyl Ester To a DMSO (2 mL) solution of the compound of Example 6, Step D was added NaH (60% dispersion in mineral oil, 33 mg, 0.83 mmol) was added methyl iodide (0.017 mL, 0.28 mmol), the mixture was stirred for 1 hour, and then an additional portion of methyl iodide (0.017 mL, 0.28 mmol) was added. After stirring 3 days, the reaction mixture was extracted from saturated aqueous sodium bicarbonate with EtOAc, and the combined extracts washed with brine, dried (MgSO$_4$) and concentrated. Purification by silica gel chromatography employing hexanes, then 1:1 EtOAc/hexanes as eluants afforded the compound of Example 203, Step A (20 mg, 29%): +APcl MS (M–$^t$Bu+1)+ 335, (M–BOC+1)$^{30}$ 291; $^1$H NMR (400 MHz, CDCl$_3$) δ: 6.93 (arom, m, 4H), 4.40 (dd, 1H), 1.50 (BOC, s, 9H), 1.13 (Me, s, 3H), 0.26 (Me, s, 3H).

B. 8a-(4-Fluoro-benzyl)-7,7-dimethyl-tetrahydro-pyrrolo[1,2-a]pyrazine-6,8-dione The compound of Example 203, Step A (20 mg, 0.061 mmol) was deprotected as described in General Procedure C to provide the secondary amine of Example 203, Step B as the HCl salt (17 mg, 85%): +APcl MS (M+1)+ 291; $^1$H NMR (400 MHz, CD$_3$OD) δ: 7.04 (arom, m, 4H), 4.56 (dd, 1H), 3.50 (d, 1H), 3.07 (d, 1H), 1.16 (Me, s, 3H), 0.16 (Me, s, 3H).

C. (1-{1(R)-Benzyloxymethyl-2-[8a(S)-(4-fluoro-benzyl)-7,7-dimethyl-6,8-dioxo-hexahydro-pyrrolo[1,2-a]pyrazin-2-yl]-2-oxo-ethylcarbamoyl}-1-methyl-ethyl)-carbamic Acid tert-Butyl Ester To a solution of the compound of Example 203, Step B (17 mg, 0.052 mmol), the acid of Example 2, Step 1 (24 mg, 0.062 mmol) and EtaN (0.036 mL, 0.26 mmol) in EtOAc (0.5 mL) at 0° C. was added PPAA (50% solution in EtOAc, 0.88 mL, 2.10 mmol). After 3 h, the reaction mixture was extracted from saturated aqueous sodium bicarbonate with EtOAc, and the combined extracts washed with brine, dried (MgSO$_4$) and concentrated. Purification by silica gel chromatography employing hexanes, then 1:1 EtOAc/hexanes as eluants afforded the less polar isomer of Example 263, Step C (4 mg, 28%) followed by the more polar isomer (6 mg, 43%). Less polar isomer of Example 203, Step C: +APcl MS (M–BOC+1)+ 553; $^1$H NMR (400 MHz, CDCl$_3$) δ: 7.40–6.80 (arom, series of m, 9H), 4.85 (d, 1H), 4.47 (Ab$_q$, 2H), 2.51 (d, 1H), 1.12 (Me, s, 3H), 0.24 (Me, s, 3H). More polar isomer: +APcl MS (M–BOC+1)+ 553; $^1$H NMR (400 MHz, CDCl$_3$) δ: 7.35–6.50 (arom, series of m, 9H), 4.85 (d, 1H), 4.55 (½Ab$_q$, 1H), 4.42 (½Ab$_q$, 1H), 2.87 (d, 1H), 2.45 (3H), 0.15 (Me, s, 3H).

D. 2-Amino-N-{1(R)-benzyloxymethyl-2-[8a(S)-(4-fluoro-benzyl)-7,7-dimethyl-6,8-dioxo-hexahydro-pyrrolo[1,2-a]pyrazin-2-yl]-2-oxo-ethyl}-2-methyl-propionamide The compound of Example 203, Step C (4 mg, 0.006 mmol) was deprotected as described in General Procedure C to provide, after trituration with ether, the compound of Example 201, Step F as its HCl salt (3 mg, 83%): +APcl MS (M+1)+ 553; $^1$H NMR (400 MHz, CD$_3$OD) δ: 7.40–6.90 (arom, series of m, 9H), 5.16 (t, 1H), 4.69 (d, 1H), 4.54 (s, 2H), 2.85 (t, 1H), 1.56 (ala Me, s, 6H), 1.12 (Me, s, 3H), 0.20 (Me, s, 3H).

The following abbreviations and notations are used in the Tables below.
Abbreviation:
Me—methyl
Et—ethyl
Ph—phenyl
Pyr—pyridyl
c-Pr—cyclopropyl
A=Mass Spec. Method is $^-$APcl
B=Mass Spec. Method is PB
C=Mass Spec. Method is $^+$APcl

EXAMPLES 204–206

The compounds of examples 204–206 were synthesized in a manner analogous to the procedures described for Example 9 using the appropriate starting materials.

| Example | R$^2$ | R$^1$ | R" | isomer | MS |
|---|---|---|---|---|---|
| 204 | Me | CH$_2$-2-Pyr | OCH$_2$Ph | d1, 2 | 510$^C$ |
| 205 | Et | CH$_2$-2-Pyr | OCH$_2$Ph | d1, 2 | 524$^C$ |
| 206 | Et | CH$_2$-2-Pyr | OCH$_2$Ph | d3, 4 | 524$^C$ |

EXAMPLES 207–230

The compounds of examples 207–230 were synthesized in a manner analogous to procedures described for Example 200 using the appropriate starting materials.

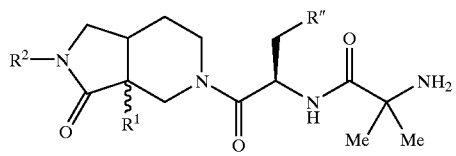

| Example | $R^2$ | $R^1$ | R" | isomer | MS |
|---|---|---|---|---|---|
| 207 | Me | $CH_2Ph$ | $OCH_2Ph$ | d1 | $507^C$ |
| 208 | Me | $CH_2Ph$ | $OCH_2Ph$ | d2 | $507^C$ |
| 209 | Me | $CH_2Ph$ | $OCH_2Ph$ | d4 | $507^C$ |
| 210 | Me | $CH_2Ph$ | $OCH_2Ph$ | d3, 4 | $507^C$ |
| 211 | c-Pr | $CH_2Ph$ | $OCH_2Ph$ | d1, 2 | $533^C$ |
| 212 | c-Pr | $CH_2Ph$ | $OCH_2Ph$ | d3 | $533^C$ |
| 213 | c-Pr | $CH_2Ph$ | $OCH_2Ph$ | d3, 4 | $533^C$ |
| 214 | Et | $CH_2Ph$ | $OCH_2Ph$ | d1, 2 | $521^C$ |
| 215 | Et | $CH_2Ph$ | $OCH_2Ph$ | d3, 4 | $521^C$ |
| 216 | Me | $CH_2$-4-F—Ph | $OCH_2Ph$ | d3, 4 | $525^C$ |
| 217 | Me | $CH_2$-4-F—Ph | $OCH_2Ph$ | d1, 2 | $525^C$ |
| 218 | $CF_3CH_2$ | $CH_2Ph$ | $OCH_2Ph$ | d3 | $575^C$ |
| 219 | $CF_3CH_2$ | $CH_2$-4-F—Ph | $OCH_2Ph$ | d3, 4 | $593^C$ |
| 220 | $CF_3CH_2$ | $CH_2Ph$ | $OCH_2Ph$ | d4 | $575^C$ |
| 221 | $CF_3CH_2$ | $CH_2$-4-F—Ph | $OCH_2Ph$ | d1, 2 | $593^C$ |
| 222 | $CF_3CH_2$ | $CH_2Ph$ | $OCH_2Ph$ | d1, 2 | $575^C$ |
| 223 | Et | $CH_2$-4-F—Ph | $OCH_2Ph$ | d1, 2 | $539^C$ |
| 224 | Et | $CH_2$-4-F—Ph | $OCH_2Ph$ | d3 | $539^C$ |
| 225 | Et | $CH_2$-4-F—Ph | $OCH_2Ph$ | d4 | $539^C$ |
| 226 | Bn | $CH_2$-4-F—Ph | $OCH_2Ph$ | d1, 2, 3, 4 | $601^C$ |
| 227 | Me | $CH_2$-2-Pyr | $OCH_2Ph$ | d1, 2 | $508^C$ |
| 228 | Et | $CH_2$-2-Pyr | $OCH_2Ph$ | d1, 2 | $522^C$ |
| 229 | H | $CH_2Ph$ | $OCH_2Ph$ | d1, 2 | $493^C$ |
| 230 | H | $CH_2Ph$ | $OCH_2Ph$ | d3, 4 | $493^C$ |

EXAMPLE 231

The compound of Example 231 was synthesized in a manner analogous to procedures described for Example 203 using the appropriate starting materials.

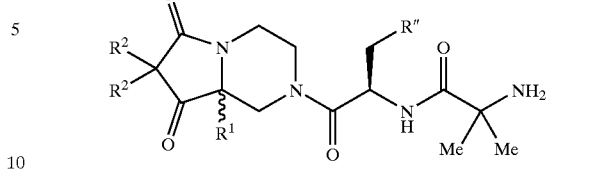

| Example | $R^2$ | $R^1$ | R" | isomer | MS |
|---|---|---|---|---|---|
| 231 | Me | $CH_2$-2-F—Ph | $OCH_2Ph$ | d2 | $553^C$ |

EXAMPLES 232–238

The compounds of examples 232–238 were synthesized in a manner analogous to procedures described for Examples 201 and 202 using the appropriate starting materials.

| Example | $R^2$ | $R^3$ | $R^1$ | R" | isomer | MS |
|---|---|---|---|---|---|---|
| 232 | H | H | $CH_2Ph$ | $OCH_2Ph$ | d1 | $493^C$ |
| 233 | H | H | $CH_2Ph$ | $OCH_2Ph$ | d2 | $493^C$ |
| 234 | H | Me | $CH_2Ph$ | $OCH_2Ph$ | d2 | $507^C$ |
| 235 | H | Me | $CH_2Ph$ | $OCH_2Ph$ | d3 | $507^C$ |
| 236 | H | Me | $CH_2Ph$ | $OCH_2Ph$ | d4 | $507^C$ |
| 237 | Me | Me | $CH_2Ph$ | $OCH_2Ph$ | d1 | $521^C$ |
| 238 | Me | Me | $CH_2Ph$ | $OCH_2Ph$ | d2 | $521^C$ |

EXAMPLES 239–240

The compounds of Examples 239–240 were synthesized in a manner analogous to procedures described for Example 199 using the appropriate starting materials.

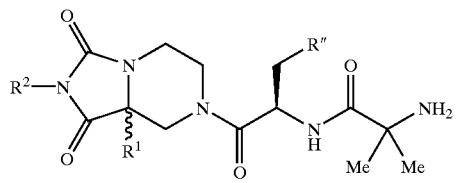

| Example | R' | $R^1$ | R" | isomer | MS |
|---|---|---|---|---|---|
| 239 | $CF_3CH_2$ | $CH_2$-2-Pyr | CH=CH-2,4-di-F—Ph | d1 | $622^C$ |
| 240 | $CF_3CH_2$ | $CH_2$-2-Pyr | CH=CH-4-Cl—Ph | d1 | $620^C$ |

EXAMPLES 241–251

The compounds of Examples 241–251 were synthesized in a manner analogous to procedures described for Examples 2, 197 and 198 using the appropriate starting materials.

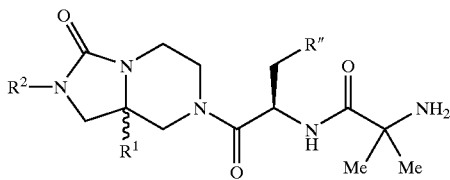

| Example | $R^2$ | $R^1$ | R" | isomer | MS |
|---|---|---|---|---|---|
| 241 | $CF_3CH_2$ | $CH_2$-2,4-di-F—Ph | $OCH_2Ph$ | d1, 2 | 612$^C$ |
| 242 | $CH_2Ph$ | $CH_2$-2,4-di-F—Ph | $OCH_2Ph$ | d1 | 620$^C$ |
| 243 | $CH_2Ph$ | $CH_2$-2,4-di-F—Ph | $OCH_2Ph$ | d2 | 620$^C$ |
| 244 | $CF_3CH_2$ | $CH_2Ph$ | $OCH_2Ph$ | d1 | 576$^C$ |
| 245 | $CF_3CH_2$ | $CH_2Ph$ | $OCH_2Ph$ | d2 | 576$^C$ |
| 246 | $CF_3CH_2$ | $CH_2$-2-Pyr | $OCH_2Ph$ | d1 | 577$^C$ |
| 247 | $CH_2Ph$ | $CH_2Ph$ | $OCH_2Ph$ | d1 | 584$^C$ |
| 248 | $CH_2Ph$ | $CH_2Ph$ | $OCH_2Ph$ | d2 | 584$^C$ |
| 249 | Me | $CH_2$-2-Pyr | $OCH_2Ph$ | d1, 2 | 509$^C$ |
| 250 | Et | $CH_2$-2-Pyr | $OCH_2Ph$ | d1, 2 | 523$^C$ |
| 251 | Bn | $CH_2$-2-Pyr | $OCH_2Ph$ | d1, 2 | 585$^C$ |

What is claimed is:

1. A compound of the formula

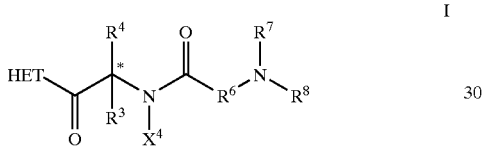

I or a stereoisomeric mixture thereof, diastereomerically enriched, diastereomerically pure, enantiomerically enriched or enantiomerically pure isomer thereof, or a prodrug of such compound, mixture or isomer thereof, or a pharmaceutically acceptable salt of the compound, mixture, isomer or prodrug, wherein HET is a heterocyclic moiety selected from the group consisting of

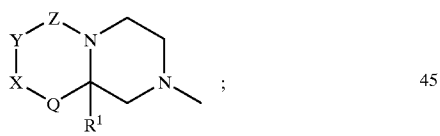

Q is a covalent bond or $CH_2$;
X is $CH_2$, C=$CH_2$ or C=O;
Y is $CH_2$, O or $NR^2$;
Z is $SO_2$;
$R^1$ is hydrogen, —CN, —$(CH_2)_qN(X^6)C(O)X^6$, —$(CH_2)_qN(X^6)C(O)(CH_2)_t$—$A^1$, —$(CH_2)_qN(X^6)S(O)_2(CH_2)_t$—$A^1$, —$(CH_2)_qN(X^6)S(O)_2X^6$, —$(CH_2)_qN(X^6)C(O)N(X^6)(CH_2)_t$—$A^1$, —$(CH_2)_qN(X^6)C(O)N(X^6)(X^6)$, —$(CH_2)_qC(O)N(X^6)(X^6)$, —$(CH_2)_qC(O)N(X^6)(CH_2)_t$—$A^1$, —$(CH_2)_qC(O)OX^6$, —$(CH_2)_qC(O)O(CH_2)_tA^1$, —$(CH_2)_qOX^6$—$(CH_2)_qOC(O)X^6$, —$(CH_2)_qOC(O)(CH_2)_t$—$A^1$, —$(CH_2)_qOC(O)N(X^6)(CH_2)_t$—$A^1$, —$(CH_2)_qOC(O)N(X^6)(X^6)$, —$(CH_2)_qC(O)X^6$, —$(CH_2)_qC(O)(CH_2)_t$—$A^1$, —$(CH_2)_qN(X^6)C(O)OX^6$, —$(CH_2)_qN(X^6)S(O)_2N(X^6)(X^6)$, —$(CH_2)_qS(O)_mX^6$, —$(CH_2)_qS(O)_m(CH_2)_t$—$A^1$, —$(C_1-C_{10})$alkyl, —$(CH_2)_t$—$A^1$, —$(CH_2)_q$—$(C_3-C_7)$cycloalkyl, —$(CH_2)_q$—$Y^1$—$(C_1-C_6)$alkyl, —$(CH_2)_q$—$Y^1$—$(CH_2)_t$—$A^1$ or —$(CH_2)_q$—$Y^1$—$(CH_2)_t$—$(C_3-C_7)$cycloalkyl;

where $A^1$ in the definition of $R^1$ is phenyl, pyridyl, thiazolyl or thienyl, optionally substituted with one to three substituents, each substituent being independently selected from the group consisting of F, Cl, $CH_3$, $OCH_3$, $OCF_2H$, $OCF_3$ and $CF_3$; and where the alkyl and cycloalkyl groups in the definition of $R^1$ are optionally substituted with $(C_1-C_4)$alkyl, hydroxy, $(C_1-C_4)$alkoxy, or 1, 2 or 3 fluoro groups;

q is 1 or 2;
t is 1 or 2;
said $(CH_2)_q$ group and $(CH_2)_t$ group in the definition of $R^1$ are optionally independently substituted with hydroxy, $(C_1-C_4)$alkoxy, carboxyl, —$CONH_2$, —$S(O)m(C_1-C_6)$alkyl, —$CO_2(C_1-C_4)$alkyl ester, 1H-tetrazol-5-yl, 1, 2 or 3 fluoro groups or 1 or 2 $(C_1-C_4)$alkyl groups;

$R^2$ is hydrogen, $(C_1-C_5)$alkyl or $(C_0-C_2)$alkyl-$(C_3-C_8)$cycloalkyl;

where the alkyl groups and the cycloalkyl groups in the definition of $R^2$ are optionally substituted with fluoro groups;

$R^3$ is phenyl-$CH_2$—O—$CH_2$—, phenyl-$CH_2$—S—$CH_2$—, pyridyl-$CH_2$—O—$CH_2$—, thienyl-$CH_2$—O—$CH_2$—, thiazolyl-$CH_2$—O—$CH_2$—, phenyl-$(CH_2)_3$— or 3-indolyl-$CH_2$—; where the carbon atom bearing the substituent $R^3$ is of the (R) configuration; where the aryl portion of the groups defined for $R^3$ is optionally substituted with one to three substituents, each substituent being independently selected from the group consisting of F, CL, $CH_3$, $OCH_3$, $OCF_2H$, $OCF_3$ and $CF_3$;

$R^4$ is hydrogen;
$X^4$ is hydrogen;

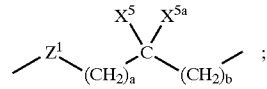

where a and b are each 0;
$X^5$ and $X^{5a}$ are each methyl;
$Z^1$ is a bond;
$R^7$ and $R^8$ are each hydrogen.

2. A compound or a stereoisomeric mixture thereof, diastereomerically enriched, diastereomerically pure, enantiomerically enriched or enantiomerically pure isomer thereof, or a prodrug of such compound, mixture or isomer thereof, or a pharmaceutically acceptable salt of the compound, mixture, isomer or prodrug according to claim 1 wherein Q is a covalent bond; X is $CH_2$; and Y is $CH_2$ or $NR^2$.

3. A compound or a stereoisomeric mixture thereof, diastereomerically enriched, diastereomerically pure, enantiomerically enriched or enantiomerically pure isomer thereof, or a prodrug of such compound, mixture or isomer thereof, or a pharmaceutically acceptable salt of the compound, mixture, isomer or prodrug according to claim 2 wherein Y is $CH_2$.

4. A compound or a stereoisomeric mixture thereof, diastereomerically enriched, diastereomerically pure, enantiomerically enriched or enantiomerically pure isomer thereof, or a prodrug of such compound, mixture or isomer thereof, or a pharmaceutically acceptable salt of the compound, mixture, isomer or prodrug according to claim 3 wherein $R^1$ is $—CH_2—A^1$ where $A^1$ is phenyl, pyridyl or thiazolyl, optionally substituted with one to three substituents, each substituent being independently selected from the group consisting of F, Cl, $CH_3$, $OCH_3$, $OCF_2H$, $OCF_3$ and $CF_3$; and $R^3$ is selected from the group consisting of 3-indolyl-$CH_2$—, phenyl-$(CH_2)_3$—, phenyl-$CH_2$—O—$CH_2$— and thiazolyl-$CH_2$—O—$CH_2$—, where the aryl portion of the groups defined for $R^3$ is optionally substituted with one to three substituents, each substituent being independently selected from the group consisting of methylenedioxy, F, Cl, $CH_3$, $OCH_3$, $OCF_3$, $OCF_2H$ and $CF_3$.

5. A compound or a prodrug of such compound or a pharmaceutically acceptable salt of the compound or a prodrug according to claim 4 where the compound is the 3a(R,S),1(R) diastereomeric mixture, the 3a(R),1(R) diastereomer or the 3a(S),1(R) diastereomer of 2-amino-N-[2-(3a-benzyl-1,1-dioxo-hexahydro-1thia-5,7a-diaza-inden-5yl)-1-benzyloxymethyl-2-oxo-ethyl]-2-methyl-propionamide.

6. A compound according to claim 1 wherein Q is a covalent bond; X is C═O; and Y is $NR^2$.

7. A compound or a stereoisomeric mixture thereof, diastereomerically enriched, diastereomerically pure, enantiomerically enriched or enantiomerically pure isomer thereof, or a prodrug of such compound, mixture or isomer thereof, or a pharmaceutically acceptable salt of the compound, mixture, isomer or prodrug according to claim 1 wherein Q is a covalent bond; X is C═O; Y is $NR^2$;

$R^1$ is hydrogen; and $R^3$ is selected from the group consisting of phenyl-$CH_2$—O—$CH_2$—, pyridyl-$CH_2$—O—$CH_2$—, phenyl-$(CH_2)_3$—, 3-indolyl-$CH_2$— and thiazolyl-$CH_2$—O—$CH_2$—, where the a groups defined for $R^3$ is optionally substituted with one to three substituents, each substituent being independently selected from the group consisting of methylenedioxy, F, Cl, $CH_3$, $OCH_3$, $OCF_3$, $OCF_2H$ and $CF_3$.

8. A pharmaceutical composition which comprises a pharmaceutically acceptable carrier and an effective amount of a compound or a stereoisomeric mixture thereof, diastereomerically enriched, diastereomerically pure, enantiomerically enriched or enantiomerically pure isomer thereof, or a prodrug of such compound, mixture or isomer thereof, or a pharmaceutically acceptable salt of the compound, mixture, isomer or prodrug according to claim 1.

9. A pharmaceutical composition useful for increasing the endogenous production or release of growth hormone in a human or other animal which comprises a pharmaceutically acceptable carrier, an effective amount of a compound or a stereoisomeric mixture thereof, diastereomerically enriched, diastereomerically pure, enantiomerically enriched or enantiomerically pure isomer thereof, or a prodrug of such compound, mixture or isomer thereof, or a pharmaceutically acceptable salt of the compound, mixture, isomer or prodrug according to claim 1 and a growth hormone secretagogue selected from the group consisting of GHRP-6, Hexarelin, GHRP-1, growth hormone releasing factor (GRF), IGF-1, IGF-2 and B-HT920 or an analog thereof.

10. A method for increasing levels of endogenous growth hormone in a human or other animal which comprises administering to such human or animal an effective amount of a compound or a stereoisomeric mixture thereof, diastereomerically enriched, diastereomerically pure, enantiomerically enriched or enantiomerically pure isomer thereof, or a prodrug of such compound, mixture or isomer thereof, or a pharmaceutically acceptable salt of the compound, mixture, isomer or prodrug according to claim 1.

11. A method for treating or preventing osteoporosis and/or frailty which comprises administering to a human or other animal in need of such treatment or prevention an amount of a compound or a stereoisomeric mixture thereof, diastereomerically enriched, diastereomerically pure, enantiomerically enriched or enantiomerically pure isomer thereof, or a prodrug of such compound, mixture or isomer thereof, or a pharmaceutically acceptable salt of the compound, mixture, isomer or prodrug according to claim 1 which is effective in treating or preventing osteoporosis and/or frailty.

12. A method for treating or preventing diseases or conditions which may be treated or prevented by growth hormone which comprises administering to a human or other animal in need of such treatment or prevention an amount of a compound or a stereoisomeric mixture thereof, diastereomerically enriched, diastereomerically pure, enantiomerically enriched or enantiomerically pure isomer thereof, or a prodrug of such compound, mixture or isomer thereof, or a pharmaceutically acceptable salt of the compound, mixture, isomer or prodrug according to claim 1 which is effective in promoting release of endogenous growth hormone.

13. A method of claim 12 wherein said condition is a sleep disorder.

14. A method according to claim 12 wherein the disease or condition is congestive heart failure, frailty associated with aging or obesity.

15. A method according to claim 14 wherein the disease or condition is congestive heart failure.

16. A method according to claim 14 wherein the disease or condition is frailty associated with aging.

17. A method for accelerating bone fracture repair, attenuating protein catabolic response after a major operation, reducing cachexia and protein loss due to chronic illness, accelerating wound healing, or accelerating the recovery of bum patients or patients having undergone major surgery, which method comprises administering to a mammal in need of such treatment an amount of a compound or a stereoisomeric mixture thereof, diastereomerically enriched, diastereomerically pure, enantiomerically enriched or enantiomerically pure isomer thereof, or a prodrug of such compound, mixture or isomer thereof, or a pharmaceutically acceptable salt of the compound, mixture, isomer or prodrug according to claim 1 which is effective in promoting release of endogenous growth hormone.

18. A method according to claim 17 wherein the method is for accelerating the recovery of patients having undergone major surgery.

19. A method according to claim 17 wherein the method is for accelerating bone fracture repair.

20. A method for improving muscle strength, mobility, maintenance of skin thickness, metabolic homeostasis or renal homeostasis, which method comprises administering to a human or other animal in need of such treatment an amount of a compound or a stereoisomeric mixture thereof, diastereomerically enriched, diastereomerically pure, enantiomerically enriched or enantiomerically pure isomer thereof, or a prodrug of such compound, mixture or isomer thereof, or a pharmaceutically acceptable salt of the compound, mixture, isomer or prodrug according to claim 1 which is effective in promoting release of endogenous growth hormone.

21. A method for the treatment or prevention of osteoporosis and/or frailty which comprises administering to a human or other animal with osteoporosis and/or frailty effective amounts of a bisphosphonate compound and a compound or a stereoisomeric mixture thereof, diastereomerically enriched, diastereomerically pure, enantiomerically enriched or enantiomerically pure isomer thereof, or a prodrug of such compound, mixture or isomer thereof, or a pharmaceutically acceptable salt of the compound, mixture, isomer or prodrug according to claim 1.

22. A method for the treatment of osteoporosis and/or frailty according to claim 21 wherein the bisphosphonate compound is alendronate.

23. A method for the treatment of osteoporosis and/or frailty according to claim 21 wherein the bisphosphonate compound is ibandronate.

24. A method for the treatment or prevention of osteoporosis and/or frailty which comprises administering to a human or other animal with osteoporosis and/or frailty effective amounts of estrogen or Premarin® and a compound or a stereoisomeric mixture thereof, diastereomerically enriched, diastereomerically pure, enantiomerically enriched or enantiomerically pure isomer thereof, or a prodrug of such compound, mixture or isomer thereof, or a pharmaceutically acceptable salt of the compound, mixture, isomer or prodrug according to claim 1 and, optionally, progesterone.

25. A method for the treatment of osteoporosis and/or frailty which comprises administering to a human or other animal with osteoporosis and/or frailty effective amounts of calcitonin and a compound or a stereoisomeric mixture thereof, diastereomerically enriched, diastereomerically pure, enantiomerically enriched or enantiomerically pure isomer thereof, or a prodrug of such compound, mixture or isomer thereof, or a pharmaceutically acceptable salt of the compound, mixture, isomer or prodrug according to claim 1.

26. A method to increase IGF-1 levels in a human or other animal deficient in IGF-1 which comprises administering to a human or other animal with IGF-1 deficiency a compound or a stereoisomeric mixture thereof, diastereomerically enriched, diastereomerically pure, enantiomerically enriched or enantiomerically pure isomer thereof, or a prodrug of such compound, mixture or isomer thereof, or a pharmaceutically acceptable salt of the compound, mixture, isomer or prodrug according to claim 1.

27. A method for the treatment of osteoporosis and/or frailty which comprises administering to a human or other animal with osteoporosis and/or frailty effective amounts of an estrogen agonist or antagonist and a compound or a stereoisomeric mixture thereof, diastereomerically enriched, diastereomerically pure, enantiomerically enriched or enantiomerically pure isomer thereof, or a prodrug of such compound, mixture or isomer thereof, or a pharmaceutically acceptable salt of the compound, mixture, isomer or prodrug according to claim 1.

28. A method according to claim 27 wherein the estrogen agonist or antagonist is tamoxifen, droloxifene, raloxifene or idoxifene.

29. A method according to claim 27 wherein the estrogen agonist or antagonist is cis-6-(4-fluoro-phenyl)-5-[4-(2-piperidin-1-yl-ethoxy)-phenyl]-5,6,7,8-tetrahydro-naphthalene-2-ol; (–)-cis-6-phenyl-5-[4-(2-pyrrolidin-1-yl-ethoxy)-phenyl]-5,6,7,8-tetrahydro-naphthalene-2-ol; cis-6-phenyl-5-[4-(2-pyrrolidin-1-yl-ethoxy)-phenyl]-5,6,7,8-tetrahydro-naphthalene-2-ol; cis-1-[6'-pyrrolodinoethoxy-3'-pyridyl]-2-phenyl-6-hydroxy-1,2,3,4-tetrahydro-naphthalene; 1-(4'-pyrrolidinoethoxyphenyl)-2-(4"-fluorophenyl)-6-hydroxy-1,2,3,4-tetrahydroisoquinoline; cis-6-(4-hydroxyphenyl)-5-[4-(2-piperidin-1-yl-ethoxy)-phenyl]-5,6,7,8-tetrahydro-naphthalene-2-ol; or 1-(4'-pyrrolidinolethoxyphenyl)-2-phenyl-6-hydroxy-1,2,3,4-tetrahydro-isoquinoline.

30. A method for enhancing growth and improving carcass quality of an animal other than humans which comprises administering to said animal an effective amount of a compound or a stereoisomeric mixture thereof, diastereomerically enriched, diastereomerically pure, enantiomerically enriched or enantiomerically pure isomer thereof, or a prodrug of such compound, mixture or isomer thereof, or a pharmaceutically acceptable salt of the compound, mixture, isomer or prodrug according to claim 1.

31. A method for enhancing feed efficiency in an animal other than humans which comprises administering to said animal an effective amount of a compound or a stereoisomeric mixture thereof, diastereomerically enriched, diastereomerically pure, enantiomerically enriched or enantiomerically pure isomer thereof, or a prodrug of such compound, mixture or isomer thereof, or a pharmaceutically acceptable salt of the compound, mixture, isomer or prodrug according to claim 1.

32. A method for increasing milk production in a female mammal which comprises administering to said female mammal an effective amount of a compound or a stereoisomeric mixture thereof, diastereomerically enriched, diastereomerically pure, enantiomerically enriched or enantiomerically pure isomer thereof, or a prodrug of such compound, mixture or isomer thereof, or a pharmaceutically acceptable salt of the compound, mixture, isomer or prodrug according to claim 1.

33. A method for increasing piglet number, increasing pregnancy rate in sows, increasing viability of piglets, increasing weight of piglets or increasing muscle fiber size in piglets which comprises administering to a sow or piglet an effective amount of a compound or a stereoisomeric mixture thereof, diastereomerically enriched, diastereomerically pure, enantiomerically enriched or enantiomerically pure isomer thereof, or a prodrug of such compound, mixture or isomer thereof, or a pharmaceutically acceptable salt of the compound, mixture, isomer or prodrug according to claim 1.

34. A method for increasing muscle mass, which method comprises administering to a human or other animal in need of such treatment an amount of a compound or a stereoisomeric mixture thereof, diastereomerically enriched, diastereomerically pure, enantiomerically enriched or enantiomerically pure isomer thereof, or a prodrug of such compound, mixture or isomer thereof, or a pharmaceutically acceptable salt of the compound, mixture, isomer or prodrug according to claim 1 which is effective in promoting release of endogenous growth hormone.

35. A method for promoting growth in growth hormone deficient children which comprises administering to a growth hormone deficient child a compound or a stereoisomeric mixture thereof, diastereomerically enriched, diastereomerically pure, enantiomerically enriched or enantiomerically pure isomer thereof, or a prodrug of such compound, mixture or isomer thereof, or a pharmaceutically acceptable salt of the compound, mixture, isomer or prodrug according to claim 1 which is effective in promoting release of endogenous growth hormone.

36. A method for the treatment or prevention of congestive heart failure, obesity or frailty associated with aging, which comprises administering to a human or other animal in need thereof effective amounts of a functional somatostatin antagonist and a compound or a stereoisomeric mixture thereof, diastereomerically enriched, diastereomerically pure, enantiomerically enriched or enantiomerically pure isomer thereof, or a prodrug of such compound, mixture or isomer thereof, or a pharmaceutically acceptable salt of the compound, mixture, isomer or prodrug according to claim 1.

37. A method according to claim 36 wherein the functional somatostatin antagonist is an alpha-2 adrenergic agonist and the other animal is a dog, cat or a horse.

38. A method according to claim 36 wherein the alpha-2 adrenergic agonist is clonidine, xylazine or medetomidine.

39. A method for treating insulin resistance in a mammal, which comprises administering to said mammal an effective amount of a compound or a stereoisomeric mixture thereof, diastereomerically enriched, diastereomerically pure, enantiomerically enriched or enantiomerically pure isomer thereof, or a prodrug of such compound, mixture or isomer thereof, or a pharmaceutically acceptable salt of the compound, mixture, isomer or prodrug according to claim 1.

40. A method for increasing the endogenous production or release of growth hormone in a human or other animal which comprises administering effective amounts of a compound or a stereoisomeric mixture thereof, diastereomerically enriched, diastereomerically pure, enantiomerically enriched or enantiomerically pure isomer thereof, or a prodrug of such compound, mixture or isomer thereof, or a pharmaceutically acceptable salt of the compound, mixture, isomer or prodrug according to claim 1 and a growth hormone secretagogue selected from the group consisting of GHRP-6, Hexarelin, GHRP-1, growth hormone releasing factor (GRF), IGF-1, IGF-2 and B-HT920 or an analog thereof.

41. A pharmaceutical composition useful for treating or preventing osteoporosis and/or frailty which comprises a pharmaceutically acceptable carrier, an amount of a bisphosphonate compound and an amount of a compound or a stereoisomeric mixture thereof, diastereomerically enriched, diastereomerically pure, enantiomerically enriched or enantiomerically pure isomer thereof, or a prodrug of such compound, mixture or isomer thereof, or a pharmaceutically acceptable salt of the compound, mixture, isomer or prodrug according to claim 1.

42. A pharmaceutical composition useful for treating or preventing osteoporosis and/or frailty which comprises a pharmaceutically acceptable carrier, an amount of estrogen or Premarin®, an amount of a compound or a stereoisomeric mixture thereof, diastereomerically enriched, diastereomerically pure, enantiomerically enriched or enantiomerically pure isomer thereof, or a prodrug of such compound, mixture or isomer thereof, or a pharmaceutically acceptable salt of the compound, mixture, isomer or prodrug according to claim 1 and, optionally, an amount of progesterone.

43. A pharmaceutical composition useful for treating osteoporosis and/or frailty which comprises a pharmaceutically acceptable carrier, an amount of calcitonin and an amount of a compound or a stereoisomeric mixture thereof, diastereomerically enriched, diastereomerically pure, enantiomerically enriched or enantiomerically pure isomer thereof, or a prodrug of such compound, mixture or isomer thereof, or a pharmaceutically acceptable salt of the compound, mixture, isomer or prodrug according to claim 1.

44. A pharmaceutical composition useful for treating preventing congestive heart failure, obesity or frailty associated with aging, which comprises a pharmaceutically acceptable carrier, an amount of an alpha-2 adrenergic agonist and an amount of a compound or a stereoisomeric mixture thereof, diastereomerically enriched, diastereomerically pure, enantiomerically enriched or enantiomerically pure isomer thereof, or a prodrug of such compound, mixture or isomer thereof, or a pharmaceutically acceptable salt of the compound, mixture, isomer or prodrug according to claim 1.

45. A pharmaceutical composition according to claim 44 wherein the alpha-2 adrenergic agonist is clonidine, xylazine or medetomidine.

46. A method for increasing levels of endogenous growth hormone, which comprises administering to a human or other animal in need thereof effective amounts of a functional somatostatin antagonist and a compound or a stereoisomeric mixture thereof, diastereomerically enriched, diastereomerically pure, enantiomerically enriched or enantiomerically pure isomer thereof, or a prodrug of such compound, mixture or isomer thereof, or a pharmaceutically acceptable salt of the compound, mixture, isomer or prodrug according to claim 1.

47. A method according to claim 39 wherein the condition associated with insulin resistance is type I diabetes, type II diabetes, hyperglycemia, impaired glucose tolerance or an insulin resistant syndrome.

48. A method according to claim 39 wherein the condition associated with insulin resistance is associated with obesity or old age.

* * * * *